US012807668B2

(12) United States Patent
Janiak et al.

(10) Patent No.: US 12,807,668 B2
(45) Date of Patent: Nov. 24, 2026

(54) CRF2 RECEPTOR AGONISTS AND THEIR USE IN THERAPY

(71) Applicant: CORTERIA PHARMACEUTICALS, Paris (FR)

(72) Inventors: Philip Janiak, Paris (FR); Marie-Laure Ozoux, Paris (FR); Daniela Roversi, Pomezia (IT); Elisabetta Bianchi, Pomezia (IT); Martina Tripepi, Pomezia (IT); Alessia Santoprete, Pomezia (IT)

(73) Assignee: CORTERIA PHARMACEUTICALS, Paris (FR)

( * ) Notice: Subject to any disclaimer, the term of this patent is extended or adjusted under 35 U.S.C. 154(b) by 2 days.

(21) Appl. No.: 18/839,784

(22) PCT Filed: Feb. 21, 2023

(86) PCT No.: PCT/EP2023/054317

§ 371 (c)(1),
(2) Date: Aug. 20, 2024

(87) PCT Pub. No.: WO2023/161229

PCT Pub. Date: Aug. 31, 2023

(65) Prior Publication Data

US 2026/0001928 A1 Jan. 1, 2026

(30) Foreign Application Priority Data

Feb. 23, 2022 (EP) .................................... 22158188

(51) Int. Cl.
*C07K 14/575* (2006.01)
*A61K 38/00* (2006.01)
*A61P 9/12* (2006.01)

(52) U.S. Cl.
CPC .............. *C07K 14/575* (2013.01); *A61P 9/12* (2018.01); *A61K 38/00* (2013.01); *C07K 2319/70* (2013.01)

(58) Field of Classification Search
None
See application file for complete search history.

(56) References Cited

U.S. PATENT DOCUMENTS

2025/0243255 A1* 7/2025 Illiano .................... A61K 38/00

FOREIGN PATENT DOCUMENTS

WO 2008047241 A2 4/2008
WO 2018013803 A1 1/2018
WO 2019140030 A1 7/2019
WO 2022038179 A1 2/2022

OTHER PUBLICATIONS

Written Opinion mailed Sep. 12, 2023, in reference to co-pending European Application No. PCT/ EP2023/054317 filed Feb. 21, 2023.
International Search Opinion mailed Sep. 12, 2023, in reference to co-pending European Application No. PCT/EP2023/054317 filed Feb. 21, 2023.
Stirrat, et al., "Cardiovascular effects of urocortin 2 and urocortin 3 in patients with chronic heart failure", British Journal of Clinical Pharmacology, vol. 82, pp. 974-982, 2016.
Greico, et al., "Natural and synthetic peptides in the cardiovascular diseases: An update on diagnostic and therapeutic potentials", Archives of Biochemistry and Biophysics, vol. 662, pp. 15-32, 2019.

* cited by examiner

*Primary Examiner* — Marianne P Allen
(74) *Attorney, Agent, or Firm* — Dinsmore & Shohl LLP

(57) ABSTRACT

The present disclosure provides compounds which are peptides comprising the amino acid sequence of the formula (I) disclosed herein or pharmaceutically acceptable salts thereof. The compounds act as agonists of the corticotropin-releasing factor receptor 2 (CRF2) and are useful in therapy, especially in the treatment or prevention of cardiovascular diseases, kidney disease, obesity, diabetes, sarcopenia, particularly obesity-linked sarcopenia, heart failure, cachexia, and pulmonary hypertension.

19 Claims, No Drawings

Specification includes a Sequence Listing.

CRF2 RECEPTOR AGONISTS AND THEIR USE IN THERAPY

CROSS-REFERENCES TO RELATED APPLICATIONS

This application is a national-stage application under 35 U.S.C. § 371 of International Application No. PCT/EP2023/054317, filed Feb. 21, 2023, which claims the benefit of priority of European Application No. 22158188.7, filed Feb. 23, 2022, the contents of which are being hereby incorporated by reference in their entirety.

SEQUENCE LISTING

A computer-readable form (CRF) sequence listing having file name CTPH0001PA_ST26.xml (672,922 bytes), created Jul. 11, 2025, is incorporated herein by reference.

FIELD

The present disclosure relates to compounds which are agonists of the corticotropin-releasing factor receptor 2 (CRF2) and their use in therapy, especially in the treatment or prevention of cardiovascular diseases, obesity, diabetes, sarcopenia, particularly obesity-linked sarcopenia, cachexia, kidney disease, heart failure and pulmonary hypertension.

BACKGROUND

Urocortins (UCNs) are endogenous peptides which act through corticotropin-releasing factor (CRF) receptors, which are type 2 G protein-coupled receptors (GPCRs). The CRF receptor family comprises CRF1 receptors, which are encoded by the CRHR1 gene, and CRF2 receptors, which are encoded by the CRHR2 gene.

There are three known endogenous urocortins found in mammals: UCN1, UCN2 and UCN3. Despite a high degree of sequence homology, the binding of these peptides to CRF1 and CRF2 is different. CRF1 and CRF2 are activated non-selectively by Corticotropin Releasing Hormone (CRH) and UCN1, whereas UCN2 and UCN3 are CRF2-selective agonists. In particular, UCN2 is a thirty-eight amino acid peptide which selectively activates the CRF2 receptor, including the known isoforms CRF2-alpha ($\alpha$), -beta ($\beta$) and -gamma ($\gamma$).

Urocortins and their receptors are involved in neurohumoral responses to various stress and pathological situations. In particular, urocortins evoke positive hemodynamic effects in both preclinical experimental heart failure models and patients with heart failure or hypertension. Urocortins and CRF receptors are expressed in the heart, the kidney and in blood vessels, with CRF2 expressed robustly and CRF1 expressed minimally if at all (see Waser et al., Peptides, 2006, 27, 3029-3038). In experimental models, urocortins acting via CRF2 activation have been shown to improve cardiovascular function via the reduction of vascular resistance, improvement in kidney function and cardiac inotropic and lusitropic actions. In clinical studies, UCN2 and UCN3 have been shown to have direct vasorelaxant actions in healthy volunteers and in patients with heart failure (see Stirrat et al., Br. J. Clin. Pharmacol., 2016, 82, 974-982), while UCN2 has also been shown to increase cardiac output and reduce vascular resistance in patients with heart failure (see Davis et al., Eur. Heart J., 2007, 28, 2589-2597; and Chan et al., JACC: Heart Failure, 2013, 1, 433-441). A recombinant acetate salt of UCN3 has been shown to improve cardiac output and reduce vascular resistance in a multicentre study of patients with chronic stable heart failure (see Gheorghiade et al., Eur. J. Heart Fail., 2013, 15, 679-89).

Recent studies have demonstrated that UCN2 and/or UCN3 gene transfer in mice improves not only cardiac function but also glucose disposal (see Giamouridis et al., JACC: Basic to Translational Science, 2018, 3, 2). In addition, subcutaneous delivery of pegylated UCN2 has been shown to improve glucose tolerance and increase glucose uptake in skeletal muscle while reducing body weight (see Borg et al., Diabetes, 2019, 1403-1414). These findings suggest that urocortins may be useful not only in the treatment of cardiovascular diseases but also in the treatment of diseases such as diabetes and obesity.

Nevertheless, the extremely short half-life of urocortins remains a major limitation to their therapeutic use (see Davies et al., JACC, 2007, 49, 461-471). To date, treatment with urocortins cannot be sustained without continuous intravenous infusion. However, the management of chronic diabetic or heart failure patients requires treatment suitable for long-standing and home self-administration.

In an attempt to overcome such limitations, various analogs of urocortins have been proposed. For instance, WO2018013803 (Alsina-Fernandez; Eli Lilly and Company) and WO2022038179 discloses analogs of UCN2 which are taught as having utility in the treatment of diseases such as chronic kidney disease and type II diabetes.

However, there remains a need for improved CRF2 receptor agonists which are useful as therapeutic agents, especially in the treatment and prevention of cardiovascular diseases, obesity and diabetes. In particular, there is a need for selective CRF2 agonists having desirable efficacy, pharmacokinetic properties (e.g., improved half-life) and/or physicochemical properties (e.g., improved stability and/or solubility), extending the possible applications to sarcopenia, kidney disease, particularly obesity-linked sarcopenia, cachexia, heart failure and pulmonary hypertension.

SUMMARY

In a first aspect, the present disclosure provides a compound which is a peptide comprising the amino acid sequence of formula (I) (SEQ ID NO: 1):

```
(I)
X1-X2-X3-X4-X5-X6-X7-X8-X9-X10-X11-X12-X13-X14-
X15-X16-X17-X18-X19-X20-X21-X22-X23-X24-X25-X26-
X27-X28-X29-X30-X31-X32-X33-X34-X35-X36-X37-X38
```

Wherein

- X1 is absent or isoleucine (I); with Isoleucine in L or D configuration
- X2 is valine (V); with valine in L or D configuration
- X3 is leucine (L)
- X4 is serine (S)
- X5 is leucine (L)
- X6 is aspartate (D)
- X7 is valine (V) or D-valine (v)
- X8 is proline (P)
- X9 is isoleucine (I)
- X10 is lysine (K), alanine (A) or glycine (G); in particular Lysine (K)
- X11 is leucine (L); isoleucine (1), alpha-methyl-leucine ($\alpha$MeL) or 2-aminoisobutyric acid (Aib)

X12 is lysine (K), wherein the epsilon-amino group of the lysine side chain is covalently bound to an albumin-binding moiety (herein also denoted as (K*))

X13 is lysine (K), glutamine (Q) or alanine (A); in particular lysine (K) or glutamine (Q); more in particular lysine (K);

X14 is isoleucine (1) or 2-aminoisobutyric acid (Aib)

X15 is leucine (L), alpha-methyl-leucine (αMeL) or 2-aminoisobutyric acid (Aib)

X16 is leucine (L)

X17 is glutamate (E) or lysine (K)

X18 is glutamine (Q)

X19 is glutamate (E)

X20 is lysine (K), arginine (R) or alanine; in particular lysine (K) or arginine (R);

X21 is glutamine (Q)

X22 is lysine (K) or alanine (A); in particular alanine (A);

X23 is lysine (K), alanine (A), glutamate (E) or 2-aminoisobutyric acid (Aib); in particular lysine (K), alanine (A), or 2-aminoisobutyric acid (Aib);

X24 is glutamine (Q)

X25 is arginine (R), alanine (A), alpha-methyl-leucine (αMeL) or 2-aminoisobutyric acid (Aib); in particular arginine (R), alpha-methyl-leucine (αMeL) or 2-aminoisobutyric acid (Aib);

X26 is glutamate (E), or 2-aminoisobutyric acid (Aib);

X27 is glutamine (Q)

X28 is alanine (A)

X29 is glutamate (E)

X30 is lysine (K) or threonine (T);

X31 asparagine (N), glutamine (Q) or alanine (A);

X32 is lysine (K), valine (V), threonine (T), 2-aminoisobutyric acid (Aib), glutamate (E), alanine (A), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); or 1-aminocyclopropanecarboxylic acid (Cpx);

X33 is glutamine (Q)

X34 is isoleucine (1)

X35 is leucine (L)

X36 is alanine (A) or glutamate (E);

X37 is glutamine (Q)

X38 is valine and wherein when X1 is isoleucine, then X7 is D-valine, and X32 is selected from valine (V), threonine (T), 2-aminoisobutyric acid (Aib), alanine (A), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); or 1-aminocyclopropanecarboxylic acid (Cpx); and said isoleucine is optionally N-terminally acetylated or N-methylated; or a pharmaceutically acceptable salt thereof.

In a second aspect of the disclosure, there is provided a pharmaceutical composition comprising a compound of the disclosure and a pharmaceutically acceptable excipient, diluent or carrier.

The compounds and pharmaceutical compositions disclosed herein are useful in therapy and may be used in the treatment or prevention of various diseases through agonism of the CRF2 receptor. Thus, in other aspects, the disclosure is directed to the use of the compounds and pharmaceutical compositions in therapy, especially in the treatment or prevention of cardiovascular diseases, obesity, diabetes, kidney disease, sarcopenia, particularly obesity-linked sarcopenia, cachexia, heart failure and pulmonary hypertension.

DETAILED DESCRIPTION

The present disclosure relates to compounds which are derivatives of UCN2 and which are useful as CRF2 receptor agonists. The compounds exhibit desirable activity and selectivity at the CRF2 receptor, as well as improved pharmacokinetic properties and beneficial in vivo effects in relevant animal models. In addition, the compounds exhibit desirable physicochemical properties, such as desirable solubility and stability, making them excellent candidates for solution formulations for subcutaneous delivery. The compounds are useful in therapy, especially in the treatment or prevention of cardiovascular diseases, kidney disease, obesity, diabetes, sarcopenia, particularly obesity-linked sarcopenia, cachexia, heart failure and pulmonary hypertension.

The desired properties of the UCN2 analogues disclosed in WO2022038179, in particular enabling once daily administration, were found to be further improved by N-terminal modification (N-methylation, acetylation or N-terminal truncation with preferably acylation or N-methylation on Val 2) of said UCN2 like peptides when combined with further modifications at position 32 as evident from the data hereinafter, shown to be key for the chemical stability of the peptides. Preferably these N-terminal modifications and modifications at position 32 are further combined with a D-valine at position 7 and further changes to lower the isoelectric point below 7 to improve the solubility of the peptides at neutral pH. In particular In case the isoelectric point of the sequence is close to 7, mutations were introduced at one or more positions where basic amino acids are present, such as in particular the positions 10, 13, 20, 22, 23 and 25 with the benefits of a) lowering the isoelectric point below 6 and improving solubility at neutral pH and b) at the same time surprisingly reduce the undesired mast cell degranulation effect resulting in pseudo-allergic reactions often observed with peptides comprising basic amino acids.

Compounds

The compounds of the disclosure are peptides comprising the amino acid sequence of the formula (I) recited above or pharmaceutically acceptable salts of said peptides.

In the present disclosure, amino acids are referred to by their name, their commonly known three-letter symbols or by the one-letter symbols recommended by the IUPAC-IUB Biochemical Nomenclature Commission. Generally accepted three-letter codes for other amino acids, such as Aib for 2-aminoisobutyric acid, may also be used. Unless otherwise indicated, all amino acids employed in the compounds of the disclosure are L-amino acids. Thus, for example, L-valine is referred to as "valine", "V" or "Val", whereas D-valine is specifically identified as such, and may be represented "v" or "D-val". In one letter symbols the D-amino acids are represented with small caps, with for example isoleucine being referred to as "i", valine being referred to as "v", serine being referred to as "s", leucine being referred to as "I", etc.

In an embodiment the present invention provides a compound which is a peptide comprising the amino acid sequence of formula (I) above; wherein;

X1 is absent or isoleucine (I); with Isoleucine in L or D configuration
X2 is valine (V); with valine in L or D configuration;
X3 is leucine (L)
X4 is serine (S)
X5 is leucine (L)
X6 is aspartate (D);
X7 is valine (V) or D-valine (v);
X8 is proline (P)
X9 is isoleucine (I)
X10 is lysine (K)
X11 is leucine (L); isoleucine (I), alpha-methyl-leucine (αMeL) or 2-aminoisobutyric acid (Aib);
X12 is lysine (K), wherein the epsilon-amino group of the lysine side chain is covalently bound to an albumin-binding moiety (K*);
X13 is lysine (K) or glutamine (Q);
X14 is isoleucine (I) or 2-aminoisobutyric acid (Aib);
X15 is leucine (L), alpha-methyl-leucine (αMeL) or 2-aminoisobutyric acid (Aib);
X16 is leucine (L)
X17 is glutamate (E) or lysine (K);
X18 is glutamine (Q)
X19 is glutamate (E)
X20 is lysine (K) or arginine (R);
X21 is glutamine (Q)
X22 is lysine (K)
X23 is lysine (K), alanine (A), glutamate (E) or 2-aminoisobutyric acid (Aib);
X24 is glutamine (Q)
X25 is arginine (R), alpha-methyl-leucine (αMeL) or 2-aminoisobutyric acid (Aib);
X26 is glutamate (E), or 2-aminoisobutyric acid (Aib);
X27 is glutamine (Q)
X28 is alanine (A)
X29 is glutamate (E)
X30 is lysine (K) or threonine (T);
X31 asparagine (N), glutamine (Q) or alanine (A);
X32 is lysine (K), valine (V), threonine (T), 2-aminoisobutyric acid (Aib), glutamate (E), alanine (A), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-amino-cyclopentane-1-carboxylic acid (Cpex); or 1-aminocyclopropanecarboxylic acid (Cpx);
X33 is glutamine (Q)
X34 is isoleucine (1)
X35 is leucine (L)
X36 is alanine (A) or glutamate (E);
X37 is glutamine (Q)
X38 is valine and wherein;

when X1 is isoleucine, then X7 is D-valine, and X32 is selected from valine (V), threonine (T), 2-aminoisobutyric acid (Aib), alanine (A), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); or 1-aminocyclopropanecarboxylic acid (Cpx); and said isoleucine is optionally N-terminally acetylated or N-methylated; in particular N-terminally acetylated; or a pharmaceutically acceptable salt thereof.

The aforementioned proviso on the selection of X32 when X1 is isoleucine, and X7 is D-valine, is applicable throughout the different embodiments herein disclosed, but for the independent embodiments hereinafter. In an embodiment of the aforementioned proviso X1 is an N-terminally acetylated or N-methylated isoleucine. In a particular embodiment of the aforementioned proviso X1 is an N-terminally acetylated isoleucine.

In an embodiment when X1 is absent, X2 is valine with valine in L or D configuration, in particular valine in L configuration (V); with said valine optionally N-terminally acylated or alkylated (e.g N-methylated). In particular when X1 is absent, X2 is valine said valine being N-terminally acylated with a C1-20alkanoyl group; more in particular said valine being N-terminally acylated with a C1-10alkanoyl group; even more in particular said valine being N-terminally acylated with an alkanoyl group selected from ethanoyl, methanoyl, propanoyl, butanoyl, pentanoyl hexanoyl, heptanoyl, decanoyl, dodecanoyl, or tetradecanoyl; more in particular selected from ethanoyl, methanoyl, propanoyl, butanoyl, pentanoyl hexanoyl or heptanoyl.

In a particular embodiment when X1 is absent, X2 is valine with valine in L or D configuration, in particular valine in L configuration (V); with said valine being N-terminally acylated or alkylated (preferably with an alkanoyl group as mentioned herein before); and X32 is selected from valine (V), threonine (T), 2-aminoisobutyric acid (Aib), alanine (A), glutamate (E), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-amino-cyclopentane-1-carboxylic acid (Cpex); or 1-aminocyclopropanecarboxylic acid (Cpx).

In an embodiment when X1 is absent, X2 is valine with valine in L or D configuration, in particular valine in L configuration (V); with said valine being N-terminally acylated or alkylated (preferably with an alkanoyl group as mentioned herein before); and X32 is selected from valine (V), threonine (T), 2-aminoisobutyric acid (Aib), alanine (A), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); or 1-aminocyclopropanecarboxylic acid (Cpx).

In another particular embodiment when X1 is absent, X2 is valine with valine in L or D configuration, in particular valine in L configuration (V); with said valine being N-terminally alkylated or N-terminally acylated with a C1-20alkanoyl group; more in particular said valine being N-terminally acylated with a C1-10alkanoyl group; even more in particular said valine being N-terminally acylated with an alkanoyl group selected from from ethanoyl, methanoyl, propanoyl, butanoyl, pentanoyl hexanoyl or heptanoyl; and X32 is selected from valine (V), threonine (T), 2-aminoisobutyric acid (Aib), alanine (A), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); or 1-aminocyclopropanecarboxylic acid (Cpx).

In an embodiment, X7 is D-valine (v).

In an embodiment, X11 alpha-methyl-leucine (αMeL) or 2-aminoisobutyric acid (Aib); in particular alpha-methyl-leucine (αMeL).

In an embodiment, X15 is alpha-methyl-leucine (αMeL) or 2-aminoisobutyric acid (Aib).

In an embodiment, X23 is alanine (A), glutamate (E) or 2-aminoisobutyric acid (Aib).

In an embodiment, X25 is alpha-methyl-leucine (αMeL) or 2-aminoisobutyric acid (Aib); in particular alpha-methyl-leucine (αMeL).

In an embodiment, X31 is glutamine (Q).

In an embodiment, X32 is selected from valine (V), threonine (T), 2-aminoisobutyric acid (Aib), alanine (A), glutamate (E), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); or 1-aminocyclopropanecarboxylic acid (Cpx); in particular X32 is selected from valine (V), threonine (T), 2-aminoisobutyric acid (Aib), alanine (A), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); or 1-aminocyclopropanecarboxylic acid (Cpx); with the proviso that when X1 is isoleucine, then X7 is D-valine, and X32 is selected from valine (V), threonine (T), 2-aminoisobutyric acid (Aib), alanine (A), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); or 1-aminocyclopropanecarboxylic acid (Cpx); in particular 2-aminoisobutyric acid (Aib), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); or 1-aminocyclopropanecarboxylic acid (Cpx), and said isoleucine is optionally N-terminally acetylated or N-methylated.

In a more particular embodiment X32 is selected from 2-aminoisobutyric acid (Aib), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); even more in particular X32 is selected from 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex).

In an embodiment, the amino acid residue at X38 is amidated.

In an independent embodiment, the present invention provides a peptide comprising the amino acid sequence of formula (I) as defined above, wherein at least one of X10, X11, X13, X15, X20, X22, X23, X25, X31 and X32 is selected as;

X10 being alanine (A) or glycine (G);

X11 being isoleucine (I), alpha-methyl-leucine (αMeL) or 2-aminoisobutyric acid (Aib); in particular alpha-methyl-leucine (αMeL) or 2-aminoisobutyric acid (Aib); more in particular alpha-methyl-leucine (αMeL);

X13 being glutamine (Q) or alanine (A);

X15 being alpha-methyl-leucine (αMeL) or 2-aminoisobutyric acid (Aib);

X20 being arginine (R) or alanine (A);

X22 being alanine (A);

X23 being alanine (A), glutamate (E) or 2-aminoisobutyric acid (Aib);

X25 being alanine (A); alpha-methyl-leucine (αMeL) or 2-aminoisobutyric acid (Aib); in particular alpha-methyl-leucine (αMeL) or 2-aminoisobutyric acid (Aib); more in particular alpha-methyl-leucine (αMeL);

X31 being glutamine (Q) or alanine (A); in particular glutamine (Q) and

X32 being glutamate (E), 2-aminoisobutyric acid (Aib), alanine (A), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); or 1-aminocyclopropanecarboxylic acid (Cpx); in particular X32 being selected from 2-aminoisobutyric acid (Aib), 2-aminobutyric acid (Abu); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); and 1-aminocyclohexanecarboxylic acid (Chx).

In a further independent embodiment X7 is D-Valine, X38 is amidated and at least one of X11, X15, X23, X25, X31 and X32 is selected as;

X11 being alpha-methyl-leucine (αMeL) or 2-aminoisobutyric acid (Aib); in particular alpha-methyl-leucine (αMeL);

X15 being alpha-methyl-leucine (αMeL) or 2-aminoisobutyric acid (Aib);

X23 being alanine (A), glutamate (E) or 2-aminoisobutyric acid (Aib);

X25 being alpha-methyl-leucine (αMeL) or 2-aminoisobutyric acid (Aib); in particular alpha-methyl-leucine (αMeL);

X31 being glutamine (Q); and

X32 being glutamate (E), 2-aminoisobutyric acid (Aib), alanine (A), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); or 1-aminocyclopropanecarboxylic acid (Cpx); in particular X32 being selected from 2-aminoisobutyric acid (Aib), 2-aminobutyric acid (Abu); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); and 1-aminocyclohexanecarboxylic acid (Chx).

In another independent embodiment X1 is and N-methylated or acetylated isoleucine (in particular an acetylated isoleucine) or absent and when absent X2 is acylated Valine, X7 is D-Valine, X38 is amidated and at least one of X11, X15, X23, X25, X31 and X32 is selected as;

X11 being alpha-methyl-leucine (αMeL) or 2-aminoisobutyric acid (Aib); in particular alpha-methyl-leucine (αMeL);
X15 being alpha-methyl-leucine (αMeL) or 2-aminoisobutyric acid (Aib);
X23 being alanine (A), glutamate (E) or 2-aminoisobutyric acid (Aib);
X25 being alpha-methyl-leucine (αMeL) or 2-aminoisobutyric acid (Aib); in particular alpha-methyl-leucine (αMeL);
X31 being glutamine (Q); and
X32 being glutamate (E), 2-aminoisobutyric acid (Aib), alanine (A), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); or 1-aminocyclopropanecarboxylic acid (Cpx); in particular X32 being selected from 2-aminoisobutyric acid (Aib), 2-aminobutyric acid (Abu); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); and 1-aminocyclohexanecarboxylic acid (Chx).

In an another independent embodiment X7 is D-Valine, X38 is amidated, X32 is selected from glutamate (E), 2-aminoisobutyric acid (Aib), alanine (A), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); or 1-aminocyclopropanecarboxylic acid (Cpx); in particular X32 being selected from 2-aminoisobutyric acid (Aib), 2-aminobutyric acid (Abu); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); and 1-aminocyclohexanecarboxylic acid (Chx); and at least one of X11, X15, X23, X25, and X31 is selected as;
X11 being alpha-methyl-leucine (αMeL) or 2-aminoisobutyric acid (Aib); in particular alpha-methyl-leucine (αMeL);
X15 being alpha-methyl-leucine (αMeL) or 2-aminoisobutyric acid (Aib);
X23 being alanine (A), glutamate (E) or 2-aminoisobutyric acid (Aib);
X25 being alpha-methyl-leucine (αMeL) or 2-aminoisobutyric acid (Aib); in particular alpha-methyl-leucine (αMeL); and
X31 being glutamine (Q).

In another independent embodiment X1 is and N-methylated or acetylated isoleucine (in particular an acetylated isoleucine) or absent and when absent X2 is acylated Valine, X7 is D-Valine, X38 is amidated, X32 is selected from glutamate (E), 2-aminoisobutyric acid (Aib), alanine (A), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); or 1-aminocyclopropanecarboxylic acid (Cpx); in particular X32 being selected from 2-aminoisobutyric acid (Aib), 2-aminobutyric acid (Abu); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); and 1-aminocyclohexanecarboxylic acid (Chx); and at least one of X11, X15, X23, X25, and X31 is selected as;
X11 being alpha-methyl-leucine (αMeL) or 2-aminoisobutyric acid (Aib); in particular alpha-methyl-leucine (αMeL);
X15 being alpha-methyl-leucine (αMeL) or 2-aminoisobutyric acid (Aib);
X23 being alanine (A), glutamate (E) or 2-aminoisobutyric acid (Aib);
X25 being alpha-methyl-leucine (αMeL) or 2-aminoisobutyric acid (Aib); in particular alpha-methyl-leucine (αMeL); and
X31 being glutamine (Q).

In an embodiment:
X1 is absent or an N-terminally acetylated or N-methylated isoleucine (I);
X2 is valine (V), wherein when X1 is absent said valine is N-terminally acylated or alkylated; in particular N-terminally acylated with an alkanoyl group selected from ethanoyl, methanoyl, propanoyl, butanoyl, pentanoyl hexanoyl or heptanoyl; more in particular N-terminally acylated with a pentanoyl group;
X7 is D-valine (v)
X9 is isoleucine (I);
X10 is lysine (K);
X11 is leucine (L) or alpha-methyl-leucine (αMeL);
X14 is isoleucine (I);
X15 is leucine (L);
X23 is lysine (K), alanine (A), glutamate (E) or 2-aminoisobutyric acid (Aib);
X25 is arginine (R);
X26 is glutamate (E);
X31 is asparagine (N);
X32 is glutamate (E), valine (V), threonine (T), 2-aminoisobutyric acid (Aib), alanine (A), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); or 1-aminocyclopropanecarboxylic acid (Cpx); in particular X32 is selected from 2-aminoisobutyric acid (Aib), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); more in particular X32 is selected from 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex).

In an embodiment:
X1 is absent or an N-terminally acetylated or N-methylated isoleucine (I);
X2 is valine (V), wherein when X1 is absent said valine is N-terminally acetylated or acylated with an alkanoyl group selected from ethanoyl, methanoyl, propanoyl, butanoyl, pentanol hexanoyl or heptanoyl; more in particular N-terminally acylated with a pentanoyl group;

X3 is leucine (L)

X4 is serine (S)

X5 is leucine (L)

X6 is aspartate (D);

X7 is valine (V) or D-valine (v); in particular D-valine (v);

X8 is proline (P)

X9 is isoleucine (I);

X10 is lysine (K);

X11 is leucine (L) or alpha-methyl-leucine (αMeL);

X12 is lysine (K), wherein the epsilon-amino group of the lysine side chain is covalently bound to an albumin-binding moiety (herein also denoted as (K*));

X13 is lysine (K) or glutamine (Q); in particular lysine (K);

X14 is isoleucine (1);

X15 is leucine (L);

X16 is leucine (L) or lysine (K); in particular leucine (L);

X17 is glutamate (E) or arginine (R); in particular glutamate (E);

X18 is glutamine (Q);

X19 is glutamate (E);

X20 is lysine (K) or arginine (R); in particular lysine (K);

X21 is glutamine (Q);

X22 is lysine (K)

X23 is lysine (K), alanine (A), glutamate (E) or 2-aminoisobutyric acid (Aib);

X24 is glutamine (Q);

X25 is arginine (R);

X26 is glutamate (E);

X27 is glutamine (Q);

X28 is alanine (A);

X29 is glutamate (E);

X30 is threonine (T) or lysine (K); in particular threonine (T);

X31 is asparagine (N);

X32 is lysine (K), 2-aminoisobutyric acid (Aib), glutamate (E), alanine (A), 2-aminobutyric acid (Abu); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); or 1-aminocyclopropanecarboxylic acid (Cpx);

X33 is glutamine (Q);

X34 is isoleucine (1)

X35 is leucine (L)

X36 is alanine (A) or glutamate (E); in particular alanine (A);

X37 is glutamine (Q);

X38 is valine (V);

wherein;

when X1 is an N-terminally acetylated or N-methylated isoleucine (1); then X7 is D-valine, and X32 is selected from 2-aminoisobutyric acid (Aib), glutamate (E), alanine (A), 2-aminobutyric acid (Abu); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); or 1-aminocyclopropanecarboxylic acid (Cpx); in particular X32 is then selected from 2-aminoisobutyric acid (Aib), 2-aminobutyric acid (Abu); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); or 1-aminocyclopropanecarboxylic acid (Cpx); even more in particular X32 is then 2-aminoisobutyric acid (Aib), when X1 is an N-terminally acetylated or N-methylated isoleucine (1); and wherein the albumin binding moiety is selected from the following groups:

-{AEEA}$_2$-gGlu-C(O)(CH$_2$)$_{16}$COOH;

-{AEEA}$_2$-gGlu-C(O)(CH$_2$)$_{18}$COOH;

-{AEEA}-gGlu-C(O)(CH$_2$)$_{16}$COOH;

-{AEEA}-gGlu-C(O)(CH$_2$)$_{18}$COOH;

-gGlu-C(O)(CH$_2$)$_{14}$COOH;

-gGlu-C(O)(CH$_2$)$_{16}$COOH;

-gGlu-C(O)(CH$_2$)$_{18}$COOH;
and

-{gGlu}$_2$-C(O)(CH$_2$)$_{18}$COOH.

or a pharmaceutically acceptable salt thereof.

In an embodiment:

X1 is absent or an N-terminally acetylated or N-methylated isoleucine (1);

X2 is valine (V), wherein when X1 is absent said valine is N-terminally acylated or alkylated; in particular N-terminally acylated with an alkanoyl group selected from ethanoyl, methanoyl, propanoyl, butanoyl, pentanoyl hexanoyl or heptanoyl; more in particular N-terminally acylated with a pentanoyl group;

X7 is D-valine (v)

X9 is isoleucine (1);

X10 is lysine (K);

X11 is leucine (L) or alpha-methyl-leucine (αMeL);

X14 is isoleucine (1);

X15 is leucine (L);

X23 is lysine (K); glutamate (E) or alanine (A);

X25 is arginine (R);

X26 is glutamate (E);

X31 is asparagine (N);

X32 is glutamate (E), 2-aminoisobutyric acid (Aib), or 4-Amino-piperidine-4-carboxylic acid (4-Pip); and wherein when X1 is an N-terminally acetylated or N-methylated isoleucine (1), X32 is selected from 2-aminoisobutyric acid (Aib), or 4-Amino-piperidine-4-carboxylic acid (4-Pip).

In an embodiment:

X1 is absent;

X2 is valine (V) N-terminally methylated or acylated with a group selected from a propanoyl group, a butanoyl group, a pentanoyl group or an isopropanoyl group and X32 is selected from glutamate (E), valine (V), threonine (T), 2-aminoisobutyric acid (Aib), alanine (A), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); or 1-aminocyclopropanecarboxylic acid (Cpx).

In an embodiment:

X1 is an N-terminally acetylated or N-methylated isoleucine (1);

X2 is valine (V);

X7 is D-valine (v);

X9 is isoleucine (1);

X10 is lysine (K);

X11 is leucine (L);

X14 is isoleucine (1);
X15 is leucine (L);
X23 is lysine (K), alanine (A), or 2-aminoisobutyric acid (Aib);
X25 is arginine (R);
X26 is glutamate (E);
X31 is asparagine (N);
X32 is glutamate (E), valine (V), threonine (T), 2-aminoisobutyric acid (Aib), alanine (A), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); or 1-aminocyclopropanecarboxylic acid (Cpx); in particular X32 is selected from 2-aminoisobutyric acid (Aib), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); more in particular X32 is selected from 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex), In an embodiment:
X1 is absent or isoleucine (I);
X2 is valine (V);
X7 is D-valine (v);
X9 is isoleucine (I);
X10 is lysine (K);
X11 is leucine (L), α-methyl-leucine (αMeL) or 2-aminoisobutyric acid (Aib); in particular X11 is leucine (L), or α-methyl-leucine (αMeL)
X14 is isoleucine (I) or glutamine (Q); in particular X14 is isoleucine (I);
X15 is leucine (L);
X16 is leucine (L);
X17 is glutamate (E) or lysine (K); in particular X17 is glutamate (E)
X23 is lysine (K), alanine (A), or 2-aminoisobutyric acid (Aib); in particular X23 is lysine (K);
X25 is arginine (R);
X26 is glutamate (E);
X30 is lysine (K) or threonine (T); in particular X30 is threonine (T);
X31 is asparagine (N);
X32 is lysine (K), glutamate (E), valine (V), threonine (T), 2-aminoisobutyric acid (Aib), alanine (A), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); or 1-aminocyclopropanecarboxylic acid (Cpx); in particular X32 is lysine selected from lysine (K), 2-aminoisobutyric acid (Aib), glutamate (E), 2-aminobutyric acid (Abu); α-methyl-lysine (αMeK); 2,3-diaminopropionic acid (Dap); 4-Amino-piperidine-4-carboxylic acid (4-Pip); wherein;

when X1 is absent, then X2 is optionally N-terminally methylated or acylated with a group selected from an acetyl group, a propanoyl group, a butanoyl group, a pentanoyl group or an isopropanoyl group; and when X1 is isoleucine (1), then X32 is glutamate (E), valine (V), threonine (T), 2-aminoisobutyric acid (Aib), alanine (A), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); or 1-aminocyclopropanecarboxylic acid (Cpx); in particular X32 is then 2-aminoisobutyric acid (Aib), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); or 1-aminocyclopropanecarboxylic acid (Cpx); more in particular X32 is 2-aminoisobutyric acid (Aib), glutamate (E), 2-aminobutyric acid (Abu); α-methyl-lysine (αMeK); 2,3-diaminopropionic acid (Dap); 4-Amino-piperidine-4-carboxylic acid (4-Pip); even more in particular X32 is then 2-aminoisobutyric acid (Aib), 2-aminobutyric acid (Abu); α-methyl-lysine (αMeK); 2,3-diaminopropionic acid (Dap); 4-Amino-piperidine-4-carboxylic acid (4-Pip)

As indicated above, the compounds of the disclosure comprise a modified lysine (K) residue at the position denoted by X12 in formula (I), in which an albumin-binding moiety is covalently bound to the epsilon-amino group of the lysine side chain.

The term "albumin-binding moiety" as used herein refers to a moiety which is capable of binding to albumin by covalent or non-covalent binding. In embodiments, the albumin-binding moiety is capable of binding to albumin by non-covalent binding. The albumin-binding moiety may comprise or consist of a group selected from fatty acids, phthalocyanines, coumarins, flavonoids, tetracyclines, naphthalenes, arylcarboxylic acids, heteroarylcarboxylic acids, lipids, alkyl amines, cyclic or linear tetrapyrroles and organometallic compounds thereof, halo-substituted aromatic acid derivatives, organic dyes, and derivatives of tryptophan and thyroxine.

In a particular embodiment, the albumin-binding moiety comprises a C10-C24 fatty acid group which is conjugated to the epsilon-amino group of the lysine side chain either by a direct bond or by a linker. The term "C10-C24 fatty acid" as used herein means a carboxylic acid having from 10 to 24 carbon atoms. The C10-C24 fatty acid can be a saturated monoacid or a saturated diacid. By "saturated" is meant that the fatty acid contains no carbon-carbon double or carbon-carbon triple bonds.

Examples of saturated C10-C24 fatty acids include capric acid (decanoic acid, a C10 monoacid), lauric acid (dodecanoic acid, a C12 monoacid), dodecanedioic acid (DDDA) (a C12 diacid), myristic acid (tetradecanoic acid; a C14 monoacid), tetradecanedioic acid (a C14 diacid), pentadecylic acid (pentadecanoic acid; a C15 monoacid), pentadecanedioic acid (a C15 diacid), palmitic acid (hexadecanoic acid; a C16 monoacid), hexadecanedioic acid (a C16 diacid), margaric acid (heptadecanoic acid; a C17 monoacid), heptadecanedioic acid (a C17 diacid), stearic acid (octadecanoic acid; a C18 monoacid), octadecanedioic acid (a C18 diacid), nonadecylic acid (nonadecanoic acid; a C19 monoacid), nonadecanedioic acid (a C19 diacid), arachadic acid (eicosanoic acid; a C20 monoacid), eicosanedioic acid (a C20 diacid), heneicosylic acid (heneicosanoic acid; a C21 monoacid), heneicosanedioic acid (a C21 diacid), behenic acid (docosanoic acid; a C22 monoacid), docosanedioic acid (a C22 diacid), tricosylic acid (tricosanoic acid, a C23 monoacid), tricosanedioic acid (a C23 diacid), lignoceric acid (tetracosanoic acid; a C24 monoacid), and tetracosanedioic acid (a C24 diacid).

In an embodiment, the C10-C24 fatty acid group is a C12-C24 fatty acid; in particular a C12-C20 fatty acid; more in particular a fatty acid selected from the group consisting of lauric acid (dodecanoic acid, a C12 monoacid), dodecanedioic acid (DDDA) (a C12 diacid), myristic acid (tetradecanoic acid; a C14 monoacid), tetradecanedioic acid (a C14 diacid), palmitic acid (hexadecanoic acid; a C16 monoacid), hexadecanedioic acid (a C16 diacid), stearic acid (octadecanoic acid; a C18 monoacid), octadecanedioic acid (a C18 diacid), arachadic acid (eicosanoic acid; a C20 monoacid) and eicosanedioic acid (a C20 diacid).

The C10-C24 fatty acid may be bound directly to the epsilon-amino group of the lysine side chain. Alternatively, the C10-C24 fatty acid may be bound to the epsilon-amino group of the lysine side chain through a linker. The linker may comprise one or more groups selected from [2-(2-aminoethoxy)ethoxy]acetyl (referred to herein as “AEEA”), glycine (Gly), N-methylglycine (N-MeGly) and gamma-glutamate (gGlu).

In an embodiment, the albumin-binding moiety is a group of the formula (II):

(II)
$-Y-Z-C(O)R^1$ wherein

Y is AEEA, $\{AEEA\}_2$, $\{AEEA\}_3$, Gly, $\{Gly\}_2$, $\{Gly\}_3$, N-MeGly, $\{N\text{-}MeGly\}_2$, $\{N\text{-}MeGly\}_3$ or absent;

Z is gGlu, $\{gGlu\}_2$ or absent; and $R^1$ is $-(CH_2)_xCOOH$ or $-(CH_2)_xCH_3$, wherein x is an integer from 10 to 22.

In an embodiment of the albumin binding moiety of formula (II) Y is {AEEA} or $\{AEEA\}_2$ and Z is gGlu or $\{gGlu\}_2$.

In an embodiment of the albumin binding moiety of formula (II), Y is absent and Z is gGlu.

In an embodiment of the albumin binding moiety of formula (II), Y and Z are both absent.

In an embodiment of the albumin binding moiety of formula (II), $R^1$ is $-(CH_2)_xCOOH$, wherein x is an integer from 12 to 18.

In an embodiment of the albumin binding moiety of formula (II), Y is {AEEA} or $\{AEEA\}_2$; Z is gGlu or $\{gGlu\}_2$; and $R^1$ is $-(CH_2)_xCOOH$, wherein x is an integer from 12 to 18

In an embodiment, the albumin-binding moiety is selected from the following groups:

$-\{AEEA\}-gGlu-C(O)(CH_2)_{10}COOH$;

$-\{AEEA\}-gGlu-C(O)(CH_2)_{12}COOH$;

$-\{AEEA\}-gGlu-C(O)(CH_2)_{14}COOH$;

$-\{AEEA\}-gGlu-C(O)(CH_2)_{16}COOH$;

$-\{AEEA\}-gGlu-C(O)(CH_2)_{18}COOH$;

$-\{AEEA\}_2-gGlu-C(O)(CH_2)_{10}COOH$;

-continued $-\{AEEA\}_2-gGlu-C(O)(CH_2)_{12}COOH$;

$-\{AEEA\}_2-gGlu-C(O)(CH_2)_{14}COOH$;

$-\{AEEA\}_2-gGlu-C(O)(CH_2)_{16}COOH$;

$-\{AEEA\}_2-gGlu-C(O)(CH_2)_{18}COOH$;

$-\{AEEA\}_2-\{gGlu\}_2-C(O)(CH_2)_{10}COOH$;

$-\{AEEA\}_2-\{gGlu\}_2-C(O)(CH_2)_{12}COOH$;

$-\{AEEA\}_2-\{gGlu\}_2-C(O)(CH_2)_{14}COOH$;

$-\{AEEA\}_2-\{gGlu\}_2-C(O)(CH_2)_{16}COOH$;

$-\{AEEA\}_2-\{gGlu\}_2-C(O)(CH_2)_{18}COOH$;

$-gGlu-C(O)(CH_2)_{10}COOH$;

$-gGlu-C(O)(CH_2)_{12}COOH$;

$-gGlu-C(O)(CH_2)_{14}COOH$;

$-gGlu-C(O)(CH_2)_{16}COOH$;

$-gGlu-C(O)(CH_2)_{18}COOH$;

$-\{gGlu\}_2-C(O)(CH_2)_{10}COOH$;

$-\{gGlu\}_2-C(O)(CH_2)_{12}COOH$;

$-\{gGlu\}_2-C(O)(CH_2)_{14}COOH$;

$-\{gGlu\}_2-C(O)(CH_2)_{16}COOH$;

and $-\{gGlu\}_2-C(O)(CH_2)_{18}COOH$.

In an embodiment, the albumin-binding moiety is selected from the following groups:

$-\{AEEA\}_2-gGlu-C(O)(CH_2)_{10}COOH$;

$-\{AEEA\}_2-gGlu-C(O)(CH_2)_{12}COOH$;

$-\{AEEA\}_2-gGlu-C(O)(CH_2)_{14}COOH$;

$-\{AEEA\}_2-gGlu-C(O)(CH_2)_{16}COOH$;

$-\{AEEA\}_2-gGlu-C(O)(CH_2)_{18}COOH$;

$-\{AEEA\}_2-\{gGlu\}_2-C(O)(CH_2)_{10}COOH$;

$-\{AEEA\}_2-\{gGlu\}_2-C(O)(CH_2)_{12}COOH$;

$-\{AEEA\}_2-\{gGlu\}_2-C(O)(CH_2)_{14}COOH$;

$-\{AEEA\}_2-\{gGlu\}_2-C(O)(CH_2)_{16}COOH$;

$-\{AEEA\}_2-\{gGlu\}_2-C(O)(CH_2)_{18}COOH$;

$-gGlu-C(O)(CH_2)_{10}COOH$;

$-gGlu-C(O)(CH_2)_{12}COOH$;

$-gGlu-C(O)(CH_2)_{14}COOH$;

$-gGlu-C(O)(CH_2)_{16}COOH$;

and $-gGlu-C(O)(CH_2)_{18}COOH$.

In an embodiment, the albumin-binding moiety is selected from the following groups:

-{AEEA}$_2$-gGlu-C(O)(CH$_2$)$_{16}$COOH;

-{AEEA}$_2$-gGlu-C(O)(CH$_2$)$_{18}$COOH;

-{AEEA}-gGlu-C(O)(CH$_2$)$_{16}$COOH;

-{AEEA}-gGlu-C(O)(CH$_2$)$_{18}$COOH;

-gGlu-C(O)(CH$_2$)$_{14}$COOH;

-gGlu-C(O)(CH$_2$)$_{16}$COOH;

-gGlu-C(O)(CH$_2$)$_{18}$COOH;

-{gGlu}$_2$-C(O)(CH$_2$)$_{16}$COOH;
and

-{gGlu}$_2$-C(O)(CH$_2$)$_{18}$COOH.

In an embodiment, the albumin-binding moiety is selected from the following groups:

-{AEEA}$_2$-gGlu-C(O)(CH$_2$)$_{16}$COOH;

-{AEEA}$_2$-gGlu-C(O)(CH$_2$)$_{18}$COOH;

-{AEEA}-gGlu-C(O)(CH$_2$)$_{16}$COOH;

-{AEEA}-gGlu-C(O)(CH$_2$)$_{18}$COOH;

-gGlu-C(O)(CH$_2$)$_{14}$COOH;

-gGlu-C(O)(CH$_2$)$_{16}$COOH;

-gGlu-C(O)(CH$_2$)$_{18}$COOH;
and

-{gGlu}$_2$-C(O)(CH$_2$)$_{18}$COOH.

The chemical structures and IUPAC names of some examples of these groups are shown in Table 1 below, in which R denotes the point of attachment of each group to the epsilon-amino group of the lysine residue at X12:

TABLE 1

| Group | Chemical structure/IUPAC name |
|---|---|
| —{AEEA}$_2$—gGlu—C(O)(CH$_2$)$_{16}$COOH | 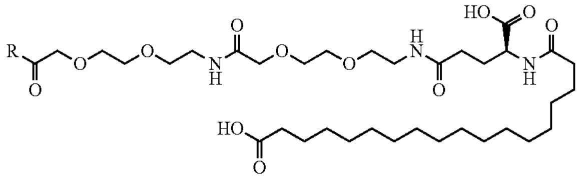 [2-[2-[2-[[2-[2-[2-[[(4S)-4-carboxy-4-(17-carboxyheptadecanoylamino)butanoyl]amino]ethoxy] ethoxy]-acetyl]amino]ethoxy]ethoxy]acetyl- |
| —{AEEA}$_2$—gGlu—C(O)(CH$_2$)$_{18}$COOH | 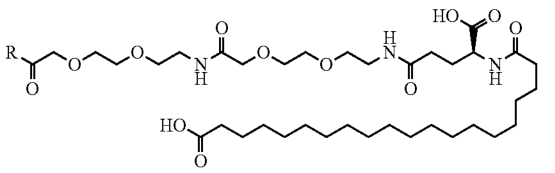 [2-[2-[2-[[2-[2-[2-[[(4S)-4-carboxy-4-(19-carboxynonadecanoylamino)butanoyl]amino]ethoxy] ethoxy]-acetyl]amino]ethoxy]ethoxy]acetyl- |
| —{AEEA}$_2$—{gGlu}$_2$—C(O)(CH$_2$)$_{16}$COOH | 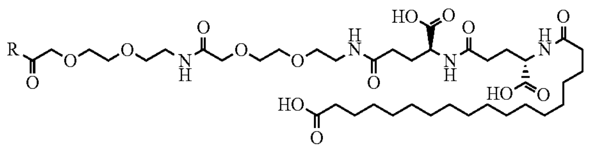 [2-[2-[2-[[2-[2-[2-[[(4S)-4-carboxy-4-[[(4S)-4-carboxy-4-(17-carboxyheptadecanoylamino) butanoyl]amino]butanoyl]amino]ethoxy]-ethoxy]acetyl]amino]ethoxy]ethoxy]acetyl- |
| —{AEEA}$_2$—{gGlu}$_2$—C(O)(CH$_2$)$_{18}$COOH | 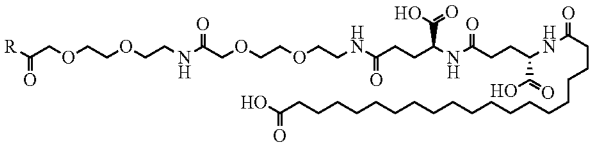 [2-[2-[2-[[2-[2-[2-[[(4S)-4-carboxy-4-[[(4S)-4-carboxy-4-(19-carboxynonadecanoylamino) butanoyl] amino]butanoyl]amino]ethoxy]-ethoxy]acetyl]amino]ethoxy]ethoxy]acetyl- |
| —gGlu—C(O)(CH$_2$)$_{16}$COOH | 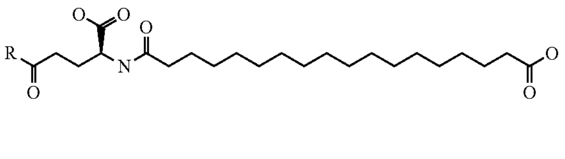 |

TABLE 1-continued
| Group | Chemical structure/IUPAC name |
|---|---|
| | 18-[[(1S)-1-carboxy-4-oxo-butyl]amino]-18-oxo-octadecanoic acid |
| —gGlu—C(O)(CH$_2$)$_{14}$COOH | 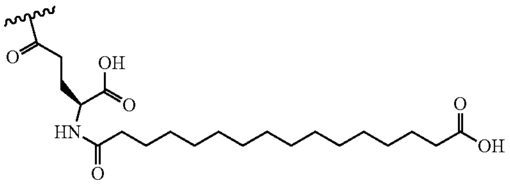 [SMILES: *C(=O)CC[C@H](NC(=O)CCCCCCCCCCCCCCC(=O)O)C(=O)O] |
| —gGlu—C(O)(CH$_2$)$_{12}$COOH | 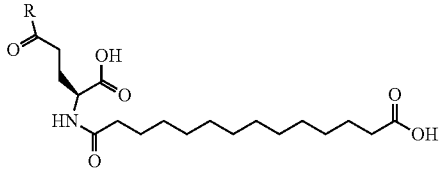 |
| —{AEEA)$_2$—gGlu—C(O)(CH$_2$)$_{12}$COOH | 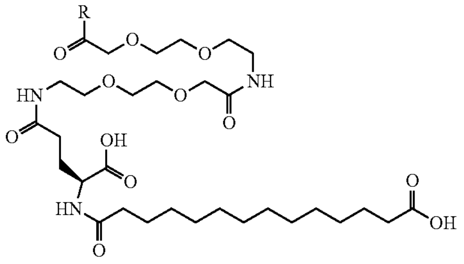 |
| {AEEA}$_2$—{gGlu}$_2$—C(O)(CH$_2$)$_{12}$COOH | 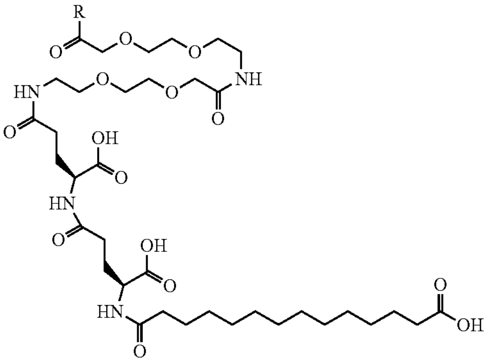 |
| —gGlu—C(O)(CH$_2$)$_{10}$COOH | 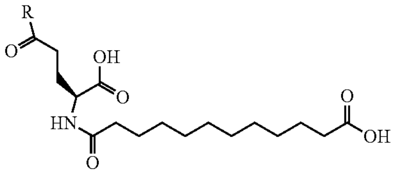 |
| —gGlu—C(O)(CH$_2$)$_{16}$COOH | 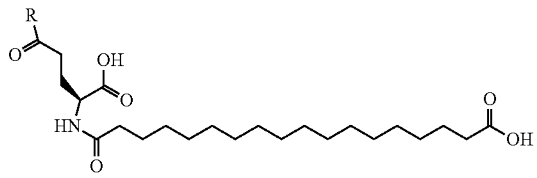 |

TABLE 1-continued
| Group | Chemical structure/IUPAC name |
| --- | --- |
| —{AEEA)$_2$—gGlu—C(O)(CH$_2$)$_{16}$COOH | 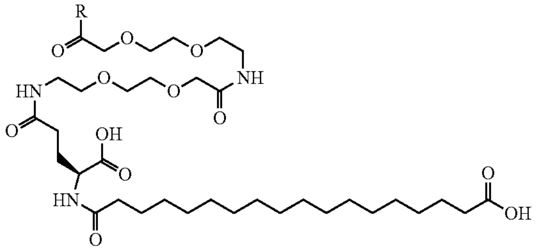 |
| —{AEEA}—{gGlu}$_2$—C(O)(CH$_2$)$_{16}$COOH | 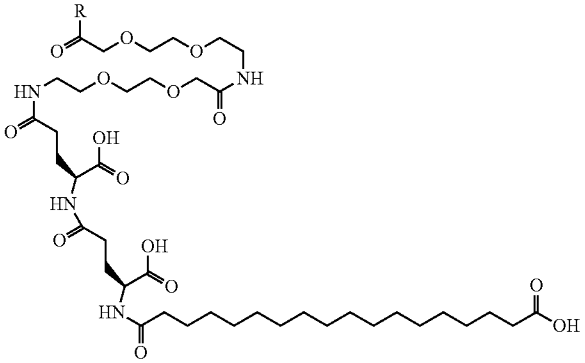 |
| —AEEA—{gGlu)$_2$—C(O)(CH$_2$)$_{16}$COOH | 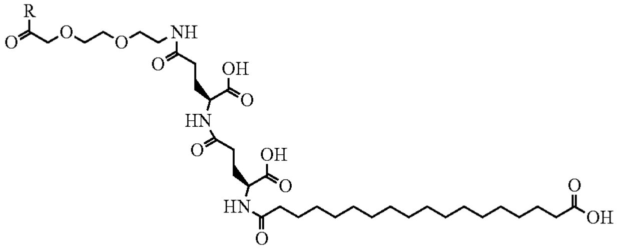 |
| —AEEA—gGlu—C(O)(CH$_2$)$_{16}$COOH | 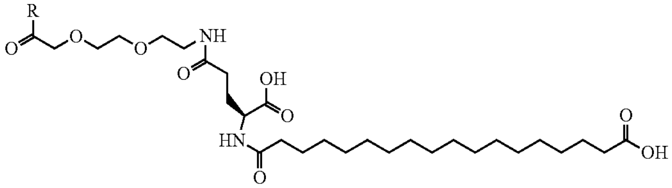 |
| —AEEA—gGlu—AEEA—gGlu—C(O)(CH$_2$)$_{16}$COOH | 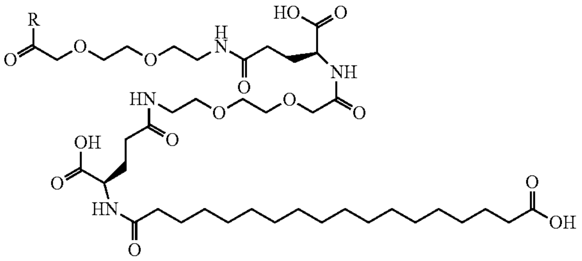 |

TABLE 1-continued

| Group | Chemical structure/IUPAC name |
|---|---|
| —{AEEA}$_3$—gGlu—C(O)(CH$_2$)$_{16}$COOH | 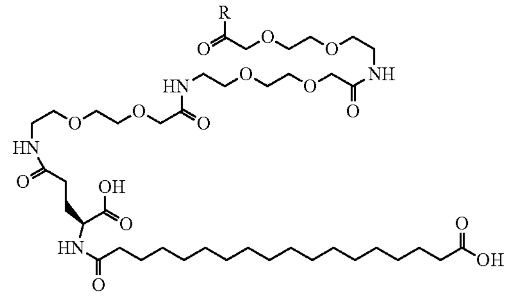 |
| —gGlu—C(O)(CH$_2$)$_{18}$COOH | 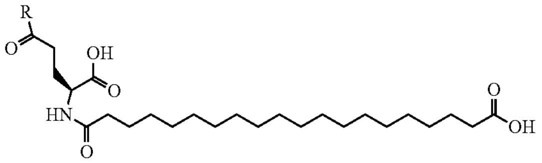 |
| —AEEA—gGlu—C(O)(CH$_2$)$_{18}$COOH | 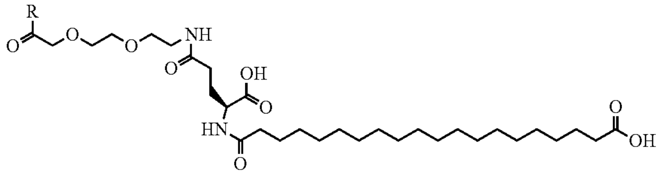 |
| —{AEEA)$_2$—gGlu—C(O)(CH$_2$)$_{18}$COOH | 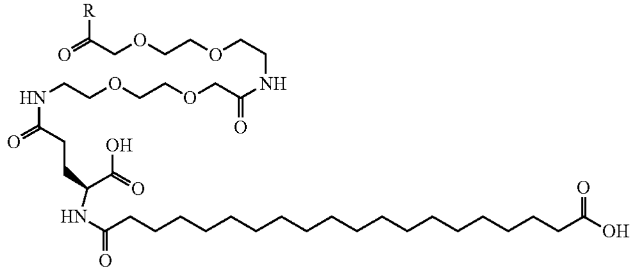 |
| —{gGlu}$_2$—C(O)(CH$_2$)$_{18}$COOH | 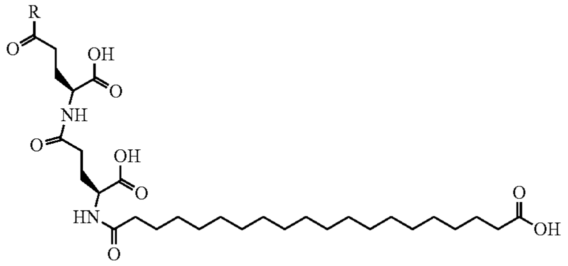 |

In an embodiment, the albumin-binding moiety is selected from the group consisting of -gGlu-C(O)(CH$_2$)$_{12}$COOH; -gGlu-C(O)(CH$_2$)$_{14}$COOH; -gGlu-C(O)(CH$_2$)$_{16}$COOH; -gGlu-C(O)(CH$_2$)$_{18}$COOH; -{AEEA}$_2$-gGlu-C(O)(CH$_2$)$_{12}$COOH, -{AEEA}$_2$-gGlu-C(O)(CH$_2$)$_{16}$COOH; -{AEEA}$_2$-gGlu-C(O)(CH$_2$)$_{18}$COOH and -{AEEA}$_2$-{gGlu}$_2$-C(O)(CH$_2$)$_{16}$COOH.

In a particular embodiment, the albumin-binding moiety is selected from the group consisting of -gGlu-C(O)(CH$_2$)$_{12}$COOH; -gGlu-C(O)(CH$_2$)$_{14}$COOH; -gGlu-C(O)(CH$_2$)$_{16}$COOH; -{AEEA}$_2$-gGlu-C(O)(CH$_2$)$_{16}$COOH and -{AEEA}$_2$-{gGlu}$_2$-C(O)(CH$_2$)$_{16}$COOH.

In another particular embodiment, the albumin-binding moiety is selected from the group consisting of -gGlu-C(O)(CH$_2$)$_{14}$COOH; -gGlu-C(O)(CH$_2$)$_{16}$COOH; and -{AEEA}$_2$-gGlu-C(O)(CH$_2$)$_{16}$COOH.

In an embodiment, the compound is a peptide comprising the amino acid sequence of any one of SEQ ID NOs 1 to 244, but for the comparative peptides, and said peptides wherein X1 is isoleucine and said isoleucine is not N-terminally acetylated or N-methylated or a pharmaceutically acceptable salt thereof.

In an embodiment, the compound is a peptide comprising the amino acid sequence of any one of SEQ ID NOs 19, 33, 34, 40, 43, 47, 51, 54, 55, 57, 64, 80, 92, 93, 96, 98, 100, 104, 110, 113, 118, 125, 131, 132, 136, 144, 145, 189, 190, 193, 203, 206, 210, 212, 213, 215, 217, 218, 219, 222, 230, 231, 233, 234, 235, 236, 237, 238, 241, 242, 243 or a pharmaceutically acceptable salt thereof.

In an embodiment, the compound is a peptide comprising the amino acid sequence of any one of SEQ ID NOs 40, 51, 57, 64, 80, 98, 110, 206, 212, 213, 215, 218, 231, 235, 237, 238, 243 or a pharmaceutically acceptable salt thereof.

In an embodiment, the compound is a peptide of the amino acid sequence of formula (I), optionally wherein the amino acid residue at X1 is acetylated and optionally wherein the amino acid residue at X38 is amidated; or a pharmaceutically acceptable salt thereof.

In an embodiment, the compound is a peptide of the amino acid sequence of formula (I) or a pharmaceutically acceptable salt thereof; wherein:

X1 is absent;

X2 is valine (V), wherein when said valine is N-terminally acylated or alkylated; in particular N-terminally acylated with an C1-10alkanoyl group; more in particular selected from ethanoyl, methanoyl, propanoyl, butanoyl, pentanoyl hexanoyl or heptanoyl;

X7 is D-valine (v)

X9 is isoleucine (1);

X10 is lysine (K);

X11 is leucine (L) or alpha-methyl-leucine (αMeL);

X14 is isoleucine (1);

X15 is leucine (L);

X23 is lysine (K), glutamate (E), alanine (A), or 2-aminoisobutyric acid (Aib);

X25 is arginine (R);

X26 is glutamate (E);

X31 is asparagine (N);

X32 is glutamate (E), valine (V), threonine (T), 2-aminoisobutyric acid (Aib), alanine (A), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); or 1-aminocyclopropanecarboxylic acid (Cpx); and optionally wherein the amino acid residue at X38 is amidated.

In an embodiment, the compound is a peptide of the amino acid sequence of formula (I) or a pharmaceutically acceptable salt thereof; wherein:

X1 is an N-terminally acetylated or N-methylated isoleucine (1);

X2 is valine (V);

X7 is D-valine (v);

X9 is isoleucine (1);

X10 is lysine (K);

X11 is leucine (L);

X14 is isoleucine (1);

X15 is leucine (L);

X23 is lysine (K), glutamate (E), alanine (A), or 2-aminoisobutyric acid (Aib);

X25 is arginine (R);

X26 is glutamate (E);

X31 is asparagine (N);

X32 is glutamate (E), valine (V), threonine (T), 2-aminoisobutyric acid (Aib), alanine (A), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); or 1-aminocyclopropanecarboxylic acid (Cpx); in particular 2-aminoisobutyric acid (Aib), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); or 1-aminocyclopropanecarboxylic acid (Cpx); and optionally wherein the amino acid residue at X38 is amidated.

In an embodiment, the compound is a peptide of any one of SEQ ID NOs 1 to 145 or SEQ ID Nos 152 to 244, or a pharmaceutically acceptable salt thereof. These peptides are listed in Table 2 below, in which K* denotes the modified lysine residue at X12, $R^a$ denotes the albumin-binding moiety, Ac— denotes that the N-terminal is acetylated, NMe- denotes that the N-terminal is N-methylated, Propanoyl- denotes that the N-terminal is alkylated with a propanoyl group, Butanoyl- denotes that the N-terminal is alkylated with a butanoyl group, Pentanoyl- denotes that the N-terminal is alkylated with a pentanoyl group, and —NH2 denotes that the C-terminal amino acid residue is amidated as a primary amide.

As used herein, N-terminally acetylated peptide is generally represented as;

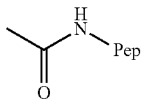

wherein Pep refers to the peptide structure.

As used herein, N-terminally acylated peptide with a propanoyl group is generally represented as;

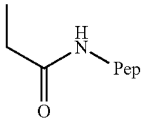

wherein Pep refers to the peptide structure.

As used herein, N-terminally acylated peptide with a butanoyl group is generally represented as;

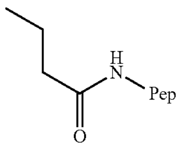

wherein Pep refers to the peptide structure.

As used herein, N-terminally acylated peptide with a pentanoyl group is generally represented as;

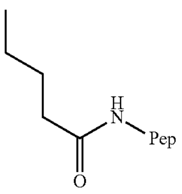

wherein Pep refers to the peptide structure.

As used herein, N-terminally acylated peptide with a isopentanoyl group is generally represented as;

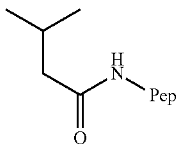

wherein Pep refers to the peptide structure.

TABLE 2

| SEQ ID NO. | Amino acid sequence | $R^a$ |
|---|---|---|
| 2 (comp) | Ac-IVLSLDvPIKLK*QILLKQERQKKQREQAEKNKQILEQV-NH2 | -gGlu-C(O)(CH$_2$)$_{14}$COOH |
| 3 | Ac-VLSLDvPIKLK*QILLKQERQKKQREQAEKNKQILEQV-NH2 | -gGlu-C(O)(CH$_2$)$_{14}$COOH |
| 4 | VLSLDvPIKLK*QILLKQERQKKQREQAEKNKQILEQV-NH2 | -gGlu-C(O)(CH$_2$)$_{14}$COOH |
| 5 (comp) | NMeIVLSLDvPIKLK*QILLKQERQKKQREQAEKNKQILEQV-NH2 | -gGlu-C(O)(CH$_2$)$_{14}$COOH |
| 6 | Propanoyl-VLSLDvPIKLK*QILLKQERQKKQREQAEKNKQILEQV-NH2 | -gGlu-C(O)(CH$_2$)$_{14}$COOH |
| 7 | Butanoyl-VLSLDvPIKLK*QILLKQERQKKQREQAEKNKQILEQV-NH2 | -gGlu-C(O)(CH$_2$)$_{14}$COOH |
| 8 | Pentanoyl-VLSLDvPIKLK*QILLKQERQKKQREQAEKNKQILEQV-NH2 | -gGlu-C(O)(CH$_2$)$_{14}$COOH |
| 9 | Isopentanoyl-VLSLDvPIKLK*QILLKQERQKKQREQAEKNKQILEQV-NH2 | -gGlu-C(O)(CH$_2$)$_{14}$COOH |
| 10 | IVLSLDvPIKLK*QILLKQERQKKQREQAEKNAibQILEQV-NH2 | -gGlu-C(O)(CH$_2$)$_{14}$COOH |
| 11 (comp) | IVLSLDvPIKLK*QILLKQERQKKQREQAEKQKQILEQV-NH2 | -gGlu-C(O)(CH$_2$)$_{14}$COOH |
| 12 (comp) | IVLSLDvPIKLK*QILLKQERQKKQREQAEKAKQILEQV-NH2 | -gGlu-C(O)(CH$_2$)$_{14}$COOH |
| 13 | IVLSLDvPIKLK*QILLKQERQKKQREQAEKNVQILEQV-NH2 | -gGlu-C(O)(CH$_2$)$_{14}$COOH |
| 14 | IVLSLDvPIKLK*QILLKQERQKKQREQAEKNTQILEQV-NH2 | -gGlu-C(O)(CH$_2$)$_{14}$COOH |
| 15 (comp) | IVLSLDvPIKLK*QILLKQERQKKQREQAETNKQILEQV-NH2 | -gGlu-C(O)(CH$_2$)$_{14}$COOH |
| 16 | Ac-IVLSLDvPIKLK*QILLKQERQKKQREQAEKNAibQILEQV-NH2 | -gGlu-C(O)(CH$_2$)$_{14}$COOH |
| 17 (comp) | Ac-IVLSLDvPIKLK*QILLKQERQKKQREQAEKNEQILEQV-NH2 | -gGlu-C(O)(CH$_2$)$_{14}$COOH |
| 18 | Ac-IVLSLDvPIKLK*QAibLLKQERQKKQREQAEKNVQILEQV-NH2 | -gGlu-C(O)(CH$_2$)$_{14}$COOH |
| 19 | Ac-IVLSLDVPIKαMeLK*QILLKQERQKKQREQAEKNAibQILEQV-NH2 | -gGlu-C(O)(CH$_2$)$_{14}$COOH |
| 20 | Ac-IVLSLDVPIKαMeLK*QAibLLKQERQKKQREQAEKNAibQILEQV-NH2 | -gGlu-C(O)(CH$_2$)$_{14}$COOH |
| 21 | Ac-IVLSLDvPIKLK*KILLKQERQKKQREQAEKNAibQILEQV-NH2 | -gGlu-C(O)(CH$_2$)$_{14}$COOH |
| 22 | Pentanoyl-VLSLDvPIKLK*QAibLLKQERQKKQREQAEKNVQILEQV-NH2 | -gGlu-C(O)(CH$_2$)$_{14}$COOH |
| 23 | NMeIVLSLDvPIKLK*QILLKQERQKKQREQAEKNAibQILEQV-NH2 | -gGlu-C(O)(CH$_2$)$_{16}$COOH |
| 24 | NMeIVLSLDvPIKLK*QILLKQERQKKQREQAEKNAQILEQV-NH2 | -gGlu-C(O)(CH$_2$)$_{16}$COOH |
| 25 | IVLSLDVPIKLK*QAibLLKQERQKKQREQAEKNAibQILEQV-NH2 | -{AEEA}$_2$-{gGlu}$_2$-C(O)(CH$_2$)$_{16}$COOH |
| 26 | Ac-IVLSLDVPIKLK*QAibLLKQERQKKQREQAEKNAibQILEQV-NH2 | -{AEEA}$_2$-{gGlu}$_2$-C(O)(CH$_2$)$_{16}$COOH |
| 27 | Ac-IVLSLDvPIKLK*QAibLLKQERQKKQREQAEKNVQILEQV-NH2 | -{AEEA}$_2$-{gGlu}$_2$-C(O)(CH$_2$)$_{16}$COOH |
| 28 | NMe-IVLSLDvPIKLK*QAibLLKQERQKKQREQAEKNVQILEQV-NH2 | -{AEEA}$_2$-{gGlu}$_2$-C(O)(CH$_2$)$_{16}$COOH |

TABLE 2-continued

| SEQ ID NO. | Amino acid sequence | $R^a$ |
|---|---|---|
| 29 | Pentanoyl-VLSLDvPIKLK*QAibLLKQERQKKQREQAEKNVQILEQV-NH2 | -{AEEA}$_2$-{gGlu}$_2$-C(O)(CH$_2$)$_{16}$COOH |
| 30 | Ac-IVLSLDvPIKLK*QILLKQERQKKQREQAEKNAibQILEQV-NH2 | -{AEEA}$_2$-{gGlu}$_2$-C(O)(CH$_2$)$_{16}$COOH |
| 31 | NMe-IVLSLDvPIKLK*QILLKQERQKKQREQAEKNAibQILEQV-NH2 | -{AEEA}$_2$-{gGlu}$_2$-C(O)(CH$_2$)$_{16}$COOH |
| 32 | Pentanoyl-VLSLDvPIKLK*QILLKQERQKKQREQAEKNAibQILEQV-NH2 | -{AEEA}$_2$-{gGlu}$_2$-C(O)(CH$_2$)$_{16}$COOH |
| 33 | Ac-VLSLDvPIKLK*KILLEQEKQKKQREQAETNKQILAQV-NH2 | -gGlu-C(O)(CH$_2$)$_{14}$COOH |
| 34 | VLSLDvPIKLK*KILLEQEKQKKQREQAETNKQILAQV-NH2 | -gGlu-C(O)(CH$_2$)$_{14}$COOH |
| 35 | Propanoyl-VLSLDvPIKLK*KILLEQEKQKKQREQAETNKQILAQV-NH2 | -gGlu-C(O)(CH$_2$)$_{14}$COOH |
| 36 | Butanoyl-VLSLDvPIKLK*KILLEQEKQKKQREQAETNKQILAQV-NH2 | -gGlu-C(O)(CH$_2$)$_{14}$COOH |
| 37 | Pentanoyl-VLSLDvPIKLK*KILLEQEKQKKQREQAETNKQILAQV-NH2 | -gGlu-C(O)(CH$_2$)$_{14}$COOH |
| 38 | IVLSLDVPIKαMeLK*KILLEQEKQKKQREQAETNAibQILAQV-NH2 | -gGlu-C(O)(CH$_2$)$_{14}$COOH |
| 39 | Ac-IVLSLDVPIKLK*KILLEQEKQKKQREQAETNAibQILAQV-NH2 | -gGlu-C(O)(CH$_2$)$_{14}$COOH |
| 40 | Ac-IVLSLDvPIKLK*KILLEQEKQKKQREQAETNAibQILAQV-NH2 | -gGlu-C(O)(CH$_2$)$_{14}$COOH |
| 41 | Ac-IVLSLDvPIKLK*KILLEQEKQKKQREQAETNAibQILAQV-NH2 | -{gGlu}$_2$-C(O)(CH$_2$)$_{14}$COOH |
| 42 | Ac-IVLSLDvPIKLK*KILLEQEKQKKQREQAETNAibQILAQV-NH2 | -{AEEA}$_2$-gGlu-C(O)(CH$_2$)$_{14}$COOH |
| 43 | Ac-IVLSLDVPIKαMeLK*KILLEQEKQKKQREQAETNAibQILAQV-NH2 | -gGlu-C(O)(CH$_2$)$_{14}$COOH |
| 44 | Ac-IVLSLDvPIKαMeLK*KILLEQEKQKKQREQAETNAibQILAQV-NH2 | -gGlu-C(O)(CH$_2$)$_{14}$COOH |
| 45 | Ac-VLSLDvPIKLK*KILLEQEKQKKQREQAETNAibQILAQV-NH2 | -gGlu-C(O)(CH$_2$)$_{14}$COOH |
| 46 | Ac-VLSLDvPIKαMeLK*KILLEQEKQKKQREQAETNAibQILAQV-NH2 | -gGlu-C(O)(CH$_2$)$_{14}$COOH |
| 47 | Ac-IVLSLDvPIKLK*KILLEQEKQKKQREQAETNAQILAQV-NH2 | -gGlu-C(O)(CH$_2$)$_{14}$COOH |
| 48 | Ac-IVLSLDvPIKLK*KILLEQEKQKKQREQAETNVQILAQV-NH2 | -gGlu-C(O)(CH$_2$)$_{14}$COOH |
| 49 | Ac-IVLSLDVPIKαMeLK*KILLEQEKQKKQREQAETNVQILAQV-NH2 | -gGlu-C(O)(CH$_2$)$_{14}$COOH |
| 50 | Ac-IVLSLDvPIKαMeLK*KILLEQEKQKKQREQAETNVQILAQV-NH2 | -gGlu-C(O)(CH$_2$)$_{14}$COOH |
| 51 | Ac-IVLSLDvPIKLK*KILLEQEKQKKQREQAETNAbuQILAQV-NH2 | -gGlu-C(O)(CH$_2$)$_{14}$COOH |
| 52 | Ac-IVLSLDvPIKLK*KILLEQEKQKKQREQAETNNvaQILAQV-NH2 | -gGlu-C(O)(CH$_2$)$_{14}$COOH |
| 53 | Ac-IVLSLDvPIKαMeLK*KILLEQEKQKKQREQAETDKQILAQV-NH2 | -gGlu-C(O)(CH$_2$)$_{14}$COOH |
| 54 | Ac-IVLSLDvPIKLK*KILLEQEKQKKQREQAETNαMeKQILAQV-NH2 | -gGlu-C(O)(CH$_2$)$_{14}$COOH |
| 55 | Ac-IVLSLDvPIKLK*KILLEQEKQKKQREQAETNDapQILAQV-NH2 | -gGlu-C(O)(CH$_2$)$_{14}$COOH |
| 56 (comp) | Ac-IVLSLDvPIKLK*KILLEQEKQKKQREQAETNEQILAQV-NH2 | -gGlu-C(O)(CH$_2$)$_{14}$COOH |
| 57 | Ac-IVLSLDvPIKLK*KILLEQEKQKKQREQAETN4-PipQILAQV-NH2 | -gGlu-C(O)(CH$_2$)$_{14}$COOH |
| 58 | Ac-IVLSLDvPIKLK*KILLEQEKQKKQREQAETNThPQILAQV-NH2 | -gGlu-C(O)(CH$_2$)$_{14}$COOH |
| 59 | Ac-IVLSLDvPIKLK*KILLEQEKQKKQREQAETNChxQILAQV-NH2 | -gGlu-C(O)(CH$_2$)$_{14}$COOH |
| 60 | Ac-IVLSLDvPIKLK*KILLEQEKQKKQREQAETNCpexQILAQV-NH2 | -gGlu-C(O)(CH$_2$)$_{14}$COOH |
| 61 | Ac-IVLSLDvPIKLK*KILLEQEKQKKQREQAETNCpxQILAQV-NH2 | -gGlu-C(O)(CH$_2$)$_{14}$COOH |
| 62 | Ac-IVLSLDvPIKLK*KILLEQEKQKAQREQAETN4PipQILAQV-NH2 | -gGlu-C(O)(CH$_2$)$_{14}$COOH |
| 63 | Ac-IVLSLDvPIKLK*KILLEQEKQKAibQREQAETN4PipQILAQV-NH2 | -gGlu-C(O)(CH$_2$)$_{14}$COOH |
| 64 | NMelVLSLDvPIKLK*KILLEQEKQKKQREQAETNAibQILAQV-NH2 | -gGlu-C(O)(CH$_2$)$_{14}$COOH |

TABLE 2-continued

| SEQ ID NO. | Amino acid sequence | $R^a$ |
|---|---|---|
| 65 | NMeIVLSLDvPIKαMeLK*KILLEQEKQKKQREQAETNAibQILAQV-NH2 | -gGlu-C(O)$(CH_2)_{14}$COOH |
| 66 | NMeIVLSLDvPIKLK*KILLEQEKQKKQREQAETNVQILAQV-NH2 | -gGlu-C(O)$(CH_2)_{14}$COOH |
| 67 | NMeIVLSLDvPIKαMeLK*KILLEQEKQKKQREQAETNVQILAQV-NH2 | -gGlu-C(O)$(CH_2)_{14}$COOH |
| 68 | NMeIVLSLDvPIKLK*KILLEQEKQKKQREQAETNAQILAQV-NH2 | -gGlu-C(O)$(CH_2)_{14}$COOH |
| 69 | NMeIVLSLDvPIKLK*KILLEQEKQKKQREQAETNAbuQILAQV-NH2 | -gGlu-C(O)$(CH_2)_{14}$COOH |
| 70 | NMeIVLSLDvPIKLK*KILLEQEKQKKQREQAETNDapQILAQV-NH2 | -gGlu-C(O)$(CH_2)_{14}$COOH |
| 71 | NMeIVLSLDvPIKLK*KILLEQEKQKKQREQAETNEQILAQV-NH2 | -gGlu-C(O)$(CH_2)_{14}$COOH |
| 72 | NMeIVLSLDvPIKLK*KILLEQEKQKKQREQAETN4-PipQILAQV-NH2 | -gGlu-C(O)$(CH_2)_{14}$COOH |
| 73 | NMeIVLSLDvPIKLK*KILLEQEKQKKQREQAETNThPQILAQV-NH2 | -gGlu-C(O)$(CH_2)_{14}$COOH |
| 74 | NMeIVLSLDvPIKLK*KILLEQEKQKAQREQAETNAibQILAQV-NH2 | -gGlu-C(O)$(CH_2)_{14}$COOH |
| 75 | NMeIVLSLDvPIKLK*KILLEQEKQKAibQREQAETNAibQILAQV-NH2 | -gGlu-C(O)$(CH_2)_{14}$COOH |
| 76 | NMeIVLSLDvPIKLK*KILLEQEKQKAQREQAETN4PipQILAQV-NH2 | -gGlu-C(O)$(CH_2)_{14}$COOH |
| 77 | NMeIVLSLDvPIKLK*KILLEQEKQKAibQREQAETN4PipQILAQV-NH2 | -gGlu-C(O)$(CH_2)_{14}$COOH |
| 78 | Propanoyl-VLSLDvPIKLK*KILLEQEKQKKQREQAETNAibQILAQV-NH2 | -gGlu-C(O)$(CH_2)_{14}$COOH |
| 79 | Butanoyl-VLSLDvPIKLK*KILLEQEKQKKQREQAETNAibQILAQV-NH2 | -gGlu-C(O)$(CH_2)_{14}$COOH |
| 80 | Pentanoyl-VLSLDvPIKLK*KILLEQEKQKKQREQAETNAibQILAQV-NH2 | -gGlu-C(O)$(CH_2)_{14}$COOH |
| 81 | Pentanoyl-VLSLDvPIKLK*KILLEQEKQKKQREQAETNVQILAQV-NH2 | -gGlu-C(O)$(CH_2)_{14}$COOH |
| 82 | Ac-IVLSLDvPIKLK*KILLEQEKQKKQREQAETNAibQILAQV-NH2 | -gGlu-C(O)$(CH_2)_{12}$COOH |
| 83 | Ac-IVLSLDvPIKLK*KILLEQEKQKKQREQAETNAbuQILAQV-NH2 | -gGlu-C(O)$(CH_2)_{12}$COOH |
| 84 | Ac-IVLSLDvPIKLK*KILLEQEKQKKQREQAETN4-PipQILAQV-NH2 | -gGlu-C(O)$(CH_2)_{12}$COOH |
| 85 (comp) | Ac-IVLSLDvPIKLK*KILLEQEKQKKQREQAETNEQILAQV-NH2 | -gGlu-C(O)$(CH_2)_{12}$COOH |
| 86 | Pentanoyl-VLSLDvPIKLK*KILLEQEKQKKQREQAETNAibQILAQV-NH2 | -gGlu-C(O)$(CH_2)_{12}$COOH |
| 87 | NMeIVLSLDvPIKLK*KILLEQEKQKKQREQAETNAibQILAQV-NH2 | -gGlu-C(O)$(CH_2)_{12}$COOH |
| 88 | NMeIVLSLDvPIKLK*KILLEQEKQKAQREQAETNAibQILAQV-NH2 | -gGlu-C(O)$(CH_2)_{12}$COOH |
| 89 | NMeIVLSLDvPIKLK*KILLEQEKQKAibQREQAETNAibQILAQV-NH2 | -gGlu-C(O)$(CH_2)_{12}$COOH |
| 90 | Ac-IVLSLDvPIKLK*KILLEQEKQKAQREQAETN4PipQILAQV-NH2 | -gGlu-C(O)$(CH_2)_{12}$COOH |
| 91 | Ac-IVLSLDvPIKLK*KILLEQEKQKAibQREQAETN4PipQILAQV-NH2 | -gGlu-C(O)$(CH_2)_{12}$COOH |
| 92 | Ac-VLSLDvPIKLK*KILLEQEKQKKQREQAETNKQILAQV-NH2 | -{AEEA}$_2$-gGlu-C(O)$(CH_2)_{16}$COOH |
| 93 | VLSLDvPIKLK*KILLEQEKQKKQREQAETNKQILAQV-NH2 | -{AEEA}$_2$-gGlu-C(O)$(CH_2)_{16}$COOH |
| 94 | Propanoyl-VLSLDVPIKLK*KILLEQEKQKKQREQAETNKQILAQV-NH2 | -{AEEA}$_2$-gGlu-C(O)$(CH_2)_{16}$COOH |
| 95 | Butanoyl-VLSLDVPIKLK*KILLEQEKQKKQREQAETNKQILAQV-NH2 | -{AEEA}$_2$-gGlu-C(O)$(CH_2)_{16}$COOH |
| 96 | Pentanoyl-VLSLDVPIKLK*KILLEQEKQKKQREQAETNKQILAQV-NH2 | -{AEEA}$_2$-gGlu-C(O)$(CH_2)_{16}$COOH |
| 97 | Ac-IVLSLDVPIKLK*KILLEQEKQKKQREQAETNAibQILAQV-NH2 | -{AEEA}$_2$-gGlu-C(O)$(CH_2)_{16}$COOH |
| 98 | Ac-IVLSLDvPIKLK*KILLEQEKQKKQREQAETNAibQILAQV-NH2 | -{AEEA}$_2$-gGlu-C(O)$(CH_2)_{16}$COOH |

TABLE 2-continued

| SEQ ID NO. | Amino acid sequence | $R^a$ |
|---|---|---|
| 99 | Ac-VLSLDvPIKLK*KILLEQEKQKKQREQAETNAibQILAQV-NH2 | -{AEEA}$_2$-gGlu-C(O)$(CH_2)_{16}$COOH |
| 100 | Ac-IVLSLDvPIKLK*KILLEQEKQKKQREQAETNAQILAQV-NH2 | -{AEEA}$_2$-gGlu-C(O)$(CH_2)_{16}$COOH |
| 101 | Ac-VLSLDvPIKLK*KILLEQEKQKKQREQAETNAQILAQV-NH2 | -{AEEA}$_2$-gGlu-C(O)$(CH_2)_{16}$COOH |
| 102 | Ac-IVLSLDVPIKLK*KILLEQEKQKKQREQAETNVQILAQV-NH2 | -{AEEA}$_2$-gGlu-C(O)$(CH_2)_{16}$COOH |
| 103 | Ac-IVLSLDvPIKLK*KILLEQEKQKKQREQAETNVQILAQV-NH2 | -{AEEA}$_2$-gGlu-C(O)$(CH_2)_{16}$COOH |
| 104 | Ac-IVLSLDvPIKLK*KILLEQEKQKKQREQAETNAbuQILAQV-NH2 | -{AEEA}$_2$-gGlu-C(O)$(CH_2)_{16}$COOH |
| 105 | Ac-IVLSLDvPIKLK*KILLEQEKQKKQREQAETNNvaQILAQV-NH2 | -{AEEA}$_2$-gGlu-C(O)$(CH_2)_{16}$COOH |
| 106 | Ac-IVLSLDvPIKLK*KILLEQEKQKKQREQAETNαMeKQILAQV-NH2 | -{AEEA}$_2$-gGlu-C(O)$(CH_2)_{16}$COOH |
| 107 | Ac-IVLSLDvPIKLK*KILLEQEKQKKQREQAETNDapQILAQV-NH2 | -{AEEA}$_2$-gGlu-C(O)$(CH_2)_{16}$COOH |
| 108 | Ac-IVLSLDvPIKLK*KILLEQEKQKKQREQAETNEQILAQV-NH2 | -{AEEA}$_2$-gGlu-C(O)$(CH_2)_{16}$COOH |
| 109 | Ac-IVLSLDvPIKLK*KILLEQEKQKKQREQAETN4-PipQILAQV-NH2 | -{AEEA}$_2$-gGlu-C(O)$(CH_2)_{16}$COOH |
| 110 | Ac-IVLSLDvPIKαMeLK*KILLEQEKQKKQREQAETNAibQILAQV-NH2 | -{AEEA}$_2$-gGlu-C(O)$(CH_2)_{16}$COOH |
| 111 | Ac-IVLSLDvPIKαMeLK*KILLEQEKQKKQREQAETNVQILAQV-NH2 | -{AEEA}$_2$-gGlu-C(O)$(CH_2)_{16}$COOH |
| 112 | Ac-IVLSLDvPIKαMeLK*KILLEQEKQKKQREQAETNAQILAQV-NH2 | -{AEEA}$_2$-gGlu-C(O)$(CH_2)_{16}$COOH |
| 113 | NMelVLSLDvPIKLK*KILLEQEKQKKQREQAETNAQILAQV-NH2 | -{AEEA}$_2$-gGlu-C(O)$(CH_2)_{16}$COOH |
| 114 | NMeIVLSLDvPIKLK*KILLEQEKQKKQREQAETNAbuQILAQV-NH2 | -{AEEA}$_2$-gGlu-C(O)$(CH_2)_{16}$COOH |
| 115 | NMeIVLSLDvPIKLK*KILLEQEKQKKQREQAETNDapQILAQV-NH2 | -{AEEA}$_2$-gGlu-C(O)$(CH_2)_{16}$COOH |
| 116 (comp) | NMelVLSLDvPIKLK*KILLEQEKQKKQREQAETNEQILAQV-NH2 | -{AEEA}$_2$-gGlu-C(O)$(CH_2)_{16}$COOH |
| 117 | NMeIVLSLDvPIKLK*KILLEQEKQKKQREQAETN4-PipQILAQV-NH2 | -{AEEA}$_2$-gGlu-C(O)$(CH_2)_{16}$COOH |
| 118 | NMeIVLSLDvPIKLK*KILLEQEKQKKQREQAETNAibQILAQV-NH2 | -{AEEA}$_2$-gGlu-C(O)$(CH_2)_{16}$COOH |
| 119 | NMelVLSLDvPIKαMeLK*KILLEQEKQKKQREQAETNAibQILAQV-NH2 | -{AEEA}$_2$-gGlu-C(O)$(CH_2)_{16}$COOH |
| 120 | Pentanoyl-VLSLDvPIKLK*KILLEQEKQKKQREQAETNAibQILAQV-NH2 | -{AEEA}$_2$-gGlu-C(O)$(CH_2)_{16}$COOH |
| 121 | Pentanoyl-VLSLDvPIKLK*KILLEQEKQKKQREQAETNVQILAQV-NH2 | -{AEEA}$_2$-gGlu-C(O)$(CH_2)_{16}$COOH |
| 122 | Pentanoyl-VLSLDvPIKLK*KILLEQEKQKKQREQAETNAQILAQV-NH2 | -{AEEA}$_2$-gGlu-C(O)$(CH_2)_{16}$COOH |
| 123 | Pentanoyl-VLSLDvPIKαMeLK*KILLEQEKQKKQREQAETNAibQILAQV-NH2 | -{AEEA}$_2$-gGlu-C(O)$(CH_2)_{16}$COOH |
| 124 | Pentanoyl-VLSLDvPIKαMeLK*KILLEQEKQKKQREQAETNVQILAQV-NH2 | -{AEEA}$_2$-gGlu-C(O)$(CH_2)_{16}$COOH |

TABLE 2-continued

| SEQ ID NO. | Amino acid sequence | $R^a$ |
|---|---|---|
| 125 | Ac-IVLSLDvPIKLK*KILLEQEKQKKQREQAETNAibQILAQV-NH2 | -gGlu-C(O)($CH_2$)$_{16}$COOH |
| 126 | Ac-IVLSLDvPIKLK*KILLEQEKQKKQREQAETNAQILAQV-NH2 | -gGlu-C(O)($CH_2$)$_{16}$COOH |
| 127 | Ac-IVLSLDvPIKLK*KILLEQEKQKKQREQAETNAbuQILAQV-NH2 | -gGlu-C(O)($CH_2$)$_{16}$COOH |
| 128 | Ac-IVLSLDvPIKLK*KILLEQEKQKKQREQAETNDapQILAQV-NH2 | -gGlu-C(O)($CH_2$)$_{16}$COOH |
| 129 | Ac-IVLSLDvPIKLK*KILLEQEKQKKQREQAETN4-PipQILAQV-NH2 | -gGlu-C(O)($CH_2$)$_{16}$COOH |
| 130 (comp) | Ac-IVLSLDvPIKLK*KILLEQEKQKKQREQAETNEQILAQV-NH2 | -gGlu-C(O)($CH_2$)$_{16}$COOH |
| 131 | Ac-IVLSLDvPIKLK*KILLEQEKQKAQREQAETN4-PipQILAQV-NH2 | -gGlu-C(O)($CH_2$)$_{16}$COOH |
| 132 | Ac-IVLSLDvPIKLK*KILLEQEKQKAibQREQAETN4-PipQILAQV-NH2 | -gGlu-C(O)($CH_2$)$_{16}$COOH |
| 133 | Ac-IVLSLDdvPIKLK*KILLEQEKQKKQREQAETNThPQILAQV-NH2 | -gGlu-C(O)($CH_2$)$_{16}$COOH |
| 134 | Ac-IVLSLDdvPIKLK*KILLEQEKQKKQREQAETNChxQILAQV-NH2 | -gGlu-C(O)($CH_2$)$_{16}$COOH |
| 135 | Ac-IVLSLDdvPIKLK*KILLEQEKQKKQREQAETNCpexQILAQV-NH2 | -gGlu-C(O)($CH_2$)$_{16}$COOH |
| 136 | Ac-IVLSLDdvPIKLK*KILLEQEKQKKQREQAETNCpxQILAQV-NH2 | -gGlu-C(O)($CH_2$)$_{16}$COOH |
| 137 | NMelVLSLDvPIKLK*KILLEQEKQKKQREQAETNAibQILAQV-NH2 | -gGlu-C(O)($CH_2$)$_{16}$COOH |
| 138 | NMeIVLSLDvPIKLK*KILLEQEKQKKQREQAETNAQILAQV-NH2 | -gGlu-C(O)($CH_2$)$_{16}$COOH |
| 139 | NMeIVLSLDvPIKLK*KILLEQEKQKKQREQAETNAbuQILAQV-NH2 | -gGlu-C(O)($CH_2$)$_{16}$COOH |
| 140 | NMeIVLSLDvPIKLK*KILLEQEKQKKQREQAETNDapQILAQV-NH2 | -gGlu-C(O)($CH_2$)$_{16}$COOH |
| 141 | NMeIVLSLDvPIKLK*KILLEQEKQKKQREQAETN4-PipQILAQV-NH2 | -gGlu-C(O)($CH_2$)$_{16}$COOH |
| 142 (comp) | NMeIVLSLDvPIKLK*KILLEQEKQKKQREQAETNEQILAQV-NH2 | -gGlu-C(O)($CH_2$)$_{16}$COOH |
| 143 | NMeIVLSLDvPIKLK*KILLEQEKQKKQREQAETNThPQILAQV-NH2 | -gGlu-C(O)($CH_2$)$_{16}$COOH |
| 144 | NMelVLSLDvPIKLK*KILLEQEKQKAQREQAETNAibQILAQV-NH2 | -gGlu-C(O)($CH_2$)$_{16}$COOH |
| 145 | NMeIVLSLDvPIKLK*KILLEQEKQKAibQREQAETNAibQILAQV-NH2 | -gGlu-C(O)($CH_2$)$_{16}$COOH |
| 146 (comp) | IVLSLDvPIKLK*QILLKQERQKKQREQAEKNKQILEQV-NH2 | -{AEEA}$_2$-{gGlu}$_2$-C(O)($CH_2$)$_{14}$COOH |
| 147 (comp) | IVLSLDvPIKLK*QILLKQERQKKQREQAEKNKQILEQV-NH2 | -{gGlu}$_2$-C(O)($CH_2$)$_{14}$COOH |
| 148 (comp) | IVLSLDvPIKLK*QILLKQERQKKQREQAEKNKQILEQV-NH2 | -{AEEA}$_2$-gGlu-C(O)($CH_2$)$_{14}$COOH |
| 149 (comp) | IVLSLDVPIKLK*KILLEQEKQKKQREQAETNKQILAQV-NH2 | -{AEEA}$_2$-gGlu-C(O)($CH_2$)$_{16}$COOH |
| 150 (comp) | IVLSLDvPIKLK*QILLKQERQKKQREQAEKNKQILEQV-NH2 | -{AEEA}$_2$-gGlu-C(O)($CH_2$)$_{16}$COOH |
| 151 (comp) | IVLSLDvPIKLK*QILLKQERQKKQREQAEKNKQILEQV-NH2 | -gGlu-C(O)($CH_2$)$_{14}$COOH |
| 152 | Ac-IVLSLDvPIKLK*KILLEQEKQKAQREQAETN4-PipQILAQV-NH2 | -gGlu-C(O)($CH_2$)$_{14}$COOH |
| 153 | Ac-IVLSLDvPIKLK*KILLEQEKQKAibQREQAETN4-PipQILAQV-NH2 | -gGlu-C(O)($CH_2$)$_{14}$COOH |
| 154 | NMeIVLSLDvPIKLK*KILLEQEKQKAQREQAETN4-PipQILAQV-NH2 | -gGlu-C(O)($CH_2$)$_{14}$COOH |
| 155 | NMelVLSLDvPIKLK*KILLEQEKQKAibQREQAETN4-PipQILAQV-NH2 | -gGlu-C(O)($CH_2$)$_{14}$COOH |
| 156 | Hexanoyl-VLSLDvPIKLK*KILLEQEKQKKQREQAETNAibQILAQV-NH2 | -gGlu-C(O)($CH_2$)$_{14}$COOH |
| 157 | Hexanoyl-VLSLDvPIKLK*KILLEQEKQKKQREQAETN4-PipQILAQV-NH2 | -gGlu-C(O)($CH_2$)$_{14}$COOH |
| 158 | Decanoyl-VLSLDvPIKLK*KILLEQEKQKKQREQAETNAibQILAQV-NH2 | -gGlu-C(O)($CH_2$)$_{14}$COOH |

TABLE 2-continued

| SEQ ID NO. | Amino acid sequence | $R^a$ |
|---|---|---|
| 159 | NMeVLSLDvPIKLK*KILLEQEKQKKQREQAETNAibQILAQV-NH2 | -gGlu-C(O)$(CH_2)_{14}$COOH |
| 160 | NMeVLSLDvPIKLK*KILLEQEKQKKQREQAETN4-PipQILAQV-NH2 | -gGlu-C(O)$(CH_2)_{14}$COOH |
| 161 | Ac-IVLSLDvPIKLK*KILLEQEKQKAQREQAETNAibQILAQV-NH2 | -gGlu-C(O)$(CH_2)_{14}$COOH |
| 162 | Ac-IVLSLDvPIKLK*KILLEQEKQKAibQREQAETNAibQILAQV-NH2 | -gGlu-C(O)$(CH_2)_{14}$COOH |
| 163 | Ac-IVLSLDvPIALK*KILLEQEKQKKQREQAETNAibQILAQV-NH2 | -gGlu-C(O)$(CH_2)_{14}$COOH |
| 164 | Ac-IVLSLDvPIKLK*AILLEQEKQKKQREQAETNAibQILAQV-NH2 | -gGlu-C(O)$(CH_2)_{14}$COOH |
| 165 | Ac-IVLSLDvPIKLK*KILLEQEAQKKQREQAETNAibQILAQV-NH2 | -gGlu-C(O)$(CH_2)_{14}$COOH |
| 166 | Ac-IVLSLDvPIKLK*KILLEQEKQAKQREQAETNAibQILAQV-NH2 | -gGlu-C(O)$(CH_2)_{14}$COOH |
| 167 | Ac-IVLSLDvPIKLK*KILLEQEKQKKQAEQAETNAibQILAQV-NH2 | -gGlu-C(O)$(CH_2)_{14}$COOH |
| 168 | Ac-IVLSLDvPIKLK*KILLEQEKQKEQREQAETNAibQILAQV-NH2 | -gGlu-C(O)$(CH_2)_{14}$COOH |
| 169 | Ac-IVLSLDvPIKLK*KILLEQEKQKAQREQAETN4-PipQILAQV-NH2 | -gGlu-C(O)$(CH_2)_{12}$COOH |
| 170 | Ac-IVLSLDvPIKLK*KILLEQEKQKAibQREQAETN4-PipQILAQV-NH2 | -gGlu-C(O)$(CH_2)_{12}$COOH |
| 171 | Ac-IVLSLDvPIKLK*KILLEQEKQKKQREQAETNAibQILAQV-NH2 | -{AEEA}$_2$-gGlu-C(O)$(CH_2)_{12}$COOH |
| 172 | Ac-IVLSLDvPIKLK*KILLEQEKQKKQREQAETN4-PipQILAQV-NH2 | -{AEEA}$_2$-gGlu-C(O)$(CH_2)_{12}$COOH |
| 173 | Ac-IVLSLDvPIKLK*KILLEQEKQKAibQREQAETN4-PipQILAQV-NH2 | -{AEEA}$_2$-gGlu-C(O)$(CH_2)_{12}$COOH |
| 174 | Ac-IVLSLDvPIKLK*KILLEQEKQKKQREQAETNAibQILAQV-NH2 | -{AEEA}-{gGlu}$_2$-C(O)$(CH_2)_{12}$COOH |
| 175 | Ac-IVLSLDvPIKLK*KILLEQEKQKKQREQAETN4-PipQILAQV-NH2 | -{AEEA}$_2$-{gGlu}$_2$-C(O)$(CH_2)_{12}$COOH |
| 176 | NMeIVLSLDvPIKLK*KILLEQEKQKAQREQAETNAibQILAQV-NH2 | -gGlu-C(O)$(CH_2)_{12}$COOH |
| 177 | NMelVLSLDvPIKLK*KILLEQEKQKAibQREQAETNAibQILAQV-NH2 | -gGlu-C(O)$(CH_2)_{12}$COOH |
| 178 | NMelVLSLDvPIKLK*KILLEQEKQKKQREQAETNAibQILAQV-NH2 | -{AEEA}$_2$-gGlu-C(O)$(CH_2)_{12}$COOH |
| 179 | NMelVLSLDvPIKLK*KILLEQEKQKKQREQAETNAibQILAQV-NH2 | -{AEEA}$_2$-{gGlu}$_2$-C(O)$(CH_2)_{12}$COOH |
| 180 | Pentanoyl-VLSLDvPIKLK*KILLEQEKQKKQREQAETNAibQILAQV-NH2 | -{AEEA}$_2$-gGlu-C(O)$(CH_2)_{12}$COOH |
| 181 | Pentanoyl-VLSLDvPIKLK*KILLEQEKQKKQREQAETNAibQILAQV-NH2 | -{AEEA}$_2$-{gGlu}$_2$-C(O)$(CH_2)_{12}$COOH |
| 182 | Ac-IVLSLDvPIKLK*KILLEQEKQKKQREQAETNAibQILAQV-NH2 | -gGlu-C(O)$(CH_2)_{10}$COOH |
| 183 | Ac-IVLSLDvPIKLK*KILLEQEKQKKQREQAETN4-PipQILAQV-NH2 | -gGlu-C(O)$(CH_2)_{10}$COOH |
| 184 | Ac-IVLSLDvPIKLK*KILLEQEKQKAibQREQAETN4-PipQILAQV-NH2 | -gGlu-C(O)$(CH_2)_{10}$COOH |
| 185 | Pentanoyl-VLSLDvPIKLK*KILLEQEKQKKQREQAETNAibQILAQV-NH2 | -gGlu-C(O)$(CH_2)_{10}$COOH |
| 186 | NMelVLSLDvPIKLK*KILLEQEKQKKQREQAETNAibQILAQV-NH2 | -gGlu-C(O)$(CH_2)_{10}$COOH |
| 187 | Ac-IVLSLDvPIKLK*KILLEQEKQKAQREQAETN4-PipQILAQV-NH2 | -gGlu-C(O)$(CH_2)_{16}$COOH |
| 188 | Ac-IVLSLDvPIKLK*KILLEQEKQKAibQREQAETN4-PipQILAQV-NH2 | -gGlu-C(O)$(CH_2)_{16}$COOH |
| 189 | Ac-IVLSLDvPIKLK*KILLEQEKQKAQREQAETNAibQILAQV-NH2 | -gGlu-C(O)$(CH_2)_{16}$COOH |
| 190 | Ac-IVLSLDvPIKLK*KILLEQEKQKAibQREQAETNAibQILAQV-NH2 | -gGlu-C(O)$(CH_2)_{16}$COOH |
| 191 | Ac-IVLSLDvPIGLK*KILLEQEKQKKQREQAETNAibQILAQV-NH2 | -gGlu-C(O)$(CH_2)_{16}$COOH |
| 192 | NMeIVLSLDvPIGLK*KILLEQEKQKKQREQAETNAibQILAQV-NH2 | -gGlu-C(O)$(CH_2)_{16}$COOH |

TABLE 2-continued

| SEQ ID NO. | Amino acid sequence | R[a] |
|---|---|---|
| 193 | Pentanoyl-VLSLDvPIKLK*KILLEQEKQKKQREQAETNAibQILAQV-NH2 | -gGlu-C(O)$(CH_2)_{16}$COOH |
| 194 | Pentanoyl-VLSLDvPIKLK*KILLEQEKQKAibQREQAETNAibQILAQV-NH2 | -gGlu-C(O)$(CH_2)_{16}$COOH |
| 195 | Pentanoyl-VLSLDvPIGLK*KILLEQEKQKKQREQAETNAibQILAQV-NH2 | -gGlu-C(O)$(CH_2)_{16}$COOH |
| 196 | Ac-IVLSLDvPIKLK*KILLEQEKQKAibQREQAETN4-PipQILAQV-NH2 | -{AEEA}$_2$-gGlu-C(O)$(CH_2)_{16}$COOH |
| 197 | Ac-IVLSLDvPIKLK*KILLEQEKQKAibQREQAETNAibQILAQV-NH2 | -{AEEA}$_2$-gGlu-C(O)$(CH_2)_{16}$COOH |
| 198 | Ac-IVLSLDvPIKLK*KILLEQEKQKKQREQAETNThpQILAQV-NH2 | -{AEEA}$_2$-gGlu-C(O)$(CH_2)_{16}$COOH |
| 199 | Ac-IVLSLDvPIKLK*KILLEQEKQKKQREQAETNThpQILAQV-NH2 | -gGlu-C(O)$(CH_2)_{16}$COOH |
| 200 | NMeIVLSLDvPIKLK*KILLEQEKQKAibQREQAETNAibQILAQV-NH2 | -{AEEA}$_2$-gGlu-C(O)$(CH_2)_{16}$COOH |
| 201 | Pentanoyl-VLSLDvPIKLK*KILLEQEKQKKQREQAETNAibQILAQV-NH2 | -{AEEA}$_2$-gGlu-C(O)$(CH_2)_{16}$COOH |
| 202 | Pentanoyl-VLSLDvPIKLK*KILLEQEKQKAibQREQAETNAibQILAQV-NH2 | -{AEEA}$_2$-gGlu-C(O)$(CH_2)_{16}$COOH |
| 203 | Ac-IVLSLDvPIKLK*KILLEQEKQKKQREQAETNAibQILAQV-NH2 | -{AEEA}-gGlu-C(O)$(CH_2)_{16}$COOH |
| 204 | Ac-IVLSLDvPIKLK*KILLEQEKQKKQREQAETNAibQILAQV-NH2 | -{AEEA}$_2$-{gGlu}$_2$-C(O)$(CH_2)_{16}$COOH |
| 205 | Ac-IVLSLDvPIKLK*KILLEQEKQKKQREQAETNAibQILAQV-NH2 | -{AEEA}-{gGlu}$_2$-C(O)$(CH_2)_{16}$COOH |
| 206 | Ac-IVLSLDvPIKLK*KILLEQEKQKKQREQAETNAibQILAQV-NH2 | -gGlu-C(O)$(CH_2)_{18}$COOH |
| 207 | Ac-IVLSLDvPIKLK*KILLEQEKQKKQREQAETN4-PipQILAQV-NH2 | -gGlu-C(O)$(CH_2)_{18}$COOH |
| 208 | Ac-IVLSLDvPIKLK*KILLEQEKQKAibQREQAETN4-PipQILAQV-NH2 | -gGlu-C(O)$(CH_2)_{18}$COOH |
| 209 | Ac-IVLSLDvPIKLK*KILLEQEKQKAibQREQAETNAibQILAQV-NH2 | -gGlu-C(O)$(CH_2)_{18}$COOH |
| 210 | Ac-IVLSLDvPIKLK*KILLEQEKQKKQREQAETNThpQILAQV-NH2 | -gGlu-C(O)$(CH_2)_{18}$COOH |
| 211 | Ac-IVLSLDvPIKLK*KILLEQEAQKKQREQAETNAibQILAQV-NH2 | -gGlu-C(O)$(CH_2)_{18}$COOH |
| 212 | Ac-IVLSLDvPIKLK*KILLEQEKQKAQREQAETNAibQILAQV-NH2 | -gGlu-C(O)$(CH_2)_{18}$COOH |
| 213 | Ac-IVLSLDvPIKLK*KILLEQEKQKEQREQAETNAibQILAQV-NH2 | -gGlu-C(O)$(CH_2)_{18}$COOH |
| 214 | NMeIVLSLDvPIKLK*KILLEQEKQKKQREQAETNAibQILAQV-NH2 | -gGlu-C(O)$(CH_2)_{18}$COOH |
| 215 | NMeIVLSLDvPIKLK*KILLEQEKQKAibQREQAETNAibQILAQV-NH2 | -gGlu-C(O)$(CH_2)_{18}$COOH |
| 216 | NMeIVLSLDvPIKLK*KILLEQEAQKKQREQAETNAibQILAQV-NH2 | -gGlu-C(O)$(CH_2)_{18}$COOH |
| 217 | NMeIVLSLDvPIKLK*KILLEQEKQKAQREQAETNAibQILAQV-NH2 | -gGlu-C(O)$(CH_2)_{18}$COOH |
| 218 | NMeIVLSLDvPIKLK*KILLEQEKQKEQREQAETNAibQILAQV-NH2 | -gGlu-C(O)$(CH_2)_{18}$COOH |
| 219 | Pentanoyl-VLSLDvPIKLK*KILLEQEKQKKQREQAETNAibQILAQV-NH2 | -gGlu-C(O)$(CH_2)_{18}$COOH |
| 220 | Pentanoyl-VLSLDvPIKLK*KILLEQEKQKAibQREQAETNAibQILAQV-NH2 | -gGlu-C(O)$(CH_2)_{18}$COOH |
| 221 | Pentanoyl-VLSLDvPIKLK*KILLEQEAQKKQREQAETNAibQILAQV-NH2 | -gGlu-C(O)$(CH_2)_{18}$COOH |
| 222 | Pentanoyl-VLSLDvPIKLK*KILLEQEKQKAQREQAETNAibQILAQV-NH2 | -gGlu-C(O)$(CH_2)_{18}$COOH |
| 223 | Decanoyl-VLSLDvPIKLK*KILLEQEKQKKQREQAETNAibQILAQV-NH2 | -gGlu-C(O)$(CH_2)_{18}$COOH |
| 224 | Dodecanoyl-VLSLDvPIKLK*KILLEQEKQKKQREQAETNAibQILAQV-NH2 | -gGlu-C(O)$(CH_2)_{18}$COOH |
| 225 | Tetradecanoyl-VLSLDvPIKLK*KILLEQEKQKKQREQAETNAibQILAQV-NH2 | -gGlu-C(O)$(CH_2)_{18}$COOH |
| 226 | Ac-IVLSLDvPIGLK*KILLEQEKQKKQREQAETNAibQILAQV-NH2 | -gGlu-C(O)$(CH_2)_{18}$COOH |

TABLE 2-continued

| SEQ ID NO. | Amino acid sequence | $R^a$ |
|---|---|---|
| 227 | Ac-IVLSLDvPIGLK*KILLEQEKQKKQREQAETN4-PipQILAQV-NH2 | -gGlu-C(O)$(CH_2)_{18}$COOH |
| 228 | Pentanoyl-VLSLDvPIGLK*KILLEQEKQKKQREQAETNAibQILAQV-NH2 | -gGlu-C(O)$(CH_2)_{18}$COOH |
| 229 | NMelVLSLDvPIGLK*KILLEQEKQKKQREQAETNAibQILAQV-NH2 | -gGlu-C(O)$(CH_2)_{18}$COOH |
| 230 | Ac-IVLSLDvPIKLK*KILLEQEKQKKQREQAETNAibQILAQV-NH2 | -{AEEA}-gGlu-C(O)$(CH_2)_{18}$COOH |
| 231 | Ac-IVLSLDvPIKLK*KILLEQEKQKEQREQAETNAibQILAQV-NH2 | -{AEEA}-gGlu-C(O)$(CH_2)_{18}$COOH |
| 232 | Ac-IVLSLDvPIKLK*KILLEQEKQKAQREQAETNAibQILAQV-NH2 | -{AEEA}-gGlu-C(O)$(CH_2)_{18}$COOH |
| 233 | NMelVLSLDvPIKLK*KILLEQEKQKEQREQAETNAibQILAQV-NH2 | -{AEEA}-gGlu-C(O)$(CH_2)_{18}$COOH |
| 234 | NMelVLSLDvPIKLK*KILLEQEKQKAibQREQAETNAibQILAQV-NH2 | -{AEEA}-gGlu-C(O)$(CH_2)_{18}$COOH |
| 235 | Pentanoyl-VLSLDvPIKLK*KILLEQEKQKKQREQAETNAibQILAQV-NH2 | -{AEEA}-gGlu-C(O)$(CH_2)_{18}$COOH |
| 236 | Ac-IVLSLDvPIKLK*KILLEQEKQKEQREQAETNAibQILAQV-NH2 | -$\{AEEA\}_2$-gGlu-C(O)$(CH_2)_{18}$COOH |
| 237 | NMelVLSLDvPIKLK*KILLEQEKQKEQREQAETNAibQILAQV-NH2 | -$\{AEEA\}_2$-gGlu-C(O)$(CH_2)_{18}$COOH |
| 238 | Ac-IVLSLDvPIKLK*KILLEQEKQKKQREQAETNAibQILAQV-NH2 | -$\{AEEA\}_2$-gGlu-C(O)$(CH_2)_{18}$COOH |
| 239 | NMeIVLSLDvPIKLK*KILLEQEKQKAibQREQAETNAibQILAQV-NH2 | -$\{AEEA\}_2$-gGlu-C(O)$(CH_2)_{18}$COOH |
| 240 | Ac-IVLSLDvPIKLK*KILLEQEKQKAQREQAETNAibQILAQV-NH2 | -$\{AEEA\}_2$-gGlu-C(O)$(CH_2)_{18}$COOH |
| 241 | Ac-IVLSLDvPIKLK*KILLEQEKQKEQREQAETNAibQILAQV-NH2 | -$\{gGlu\}_2$-C(O)$(CH_2)_{18}$COOH |
| 242 | NMelVLSLDvPIKLK*KILLEQEKQKEQREQAETNAibQILAQV-NH2 | -$\{gGlu\}_2$-C(O)$(CH_2)_{18}$COOH |
| 243 | Ac-IVLSLDvPIKLK*KILLEQEKQKKQREQAETNAibQILAQV-NH2 | -$\{gGlu\}_2$-C(O)$(CH_2)_{18}$COOH |
| 244 | Ac-IVLSLDvPIKLK*KILLEQEKQKAQREQAETNAibQILAQV-NH2 | -$\{gGlu\}_2$-C(O)$(CH_2)_{18}$COOH |

In an embodiment, the compound is a peptide of the following amino acid sequence (SEQ ID NO: 19):

```
Ac-IVLSLDVPIKαMELK*QILLKQERQKKQREQAEKNAibQILEQV-
NH2
```

wherein the K residue at position 12 (denoted as K*) is chemically modified such that the epsilon-amino group of its side chain is covalently bound to -gGlu-C(O)$(CH_2)_{14}$COOH;

—NH2 denotes that the C-terminal amino acid residue is amidated as a primary amide; and Ac— denotes that the N-terminal amino acid residue is acetylated;

or a pharmaceutically acceptable salt thereof.

In an embodiment, the compound is a peptide of the following amino acid sequence (SEQ ID NO: 33):

```
Ac-VLSLDvPIKLK*KILLEQEKQKKQREQAETNKQILAQV-NH2
```

wherein the K residue at position 11 (denoted as K*) is chemically modified such that the epsilon-amino group of its side chain is covalently bound to -gGlu-C(O)$(CH_2)_{14}$COOH;

—NH2 denotes that the C-terminal amino acid residue is amidated as a primary amide; and Ac— denotes that the N-terminal amino acid residue is acetylated;

or a pharmaceutically acceptable salt thereof.

In an embodiment, the compound is a peptide of the following amino acid sequence (SEQ ID NO: 34):

```
VLSLDvPIKLK*KILLEQEKQKKQREQAETNKQILAQV-NH2
```

wherein the K residue at position 11 (denoted as K*) is chemically modified such that the epsilon-amino group of its side chain is covalently bound to -gGlu-C(O)$(CH_2)_{14}$COOH;

—NH2 denotes that the C-terminal amino acid residue is amidated as a primary amide; and Ac— denotes that the N-terminal amino acid residue is acetylated;

or a pharmaceutically acceptable salt thereof.

In an embodiment, the compound is a peptide of the following amino acid sequence (SEQ ID NO: 40):

Ac-IVLSLDvPIKLK*KILLEQEKQKKQREQAETNAibQILAQV-NH2 wherein the K residue at position 12 (denoted as K*) is chemically modified such that the epsilon-amino group of its side chain is covalently bound to -gGlu-C(O)$(CH_2)_{14}$COOH;

—NH2 denotes that the C-terminal amino acid residue is amidated as a primary amide; and Ac— denotes that the N-terminal amino acid residue is acetylated;

or a pharmaceutically acceptable salt thereof.

In an embodiment, the compound is a peptide of the following amino acid sequence (SEQ ID NO: 43):

Ac-IVLSLDVPIKαMELK*KILLEQEKQKKQREQAETNAibQILAQV-NH2 wherein the K residue at position 12 (denoted as K*) is chemically modified such that the epsilon-amino group of its side chain is covalently bound to -gGlu-C(O)$(CH_2)_{14}$COOH;

—NH2 denotes that the C-terminal amino acid residue is amidated as a primary amide; and Ac— denotes that the N-terminal amino acid residue is acetylated;

or a pharmaceutically acceptable salt thereof.

In an embodiment, the compound is a peptide of the following amino acid sequence (SEQ ID NO: 47):

Ac-IVLSLDvPIKLK*KILLEQEKQKKQREQAETNAQILAQV-NH2 wherein the K residue at position 12 (denoted as K*) is chemically modified such that the epsilon-amino group of its side chain is covalently bound to -gGlu-C(O)$(CH_2)_{14}$COOH;

—NH2 denotes that the C-terminal amino acid residue is amidated as a primary amide; and Ac— denotes that the N-terminal amino acid residue is acetylated;

or a pharmaceutically acceptable salt thereof.

In an embodiment, the compound is a peptide of the following amino acid sequence (SEQ ID NO: 51):

Ac-IVLSLDvPIKLK*KILLEQEKQKKQREQAETNAbuQILAQV-NH2 wherein the K residue at position 12 (denoted as K*) is chemically modified such that the epsilon-amino group of its side chain is covalently bound to -gGlu-C(O)$(CH_2)_{14}$COOH;

—NH2 denotes that the C-terminal amino acid residue is amidated as a primary amide; and Ac— denotes that the N-terminal amino acid residue is acetylated;

or a pharmaceutically acceptable salt thereof.

In an embodiment, the compound is a peptide of the following amino acid sequence (SEQ ID NO: 54):

Ac-IVLSLDvPIKLK*KILLEQEKQKKQREQAETNaMeKQILAQV-NH2 wherein the K residue at position 12 (denoted as K*) is chemically modified such that the epsilon-amino group of its side chain is covalently bound to -gGlu-C(O)$(CH_2)_{14}$COOH;

—NH2 denotes that the C-terminal amino acid residue is amidated as a primary amide; and Ac— denotes that the N-terminal amino acid residue is acetylated;

or a pharmaceutically acceptable salt thereof.

In an embodiment, the compound is a peptide of the following amino acid sequence (SEQ ID NO: 55):

Ac-IVLSLDvPIKLK*KILLEQEKQKKQREQAETNDapQILAQV-NH2 wherein the K residue at position 12 (denoted as K*) is chemically modified such that the epsilon-amino group of its side chain is covalently bound to -gGlu-C(O)$(CH_2)_{14}$COOH;

—NH2 denotes that the C-terminal amino acid residue is amidated as a primary amide; and Ac— denotes that the N-terminal amino acid residue is acetylated;

or a pharmaceutically acceptable salt thereof.

In a comparative embodiment, the compound is a peptide of the following amino acid sequence (SEQ ID NO: 56):

Ac-IVLSLDvPIKLK*KILLEQEKQKKQREQAETNEQILAQV-NH2 wherein the K residue at position 12 (denoted as K*) is chemically modified such that the epsilon-amino group of its side chain is covalently bound to -gGlu-C(O)$(CH_2)_{14}$COOH;

—NH2 denotes that the C-terminal amino acid residue is amidated as a primary amide; and Ac— denotes that the N-terminal amino acid residue is acetylated;

or a pharmaceutically acceptable salt thereof.

In an embodiment, the compound is a peptide of the following amino acid sequence (SEQ ID NO: 57):

Ac-IVLSLDvPIKLK*KILLEQEKQKKQREQAETN4-PipQILAQV-NH2 wherein the K residue at position 12 (denoted as K*) is chemically modified such that the epsilon-amino group of its side chain is covalently bound to -gGlu-C(O)$(CH_2)_{14}$COOH;

—NH2 denotes that the C-terminal amino acid residue is amidated as a primary amide; and Ac— denotes that the N-terminal amino acid residue is acetylated;

or a pharmaceutically acceptable salt thereof.

In an embodiment, the compound is a peptide of the following amino acid sequence (SEQ ID NO: 64):

```
NMeIVLSLDvPIKLK*KILLEQEKQKKQREQAETNAibQILAQV-
NH2
```

wherein the K residue at position 12 (denoted as K*) is chemically modified such that the epsilon-amino group of its side chain is covalently bound to -gGlu-C(O)$(CH_2)_{14}$COOH;

—NH2 denotes that the C-terminal amino acid residue is amidated as a primary amide; and NMe- denotes that the N-terminal amino acid residue is N-methylated;

or a pharmaceutically acceptable salt thereof.

In an embodiment, the compound is a peptide of the following amino acid sequence (SEQ ID NO: 80):

```
Pentanoyl-VLSLDvPIKLK*KILLEQEKQKKQREQAETNAibQILAQV-
NH2
```

wherein the K residue at position 11 (denoted as K*) is chemically modified such that the epsilon-amino group of its side chain is covalently bound to -gGlu-C(O)$(CH_2)_{14}$COOH;

—NH2 denotes that the C-terminal amino acid residue is amidated as a primary amide; and Pentanoyl- denotes that the N-terminal amino acid residue is acylated with a pentanoyl group;

or a pharmaceutically acceptable salt thereof.

In an embodiment, the compound is a peptide of the following amino acid sequence (SEQ ID NO: 92):

```
Ac-VLSLDvPIKLK*KILLEQEKQKKQREQAETNKQILAQV-NH2
```

wherein the K residue at position 11 (denoted as K*) is chemically modified such that the epsilon-amino group of its side chain is covalently bound to -{AEEA}2-gGlu-C(O)$(CH_2)_{16}$COOH;

—NH2 denotes that the C-terminal amino acid residue is amidated as a primary amide; and Ac— denotes that the N-terminal amino acid residue is acetylated;

or a pharmaceutically acceptable salt thereof.

In an embodiment, the compound is a peptide of the following amino acid sequence (SEQ ID NO: 93):

```
VLSLDvPIKLK*KILLEQEKQKKQREQAETNKQILAQV-NH2
```

wherein the K residue at position 11 (denoted as K*) is chemically modified such that the epsilon-amino group of its side chain is covalently bound to -{AEEA}2-gGlu-C(O)$(CH_2)_{16}$COOH;

—NH2 denotes that the C-terminal amino acid residue is amidated as a primary amide;

or a pharmaceutically acceptable salt thereof.

In an embodiment, the compound is a peptide of the following amino acid sequence (SEQ ID NO: 96):

```
Butanoyl-VLSLDVPIKLK*KILLEQEKQKKQREQAETNKQILAQV-
NH2
```

wherein the K residue at position 11 (denoted as K*) is chemically modified such that the epsilon-amino group of its side chain is covalently bound to -{AEEA}2-gGlu-C(O)$(CH_2)_{16}$COOH;

—NH2 denotes that the C-terminal amino acid residue is amidated as a primary amide; and Butanoyl- denotes that the N-terminal amino acid residue is acylated with a butanoyl group;

or a pharmaceutically acceptable salt thereof.

In an embodiment, the compound is a peptide of the following amino acid sequence (SEQ ID NO: 100):

```
Ac-IVLSLDvPIKLK*KILLEQEKQKKQREQAETNAQILAQV-NH2
```

wherein the K residue at position 12 (denoted as K*) is chemically modified such that the epsilon-amino group of its side chain is covalently bound to -$\{AEEA\}_2$-gGlu-C(O)$(CH_2)_{16}$COOH; and —NH2 denotes that the C-terminal amino acid residue is amidated as a primary amide; and Ac— denotes that the N-terminal amino acid residue is acetylated;

or a pharmaceutically acceptable salt thereof.

In an embodiment, the compound is a peptide of the following amino acid sequence (SEQ ID NO: 104):

```
Ac-IVLSLDvPIKLK*KILLEQEKQKKQREQAETNAbuQILAQV-NH2
```

wherein the K residue at position 12 (denoted as K*) is chemically modified such that the epsilon-amino group of its side chain is covalently bound to -$\{AEEA\}_2$-gGlu-C(O)$(CH_2)_{16}$COOH; and —NH2 denotes that the C-terminal amino acid residue is amidated as a primary amide; and Ac— denotes that the N-terminal amino acid residue is acetylated;

or a pharmaceutically acceptable salt thereof.

In an embodiment, the compound is a peptide of the following amino acid sequence (SEQ ID NO: 110):

```
Ac-IVLSLDvPIKαMELK*KILLEQEKQKKQREQAETNAibQILAQV-
NH2
```

wherein the K residue at position 12 (denoted as K*) is chemically modified such that the epsilon-amino group of its side chain is covalently bound to -$\{AEEA\}_2$-gGlu-C(O)$(CH_2)_{16}$COOH; and —NH2 denotes that the C-terminal amino acid residue is amidated as a primary amide; and Ac— denotes that the N-terminal amino acid residue is acetylated;

or a pharmaceutically acceptable salt thereof.

In an embodiment, the compound is a peptide of the following amino acid sequence (SEQ ID NO: 113):

NMeIVLSLDvPIKLK*KILLEQEKQKKQREQAETNAQILAQV-NH2 wherein the K residue at position 12 (denoted as K*) is chemically modified such that the epsilon-amino group of its side chain is covalently bound to -{AEEA}2-gGlu-C(O)$(CH_2)_{16}$COOH; and —NH2 denotes that the C-terminal amino acid residue is amidated as a primary amide; and NMe- denotes that the N-terminal amino acid residue is N-methylated;

or a pharmaceutically acceptable salt thereof.

In an embodiment, the compound is a peptide of the following amino acid sequence (SEQ ID NO: 118):

NMeIVLSLDvPIKLK*KILLEQEKQKKQREQAETNAibQILAQV-NH2 wherein the K residue at position 12 (denoted as K*) is chemically modified such that the epsilon-amino group of its side chain is covalently bound to -$\{AEEA\}_2$-gGlu-C(O)$(CH_2)_{16}$COOH; and —NH2 denotes that the C-terminal amino acid residue is amidated as a primary amide; and NMe- denotes that the N-terminal amino acid residue is N-methylated;

or a pharmaceutically acceptable salt thereof.

In an embodiment, the compound is a peptide of the following amino acid sequence (SEQ ID NO: 125):

Ac-IVLSLDvPIKLK*KILLEQEKQKKQREQAETNAibQILAQV-NH2 wherein the K residue at position 12 (denoted as K*) is chemically modified such that the epsilon-amino group of its side chain is covalently bound to -gGlu-C(O)$(CH_2)_{14}$COOH;

—NH2 denotes that the C-terminal amino acid residue is amidated as a primary amide; and Ac— denotes that the N-terminal amino acid residue is acetylated;

or a pharmaceutically acceptable salt thereof.

In an embodiment, the compound is a peptide of the following amino acid sequence (SEQ ID NO: 131):

Ac-IVLSLDvPIKLK*KILLEQEKQKAQREQAETN4PipQILAQV-NH2 wherein the K residue at position 12 (denoted as K*) is chemically modified such that the epsilon-amino group of its side chain is covalently bound to -gGlu-C(O)$(CH_2)_{16}$COOH;

—NH2 denotes that the C-terminal amino acid residue is amidated as a primary amide; and Ac— denotes that the N-terminal amino acid residue is acetylated;

or a pharmaceutically acceptable salt thereof.

In an embodiment, the compound is a peptide of the following amino acid sequence (SEQ ID NO: 132):

Ac-IVLSLDvPIKLK*KILLEQEKQKAibQREQAETN4PipQILAQV-NH2 wherein the K residue at position 12 (denoted as K*) is chemically modified such that the epsilon-amino group of its side chain is covalently bound to -gGlu-C(O)$(CH_2)_{16}$COOH;

—NH2 denotes that the C-terminal amino acid residue is amidated as a primary amide; and Ac— denotes that the N-terminal amino acid residue is acetylated;

or a pharmaceutically acceptable salt thereof.

In an embodiment, the compound is a peptide of the following amino acid sequence (SEQ ID NO: 136):

Ac-IVLSLDdvPIKLK*KILLEQEKQKKQREQAETNCpxQILAQV-NH2 wherein the K residue at position 12 (denoted as K*) is chemically modified such that the epsilon-amino group of its side chain is covalently bound to -gGlu-C(O)$(CH_2)_{16}$COOH;

—NH2 denotes that the C-terminal amino acid residue is amidated as a primary amide; and Ac— denotes that the N-terminal amino acid residue is acetylated;

or a pharmaceutically acceptable salt thereof.

In an embodiment, the compound is a peptide of the following amino acid sequence (SEQ ID NO: 144):

NMeIVLSLDvPIKLK*KILLEQEKQKAQREQAETNAibQILAQV-NH2 wherein the K residue at position 12 (denoted as K*) is chemically modified such that the epsilon-amino group of its side chain is covalently bound to -gGlu-C(O)$(CH_2)_{16}$COOH;

—NH2 denotes that the C-terminal amino acid residue is amidated as a primary amide; and NMe- denotes that the N-terminal amino acid residue is N-methylated;

or a pharmaceutically acceptable salt thereof.

In an embodiment, the compound is a peptide of the following amino acid sequence (SEQ ID NO: 145):

NMelVLSLDvPIKLK*KILLEQEKQKAibQREQAETNAibQILAQV-NH2 wherein the K residue at position 12 (denoted as K*) is chemically modified such that the epsilon-amino group of its side chain is covalently bound to -gGlu-C(O)$(CH_2)_{16}$COOH;

—NH2 denotes that the C-terminal amino acid residue is amidated as a primary amide; and NMe- denotes that the N-terminal amino acid residue is N-methylated;

or a pharmaceutically acceptable salt thereof.

In an embodiment, the compound is a peptide of the following amino acid sequence (SEQ ID NO: 189):

```
Ac-IVLSLDvPIKLK*KILLEQEKQKAQREQAETNAibQILAQV-NH2
```

wherein the K residue at position 12 (denoted as K*) is chemically modified such that the epsilon-amino group of its side chain is covalently bound to -gGlu-C(O)$(CH_2)_{16}$COOH;

—NH2 denotes that the C-terminal amino acid residue is amidated as a primary amide; and Ac— denotes that the N-terminal amino acid residue is Acetylated or a pharmaceutically acceptable salt thereof.

In an embodiment, the compound is a peptide of the following amino acid sequence (SEQ ID NO: 190):

```
Ac-IVLSLDvPIKLK*KILLEQEKQKAibQREQAETNAibQILAQV-NH2
```

wherein the K residue at position 12 (denoted as K*) is chemically modified such that the epsilon-amino group of its side chain is covalently bound to -gGlu-C(O)$(CH_2)_{16}$COOH;

—NH2 denotes that the C-terminal amino acid residue is amidated as a primary amide; and Ac— denotes that the N-terminal amino acid residue is Acetylated or a pharmaceutically acceptable salt thereof.

In an embodiment, the compound is a peptide of the following amino acid sequence (SEQ ID NO: 193):

```
Pentanoyl-VLSLDvPIKLK*KILLEQEKQKKQREQAETNAibQILAQ
V-NH2
```

wherein the K residue at position 11 (denoted as K*) is chemically modified such that the epsilon-amino group of its side chain is covalently bound to -gGlu-C(O)$(CH_2)_{16}$COOH;

—NH2 denotes that the C-terminal amino acid residue is amidated as a primary amide; and Pentanoyl- denotes that the N-terminal amino acid residue is acylated with a pentanoyl group;

or a pharmaceutically acceptable salt thereof.

In an embodiment, the compound is a peptide of the following amino acid sequence (SEQ ID NO: 203):

```
Ac-IVLSLDvPIKLK*KILLEQEKQKKQREQAETNAibQILAQV-NH2
```

wherein the K residue at position 12 (denoted as K*) is chemically modified such that the epsilon-amino group of its side chain is covalently bound to -{AEEA}-gGlu-C(O)$(CH_2)_{16}$COOH;

—NH2 denotes that the C-terminal amino acid residue is amidated as a primary amide; and Ac— denotes that the N-terminal amino acid residue is acetylated or a pharmaceutically acceptable salt thereof.

In an embodiment, the compound is a peptide of the following amino acid sequence (SEQ ID NO: 206):

```
Ac-IVLSLDvPIKLK*KILLEQEKQKKQREQAETNAibQILAQV-NH2
```

wherein the K residue at position 12 (denoted as K*) is chemically modified such that the epsilon-amino group of its side chain is covalently bound to -gGlu-C(O)$(CH_2)_{18}$COOH;

—NH2 denotes that the C-terminal amino acid residue is amidated as a primary amide; and Ac— denotes that the N-terminal amino acid residue is Acetylated;

or a pharmaceutically acceptable salt thereof.

In an embodiment, the compound is a peptide of the following amino acid sequence (SEQ ID NO: 210):

```
Ac-IVLSLDvPIKLK*KILLEQEKQKKQREQAETNThpQILAQV-NH2
```

wherein the K residue at position 12 (denoted as K*) is chemically modified such that the epsilon-amino group of its side chain is covalently bound to -gGlu-C(O)$(CH_2)_{18}$COOH;

—NH2 denotes that the C-terminal amino acid residue is amidated as a primary amide; and Ac— denotes that the N-terminal amino acid residue is Acetylated;

or a pharmaceutically acceptable salt thereof.

In an embodiment, the compound is a peptide of the following amino acid sequence (SEQ ID NO: 212):

```
Ac-IVLSLDvPIKLK*KILLEQEKQKAQREQAETNAibQILAQV-NH2
```

wherein the K residue at position 12 (denoted as K*) is chemically modified such that the epsilon-amino group of its side chain is covalently bound to -gGlu-C(O)$(CH_2)_{18}$COOH;

—NH2 denotes that the C-terminal amino acid residue is amidated as a primary amide; and Ac— denotes that the N-terminal amino acid residue is Acetylated;

or a pharmaceutically acceptable salt thereof.

In an embodiment, the compound is a peptide of the following amino acid sequence (SEQ ID NO: 213):

```
Ac-IVLSLDvPIKLK*KILLEQEKQKEQREQAETNAibQILAQV-NH2
```

wherein the K residue at position 12 (denoted as K*) is chemically modified such that the epsilon-amino group of its side chain is covalently bound to -gGlu-C(O)$(CH_2)_{18}$COOH;

—NH2 denotes that the C-terminal amino acid residue is amidated as a primary amide; and Ac— denotes that the N-terminal amino acid residue is Acetylated;

or a pharmaceutically acceptable salt thereof.

In an embodiment, the compound is a peptide of the following amino acid sequence (SEQ ID NO: 215):

```
NMeIVLSLDvPIKLK*KILLEQEKQKAibQREQAETNAibQILAQV-NH2
```

wherein the K residue at position 12 (denoted as K*) is chemically modified such that the epsilon-amino group of its side chain is covalently bound to -gGlu-C(O)$(CH_2)_{18}$COOH;

—NH2 denotes that the C-terminal amino acid residue is amidated as a primary amide; and NMe- denotes that the N-terminal amino acid residue is N-methylated;

or a pharmaceutically acceptable salt thereof.

In an embodiment, the compound is a peptide of the following amino acid sequence (SEQ ID NO: 217):

```
NMeIVLSLDvPIKLK*KILLEQEKQKAQREQAETNAibQILAQV-NH2
```

wherein the K residue at position 12 (denoted as K*) is chemically modified such that the epsilon-amino group of its side chain is covalently bound to -gGlu-C(O)$(CH_2)_{18}$COOH;

—NH2 denotes that the C-terminal amino acid residue is amidated as a primary amide; and NMe- denotes that the N-terminal amino acid residue is N-methylated;

or a pharmaceutically acceptable salt thereof.

In an embodiment, the compound is a peptide of the following amino acid sequence (SEQ ID NO: 218):

```
NMeIVLSLDvPIKLK*KILLEQEKQKEQREQAETNAibQILAQV-NH2
```

wherein the K residue at position 12 (denoted as K*) is chemically modified such that the epsilon-amino group of its side chain is covalently bound to -gGlu-C(O)$(CH_2)_{18}$COOH;

—NH2 denotes that the C-terminal amino acid residue is amidated as a primary amide; and NMe- denotes that the N-terminal amino acid residue is N-methylated;

or a pharmaceutically acceptable salt thereof.

In an embodiment, the compound is a peptide of the following amino acid sequence (SEQ ID NO: 219):

```
Pentanoyl-VLSLDvPIKLK*KILLEQEKQKKQREQAETNAibQILAQ

V-NH2
```

wherein the K residue at position 11 (denoted as K*) is chemically modified such that the epsilon-amino group of its side chain is covalently bound to -gGlu-C(O)$(CH_2)_{18}$COOH;

—NH2 denotes that the C-terminal amino acid residue is amidated as a primary amide; and Pentanoyl- denotes that the N-terminal amino acid residue is acylated with a pentanoyl group;

or a pharmaceutically acceptable salt thereof.

In an embodiment, the compound is a peptide of the following amino acid sequence (SEQ ID NO: 222):

```
Pentanoyl-VLSLDvPIKLK*KILLEQEKQKAQREQAETNAibQILAQ

V-NH2
```

wherein the K residue at position 11 (denoted as K*) is chemically modified such that the epsilon-amino group of its side chain is covalently bound to -gGlu-C(O)$(CH_2)_{18}$COOH;

—NH2 denotes that the C-terminal amino acid residue is amidated as a primary amide; and Pentanoyl- denotes that the N-terminal amino acid residue is acylated with a pentanoyl group;

or a pharmaceutically acceptable salt thereof.

In an embodiment, the compound is a peptide of the following amino acid sequence (SEQ ID NO: 230):

```
Ac-IVLSLDvPIKLK*KILLEQEKQKKQREQAETNAibQILAQV-NH2
```

wherein the K residue at position 12 (denoted as K*) is chemically modified such that the epsilon-amino group of its side chain is covalently bound to -{AEEA}-gGlu-C(O)$(CH_2)_{18}$COOH;

—NH2 denotes that the C-terminal amino acid residue is amidated as a primary amide; and Ac— denotes that the N-terminal amino acid residue is Acetylated;

or a pharmaceutically acceptable salt thereof.

In an embodiment, the compound is a peptide of the following amino acid sequence (SEQ ID NO: 231):

```
Ac-IVLSLDvPIKLK*KILLEQEKQKEQREQAETNAibQILAQV-NH2
```

wherein the K residue at position 12 (denoted as K*) is chemically modified such that the epsilon-amino group of its side chain is covalently bound to -{AEEA}-gGlu-C(O)$(CH_2)_{18}$COOH;

—NH2 denotes that the C-terminal amino acid residue is amidated as a primary amide; and Ac— denotes that the N-terminal amino acid residue is Acetylated;

or a pharmaceutically acceptable salt thereof.

In an embodiment, the compound is a peptide of the following amino acid sequence (SEQ ID NO: 233):

```
NMeIVLSLDvPIKLK*KILLEQEKQKEQREQAETNAibQILAQV-NH2
```

wherein the K residue at position 12 (denoted as K*) is chemically modified such that the epsilon-amino group of its side chain is covalently bound to -{AEEA}-gGlu-C(O)$(CH_2)_{18}$COOH;

—NH2 denotes that the C-terminal amino acid residue is amidated as a primary amide; and NMe- denotes that the N-terminal amino acid residue is N-methylated;

or a pharmaceutically acceptable salt thereof.

In an embodiment, the compound is a peptide of the following amino acid sequence (SEQ ID NO: 234):

```
NMelVLSLDvPIKLK*KILLEQEKQKAibQREQAETNAibQILAQV-NH2
```

wherein the K residue at position 12 (denoted as K*) is chemically modified such that the epsilon-amino group of its side chain is covalently bound to -{AEEA}-gGlu-C(O)$(CH_2)_{18}$COOH;

—NH2 denotes that the C-terminal amino acid residue is amidated as a primary amide; and NMe- denotes that the N-terminal amino acid residue is N-methylated;

or a pharmaceutically acceptable salt thereof.

In an embodiment, the compound is a peptide of the following amino acid sequence (SEQ ID NO: 235):

```
Pentanoyl-VLSLDvPIKLK*KILLEQEKQKKQREQAETNAibQILAQ
V-NH2
```

wherein the K residue at position 11 (denoted as K*) is chemically modified such that the epsilon-amino group of its side chain is covalently bound to -{AEEA}-gGlu-C(O)$(CH_2)_{18}$COOH;

—NH2 denotes that the C-terminal amino acid residue is amidated as a primary amide; and Pentanoyl- denotes that the N-terminal amino acid residue is acylated with a pentanoyl group;

or a pharmaceutically acceptable salt thereof.

In an embodiment, the compound is a peptide of the following amino acid sequence (SEQ ID NO: 236):

```
Ac-IVLSLDvPIKLK*KILLEQEKQKEQREQAETNAibQILAQV-NH2
```

wherein the K residue at position 12 (denoted as K*) is chemically modified such that the epsilon-amino group of its side chain is covalently bound to -$\{AEEA\}_2$-gGlu-C(O)$(CH_2)_{18}$COOH;

—NH2 denotes that the C-terminal amino acid residue is amidated as a primary amide; and Ac— denotes that the N-terminal amino acid residue is Acetylated;

or a pharmaceutically acceptable salt thereof.

In an embodiment, the compound is a peptide of the following amino acid sequence (SEQ ID NO: 237):

```
NMeIVLSLDvPIKLK*KILLEQEKQKEQREQAETNAibQILAQV-NH2
```

wherein the K residue at position 12 (denoted as K*) is chemically modified such that the epsilon-amino group of its side chain is covalently bound to -$\{AEEA\}_2$-gGlu-C(O)$(CH_2)_{18}$COOH;

—NH2 denotes that the C-terminal amino acid residue is amidated as a primary amide; and NMe- denotes that the N-terminal amino acid residue is N-Methylated;

or a pharmaceutically acceptable salt thereof.

In an embodiment, the compound is a peptide of the following amino acid sequence (SEQ ID NO: 238):

```
Ac-IVLSLDvPIKLK*KILLEQEKQKKQREQAETNAibQILAQV-NH2
```

wherein the K residue at position 12 (denoted as K*) is chemically modified such that the epsilon-amino group of its side chain is covalently bound to -$\{AEEA\}_2$-gGlu-C(O)$(CH_2)_{18}$COOH;

—NH2 denotes that the C-terminal amino acid residue is amidated as a primary amide; and Ac— denotes that the N-terminal amino acid residue is Acetylated;

or a pharmaceutically acceptable salt thereof.

In an embodiment, the compound is a peptide of the following amino acid sequence (SEQ ID NO: 241):

```
Ac-IVLSLDvPIKLK*KILLEQEKQKEQREQAETNAibQILAQV-NH2
```

wherein the K residue at position 12 (denoted as K*) is chemically modified such that the epsilon-amino group of its side chain is covalently bound to -$\{gGlu\}_2$-C(O)$(CH_2)_{18}$COOH;

—NH2 denotes that the C-terminal amino acid residue is amidated as a primary amide; and Ac— denotes that the N-terminal amino acid residue is Acetylated;

or a pharmaceutically acceptable salt thereof.

In an embodiment, the compound is a peptide of the following amino acid sequence (SEQ ID NO: 242):

```
NMeIVLSLDvPIKLK*KILLEQEKQKEQREQAETNAibQILAQV-NH2
```

wherein the K residue at position 12 (denoted as K*) is chemically modified such that the epsilon-amino group of its side chain is covalently bound to -$\{gGlu\}_2$-C(O)$(CH_2)_{18}$COOH;

—NH2 denotes that the C-terminal amino acid residue is amidated as a primary amide; and NMe- denotes that the N-terminal amino acid residue is N-Methylated;

or a pharmaceutically acceptable salt thereof.

In an embodiment, the compound is a peptide of the following amino acid sequence (SEQ ID NO: 243):

```
Ac-IVLSLDvPIKLK*KILLEQEKQKKQREQAETNAibQILAQV-NH2
```

wherein the K residue at position 12 (denoted as K*) is chemically modified such that the epsilon-amino group of its side chain is covalently bound to -$\{gGlu\}_2$-C(O)$(CH_2)_{18}$COOH;

—NH2 denotes that the C-terminal amino acid residue is amidated as a primary amide; and Ac— denotes that the N-terminal amino acid residue is Acetylated;

or a pharmaceutically acceptable salt thereof.

The compounds of the disclosure may be prepared and utilised in the form of pharmaceutically acceptable salts. Pharmaceutically acceptable salts and methods for their preparation are well known in the art (see, e.g., Stahl, et al. "Handbook of Pharmaceutical Salts: Properties, Selection and Use", Second Revised Edition, Wiley-VCH, 2011; and Berge, et al., "Pharmaceutical Salts," Journal of Pharmaceutical Sciences, 1977, 66, 1). Examples of pharmaceutically acceptable salts include trifluoroacetate salts, sodium salts, acetate salts and hydrochloride salts.

Compound Synthesis

A variety of methods can be used to prepare the compounds of the disclosure. The compounds may be prepared by synthesis in solution or on a solid support, with subsequent isolation and purification. Alternatively, the peptides can be prepared by gene expression in a host cell in which a DNA sequence encoding the peptide has been introduced.

Gene expression can also be achieved without utilising a cell system. Combinations of methods may also be used.

In particular, the compounds may be prepared by solid phase synthesis on a suitable resin. Solid phase peptide synthesis is a well-established methodology (see, e.g., Stewart and Young, "Solid Phase Peptide Synthesis", Pierce Chemical Co., Rockford, Ill., 1984; and Atherton and Sheppard, "Solid Phase Peptide Synthesis: A Practical Approach", Oxford-IRL Press, New York, 1989).

Standard manual or automated solid phase synthesis procedures can be used to prepare the compounds. Automated peptide synthesisers are commercially available from, e.g., Applied Biosystems (Foster City, CA) and Protein Technologies Inc. (Tucson, AZ). Reagents for solid phase synthesis are readily available from commercial sources. Solid phase synthesisers can be used according to the manufacturer's instructions for blocking interfering groups, protecting amino acids during reaction, coupling, deprotecting, and capping of unreacted amino acids.

Solid phase synthesis may be initiated by attaching an N-terminally protected amino acid with its carboxy terminus to an inert solid support carrying a cleavable linker. The solid support can be any polymer that allows coupling of the initial amino acid, e.g. a trityl resin, a chlorotrityl resin, a Wang resin or a Rink resin in which the linkage of the carboxy group (or carboxamide group for a Rink resin) to the resin is sensitive to acid (when a Fmoc strategy is used). The support must be one which is stable under the conditions used to deprotect the $\alpha$-amino group during the peptide synthesis.

After the N-terminally protected first amino acid has been coupled to the solid support, the $\alpha$-amino protecting group of this amino acid is removed using a reagent such as trifluoroacetic acid (TFA) or piperidine, for example. The remaining protected amino acids are then coupled one after the other or added as a preformed dipeptide, tripeptide or tetrapeptide in the order represented by the peptide sequence using appropriate amide coupling reagents. Examples of coupling reagents include benzotriazol-1-yloxytris (dimethylamino)phosphonium hexafluorophosphate (BOP), hexafluorophosphate benzotriazole tetramethyl uronium (HBTU), hexafluorophosphate azabenzotriazole tetramethyl uronium (HATU), diisopropyl-carbodiimide (DIC), 1-hydroxybenzotriazole (HOBt) and 1-hydroxy-7-azabenzotriazole, and combinations thereof. Typically, couplings are performed at room temperature in an inert solvent such as dimethylformamide (DMF), N-methylpyrrolidone (NMP) or dichloromethane (DCM).

Usually, reactive side chain groups of the amino acids are protected with suitable blocking groups. These protecting groups are removed after the desired peptides have been assembled and they may be removed concomitantly with cleavage of the desired product from the resin under the same conditions. Protecting groups and procedures for their introduction are well known in the art (see, e.g., Greene and Wuts, "Protective Groups in Organic Synthesis", 3rd ed., 1999, Wiley & Sons). Examples of protecting groups include tert-butyloxycarbonyl (tBoc) and fluorenylmethoxycarbonyl (Fmoc).

The albumin-binding moiety may be introduced by selectively functionalising the lysine (K) residue at the position denoted by X12. Thus, the lysine residue may comprise a side chain protecting group which can be selectively removed while other side chain protecting groups remain intact, such that the deprotected lysine residue can be selectively functionalised by the albumin-binding moiety. Conjugation of the albumin-binding moiety to the epsilon-amino group of the lysine side chain may be achieved through an acylation reaction or other suitable reactions known in the art.

By way of illustration, the lysine residue may be protected with a 1-(4,4-dimethyl-2,6-dioxocyclohex-1-ylidene)-3-methylbutyl ("ivDde") protecting group, which is labile to highly nucleophilic bases such as 4% hydrazine in DMF (see Chhabra et al., Tetrahedron Lett. 1998, 39, 1603). Thus, if the N-terminal amino group and all side chain functionalities are protected with acid labile protecting groups, the ivDde group can be selectively removed using a highly nucleophilic base. The resulting free amino group can then be conjugated to the albumin-binding moiety, for example by acylation. Alternatively, the lysine residue may be protected with a (4-methoxyphenyl) diphenylmethyl ("Mmt") protecting group, which is labile to very mild acids such as acetic acid and trifluoroethanol in dichloromethane (see Dubowchik et al., Tetrahedron Lett., 1997, 38(30), 5257). Thus, if the N-terminal amino group and all side chain functionalities are protected with protecting groups only labile to strong acids, the Mmt group can be selectively removed using, e.g., a mixture of acetic acid and trifluoroethanol in dichloromethane (e.g., in a 1:2:7 ratio). The resulting free amino group can then be conjugated to the albumin-binding moiety, for example by acylation.

Alternatively, the albumin binding moiety can be introduced together with the lysine during peptide synthesis by using a prefunctionalized building block as a coupling partner. Examples of such prefunctionalized building blocks include Fmoc-L-Lys[gGlu(OtBu)-C(O)$(CH_2)_{18}$—C(O)OtBu]-OH, Fmoc-L-Lys[gGlu(OtBu)-C(O)$(CH_2)_{16}$—C(O)OtBu]-OH, Fmoc-L-Lys[gGlu(OtBu)-C(O)$(CH_2)_{14}$—C(O)OtBu]-OH and Fmoc-L-Lys[$\{AEEA\}_2$-gGlu(OtBu)-C(O)$(CH_2)_{16}$—C(O)OtBu]-OH.

If desired, the N-terminus of the peptide chain can be modified, for example by acetylation. For the synthesis of C-terminal amide peptides, resins incorporating Rink amide 4-methylbenzhydrylamine (MBHA) or Rink amide AM linkers are typically used with Fmoc synthesis, while MBHA resin is generally used with tBoc synthesis.

After completion of synthesis, peptides are cleaved from the solid-phase support with simultaneous side-chain deprotection using standard treatment methods. This can be achieved by using King's cocktail (King et al., Int. J. Peptide Protein Res., 1990, 36, 255-266) or similar cleavage cocktails known in the art.

The raw material can be purified by chromatography (e.g., by preparative RP-HPLC) if necessary. Crude peptides typically are purified using RP-HPLC on C8 or C18 columns using water-acetonitrile gradients in 0.05 to 0.1% trifluoroacetic acid (TFA). The purity of the peptides can be verified by analytical RP-HPLC. The identity of the peptides can be verified by mass spectrometry. The compounds may be isolated in solid form (e.g., as dry powders) using techniques such as lyophilization.

The present disclosure also relates to intermediate compounds for use in synthesising the present compounds. In particular, there is provided a compound which is a peptide comprising the amino acid sequence of formula (I) disclosed herein, in which residues X1 to X11 and X13 to X38 have the meanings recited in connection with formula (I) and X12 is lysine (K); or a salt thereof. Said compound may be used as an intermediate in the preparation of the compounds of the disclosure, which can be obtained by conjugating the albumin-binding moiety to the epsilon-amino group of the lysine side chain at X12. Addition of the albumin-binding moiety may be performed while the peptide is still attached to the solid phase. After adding the albumin-binding moiety, the peptide may be released from the resin and purified.

Particular processes for preparing the compounds of the disclosure are described in the examples below. The specific synthetic steps for each of the routes described may be combined in different ways to prepare the compounds. The reagents and starting materials are readily available or can be prepared by methods known in the art.

Pharmaceutical Compositions

Also disclosed herein are pharmaceutical compositions comprising a compound of the disclosure and a pharmaceutically acceptable carrier or excipient.

A pharmaceutical composition may contain from about 0.1% to about 99.9% by weight of a compound of the disclosure and from about 99.9% to about 0.1% by weight of one or more pharmaceutically acceptable carriers, excipients or diluents. In one example, a pharmaceutical composition comprises from about 5% and about 75% by weight of the compound of the disclosure, with the rest being suitable pharmaceutical carriers, diluents or excipients. Methods of preparing pharmaceutical compositions are known, or will be apparent, to those skilled in this art, e.g., from literature such as Remington: The Science and Practice of Pharmacy, $22^{nd}$ Edition, Pharmaceutical Press.

In an embodiment, the pharmaceutical composition further comprises one or more additional therapeutic agents.

The pharmaceutical composition may be suitable for administration by oral, inhalation or parenteral route, e.g., subcutaneous, intravenous, intraperitoneal, intramuscular or transdermal administration. In particular, the pharmaceutical composition may be suitable for subcutaneous administration. In an embodiment, the pharmaceutical composition is a ready-to-use composition suitable for administration by a pen or autoinjector device.

The compounds may exhibit desirable solubility, chemical stability and/or physical stability, especially in solvents at physiological pH values and solvents containing antimicrobial preservatives such as phenol or meta-cresol. As a consequence, the compounds may be particularly suitable for use in pharmaceutical compositions in solution form.

In a particular embodiment, the pharmaceutical composition is a solution comprising a solvent and, dissolved therein, a compound of the disclosure and an antimicrobial preservative selected from phenol and meta-cresol; wherein the compound of the disclosure is present in an amount of at least 1 mg/ml, at least 5 mg/ml, at least 10 mg/ml or at least 20 mg/ml; and wherein the solution has a pH of from pH 6 to 8 (e.g., pH 7.0 or pH 7.4) measured at 25° C.

Use in Therapy

The compounds of the disclosure are useful in therapy and may be used to treat or prevent a variety of diseases. Thus, in other aspects, the disclosure is directed to the use of the compounds in therapy and to therapeutic methods in which an effective amount of a compound of the disclosure is administered to a patient. The disclosure is also directed to the use of the compounds for the manufacture of medicaments for use in therapy. The compounds are especially useful in the therapy of diseases which can be treated or prevented by agonism of the CRF2 receptor.

The term "therapy" as used herein refers to the treatment or prevention of a disease in a patient.

The term "treat" or "treating" as used herein includes prohibiting, restraining, slowing, stopping, or reversing the progression or severity of an existing disease in a patient. Treatment may eliminate a disease; arrest or slow a disease in a patient; inhibit or slow the development of a new disease in a patient; decrease the frequency or severity of symptoms and/or recurrences in a patient who currently has or who previously has had a disease; and/or prolong, i.e., increase, the lifespan of the patient. In particular, treatment of a disease may result in curing, shortening the duration, ameliorating, slowing down or inhibiting progression or worsening of a disease or the symptoms thereof.

The term "prevent" or "preventing" as used herein refers to inhibiting or delaying the onset of a disease or disease in a patient.

The term "disease" as used herein refers to any condition or disorder that damages or interferes with the normal function of a cell, tissue or organ.

The term "patient" as used herein refers to a mammal, such as a human, mouse, guinea pig, rat, dog or cat. In a particular embodiment, the patient is a human patient.

The term "effective amount" as used herein refers to the amount or dose of compound of the disclosure which, upon single or multiple dose administration to the patient, provides the desired effect in the patient. An effective amount can be readily determined by the attending diagnostician by the use of known techniques and by observing results obtained under analogous circumstances. In determining the effective amount for a patient, a number of factors are considered by the attending diagnostician, including, but not limited to: the species of mammal; its size, age, and general health; the specific disease or disease involved; the degree of or involvement or the severity of the disease or disease; the response of the individual patient; the particular compound administered; the mode of administration; the bioavailability characteristics of the preparation administered; the dose regimen selected; the use of concomitant medication; and other relevant circumstances.

The compounds of the disclosure may be effective over a wide dosage range. For example, unitary dosages may fall within the range of about 0.1 μg/kg to about 50 mg/kg of body weight. For example for oral administration the unitary dosages may fall within the range of about 500 μg/kg to about 50 mg/kg. For the parenteral route of administration, e.g., by subcutaneous, intravenous, intraperitoneal, intramuscular or transdermal administration, the unitary dosages may fall within the range of about 0.1 μg/kg to about 300 μg/kg, and for inhalation as the route of administration the unitary dosages may fall within the range of about 1 μg/kg to about 1 mg/kg; in particular within the range of about 30 μg/kg to about 300 μg/kg, In embodiments, the compounds are administered by once daily administration, once weekly, bi-monthly or monthly administration.

The compounds may be administered in combination with one or more additional therapeutic agents. The term "in combination with" as used herein means administration of the compound of the disclosure either simultaneously, sequentially or in a single combined formulation with the one or more additional therapeutic agents.

The compounds of the disclosure may be administered orally or by a parenteral route, e.g., by subcutaneous, intravenous, intraperitoneal, intramuscular or transdermal administration or by inhalation.

In a particular embodiment, the compounds are administered by subcutaneous administration. The compounds may be administered by a physician, a nurse or self-administered using an injection device. It is understood the gauge size and amount of injection volume is determined by the skilled practitioner. In one embodiment, the amount of injection volume is less than or equal to 2 ml, e.g., less than or equal to 1 ml. In another embodiment, a needle gauge of greater than or equal to 27, e.g., greater than or equal to 29, is used. Administration may be accomplished using an autoinjector or multidose delivery device.

The compounds of the disclosure may be useful in the therapy of diseases which can be treated or prevented by agonism of the CRF2 receptor.

The compounds are particularly useful in the treatment or prevention of cardiovascular diseases, obesity and diabetes. Thus, embodiments of the disclosure relate to the use of the compounds in the treatment or prevention of a cardiovascular diseases, obesity, diabetes, sarcopenia, particularly obesity-linked sarcopenia, cachexia, heart failure and pulmonary hypertension, in a patient.

The disclosure also relates to methods of treating or preventing a cardiovascular diseases, obesity, diabetes, kidney disease, sarcopenia, particularly obesity-linked sarcopenia, cachexia, heart failure and pulmonary hypertension in a patient which comprises administering an effective amount of a compound of the disclosure to the patient. In addition, the disclosure relates to the use of the compounds in the manufacture of a medicament for the treatment or prevention of a cardiovascular diseases, obesity, diabetes, kidney disease, sarcopenia, particularly obesity-linked sarcopenia, cachexia, heart failure and pulmonary hypertension in a patient.

Examples of cardiovascular diseases which may be treated or prevented using the present compounds include heart failure, hypertension, dyslipidaemia, atherosclerosis, arteriosclerosis, coronary heart disease, and stroke. The effect of the compounds in these conditions may be as a result of or associated with their effect on body weight or may be independent thereof. In a particular embodiment, the compounds are used to treat or prevent heart failure alone or on top of standard of care including but not exclusively angiotensin enzyme inhibitors, angiotensin II receptor antagonists, angiotensin receptor/neprilysin inhibitor (ARNi), beta-blockers, mineralocorticoid antagonists, SGLT1 inhibitors, SGLT2 inhibitors, diuretics.

The compounds may also be useful in the treatment or prevention of obesity and other diseases caused or characterised by excess body weight, such as obesity-linked inflammation, obesity-linked sarcopenia, obesity-linked gallbladder disease and obesity-induced sleep apnoea. In terms of a human adult patient, obesity can be defined as a body mass index (BMI) greater than or equal to 30 $kg/m^2$. The BMI is a simple index of weight-for-height that is commonly used to classify overweight and obesity in adults. It is defined as a person's weight in kilograms divided by the square of his/her height in meters and hence is expressed in units of $kg/m^2$. The compound may be administered in combination with one or more additional therapeutic agents useful in the treatment of obesity. Alternatively or additionally, the treatment may be combined with diet and exercise.

The compounds may also be used in the treatment or prevention of diabetes, especially type II diabetes. The compounds may be administered alone or in combination with one or more additional therapeutic agents useful in the treatment of diabetes, for example one or more agents selected from metformin, thiazolidinediones (TZDs), sulfonylureas (SUs), dipeptidyl peptidase-IV (DPP-IV) inhibitors, glucagon-like peptide-1 (GLP1) agonists, and sodium glucose co-transporters (SGLTs) inhibitors. Alternatively or additionally, treatment may be combined with diet and exercise. The compounds may also be used to treat or prevent hyperglycaemia, type I diabetes and impaired glucose tolerance.

The compounds may also be useful in the treatment or prevention of other diseases such as metabolic syndrome, kidney disease, degenerative diseases (e.g., neurodegenerative diseases) or diseases accompanied by nausea or vomiting. In particular in the treatment or prevention of sarcopenia, particularly obesity-linked sarcopenia, cachexia, heart failure and pulmonary hypertension alone or on top of standard of care.

The present invention is further illustrated by the following examples, which are provided for illustrative purposes only. The examples are not to be construed as limiting the scope or content of the disclosure in any way.

EXAMPLES

Abbreviations

Certain abbreviations are used in the examples and elsewhere herein:

"AA" refers to amino acid;
"AEEA" refers to [2-(2-aminoethoxy)ethoxy]acetyl;
"Aib" refers to 2-amino-isobutyric acid;
"AUC" refers to area under the curve;
"cAMP" refers to cyclic adenosine monophosphate;
"Boc" refers to tert-butyloxycarbonyl;
"BOP" refers to (benzotriazol-1-yloxy)tris(dimethylamino)phosphonium hexafluorophosphate;
"BSA" refers to bovine serum albumin;
"tBu" refers to tertiary butyl;
"DCM" refers to dichloromethane;
"Dde" refers to 1-(4,4-dimethyl-2,6-dioxocyclohexylidene)-ethyl;
"IvDde" refers to 1-(4,4-dimethyl-2,6-dioxocyclohexylidene)-3-methyl-butyl;
"DIC" refers to N,N'-diisopropylcarbodiimide;
"DIPEA" refers to N,N-diisopropylethylamine;
"DMEM" refers to Dulbecco's modified Eagle's medium;
"DMF" refers to dimethyl formamide;
"DMSO" refers to dimethyl sulfoxide;
"EDT" refers to ethane dithiol;
"FA" refers to formic acid;
"FBS" refers to fetal bovine serum;
"Fmoc" refers to fluorenylmethyloxycarbonyl;
"gGlu" refers to gamma-glutamate (γE);
"HATU" refers to O-(7-azabenzotriazol-1-yl)-N,N,N',N'-tetramethyluronium hexafluorophosphate;
"HBSS" refers to Hanks' Balanced Salt Solution;
"HBTU" refers to 2-(1H-benzotriazol-1-yl)-1,1,3,3-tetramethyluronium hexafluorophosphate;
"HEPES" refers to 2-[4-(2-hydroxyethyl)piperazin-1-yl] ethanesulfonic acid;
"HOAt" refers to 1-hydroxy-7-azabenzotriazole;
"HOBt" refers to 1-hydroxybenzotriazole;
"HOSu" refers to N-hydroxysuccinimide;
"HPLC" refers to High Performance Liquid Chromatography;
"hr" refers to hour;
"HTRF" refers to Homogenous Time Resolved Fluorescence;
"IBMX" refers to 3-isobutyl-1-methylxanthine;
"i.v." refers to intravenous;
"kDa" refers to kilodaltons;
"LC/MS" refers to Liquid Chromatography/Mass Spectrometry;
"Mmt" refers to monomethoxy-trityl;
"MS" refers to mass spectrometry;
"OtBu" refers to O-tert-butyl;

"Palm" refers to palmitoyl;

"Pbf" refers to 2,2,4,6,7-pentamethyldihydrobenzofuran-5-sulfonyl;

"PBS" refers to phosphate buffered saline;

"PK" refers to pharmacokinetic;

"RP-HPLC" refers to reversed-phase high performance liquid chromatography;

"s.c." refers to subcutaneous;

"SEM" refers to standard error of the mean;

"Stea" refers to stearyl;

"TIPS" refers to triisopropylsilane;

"TFA" refers to trifluoroacetic acid;

"Trt" refers to trityl; and

"UV" refers to ultraviolet.

Materials and Methods

The following starting materials and methods were employed in the synthetic procedures described in the examples.

Rink Amide AM Resin LL 0.29 mmol/g (4-(2',4'-Dimethoxyphenyl-Fmoc-aminomethyl)-phenoxyacetamido-norleucylaminomethyl resin, Novabiochem), 100-200 mesh was used for the synthesis of all the peptide amides.

Fmoc-protected natural amino acids were purchased from Novabiochem, Iris Biotech, Bachem or Chem-Impex International. The following standard amino acids were used in the synthesis: Fmoc-L-Ala-OH, Fmoc-L-Arg(Pbf)-OH, Fmoc-L-Asn(Trt)-OH, Fmoc-L-Asp(OMpe)-OH, Fmoc-L-Gln(Trt)-OH, Fmoc-L-Glu(OtBu)-OH, Fmoc-L-Ile-OH, Fmoc-L-Leu-OH, Fmoc-L-Lys(Boc)-OH, Fmoc-L-Pro-OH, Fmoc-L-Ser(tBu)-OH, Fmoc-L-Thr(tBu)-OH, Fmoc-L-Val-OH.

In addition, the following amino acids were purchased from Novabiochem, Iris Biotech, Bachem, Chem-Impex International, FluoroChem, GL Biochem, Alchem Pharmtech or Aurum Pharmatech: Fmoc-L-Lys(Dde)-OH, Fmoc-Aib-OH, Fmoc-D-Val-OH, Fmoc-D-Ile-OH, Fmoc-D-Leu-OH, Fmoc-D-Ser(tBu)-OH, Fmoc-N-methyl-L-Ile, Fmoc-L-Abu-OH, Fmoc-L-Asn(Me2)-OH, Fmoc-L-HSer (Trt)-OH, N-Boc-4-(Fmoc-amino)piperidine-4-carboxylic acid, Fmoc-L-Nva-OH, Fmoc-α-Me-L-Lys(Boc)-OH, Fmoc-α-Me-L-Leu-OH, Fmoc-L-Dap(Boc)-OH, Fmoc-4-amino-tetrahydropyran-4-carboxylic acid, 1-(Fmoc-amino) cyclohexanecarboxylic acid, Fmoc-1-aminocyclopentane-1-carboxylic acid, 1-(Fmoc-amino)cyclopropanecarboxylic acid.

The following side chain building blocks were acquired from Iris Biotech, TCI, Merck, BLD pharm: Fmoc-AEEA-OH, Fmoc-L-Glu-OtBu, Tetradecanedioic acid (HO—C(O)$(CH_2)_{12}$COOH), 16-(tert-Butoxy)-16-oxohexadecanoic acid (HO—C(O)$(CH_2)_{16}$COOtBu), 18-(Tert-butoxy)-18-oxooctadecanoic acid (HO—C(O)$(CH_2)_{16}$COOtBu), Icosanedioic acid (HO—C(O)$(CH_2)_{18}$COOH).

Propionic acid, butyric acid, valeric acid, 3-methylbutanoic acid, tert-butoxycarbonyl tert-butyl carbonate and acetic anhydride were purchased from TCI, FluoroChem, Fluka or Sigma-Aldrich.

Crude peptides were purified on a preparative HPLC Waters system with a C4 column. Specifically, the following column was used: Reprosil (Dr. Maish) Gold C4 Prep, 250×40 mm, 120 Å, 5 μm.

Acetonitrile+0.1% TFA and water+0.1% TFA were employed as eluents. Product containing fractions were collected and lyophilized to obtain the purified product, typically as a TFA salt.

TFA to HCl ion exchange was performed with the following protocol: 10 equivalents of HCl 50 mM were added to the peptide. The final concentration of 1 mg/ml was reached by diluting the samples with a solution of H2O/ACN 80:20. After lyophilization, peptides were dissolved in H2O/ACN 80:20 and lyophilized again. The completeness of the ion exchange was checked with 19F NMR.

Crude and purified peptides were analyzed by Ultra-high performance liquid chromatography with UV and mass spectrometry detection (UPLC-UV-MS). Analytical UPLC was performed according to one of the following methods:

| | |
|---|---|
| Method A: | Detection at 214 nm |
| Column: | Acquity Waters BEH C4, 300 Å, 1.7 μm (2.1 × 100 mm) at 45° C. |
| Solvent: | H2O + 0.1% TFA:ACN + 0.1% TFA (flow 0.4 ml/min) |
| Gradient: | 70:30 (0 min) to 70:30 (1 min) to 50:50 (5 min) to 10:90 (5.2 min) to 10:90 (5.5 min) to 70:30 (5.7 min) to 70:30 (6 min) |
| Mass analyzer: | Waters SQ Detector with electrospray ionization in positive ion detection mode |
| Method B: | Detection at 214 nm |
| Column: | Acquity Waters BEH C4, 300 Å, 1.7 μm (2.1 × 100 mm) at 45° C. |
| Solvent: | H2O + 0.1% TFA:ACN + 0.1% TFA (flow 0.4 ml/min) |
| Gradient: | 65:35 (0 min) to 65:35 (1 min) to 45:55 (5 min) to 10:90 (5.2 min) to 10:90 (5.5 min) to 65:35 (5.7 min) to 65:35 (6 min) |
| Mass analyzer: | Waters SQ Detector with electrospray ionization in positive ion detection mode. |

Example 1: General Synthesis Procedure SEQ ID NO: 1-145

The synthesis of all the peptides (SEQ ID NO: 1-145) was performed by standard Fmoc stepwise solid phase synthesis (SPPS) on a Liberty Blue microwave synthesizer (CEM corp.). The assembly was performed using a Rink amide AM Resin LL 0.29 mmol/g on a 0.1 mmol scale, with DIC/Oxyma activation. DMF was used as the solvent. Sequences were assembled with single couplings except for Arginine and for the amino acid introduced after an alpha methylated one, which underwent double coupling. For the modified lysine side chain, Fmoc-L-Lys(Dde)-OH was used at position 12.

The following conditions were employed:

Standard deprotection: 20% piperidine in DMF for 2×120 s, 90° C.

Washes: 4×DMF.

Standard Single coupling: 5 eq. AA 0.4 M/5 eq. DIC 1M/5 eq. Oxyma 1M, 120 s, 90° C.

Washes: 4×DMF.

At the end of the assembly, N-terminus of the peptide was modified as reported in Examples 2-9 according to the peptide sequence.

The removal of Dde group on Lys12 was achieved by dropping 2% hydrazine monohydrate and washing the resins with DMF/DCM/DMF (6/6/6 time each).

After the removal of the Dde group, the resins were treated as reported in Examples 2-9 according to the peptide sequence side chain derivatization.

Cleavage of the peptides from the resin was performed using the following cleavage cocktail: 87.5% TFA, 5% phenol, 5% water, 2.5% TIPS for 1.5 to 2.5 hours. The resin employed in the synthesis was such that the C-terminal was cleaved from the resin as a primary amide.

The cleavage mixture was collected by filtration, the crude peptides were precipitated in methyl tert-butyl ether, centrifuged, the supernatant was removed, fresh diethyl ether was added to the peptides and re-centrifuged, twice; the crude peptides were then lyophilized.

Peptides were analyzed by analytical UPLC and verified by $ESI^+$ mass spectrometry. Crude peptides were purified by a conventional preparative RP-HPLC purification procedure.

Example 2: Synthesis of the Peptide with Seq ID 125

The compound with seq ID 125, was prepared following the procedure described in Example 1. A Novabiochem Rink amide AM Resin LL 0.29 mmol/g (4-(2',4'-Dimethoxyphenyl-Fmoc-aminomethyl)-phenoxyacetamido-norleucylaminomethyl resin), 100-200 mesh was used. The automated Fmoc-synthesis strategy was applied with DIC/Oxyma-activation. In position 12, Fmoc-L-Lys(Dde)-OH was used in the solid phase synthesis protocol.

At the end of the assembly, N-terminus of the peptide was reacted with acetic anhydride (10 equivalent excess with respect to resin loading, Sigma-Aldrich) in DMF; the mixture was shaken at room temperature for 30 minutes and the reaction was monitored by Kaiser Test.

Dde protecting group on Lys12 was removed as reported in Example 1.

The γ-carboxyl end of glutamic acid was attached to the epsilon-amino group of Lys using a Fmoc-L-Glu-OtBu with DIC/HOAt method (4 equivalent excess with respect to resin loading) in DMF. The mixture was shaken at room temperature for 1 h and the reaction was monitored by Kaiser Test. The resin was filtered and washed with DMF/DCM/DMF (6/6/6 time each). The Fmoc group on the glutamic acid was removed by treating it three times with 20% (v/v) piperidine/DMF solution for 3 minutes. The resin was washed with DMF/DCM/DMF (6/6/6 time each). A Kaiser test on peptide resin aliquot upon completion of Fmoc-deprotection was positive.

Attachment of the albumin-binding moiety was performed using 18-(Tert-butoxy)-18-oxooctadecanoic acid ($HO—C(O)(CH_2)_{16}COOtBu$) with DIC/HOAt method (5 equivalent excess with respect to resin loading) in DMF. The mixture was shaken at room temperature for 1 h and the reaction was monitored by Kaiser Test. The resin was filtered and washed with DMF/DCM/DMF (6/6/6 time each).

The peptide was cleaved from the resin as described in the Example 1. The crude product was purified via preparative RP-HPLC on a Reprosil Gold C4 Prep (Dr Maisch), 250×40 mm, 120 Å, 5 μm using an acetonitrile/water gradient (with 0.1% TFA). The purified peptide was analyzed by LC/MS as reported in example 10.

Example 3: Synthesis of the Peptide with Seq ID 9

The compound with seq ID 9, was prepared following the procedure described in Example 1. A Novabiochem Rink amide AM Resin LL 0.29 mmol/g (4-(2',4'-Dimethoxyphenyl-Fmoc-aminomethyl)-phenoxyacetamido-norleucylaminomethyl resin), 100-200 mesh was used. The automated Fmoc-synthesis strategy was applied with DIC/Oxyma-activation. In position 12, Fmoc-L-Lys(Dde)-OH was used in the solid phase synthesis protocol.

At the end of the assembly, N-terminus of the peptide was reacted with 3-methylbutanoic acid with DIC/HOAt method (4 equivalent excess with respect to resin loading, Sigma-Aldrich) in DMF; the mixture was shaken at room temperature for 1 h and the reaction was monitored by Kaiser Test.

Dde protecting group on Lys12 was removed as reported in Example 1.

The γ-carboxyl end of glutamic acid was attached to the epsilon-amino group of Lys using a Fmoc-L-Glu-OtBu with DIC/HOAt method (4 equivalent excess with respect to resin loading) in DMF. The mixture was shaken at room temperature for 1 h and the reaction was monitored by Kaiser Test. The resin was filtered and washed with DMF/DCM/DMF (6/6/6 time each). The Fmoc group on the glutamic acid was removed by treating it three times with 20% (v/v) piperidine/DMF solution for 3 minutes. The resin was washed with DMF/DCM/DMF (6/6/6 time each). A Kaiser test on peptide resin aliquot upon completion of Fmoc-deprotection was positive.

Attachment of the albumin-binding moiety was performed using 16-(tert-Butoxy)-16-oxohexadecanoic acid ($HO—C(O)(CH_2)_{16}COOtBu$) with DIC/HOAt method (5 equivalent excess with respect to resin loading) in DMF. The mixture was shaken at room temperature for 1 h and the reaction was monitored by Kaiser Test. The resin was filtered and washed with DMF/DCM/DMF (6/6/6 time each).

The peptide was cleaved from the resin as described in the Example 1. The crude product was purified via preparative RP-HPLC on a Reprosil Gold C4 Prep (Dr Maisch), 250×40 mm, 120 Å, 5 μm using an acetonitrile/water gradient (with 0.1% TFA). The purified peptide was analyzed by LC/MS as reported in example 10.

Example 4: Synthesis of the Peptide with Seq ID 7

The compound with seq ID 7, was prepared following the procedure described in Example 1. A Novabiochem Rink amide AM Resin LL 0.29 mmol/g (4-(2',4'-Dimethoxyphenyl-Fmoc-aminomethyl)-phenoxyacetamido-norleucylaminomethyl resin), 100-200 mesh was used. The automated Fmoc-synthesis strategy was applied with DIC/Oxyma-activation. In position 12, Fmoc-L-Lys(Dde)-OH was used in the solid phase synthesis protocol.

At the end of the assembly, N-terminus of the peptide was acylated with butyric acid with DIC/HOAt method (4 equivalent excess with respect to resin loading, TCI) in DMF; the mixture was shaken at room temperature for 1 h and the reaction was monitored by Kaiser Test.

Dde protecting group on Lys12 was removed as reported in Example 1.

The γ-carboxyl end of glutamic acid was attached to the epsilon-amino group of Lys using a Fmoc-L-Glu-OtBu with DIC/HOAt method (4 equivalent excess with respect to resin loading) in DMF. The mixture was shaken at room temperature for 1 h and the reaction was monitored by Kaiser Test. The resin was filtered and washed with DMF/DCM/DMF (6/6/6 time each). The Fmoc group on the glutamic acid was removed by treating it three times with 20% (v/v) piperidine/DMF solution for 3 minutes. The resin was washed with DMF/DCM/DMF (6/6/6 time each). A Kaiser test on peptide resin aliquot upon completion of Fmoc-deprotection was positive.

Attachment of the albumin-binding moiety was performed using 16-(tert-Butoxy)-16-oxohexadecanoic acid ($HO—C(O)(CH_2)_{16}COOtBu$) with DIC/HOAt method (5 equivalent excess with respect to resin loading) in DMF. The mixture was shaken at room temperature for 1 h and the reaction was monitored by Kaiser Test. The resin was filtered and washed with DMF/DCM/DMF (6/6/6 time each).

The peptide was cleaved from the resin as described in the Example 1. The crude product was purified via preparative RP-HPLC on a Reprosil Gold C4 Prep (Dr Maisch), 250×40 mm, 120 Å, 5 μm using an acetonitrile/water gradient (with 0.1% TFA). The purified peptide was analyzed by LC/MS as reported in example 10.

Example 5: Synthesis of the Peptide with Seq ID 86

The compound with seq ID 86, was prepared following the procedure described in Example 1. A Novabiochem Rink amide AM Resin LL 0.29 mmol/g (4-(2',4'-Dimethoxyphenyl-Fmoc-aminomethyl)-phenoxyacetamido-norleucylaminomethyl resin), 100-200 mesh was used. The automated Fmoc-synthesis strategy was applied with DIC/Oxyma-activation. In position 12, Fmoc-L-Lys(Dde)-OH was used in the solid phase synthesis protocol.

At the end of the assembly N-terminus of the peptide was acylated with valeric acid with DIC/HOAt method (4 equivalent excess with respect to resin loading, Sigma-Aldrich) in DMF; the mixture was shaken at room temperature for 1 h and the reaction was monitored by Kaiser Test.

Dde protecting group on Lys12 was removed as reported in Example 1.

The γ-carboxyl end of glutamic acid was attached to the epsilon-amino group of Lys using a Fmoc-L-Glu-OtBu with DIC/HOAt method (4 equivalent excess with respect to resin loading) in DMF. The mixture was shaken at room temperature for 1 h and the reaction was monitored by Kaiser Test. The resin was filtered and washed with DMF/DCM/DMF (6/6/6 time each). The Fmoc group on the glutamic acid was removed by treating it twice with 20% (v/v) piperidine/DMF solution for 5 minutes (25 ml each). The resin was washed with NMP/DCM/NMP (6/6/6 time each). A Kaiser test on peptide resin aliquot upon completion of Fmoc-deprotection was positive.

Attachment of the albumin-binding moiety was performed using Tetradecanedioic acid (HO—C(O)$(CH_2)_{12}$COOH) with DIC/HOAt method (5 equivalent excess with respect to resin loading) in NMP. The mixture was shaken at room temperature for 1 h and the reaction was monitored by Kaiser Test. The resin was filtered and washed with NMP/DCM/NMP (6/6/6 time each).

The peptide was cleaved from the resin as described in the Example 1. The crude product was purified via preparative RP-HPLC on a Reprosil Gold C4 Prep (Dr Maisch), 250×40 mm, 120 Å, 5 μm using an acetonitrile/water gradient (with 0.1% TFA). The purified peptide was analyzed by LC/MS as reported in example 10.

Example 6: Synthesis of the Peptide with Seq ID 42

The compound with seq ID 42, was prepared following the procedure described in Example 1. A Novabiochem Rink amide AM Resin LL 0.29 mmol/g (4-(2',4'-Dimethoxyphenyl-Fmoc-aminomethyl)-phenoxyacetamido-norleucylaminomethyl resin), 100-200 mesh was used. The automated Fmoc-synthesis strategy was applied with DIC/Oxyma-activation. In position 12, Fmoc-L-Lys(Dde)-OH was used in the solid phase synthesis protocol.

At the end of the assembly, N-terminus of the peptide was reacted with acetic anhydride (10 equivalent excess with respect to resin loading, Sigma-Aldrich) in DMF; the mixture was shaken at room temperature for 30 minutes and the reaction was monitored by Kaiser Test.

Dde protecting group on Lys12 was removed as reported in Example 1.

Fmoc-AEEA-OH was attached to the epsilon-amino group of Lys with DIC/HOAt method (4 equivalent excess with respect to resin loading) in DMF. The mixture was shaken at room temperature for 1 h and the reaction was monitored by Kaiser Test. The resin was filtered and washed with DMF/DCM/DMF (6/6/6 time each). The Fmoc group on AEEA was removed by treating the resin three times with 20% (v/v) piperidine/DMF solution for 3 minutes. The resin was washed with DMF/DCM/DMF (6/6/6 time each). A Kaiser test on peptide resin aliquot upon completion of Fmoc-deprotection was positive.

A second Fmoc-AEEA-OH was attached to the deprotected amino group with DIC/HOAt method in DMF and then deprotected from Fmoc as reported above.

The γ-carboxyl end of glutamic acid was attached to the deprotected amino group using a Fmoc-L-Glu-OtBu with DIC/HOAt method (4 equivalent excess with respect to resin loading) in DMF. The mixture was shaken at room temperature for 1 h and the reaction was monitored by Kaiser Test. The resin was filtered and washed with DMF/DCM/DMF (6/6/6 time each). The Fmoc group on the glutamic acid was removed by treating it three times with 20% (v/v) piperidine/DMF solution for 3 minutes. The resin was washed with DMF/DCM/DMF (6/6/6 time each). A Kaiser test on peptide resin aliquot upon completion of Fmoc-deprotection was positive.

Attachment of the albumin-binding moiety was performed using 16-(tert-Butoxy)-16-oxohexadecanoic acid (HO—C(O)$(CH_2)_{16}$COOtBu) with DIC/HOAt method (5 equivalent excess with respect to resin loading) in DMF. The mixture was shaken at room temperature for 1 h and the reaction was monitored by Kaiser Test. The resin was filtered and washed with DMF/DCM/DMF (6/6/6 time each).

The peptide was cleaved from the resin as described in the Example 1. The crude product was purified via preparative RP-HPLC on a Reprosil Gold C4 Prep (Dr Maisch), 250×40 mm, 120 Å, 5 μm using an acetonitrile/water gradient (with 0.1% TFA). The purified peptide was analyzed by LC/MS as reported in example 10.

Example 7: Synthesis of the Peptide with Seq ID 94

The compound with seq ID 94, was prepared following the procedure described in Example 1. A Novabiochem Rink amide AM Resin LL 0.29 mmol/g (4-(2',4'-Dimethoxyphenyl-Fmoc-aminomethyl)-phenoxyacetamido-norleucylaminomethyl resin), 100-200 mesh was used. The automated Fmoc-synthesis strategy was applied with DIC/Oxyma-activation. In position 12, Fmoc-L-Lys(Dde)-OH was used in the solid phase synthesis protocol.

At the end of the assembly, N-terminus of the peptide was acylated with propionic acid with DIC/HOAt method (4 equivalent excess with respect to resin loading, Sigma-Aldrich) in DMF; the mixture was shaken at room temperature for 1 h and the reaction was monitored by Kaiser Test.

Dde protecting group on Lys12 was removed as reported in Example 1.

Fmoc-AEEA-OH was attached to the epsilon-amino group of Lys with DIC/HOAt method (4 equivalent excess with respect to resin loading) in DMF. The mixture was shaken at room temperature for 1 h and the reaction was monitored by Kaiser Test. The resin was filtered and washed with DMF/DCM/DMF (6/6/6 time each). The Fmoc group on AEEA was removed by treating the resin three times with 20% (v/v) piperidine/DMF solution for 3 minutes. The resin was washed with DMF/DCM/DMF (6/6/6 time each). A Kaiser test on peptide resin aliquot upon completion of Fmoc-deprotection was positive.

A second Fmoc-AEEA-OH was attached to the deprotected amino group with DIC/HOAt method in DMF and then deprotected from Fmoc as reported above.

The γ-carboxyl end of glutamic acid was attached to the deprotected amino group using a Fmoc-L-Glu-OtBu with DIC/HOAt method (4 equivalent excess with respect to resin loading) in DMF. The mixture was shaken at room temperature for 1 h and the reaction was monitored by Kaiser Test. The resin was filtered and washed with DMF/DCM/DMF (6/6/6 time each). The Fmoc group on the glutamic acid was removed by treating it three times with 20% (v/v) piperidine/DMF solution for 3 minutes. The resin was washed with DMF/DCM/DMF (6/6/6 time each). A Kaiser test on peptide resin aliquot upon completion of Fmoc-deprotection was positive.

Attachment of the albumin-binding moiety was performed using 18-(Tert-butoxy)-18-oxooctadecanoic acid (HO—C(O)$(CH_2)_{16}$COOtBu) with DIC/HOAt method (5 equivalent excess with respect to resin loading) in DMF. The mixture was shaken at room temperature for 1 h and the reaction was monitored by Kaiser Test. The resin was filtered and washed with DMF/DCM/DMF (6/6/6 time each).

The peptide was cleaved from the resin as described in the Example 1. The crude product was purified via preparative RP-HPLC on a Reprosil Gold C4 Prep (Dr Maisch), 250×40 mm, 120 Å, 5 μm using an acetonitrile/water gradient (with 0.1% TFA). The purified peptide was analyzed by LC/MS as reported in example 10.

Example 8: Synthesis of the Comparative Peptide Comp3 with Seq ID 146

A comparative compound (comp3) with the following peptide sequence,

```
                                        (SEQ ID 146)
IVLSLDvPIKLK*QILLKQERQKKQREQAEKNKQILEQV-NH2
```

wherein

- the K residue at position 12 (denoted as K*) is chemically modified such that the epsilon-amino group of its side chain is covalently bound to -{AEEA}$_2$-{gGlu}$_2$-C(O)$(CH_2)_{14}$COOH;
- —NH2 denotes that the C-terminal amino acid residue is amidated as a primary amide;

was prepared following the procedure described in Example 1. A Novabiochem Rink amide AM Resin LL 0.29 mmol/g (4-(2',4'-Dimethoxyphenyl-Fmoc-aminomethyl)-phenoxyacetamido-norleucylaminomethyl resin), 100-200 mesh was used. The automated Fmoc-synthesis strategy was applied with DIC/Oxyma-activation. In position 12, Fmoc-L-Lys (Dde)-OH was used in the solid phase synthesis protocol.

At the end of the assembly, N-terminus of the peptide was protected using tert-butoxycarbonyl tert-butyl carbonate (10 equivalent excess with respect to resin loading, FluoroChem) in DMF; the mixture was shaken at room temperature for 30 minutes and the reaction was monitored by Kaiser Test.

Dde protecting group on Lys12 was removed as reported in Example 1.

Fmoc-AEEA-OH was attached to the epsilon-amino group of Lys with DIC/HOAt method (4 equivalent excess with respect to resin loading) in DMF. The mixture was shaken at room temperature for 1 h and the reaction was monitored by Kaiser Test. The resin was filtered and washed with DMF/DCM/DMF (6/6/6 time each). The Fmoc group on AEEA was removed by treating the resin three times with 20% (v/v) piperidine/DMF solution for 3 minutes. The resin was washed with DMF/DCM/DMF (6/6/6 time each). A Kaiser test on peptide resin aliquot upon completion of Fmoc-deprotection was positive.

A second Fmoc-AEEA-OH was attached to the deprotected amino group with DIC/HOAt method in DMF and then deprotected from Fmoc as reported above.

The γ-carboxyl end of glutamic acid was attached to the deprotected amino group using a Fmoc-L-Glu-OtBu with DIC/HOAt method (4 equivalent excess with respect to resin loading) in DMF. The mixture was shaken at room temperature for 1 h and the reaction was monitored by Kaiser Test. The resin was filtered and washed with DMF/DCM/DMF (6/6/6 time each). The Fmoc group on the glutamic acid was removed by treating it three times with 20% (v/v) piperidine/DMF solution for 3 minutes. The resin was washed with DMF/DCM/DMF (6/6/6 time each). A Kaiser test on peptide resin aliquot upon completion of Fmoc-deprotection was positive.

A second Fmoc-L-Glu-OtBu was attached to the deprotected amino group with DIC/HOAt method in DMF and then deprotected from Fmoc as reported above. The resin was washed with DMF/DCM/DMF (6/6/6 time each).

Attachment of the albumin-binding moiety was performed using 16-(tert-Butoxy)-16-oxohexadecanoic acid (HO—C(O)$(CH_2)_{16}$COOtBu) with DIC/HOAt method (5 equivalent excess with respect to resin loading) in DMF. The mixture was shaken at room temperature for 1 h and the reaction was monitored by Kaiser Test. The resin was filtered and washed with DMF/DCM/DMF (6/6/6 time each).

The peptide was cleaved from the resin as described in the Example 1. The crude product was purified via preparative RP-HPLC on a Reprosil Gold C4 Prep (Dr Maisch), 250×40 mm, 120 Å, 5 μm using an acetonitrile/water gradient (with 0.1% TFA). The purified peptide was analyzed by LC/MS as reported in example 10.

Example 9: Synthesis of the Peptide with Seq ID 41

The compound with seq ID 41, was prepared following the procedure described in Example 1. A Novabiochem Rink amide AM Resin LL 0.29 mmol/g (4-(2',4'-Dimethoxyphenyl-Fmoc-aminomethyl)-phenoxyacetamido-norleucylaminomethyl resin), 100-200 mesh was used. The automated Fmoc-synthesis strategy was applied with DIC/Oxyma-activation. In position 12, Fmoc-L-Lys(Dde)-OH was used in the solid phase synthesis protocol.

At the end of the assembly, N-terminus of the peptide was reacted with acetic anhydride (10 equivalent excess with respect to resin loading, Sigma-Aldrich) in DMF; the mixture was shaken at room temperature for 30 minutes and the reaction was monitored by Kaiser Test.

The protecting group on Lys12 was removed as reported in Example 1.

The γ-carboxyl end of glutamic acid was attached to the deprotected amino group using a Fmoc-L-Glu-OtBu with DIC/HOAt method (4 equivalent excess with respect to resin loading) in DMF. The mixture was shaken at room temperature for 1 h and the reaction was monitored by Kaiser Test. The resin was filtered and washed with DMF/DCM/DMF (6/6/6 time each). The Fmoc group on the glutamic acid was removed by treating it three times with 20% (v/v) piperidine/DMF solution for 3 minutes. The resin was washed with DMF/DCM/DMF (6/6/6 time each). A Kaiser test on peptide resin aliquot upon completion of Fmoc-deprotection was positive.

A second Fmoc-L-Glu-OtBu was attached to the deprotected amino group with DIC/HOAt method in DMF and then deprotected from Fmoc as reported above. The resin was washed with DMF/DCM/DMF (6/6/6 time each).

Attachment of the albumin-binding moiety was performed using 16-(tert-Butoxy)-16-oxohexadecanoic acid (HO—C(O)$(CH_2)_{16}$COOtBu) with DIC/HOAt method (5 equivalent excess with respect to resin loading) in DMF. The mixture was shaken at room temperature for 1 h and the reaction was monitored by Kaiser Test. The resin was filtered and washed with DMF/DCM/DMF (6/6/6 time each).

The peptide was cleaved from the resin as described in the Example 1. The crude product was purified via preparative RP-HPLC on a Reprosil Gold C4 Prep (Dr Maisch), 250×40 mm, 120 Å, 5 μm using an acetonitrile/water gradient (with 0.1% TFA). The purified peptide was analyzed by LC/MS as reported in example 10.

Example 10: Synthesis of Further Peptides

The following peptides were synthesized following the procedures described in Examples 1-9. In addition to comparative peptide comp3 above, it includes two further comparative peptides, i.e. camp 1 with seq ID 147 and comp2 with Seq ID 148 respectively

| SEQ ID NO. | Peptide | Amino acid sequence | $R^a$ |
|---|---|---|---|
| 147 | Comp 1 | IVLSLDvPIKLK*QILLKQERQ KKQREQAEKNKQILEQV-NH2 | —{gGlu}$_2$—C(O) $(CH_2)_{14}$COOH |
| 148 | Comp 2 | IVLSLDvPIKLK*QILLKQERQ KKQREQAEKNKQILEQV-NH2 | —{AEEA}$_2$— gGlu—C(O) $(CH_2)_{14}$COOH |

Table legend:
K* = position of side chain derivatization;
v = D-Valine;
$R^a$ = side chain derivatization for K *;
R* structures are reported in FIG. 1

The calculated and found masses and retention times of these peptides are indicated in Table 3 below, along with those of the compounds of Examples 2-9:

TABLE 3

| SEQ ID NO. | Calc. mass (M/4 + H)+ | Found mass (M/4 + H)+ | Retention Time (min) | Method |
|---|---|---|---|---|
| 146 | 1271.0 | 1271.6 | 3.42 | A |
| 147 | 1311.3 | 1312.0 | 3.50 | A |

TABLE 3-continued

| SEQ ID NO. | Calc. mass (M/4 + H)+ | Found mass (M/4 + H)+ | Retention Time (min) | Method |
|---|---|---|---|---|
| 148 | 1343.6 | 1343.8 | 3.39 | A |
| 2 | 1249.3 | 1249.6 | 3.48 | B |
| 3 | 1221.0 | 1221.4 | 4.10 | A |
| 4 | 1210.6 | 1211.0 | 3.47 | A |
| 5 | 1242.2 | 1242.5 | 3.70 | A |
| 6 | 1224.5 | 1224.8 | 3.28 | B |
| 7 | 1228.0 | 1228.8 | 3.35 | B |
| 8 | 1231.5 | 1232.3 | 3.52 | B |
| 9 | 1231.5 | 1231.7 | 3.57 | B |
| 10 | 1228.0 | 1228.2 | 3.76 | A |
| 13 | 1231.5 | 1231.7 | 3.78 | A |
| 14 | 1232.0 | 1232.2 | 3.74 | A |
| 16 | 1238.5 | 1238.5 | 4.53 | A |
| 17 | 1249.5 | 1249.8 | 3.34 | B |
| 18 | 1235.0 | 1235.0 | 3.50 | B |
| 19 | 1242.0 | 1242.0 | 3.34 | B |
| 20 | 1235.0 | 1234.9 | 3.21 | B |
| 21 | 1238.6 | 1238.4 | 3.30 | B |
| 22 | 1217.2 | 1217.3 | 3.63 | B |
| 23 | 1238.5 | 1238.3 | 2.93 | B |
| 24 | 1235.0 | 1234.8 | 3.98 | A |
| 25 | 1300.5 | 1300.6 | 3.62 | A |
| 26 | 1311.1 | 1310.9 | 3.42 | B |
| 27 | 1314.6 | 1314.7 | 3.62 | A |
| 28 | 1307.6 | 1307.6 | 3.89 | A |
| 29 | 1296.8 | 1296.8 | 3.77 | B |
| 30 | 1318.1 | 1317.9 | 3.71 | B |
| 31 | 1311.1 | 1310.9 | 3.94 | A |
| 32 | 1300.3 | 1300.1 | 3.78 | B |
| 33 | 1192.9 | 1193.8 | 3.00 | B |
| 34 | 1182.4 | 1182.5 | 3.46 | A |
| 35 | 1196.4 | 1196.5 | 4.31 | A |
| 36 | 1200.0 | 1200.0 | 4.45 | A |
| 37 | 1203.5 | 1203.5 | 4.62 | A |
| 38 | 1203.4 | 1203.5 | 3.59 | A |
| 39 | 1210.7 | 1210.4 | 3.36 | B |
| 40 | 1210.5 | 1210.5 | 3.57 | B |
| 41 | 1242.7 | 1243.1 | 3.06 | B |
| 42 | 1283.0 | 1283.0 | 3.37 | B |
| 43 | 1214.0 | 1213.9 | 3.37 | B |
| 44 | 1214.0 | 1213.8 | 3.58 | B |
| 45 | 1182.2 | 1182.1 | 4.21 | A |
| 46 | 1185.9 | 1185.6 | 4.30 | A |
| 47 | 1207.0 | 1207.2 | 3.36 | B |
| 48 | 1214.0 | 1213.9 | 4.63 | A |
| 49 | 1217.5 | 1217.5 | 3.44 | B |
| 50 | 1217.5 | 1217.5 | 3.63 | B |
| 51 | 1210.5 | 1210.4 | 3.55 | B |
| 52 | 1214.0 | 1213.9 | 3.60 | B |
| 53 | 1225.0 | 1225.0 | 3.47 | B |
| 54 | 1224.7 | 1224.6 | 3.45 | B |
| 55 | 1210.7 | 1211.1 | 3.25 | B |
| 56 | 1221.5 | 1221.2 | 3.55 | B |
| 57 | 1220.7 | 1221.0 | 3.27 | B |
| 58 | 1221.0 | 1220.8 | 3.45 | B |
| 59 | 1220.5 | 1220.1 | 3.54 | B |
| 60 | 1217.0 | 1216.7 | 3.49 | B |
| 61 | 1210.0 | 1209.7 | 3.42 | B |
| 64 | 1203.5 | 1203.5 | 3.79 | A |
| 65 | 1207.0 | 1206.9 | 3.85 | A |
| 66 | 1207.0 | 1206.9 | 3.85 | A |
| 67 | 1210.5 | 1210.4 | 3.88 | A |
| 68 | 1200.0 | 1199.7 | 3.69 | A |
| 69 | 1203.4 | 1203.3 | 3.69 | A |
| 70 | 1203.7 | 1203.4 | 3.59 | A |
| 71 | 1214.4 | 1214.2 | 3.66 | A |
| 72 | 1213.7 | 1213.9 | 2.44 | B |
| 73 | 1213.9 | 1213.6 | 3.83 | B |
| 74 | 1189.2 | 1188.8 | 3.87 | A |
| 75 | 1192.7 | 1192.4 | 3.89 | A |
| 78 | 1185.7 | 1185.5 | 3.37 | B |
| 79 | 1189.2 | 1189.0 | 3.45 | B |
| 80 | 1192.7 | 1192.9 | 3.68 | B |
| 81 | 1196.2 | 1196.2 | 3.71 | B |
| 82 | 1203.4 | 1203.5 | 4.19 | A |
| 83 | 1203.4 | 1203.5 | 4.19 | A |

TABLE 3-continued

| SEQ ID NO. | Calc. mass (M/4 + H)+ | Found mass (M/4 + H)+ | Retention Time (min) | Method |
|---|---|---|---|---|
| 84 | 1213.7 | 1213.7 | 4.04 | A |
| 85 | 1214.5 | 1214.1 | 3.22 | B |
| 86 | 1185.7 | 1185.3 | 3.40 | B |
| 87 | 1196.4 | 1196.1 | 3.53 | A |
| 92 | 1272.5 | 1273.3 | 3.33 | B |
| 93 | 1262.0 | 1262.5 | 3.67 | A |
| 94 | 1276.0 | 1275.9 | 3.23 | B |
| 95 | 1279.6 | 1279.4 | 3.39 | B |
| 96 | 1283.0 | 1283.0 | 3.58 | B |
| 97 | 1290.0 | 1289.9 | 3.54 | B |
| 98 | 1290.1 | 1289.8 | 3.62 | B |
| 99 | 1261.8 | 1262.1 | 3.15 | B |
| 100 | 1286.5 | 1286.4 | 3.68 | B |
| 101 | 1258.3 | 1258.0 | 3.33 | B |
| 102 | 1293.6 | 1293.5 | 3.62 | B |
| 103 | 1293.6 | 1293.6 | 3.76 | B |
| 104 | 1290.0 | 1290.0 | 3.70 | B |
| 105 | 1293.6 | 1293.5 | 3.73 | B |
| 106 | 1304.3 | 1304.5 | 3.39 | B |
| 107 | 1290.3 | 1290.1 | 3.60 | B |
| 108 | 1301.0 | 1300.9 | 3.66 | B |
| 109 | 1300.3 | 1300.1 | 3.47 | B |
| 110 | 1293.5 | 1293.4 | 3.71 | B |
| 111 | 1297.1 | 1297.1 | 3.80 | B |
| 112 | 1290.0 | 1289.8 | 3.71 | B |
| 113 | 1279.5 | 1279.4 | 3.94 | A |
| 114 | 1283.0 | 1282.8 | 3.90 | A |
| 115 | 1283.3 | 1283.1 | 3.80 | A |
| 116 | 1294.0 | 1293.8 | 3.84 | A |
| 117 | 1293.3 | 1293.1 | 2.64 | B |
| 118 | 1283.0 | 1283.0 | 3.99 | A |
| 119 | 1286.6 | 1286.4 | 4.03 | A |
| 120 | 1272.3 | 1272.3 | 3.87 | B |
| 121 | 1275.8 | 1275.7 | 3.91 | B |
| 122 | 1268.8 | 1268.6 | 3.84 | B |
| 123 | 1275.8 | 1275.7 | 3.88 | B |
| 124 | 1279.3 | 1279.9 | 3.94 | B |
| 125 | 1217.5 | 1217.3 | 3.80 | B |
| 126 | 1214.0 | 1213.8 | 3.76 | B |
| 127 | 1217.5 | 1217.3 | 3.92 | B |
| 128 | 1217.7 | 1217.8 | 3.74 | B |
| 129 | 1227.7 | 1227.5 | 3.66 | B |
| 130 | 1228.5 | 1228.3 | 3.88 | B |
| 131 | 1228 | 1227.6 | 3.77 | B |
| 132 | 1227.5 | 1227.2 | 3.86 | B |
| 133 | 1224.0 | 1223.8 | 3.82 | B |
| 134 | 1217.0 | 1216.8 | 3.75 | B |
| 135 | 1210.4 | 1210.3 | 2.95 | B |
| 136 | 1207.0 | 1207.1 | 2.98 | B |
| 137 | 1210.5 | 1210.2 | 2.96 | B |
| 138 | 1210.7 | 1210.4 | 3.93 | A |
| 139 | 1220.7 | 1220.8 | 2.88 | B |
| 142 | 1221.5 | 1221.3 | 3.98 | A |
| 143 | 1220.9 | 1220.6 | 4.18 | B |
| 144 | 1196.1 | 1196.2 | 3.21 | A |
| 145 | 1199.7 | 1199.7 | 4.27 | A |
| 152 | 1206.4 | 1206.2 | 3.69 | A |
| 153 | 1209.9 | 1209.6 | 3.74 | A |
| 169 | 1199.4 | 1199.2 | 3.34 | A |
| 170 | 1202.9 | 1202.8 | 3.36 | A |
| 187 | 1213.4 | 1213 | 4.09 | A |
| 188 | 1216.9 | 1216.5 | 4.09 | A |
| 154 | 1199.4 | 1199.2 | 3.90 | B |
| 155 | 1202.9 | 1202.7 | 3.93 | B |
| 176 | 1182.2 | 1182.0 | 3.71 | B |
| 177 | 1185.7 | 1185.4 | 3.72 | B |
| 159 | 1175.2 | 1174.7 | 3.66 | B |
| 160 | 1185.4 | 1185 | 3.53 | B |
| 156 | 1196.2 | 1195.7 | 3.99 | A |
| 157 | 1206.4 | 1206 | 3.86 | A |
| 182 | 1196.4 | 1196.1 | 3.98 | B |
| 183 | 1206.7 | 1206.2 | 3.85 | B |
| 185 | 1178.7 | 1178.3 | 3.04 | A |
| 186 | 1189.4 | 1189.9 | 3.14 | B |
| 206 | 1224.4 | 1224.0 | 3.32 | C |
| 207 | 1234.7 | 1234.5 | 4.26 | A |

TABLE 3-continued

| SEQ ID NO. | Calc. mass (M/4 + H)+ | Found mass (M/4 + H)+ | Retention Time (min) | Method |
|---|---|---|---|---|
| 219 | 1206.7 | 1206.3 | 3.53 | C |
| 214 | 1217.4 | 1217.0 | 3.48 | A |
| 171 | 1276.0 | 1275.6 | 3.08 | A |
| 172 | 1286.3 | 1286.1 | 4.00 | B |
| 180 | 1258.2 | 1257.9 | 3.21 | A |
| 178 | 1269.0 | 1268.6 | 3.42 | B |
| 161 | 1196.1 | 1195.6 | 3.86 | A |
| 162 | 1199.7 | 1199.2 | 3.84 | A |
| 189 | 1203.2 | 1202.7 | 4.20 | A |
| 190 | 1206.7 | 1206.3 | 3.16 | C |
| 163 | 1196.2 | 1195.9 | 4.05 | A |
| 164 | 1196.2 | 1195.9 | 3.77 | A |
| 165 | 1196.2 | 1195.7 | 3.77 | A |
| 166 | 1196.1 | 1195.8 | 3.97 | A |
| 167 | 1189.1 | 1188.8 | 3.78 | A |
| 208 | 1223.9 | 1223.6 | 3.44 | A |
| 215 | 1206.7 | 1206.4 | 3.72 | C |
| 200 | 1272.2 | 1272.3 | 4.17 | B |
| 184 | 1195.9 | 1195.8 | 4.02 | B |
| 173 | 1275.5 | 1275.1 | 4.20 | B |
| 196 | 1289.5 | 1289.1 | 3.87 | A |
| 192 | 1192.6 | 1192.3 | 3.54 | A |
| 201 | 1272.3 | 1271.9 | 3.93 | A |
| 203 | 1253.8 | 1253.7 | 3.81 | A |
| 204 | 1322.3 | 1321.9 | 3.63 | A |
| 197 | 1279.2 | 1278.9 | 3.99 | A |
| 202 | 1261.4 | 1261.2 | 3.05 | C |
| 209 | 1213.7 | 1213.2 | 3.58 | C |
| 226 | 1206.7 | 1206.1 | 3.78 | C |
| 227 | 1216.9 | 1216.8 | 3.65 | C |
| 220 | 1195.9 | 1196.0 | 3.66 | C |
| 228 | 1188.9 | 1188.9 | 3.86 | C |
| 229 | 1199.7 | 1199.2 | 3.92 | A |
| 193 | 1199.7 | 1199.7 | 4.11 | A |
| 194 | 1188.9 | 1189.1 | 4.32 | A |
| 195 | 1181.9 | 1181.5 | 3.48 | C |
| 191 | 1199.7 | 1199.1 | 3.34 | C |
| 205 | 1286.0 | 1285.7 | 3.67 | C |
| 174 | 1308.1 | 1307.8 | 3.97 | B |
| 175 | 1318.3 | 1318.7 | 3.82 | B |
| 181 | 1290.3 | 1290.5 | 4.05 | B |
| 179 | 1301.1 | 1301.4 | 3.22 | B |
| 210 | 1234.9 | 1234.8 | 3.35 | C |
| 158 | 1210.0 | 1210.0 | 3.70 | C |
| 198 | 1300.6 | 1300.8 | 3.74 | A |
| 230 | 1260.7 | 1260.5 | 3.19 | C |
| 234 | 1243.0 | 1243.1 | 3.59 | A |
| 235 | 1242.9 | 1242.7 | 3.36 | C |
| 211 | 1210.2 | 1210.5 | 3.43 | C |
| 216 | 1203.2 | 1203.0 | 3.62 | A |
| 221 | 1192.4 | 1192.3 | 3.62 | C |
| 212 | 1210.2 | 1210.0 | 3.54 | C |
| 217 | 1203.2 | 1203.1 | 3.71 | A |
| 222 | 1192.5 | 1192.4 | 3.71 | C |
| 223 | 1224.2 | 1224.2 | 4.44 | C |
| 224 | 1231.3 | 1231.6 | 3.7 | D |
| 225 | 1238.3 | 1238.3 | 4.10 | D |
| 238 | 1297.1 | 1296.9 | 4.16 | A |
| 243 | 1256.8 | 1256.6 | 3.08 | C |
| 218 | 1217.7 | 1217.6 | 4 | A |
| 239 | 1279.3 | 1279.4 | 3.57 | A |
| 213 | 1224.7 | 1224.8 | 3.55 | C |
| 236 | 1297.3 | 1297.6 | 3.28 | C |
| 241 | 1257.0 | 1257.3 | 4.22 | A |
| 237 | 1290.3 | 1290.7 | 3.48 | A |
| 242 | 1250.0 | 1250.3 | 3.39 | A |
| 233 | 1254.0 | 1254.1 | 3.6 | A |
| 231 | 1261.0 | 1260.9 | 3.39 | C |
| 168 | 1210.7 | 1211.2 | 3.77 | A |
| 232 | 1246.5 | 1247.0 | 4.36 | A |
| 240 | 1282.8 | 1283.2 | 4.31 | A |
| 244 | 1242.5 | 1242.9 | 4.21 | A |

Example 11: Assessment of Activity at Human CRF2α Receptor

Agonism of compounds for human corticotropin-releasing factor 2α (CRF2α receptor) was determined by a functional assay measuring cAMP modulation upon treatment of TeloHEAC cells stably expressing human CRF2α receptor.

Compounds were dissolved at 0.5 mM in 100% DMSO and serially diluted (1:2) in 100% DMSO for 16 dilutions. 20 nL of each dilution was then transferred to 384-well assay plate using an acoustic droplet ejection instrument. 5 μL of compound buffer (1×HBSS; 20 mM HEPES,) were then added to each well.

Prior to use, frozen cells were thawed quickly at 37° C. and washed (5 min at 900 rpm) with 20 mL cell buffer (1×HBSS; 20 mM HEPES). Cells were resuspended in cell buffer added with 2 mM IBMX and adjusted to a cell density of 2M cells/ml.

5 μL cells (final dell density: 10000 cells/well) were dispensed in the compound-containing 384-well assay plate and incubated for 30 minutes 37° C.

The cAMP level in treated cells was determined using the Cisbio 62AM4PEC kit according to manufacturer's instruction. Finally, plates were incubated for 1 h at room temperature before measuring the fluorescence ratio between 665/620 nm.

The percent activity value (E %) was calculated by setting 100 nM of urocortin 2 (UCN2) as 100%. The in vitro potency of the compounds was quantified by determining the concentrations that caused 50% activation of maximal response (EC50) relative to urocortin 2.

Representative EC50 values are provided in Table 4 below:

TABLE 4

| SEQ ID No. | EC50 [nM] |
|---|---|
| 149 (Comp Y) | 0.44 |
| 150 (Comp Z) | 0.25 |
| 151 (Comp X) | 0.12 |
| 146 (Comp 1) | 0.1 |
| 147 (Comp 2) | 0.18 |
| 148 (Comp 3) | 0.65 |
| 2 (Comp 4) | 0.07 |
| 5 (Comp 5) | 0.09 |
| 56 (Comp 10) | 0.3 |
| 116 (comp 12) | 0.37 |
| 130 (Comp 13 | 0.08 |
| 142 (Comp 14) | 0.07 |
| 4 | 0.44 |
| 8 | 0.14 |
| 3 | 0.16 |
| 6 | 0.09 |
| 9 | 0.16 |
| 7 | 0.06 |
| 10 | 0.17 |
| 13 | 0.15 |
| 14 | 0.26 |
| 92 | 2.3 |
| 93 | 5.08 |
| 33 | 0.47 |
| 34 | 1.61 |
| 94 | 1.48 |
| 96 | 0.49 |
| 95 | 0.76 |
| 25 | 5.02 |
| 26 | 18.63 |
| 97 | 3.17 |
| 19 | 0.28 |
| 20 | 1.09 |
| 39 | 0.53 |
| 38 | 0.49 |

TABLE 4-continued

| SEQ ID No. | EC50 [nM] |
|---|---|
| 43 | 0.3 |
| 102 | 17.59 |
| 49 | 0.92 |
| 40 | 0.25 |
| 64 | 0.19 |
| 118 | 0.6 |
| 80 | 0.35 |
| 120 | 1.33 |
| 66 | 1.05 |
| 81 | 0.8 |
| 121 | 5.76 |
| 18 | 3.55 |
| 22 | 4.44 |
| 35 | 0.23 |
| 36 | 0.14 |
| 37 | 0.13 |
| 103 | 3.09 |
| 48 | 1.35 |
| 111 | 2.58 |
| 27 | 16.89 |
| 28 | 2.2 |
| 29 | 37.17 |
| 16 | 0.13 |
| 44 | 0.25 |
| 50 | 0.26 |
| 53 | 8.05 |
| 46 | 0.7 |
| 65 | 0.1 |
| 67 | 0.34 |
| 110 | 0.3 |
| 125 | 0.15 |
| 119 | 1.62 |
| 123 | 0.7 |
| 124 | 0.38 |
| 45 | 0.96 |
| 100 | 0.41 |
| 104 | 0.47 |
| 105 | 0.87 |
| 113 | 0.35 |
| 122 | 0.67 |
| 30 | 0.29 |
| 31 | 0.23 |
| 32 | 1.04 |
| 42 | 3.08 |
| 41 | 1.85 |
| 106 | 0.35 |
| 107 | 1.43 |
| 108 | 1.14 |
| 54 | 0.12 |
| 55 | 0.42 |
| 51 | 0.12 |
| 52 | 0.17 |
| 17 | 0.21 |
| 21 | 0.34 |
| 47 | 0.09 |
| 57 | 0.39 |
| 78 | 0.73 |
| 79 | 0.38 |
| 99 | 6.07 |
| 112 | 0.28 |
| 101 | 1.74 |
| 98 | 0.55 |
| 109 | 1 |
| 68 | 0.05 |
| 71 | 0.21 |
| 72 | 0.14 |
| 126 | 0.05 |
| 127 | 0.08 |
| 129 | 0.14 |
| 137 | 0.07 |
| 69 | 0.09 |
| 70 | 0.17 |
| 128 | 0.17 |
| 115 | 0.76 |
| 114 | 0.18 |
| 140 | 0.17 |
| 139 | 0.05 |
| 117 | 0.63 |

TABLE 4-continued

| SEQ ID No. | EC50 [nM] |
|---|---|
| 138 | 0.05 |
| 141 | 0.16 |
| 23 | 0.33 |
| 24 | 0.04 |
| 58 | 0.41 |
| 133 | 0.16 |
| 59 | 0.81 |
| 134 | 0.5 |
| 60 | 0.34 |
| 135 | 0.19 |
| 61 | 0.36 |
| 136 | 0.16 |
| 74 | 0.15 |
| 75 | 0.19 |
| 152 | 0.51 |
| 153 | 0.41 |
| 154 | 0.52 |
| 155 | 0.51 |
| 156 | 0.29 |
| 157 | 0.32 |
| 158 | 0.04) |
| 159 | 2.97 |
| 160 | 2.08 |
| 161 | 0.32 |
| 162 | 0.49 |
| 163 | 0.3 |
| 164 | 2.43 |
| 165 | 0.64 |
| 166 | 0.77 |
| 167 | 1.15 |
| 168 | 0.8 |
| 169 | 1.34 |
| 170 | 1.28 |
| 171 | 5.79 |
| 172 | 16.13 |
| 173 | 28.14 |
| 174 | 16.18 |
| 175 | 18.85 |
| 176 | 0.99 |
| 177 | 0.86 |
| 178 | 6.5 |
| 179 | 15.55 |
| 180 | 10.67 |
| 181 | 24.68 |
| 182 | 1.88 |
| 183 | 2.47 |
| 184 | 4.25 |
| 185 | 3.54 |
| 186 | 0.79 |
| 187 | 0.26 |
| 188 | 0.28 |
| 189 | 0.29 |
| 190 | 0.3 |
| 191 | 0.18 |
| 192 | 0.11 |
| 193 | 0.17 |
| 194 | 0.44 |
| 195 | 0.21 |
| 196 | 2.2 |
| 197 | 1.28 |
| 198 | 1.7 |
| 199 | 0.16 |
| 200 | 0.71 |
| 201 | 1.37 |
| 202 | 1.73 |
| 203 | 0.43 |
| 204 | 1.84 |
| 205 | 1.43 |
| 206 | 0.11 |
| 207 | 0.12 |
| 208 | 0.15 |
| 209 | 0.22 |
| 210 | 0.21 |
| 211 | 0.15 |
| 212 | 0.11 |
| 213 | 0.22 |
| 214 | 0.12 |
| 215 | 0.12 |

TABLE 4-continued

| SEQ ID No. | EC50 [nM] |
|---|---|
| 216 | 0.05 |
| 217 | 0.09 |
| 218 | 0.11 |
| 219 | 0.16 |
| 220 | 0.27 |
| 221 | 0.18 |
| 222 | 0.14 |
| 223 | 0.08 |
| 224 | 0.07 |
| 225 | 0.09 |
| 226 | 0.18 |
| 227 | 0.2 |
| 228 | 0.19 |
| 229 | 0.11 |
| 230 | 0.16 |
| 231 | 0.28 |
| 232 | 0.12 |
| 233 | 0.12 |
| 234 | 0.09 |
| 235 | 0.16 |
| 236 | 0.54 |
| 237 | 0.41 |
| 238 | 0.11 |
| 239 | 0.11 |
| 240 | 0.22 |
| 241 | 0.56 |
| 242 | 0.22 |
| 243 | 0.13 |
| 244 | 0.28 |

Example 12: Assessment of Activity at Anti-Target CFR1R Receptor

Assessment of activity at anti-target CFR1R receptor is done using the same procedure as the one described for the TeloHEAC cell line.

The CRF1R-overexpression CHO-K1 cell line clone 2 was purchased from PerkinElmer.

Cells were grown in a 10 cm dish at 37° C./5% $CO_2$ in medium (F12 (Hams)/10% FBS/400 µg/ml G418) to near confluence. At that stage, cells were harvested, resuspended to 10 million/mL in culture medium without G418 and with 10% DMSO. 1 mL vial aliquots were slowly frozen to −80° C. in isopropanol and then transferred in liquid nitrogen for storage. These vials were used to run the experiment following the procedure reported in the previous paragraph, except for the compound used in the control well to define the 100% activation (Sauvagine at 100 nM) and the cell density (final cell density: 4000 cells/well)

Representative EC50 values are provided in Table 5 below:

TABLE 5

| SEQ ID No. | EC50 [nM] | Emax (% I) |
|---|---|---|
| 149 (CompY) | >250 | 4 |
| 150 (CompZ) | >250 | 38 |
| 151 (CompX) | 25.3 | 53 |
| 146 (Comp1) | 100 | 27 |
| 147 (Comp2) | 100 | 22 |
| 148 (Comp3) | 100 | 13 |
| 2 (Comp 4) | 95.41 | 63 |
| 5 (Comp 5) | 157.6 | 48 |
| 56 (Comp 10) | >250 | 3 |
| 116 (Comp 12) | >250 | 0 |
| 130 (Comp 13) | >250 | 4 |
| 142 (Comp 14) | >250 | 3 |
| 4 | >250 | 4 |
| 8 | 186.26 | 50 |

TABLE 5-continued

| SEQ ID No. | EC50 [nM] | Emax (% I) |
|---|---|---|
| 3 | >250 | 27 |
| 6 | 166.13 | 56 |
| 9 | 28.24 | 77 |
| 7 | 101.16 | 59 |
| 10 | >250 | 26 |
| 13 | >250 | 24 |
| 14 | >250 | 24 |
| 92 | >250 | 5 |
| 93 | >250 | 6 |
| 33 | >250 | 13 |
| 34 | >250 | 0 |
| 94 | >250 | 0 |
| 96 | >250 | 4 |
| 95 | >250 | 5 |
| 25 | >250 | 6 |
| 26 | >250 | 1 |
| 97 | >250 | 0 |
| 19 | >250 | 6 |
| 20 | >250 | 3 |
| 39 | >250 | 2 |
| 38 | >250 | 6 |
| 43 | >250 | 1 |
| 102 | >250 | −5 |
| 49 | >250 | −3 |
| 40 | >250 | 0 |
| 64 | >250 | 4 |
| 118 | >250 | 7 |
| 80 | >250 | 10 |
| 120 | >250 | 3 |
| 66 | >250 | 4 |
| 81 | >250 | 6 |
| 121 | >250 | 6 |
| 18 | >250 | 10 |
| 22 | >250 | 3 |
| 35 | >250 | 13 |
| 36 | >250 | 22 |
| 37 | >250 | 22 |
| 103 | >250 | 3 |
| 48 | >250 | 4 |
| 111 | >250 | −3 |
| 27 | >250 | 7 |
| 28 | >250 | 6 |
| 29 | >250 | 6 |
| 16 | 185.15 | 47 |
| 44 | >250 | 5 |
| 50 | >250 | 9 |
| 53 | >250 | 5 |
| 46 | >250 | 6 |
| 65 | >250 | 10 |
| 67 | >250 | 8 |
| 110 | >250 | 9 |
| 125 | >250 | 18 |
| 119 | >250 | 5 |
| 123 | >250 | 14 |
| 124 | >250 | 14 |
| 45 | >250 | 5 |
| 100 | >250 | 8 |
| 104 | >250 | 5 |
| 105 | >250 | 10 |
| 113 | >250 | 6 |
| 122 | >250 | 5 |
| 30 | >250 | 15 |
| 31 | >250 | 14 |
| 32 | >250 | 5 |
| 42 | >250 | 1 |
| 41 | >250 | 7 |
| 106 | >250 | 6 |
| 107 | >250 | 0 |
| 108 | >250 | 4 |
| 54 | >250 | 20 |
| 55 | >250 | 5 |
| 51 | >250 | 9 |
| 52 | >250 | 7 |
| 17 | >250 | 12 |
| 21 | >250 | 5 |
| 47 | >250 | 10 |
| 57 | >250 | 24 |
| 78 | >250 | 7 |

TABLE 5-continued

| SEQ ID No. | EC50 [nM] | Emax (% I) |
|---|---|---|
| 79 | >250 | 10 |
| 99 | >250 | 0 |
| 112 | >250 | 3 |
| 101 | >250 | 0 |
| 98 | >250 | −2 |
| 109 | >250 | 4 |
| 68 | >250 | 8 |
| 71 | >250 | −4 |
| 72 | >250 | 18 |
| 126 | >250 | 20 |
| 127 | >250 | 11 |
| 129 | 235.62 | 39 |
| 137 | >250 | 9 |
| 69 | >250 | 3 |
| 70 | >250 | 0 |
| 128 | >250 | 10 |
| 115 | >250 | 4 |
| 114 | >250 | 6 |
| 140 | >250 | 14 |
| 139 | >250 | 13 |
| 117 | >250 | 3 |
| 138 | >250 | 10 |
| 141 | >250 | 32 |
| 23 | >250 | 35 |
| 24 | >250 | 37 |
| 58 | >250 | 6 |
| 133 | >250 | 11 |
| 59 | >250 | 9 |
| 134 | >250 | 10 |
| 60 | >250 | 5 |
| 135 | >250 | 15 |
| 61 | >250 | 3 |
| 136 | >250 | 5 |
| 74 | >250 | 7 |
| 75 | >250 | 3 |
| 152 | >250 | 25 |
| 153 | >250 | 22 |
| 154 | >250 | 24 |
| 155 | >250 | 26 |
| 156 | >250 | 8 |
| 157 | >250 | 30 |
| 158 | 98.7 | 54 |
| 159 | >250 | 4 |
| 160 | >250 | 2 |
| 161 | >250 | 3 |
| 162 | >250 | 0 |
| 163 | 189.69 | 53 |
| 164 | >250 | 14 |
| 165 | >250 | 14 |
| 166 | >250 | 5 |
| 167 | >250 | 7 |
| 168 | >250 | 3 |
| 169 | >250 | 13 |
| 170 | >250 | 5 |
| 171 | >250 | 0 |
| 172 | >250 | −6 |
| 173 | >250 | −1 |
| 174 | >250 | 11 |
| 175 | >250 | 5 |
| 176 | >250 | 8 |
| 177 | >250 | 10 |
| 178 | >250 | 1 |
| 179 | >250 | −4 |
| 180 | >250 | 2 |
| 181 | >250 | 9 |
| 182 | >250 | 1 |
| 183 | >250 | 11 |
| 184 | >250 | 3 |
| 185 | >250 | 2 |
| 186 | >250 | 2 |
| 187 | 195.24 | 37 |
| 188 | >250 | 32 |
| 189 | >250 | 9 |
| 190 | >250 | 9 |
| 191 | 92.86 | 54 |
| 192 | >250 | 19 |
| 193 | >250 | 20 |
| 194 | >250 | 10 |

TABLE 5-continued

| SEQ ID No. | EC50 [nM] | Emax (% I) |
|---|---|---|
| 195 | *180.45 | 42 |
| 196 | >250 | 9 |
| 197 | >250 | 5 |
| 198 | >250 | 8 |
| 199 | >250 | 11 |
| 200 | >250 | 2 |
| 201 | >250 | 5 |
| 202 | >250 | 8 |
| 203 | >250 | 3 |
| 204 | >250 | −2 |
| 205 | >250 | 1 |
| 206 | 224.24 | 42 |
| 207 | 61.36 | 65 |
| 208 | 83.93 | 63 |
| 209 | >250 | 21 |
| 210 | >250 | 35 |
| 211 | 39.91 | 73 |
| 212 | 228.55 | 41 |
| 213 | >250 | 27 |
| 214 | >250 | 34 |
| 215 | >250 | 19 |
| 216 | 80.27 | 61 |
| 217 | >250 | 33 |
| 218 | >250 | 24 |
| 219 | 222.27 | 48 |
| 220 | >250 | 32 |
| 221 | 22.53 | 79 |
| 222 | 196.44 | 50 |
| 223 | 152 | 58 |
| 224 | 39.53 | 66 |
| 225 | 73.42 | 70 |
| 226 | 42.15 | 82 |
| 227 | 1.74 | 97 |
| 228 | 90.55 | 62 |
| 229 | 202.93 | 43 |
| 230 | >250 | 30 |
| 231 | >250 | 10 |
| 232 | >250 | 13 |
| 233 | >250 | 8 |
| 234 | >250 | 15 |
| 235 | >250 | 27 |
| 236 | >250 | 7 |
| 237 | >250 | 6 |
| 238 | >250 | 12 |
| 239 | >250 | 0 |
| 240 | >250 | 4 |
| 241 | >250 | 7 |
| 242 | >250 | 6 |
| 243 | >250 | 8 |
| 244 | >250 | 8 |

Example 13: Assessment of Activity at Rat CRF2 α

The A7R5 rat aortic smooth muscle cell line used in this study was purchased from ATCC.

Cells were grown in a 10 cm dish at 37° C./5% CO2 in medium (DMEM/10% FBS) to near confluence. At that stage, cells were harvested, resuspended to 10 million/mL in culture medium and with 5% DMSO. 1 mL vial aliquots were slowly frozen to −80° C. in isopropanol and then transferred in liquid nitrogen for storage.

These vials were used to run the experiment following the procedure reported in the previous paragraph, except for the compound used in the control well to define the 100% activation (Sauvagine at 100 nM) and the cell density (final cell density: 5000 cells/well).

Representative EC50 values compared to comparative peptide 11 (Seq ID 85 in Table 2) are provided in Table 6 below:

TABLE 6

| SEQ ID | $EC_{50}$ [nM] 0% HSA |
|---|---|
| 85 (Comp 11) | 1.01 |
| 40 | 0.59 |
| 144 | 0.06 |
| 145 | 0.05 |
| 86 | 0.68 |
| 87 | 0.32 |
| 206 | 0.06 |
| 189 | 0.15 |
| 215 | 0.04 |
| 230 | 0.11 |
| 234 | 0.05 |
| 235 | 0.17 |
| 212 | 0.08 |
| 217 | 0.06 |
| 222 | 0.18 |
| 238 | 0.09 |
| 243 | 0.09 |
| 218 | 0.13 |
| 213 | 0.45 |
| 236 | 2.81 |
| 241 | 3.52 |
| 237 | 0.63 |
| 242 | 0.40 |
| 233 | 0.37 |
| 231 | 1.32 |
| 168 | 3.23 |
| 232 | 0.40 |
| 240 | 2.30 |
| 244 | 1.77 |

Example 14: Assessment of Solubility, Chemical, Catabolic Stability and PK Properties of the Peptides According to the Invention The effect on solubility, chemical, catabolic stability and PK properties of the peptides according to the invention were studied by means of solubility, chemical stability, plasma and SC extract stability, and pharmacokinetics studies. As comparative peptides the following peptides (Table 7) were included in the assays;

| SEQ ID NO. | Comp Number | Amino acid sequence | $R^a$ |
|---|---|---|---|
| 149 | Comp Y | IVLSLDVPIKLK*KILLEQEKQKKQREQAETNKQI-LAQV-NH2 | {AEEA}$_2$-gGlu-C(O)$(CH_2)_{16}$COOH |
| 150 | Comp Z | IVLSLDVPIKLK*QILLKQERQKKQREQAEKNKQI-LEQV-NH2 | {AEEA}2-gGlu-C(O)$(CH_2)_{16}$COOH |

-continued

| SEQ ID NO. | Comp Number | Amino acid sequence | $R^a$ |
|---|---|---|---|
| 151 | Comp X | IVLSLDVPIKLK*QILLKQERQKKQREQAEKNKQI-LEQV-NH2 | gGlu-C(O)(CH$_2$)$_{14}$COOH |

Legend:
V = D-Valine;
K* = position of side chain derivatization

In Vitro Plasma Stability

In vitro plasma metabolic stability was studied in male Sprague Dawley rats and human. Test compounds were incubated at 3 M for 2 hours at 37° C. At each time point (0, 0.25, 1 and 2 h), samples were prepared for analysis by means of a single step protein precipitation technique by adding 150 μL of ethanol, 0.1% formic acid to 50 μL aliquots of plasma. Samples were mixed by vortex for homogeneity and then subjected to centrifugation at 14000 rpm for 15 min. The supernatant (100 μL) was collected, diluted with 100 μL of water, 0.1% formic acid and analyzed by LC-HRMS (TripleTOF 6600+, AB Sciex). For each test compound, the area ratios at each time point were compared to the 0 h area ratio and converted to a percentage remaining.

Plasma stability was initially included in the ADME screening funnel. However, all compounds showed high stability in human, rat and minipig or dog plasma some representative examples are provided in (Table 8). Good stability results indicate that differences in N-terminal protective group or in the linker did not affect stability.

Human, rat and minipig or dog plasma stability data of representative compounds:

TABLE 8

| SEQ ID No. | Species | % remaining at 2 hours |
|---|---|---|
| 118 | Human PLM | 91 |
| | Rat PLM | 128 |
| | Minipig PLM | 126 |
| 80 | Human PLM | 101 |
| | Rat PLM | 98 |
| | Minipig PLM | 104 |
| 110 | Human PLM | 97 |
| | Rat PLM | 95 |
| | Minipig PLM | 106 |
| 125 | Human PLM | 93 |
| | Rat PLM | 108 |
| | Minipig PLM | 110 |
| ~~56~~ | ~~Human PLM~~ | ~~102~~ |
| | ~~Rat PLM~~ | ~~91~~ |
| | ~~Minipig PLM~~ | ~~123~~ |
| 51 | Human PLM | 102 |
| | Rat PLM | 73 |
| | Minipig PLM | 97 |
| 57 | Human PLM | 104 |
| | Rat PLM | 96 |
| | Minipig PLM | 81 |
| 218 | Human PLM | 99 |
| | Rat PLM | 109 |
| | Dog PLM | 102 |
| 213 | Human PLM | 99 |
| | Rat PLM | 99 |
| | Dog PLM | 102 |
| 237 | Human PLM | 83 |
| | Rat PLM | 84 |
| | Dog PLM | 86 |
| 233 | Human PLM | 100 |
| | Rat PLM | 106 |
| | Dog PLM | 99 |

In Vitro Subcutaneous Tissue Supernatant Stability and Metabolite Identification In vitro metabolic stability in subcutaneous tissue supernatant (SCts) was studied in male Sprague Dawley rats. Test compounds were incubated at 3 mM for 2 hours at 37° C. At each time point (0, 0.25, 1 and 2 h), samples were prepared for analysis by means of a single step protein precipitation technique by adding 150 μL of ethanol, 0.1% formic acid to 50 μL aliquots of SCts. Samples were mixed by vortex for homogeneity and then subjected to centrifugation at 14000 rpm for 15 min. The supernatant (100 μL) was collected, diluted with 100 μL of water, 0.1% formic acid and analyzed by LC-HRMS either with a TripleTOF 6600$^+$ (Sciex) or Orbitrap Q Exactive (Thermo). For each test compound, the area ratios at each time point were compared to the 0 h area ratio and converted to a percentage remaining.

Software aided in vitro metabolite identification on SCts stability samples was performed using either Metabolite Pilot (Sciex) or Biopharma Finder (Thermo). In addition, metabolite identification using Metabolite Pilot was performed on plasma samples of Comp Y following SC administration to rat at 1 mg/kg.

Representative SCts stability data are provided in Table 9. The first analogs of the Comparative peptides that were tested showed a poor metabolic stability in rat SCts (<5% remaining at 2 hours). In vitro soft spot identification on Comp X and Comp Y, and in vivo metabolite ID of Comp Y identified the N-terminus as the major metabolic soft spot both in vitro (rat) and in vivo.

Acetylation or N-methylation of Ile1 at the N-terminus resulted in a substantial improvement of the rat SCts stability (>50% remaining at 2 hours). Finally, N-terminus stabilization translated into better SC pharmacokinetic profiles in rat (see "Pharmacokinetics" section below). All the tested compounds showed a good SCts stability in all the species (human, rat, minipig and dog) investigated confirming that N-terminus modification did improve SCts stability. Otherwise, chemical nature of the Lys12 linker (gEC16OH, gEC20OH, PEG2-gE-C20OH and PEG2-PEG2-gE-C20OH e.g.) did not significantly affect the stability of these peptides.

Representative rat SCts stability data.

TABLE 9

| SEQ ID N | Species | % remaining at 2 h |
|---|---|---|
| 149 (CompY) | Rat | 4 |
| 151 (CompX) | Rat | 0 |
| 40 | Rat | 79 |
| 110 | Rat | 77 |
| 125 | Rat | 79 |
| 98 | Rat | 74 |
| 199 | Rat | 83 |
| 136 | Rat | 78 |
| 144 | Rat | 74 |
| 145 | Rat | 76 |
| 82 | Rat | 82 |

TABLE 9-continued

| SEQ ID N | Species | % remaining at 2 h |
|---|---|---|
| 187 | Rat | 82 |
| 188 | Rat | 77 |
| 206 | Rat | 73 |
| 219 | Rat | 71 |
| 214 | Rat | 72 |
| 161 | Rat | 59 |
| 189 | Rat | 67 |
| 190 | Rat | 95 |
| 165 | Rat | 72 |
| 215 | Rat | 84 |
| 203 | Rat | 65 |
| 193 | Rat | 56 |
| 210 | Rat | 72 |
| 234 | Rat | 68 |
| 235 | Rat | 66 |
| 121 | Rat | 77 |
| 217 | Rat | 76 |
| 222 | Rat | 62 |
| 223 | Rat | 79 |
| 218 | Rat | 71 |
| 213 | Rat | 74 |
| 236 | Rat | 75 |
| 241 | Rat | 68 |
| 237 | Rat | 60 |
| 233 | Rat | 56 |
| 231 | Rat | 65 |
| 242 | Rat | 68 |

Solubility and Chemical Stability

Solubility and chemical stability were studied in 100 mM phosphate buffer (pH 7.4) and 100 mM acetate buffer (pH 4.5). Test compound powders were dissolved in both buffers at a target concentration of 10 mg/mL and incubated for 1 hour at room temperature. After centrifugation at 2500 rcf for 15 minutes, 10 μL of supernatant was diluted with 190 μL of the incubation buffer and analyzed by LC-UV (Acquity UPLC-DAD, Waters). Solubility was calculated by comparing the peak area of the test compound in the buffer sample with the peak area of the same compound dissolved at 0.5 mg/mL in water:acetonitrile 1:1, 0.1% formic acid.

From the centrifuged supernatant, two additional 80 μL aliquots were collected and diluted with 160 μL of incubation buffer. One aliquot was stored at 5° C., while the other was stored at 40° C. After 14 or 28 days, the samples were analyzed by LC-UV. Chemical stability was calculated as % loss using the following equations:

$$\text{Chemical stability (as \% loss)} = [(\text{purity after 14 or 28 days at } 5^\circ\text{ C.}) - (\text{purity after 28 days at } 40^\circ\text{ C.})] \times 100/(\text{purity after 28 days at } 5^\circ\text{ C.})$$

$$\text{\% purity} = [(\text{peak area compound}) \times 100/(\text{total peak area})]$$

Representative buffer stability data are provided in Table 10 below. Solubility was generally good at both pH (data not shown), as most of the peptides showed values close to the target concentration (10 mg/mL). The peptides showed a good chemical stability at pH 4.5 but a relevant degradation at pH 7.4, probably related to isomerization of Asn31 (observed and confirmed at by high-resolution mass spectrometry). To block or reduce this degradation pathway, bulky amino acids were introduced in substitution of Lys32. In particular, the use of Aib, Abu, and 4-Pip provided a good chemical stabilization with no loss of purity observed after 2 weeks.

TABLE 10

| SEQ ID No. | Buffer stability pH 7.4/4.5 % purity loss |
|---|---|
| 149 (CompY) | 17/— |
| 92 | 16.8/0 |
| 93 | 19/0 |
| 33 | 18.8/0 |
| 34 | 4.5/0 |
| 96 | nd/0 |
| 19 | 0/0 |
| 43 | 0/nd |
| 40 | 0/nd |
| 64 | nd/0 |
| 118 | 0/0 |
| 80 | 0/nd |
| 110 | 0/nd |
| 125 | 0/nd |
| 100 | 13.2/0 |
| 104 | 0/0 |
| 113 | 14.7/0 |
| 54 | nd/0 |
| 55 | 73.5/28.9 |
| 51 | 0/0 |
| 47 | 9.0/0 |
| 57 | 0/0 |
| 98 | 0.0/0.0 |
| 137 | Not Tested/Not Tested |
| 141 | Not Tested/Not Tested |
| 199 | 0/Not Tested |
| 135 | Not Tested/Not Tested |
| 136 | 24.3/0.0 |
| 144 | 0.0/Not Tested |
| 145 | 0.0/Not Tested |
| 82 | 0.0/Not Tested |
| 187 | 0.0/0.0 |
| 188 | 0.0/0.0 |
| 206 | 0.0/0.0 |
| 219 | −2.1/Not Tested |
| 214 | 0.0/0.0 |
| 161 | 0.6/Not Tested |
| 189 | 0.0/Not Tested |
| 190 | 0.0/Not Tested |
| 165 | 0.0/Not Tested |
| 215 | 0.0/Not Tested |
| 203 | 0.0/0.0 |
| 193 | 0.0/Not Tested |
| 210 | 0.0/0.0 |
| 234 | −0.1/0.0 |
| 235 | 0.0/−1.6 |
| 212 | 0.3/Not Tested |
| 217 | 1.8/Not Tested |
| 222 | 0.0/Not Tested |
| 223 | −0.1/Not Tested |
| 218 | 0.0/Not Tested |
| 239 | 0.0/2.6 |
| 213 | −0.1/Not Tested |
| 236 | 3.8/Not Tested |
| 241 | 2.0/Not Tested |
| 237 | 0.0/Not Tested |
| 242 | 0.0/Not Tested |
| 233 | 0.0/Not Tested |
| 231 | 0.0/Not Tested |

Pharmacokinetics

The pharmacokinetics of UCN-2 derivatives was studied in male Sprague Dawley rats after subcutaneous administration (SC) at 0.05, 0.1, 0.3 or 1 mg/kg. Peptides were formulated as a solution in 10 mM phosphate pH 7.4 buffer+glycerol 85% (2.3% v/v)). Plasma samples obtained from dosed animals were prepared for analysis by means of a single step protein precipitation technique by adding 200 μL of methanol, 0.1% trifluoroacetic acid to 50 μL aliquots of individual subject samples. Samples were mixed by vortex for homogeneity and then subjected to centrifugation at 16000 rpm for 15 min. The supernatant (200 μL) was analyzed by LC-MSMS. Pharmacokinetic parameters were calculated using established non-compartmental methods.

The area under the plasma concentration curve versus time (AUC) was determined using Watson LIMS (version 7.6), with linear trapezoidal interpolation in the ascending slope and logarithmic trapezoidal interpolation in the descending slope. The portion of the AUC from the last measurable concentration to infinity was estimated from the equation, Ct/kel, where Ct represents the last measurable concentration and kel is the elimination rate constant. The latter was determined from the concentration curve versus time by linear regression at the terminal phase of the semi-logarithmic plot.

In line with what has been observed for the chemical stability date, improved PK properties were obtained by stabilization of the N-terminus via acetylation or N-methylation of Ile-1 or in case lie-1 is removed via acetylation from Val-2 resulting in extended half-life in rat up to 8.6 h (Data not shown).

Further improvements in terms of catabolic stability were obtained introducing substitution of lysine-32 with bulky residues (e.i. Aib, Abu or 4-Pip). Data of some representative peptides are provided in Table 11. Compared to Comp Y at much lower dosage half-life significantly increased.

In addition, and consistently with the higher albumin binding generally observed in peptides with a longer fatty acid chain, C20-OH analogues exhibited a prolonged SC half-life compared to C16-OH analogues and C18-OH analogues.

TABLE 11

Rat PK results of representative peptides in comparison to Comp Y.

| SEQ ID N | Dose (mg/kg) | Route | $T_{1/2}$ (h) | Cmax (ng/mL) | Tmax (h) | AUClast (ng*h/mL) |
|---|---|---|---|---|---|---|
| 149 (Comp Y) | 0.1 | IV | 4.3 | — | — | 2760 |
| | 1.0 | SC | 4 | 1045 | 2 | 14500 |
| 82 | 0.05 | SC | 1.4 | 64 | 0.75 | 221 |
| 199 | 0.05 | SC | 10.2 | 111 | 6 | 1625 |
| 187 | 0.05 | SC | 9.7 | 137 | 7 | 2100 |
| 188 | 0.05 | SC | 10.6 | 138 | 6 | 2270 |
| 189 | 0.05 | IV | 7.5 | — | — | 5035 |
| 190 | 0.05 | SC | 5.7 | 112 | 5 | 1930 |
| 203 | 0.05 | IV | 6.2 | — | — | 4865 |
| 110 | 0.05 | IV | 4.8 | — | — | 3880 |
| | 0.1 | SC | 5 | 291 | 5 | 4430 |
| 98 | 0.05 | SC | 5.8 | 159 | 5 | 2710 |
| 144 | 0.05 | SC | 12.6 | 105 | 6 | 1710 |
| 145 | 0.05 | IV | 5.8 | — | — | 4105 |
| | 0.1 | SC | NC | 295 | 8 | 4202 |
| 118 | 0.05 | IV | 5.2 | — | — | 3900 |
| | 0.1 | SC | 5.2 | 225 | 8 | 3540 |
| 193 | 0.05 | IV | 4.9 | — | — | 2340 |
| 206 | 0.05 | IV | 8 | — | — | 8105 |
| | 0.1 | SC | 8 | 197 | 8 | 5770 |
| 210 | 0.05 | IV | 8.4 | — | — | 7785 |
| 212 | 0.025 | IV | 8 | — | — | 4840 |
| | 0.05 | SC | 8 | 154 | 14 | 4685 |
| 241 | 0.05 | IV | 15 | — | — | 6210 |
| 236 | 0.05 | IV | 15 | — | — | 8250 |
| 215 | 0.05 | IV | 8 | — | — | 7320 |
| | 0.1 | SC | 10 | 325 | 7 | 9410 |
| 234 | 0.025 | IV | 7 | — | — | 2705 |
| | 0.05 | SC | 7.5 | 95 | 6 | 2730 |
| 217 | 0.025 | IV | 8 | — | — | 4120 |
| | 0.05 | SC | 12 | 138 | 8 | 4035 |
| 218 | 0.05 | IV | 11 | — | — | 6735 |
| | 0.1 | SC | NC | 115 | 24 | 4125 |
| 242 | 0.05 | IV | 14 | — | — | 7970 |
| 233 | 0.05 | IV | 9 | — | — | 4880 |
| 237 | 0.05 | IV | 11 | — | — | 4160 |
| 219 | 0.05 | IV | 6 | — | — | 5325 |
| | 0.1 | SC | 15 | 156 | 8 | 4520 |

TABLE 11-continued

Rat PK results of representative peptides in comparison to Comp Y.

| SEQ ID N | Dose (mg/kg) | Route | $T_{1/2}$ (h) | Cmax (ng/mL) | Tmax (h) | AUClast (ng*h/mL) |
|---|---|---|---|---|---|---|
| 222 | 0.025 | IV | 7 | — | — | 3315 |
| | 0.05 | SC | 12 | 113 | 8 | 2890 |
| 235 | 0.025 | IV | 8 | — | — | 4510 |
| 223 | 0.025 | IV | 2.8 | — | — | 1925 |
| | 0.05 | SC | 6.5 | 67 | 2 | 698 |

Example 15: Assessment of Degranulation Potential of the Peptides According to the Invention in Human LAD2 Cells Non-allergic (anaphylactoid) reactions are acute adverse drug reactions that can exacerbate a patient's condition and produce effects that may become life-threatening. The main mechanism involves the direct stimulation of mast cells or basophils leading to the release of anaphylactic mediators such as histamine and R-hexosaminidase. A recent study by McNeil et al. (McNeil B D et al., Nature, 12, 519 (2015)) reported that MrgprX2, a specific membrane receptor on human mast cells, plays a major role in non-allergic reactions induced by small molecule drugs, including neuromuscular blocking agents and insect venom, neuropeptides and peptide therapeutics.

LAD2 (Laboratory of Allergic Diseases 2) cell is a human mast cell line commonly employed to study anaphylactic and anaphylactoid reactions, because its biological properties are identical to those of primary human mast cells, including the functional expression of the MrgprX2 receptor.

LAD2 cells are derived from CD34+ cells isolated from patient with aggressive mastocytosis, without any detectable KIT mutation (Kirshenbaum et al., Leukemia Res. 27, 677 (2003)). LAD2 cells stably express IgE receptor type 1 (FceR1), display a granular phenotype and have been reported to be more sensitive than primary human mast cells to degranulating peptides (Kulka et al., Immunology 123, 398 (2008)).

As such, the LAD2 cell line is considered as reasonably resembling normal human mast cells. LAD2 cell degranulation is quantified through the release of anaphylactic mediators such as β-hexosaminidase by fluorometric quantification.

Human LAD2 cells were obtained after Licensing Agreement with NIH and cultured following the NIH's instructions.

LAD2 cells (20000 cells/well, 96-well plates and 10,000 cells/well in 384-well plates) were incubated with compounds for 30 min. The R-hexosaminidase released into the supernatants and in cell lysates was quantified using the fluorogenic substrate 4-methylumbelliferyl-N-acetyl-b-D-glucosaminide.

On the day of the assay, the lyophilized peptides were dissolved in DMSO and/or PBS 1× pH 7.4, to obtain stock solutions. The stock solutions were used to prepare working serial dilutions to have final concentrations in assay ranging from 50, 100 or 300 to 0.1 or 0.001 μM. Each peptide was tested in biological duplicates. When compounds were dissolved in DMSO, the final solvent concentration in assay was 0.5% (v/v).

The percentage of degranulation, expressed as % of R-hexosaminidase release, was calculated by dividing the fluorescence signal of the supernatant by the sum of the signals from the supernatant and cell pellet (lysed with Triton X-100, final 1%) and multiplying by 100.

Dose-response curves were generated by plotting the % of R-hexosaminidase release versus total release of cells treated with triton (y-axis) against the concentrations of peptides tested (x-axis). The Mast Cell Degranulation (MCD) EC50 values and standard errors were calculated using XLfit 5.5.0.5 based on the following equation:

4 Parameter Sigmoidal Model: $f=(A+((B-A)/(1+((C/x)^D))))$ where A=Emin, B=Emax, C=EC50 and D=slope Potency (EC50) and % β-Hexosaminidase release at highest concentration of all peptides tested in LAD2 cells is summarized in Table 12 below.

Substance P and Icatibant were included as positive and GLP-1 as negative controls, respectively. Also the prior art peptides Comp 10 (SEQ ID No 56), Comp Y (SEQ ID No 149) and Comp X (SEQ ID No 151) were included in this study.

TABLE 12

MCD data of representative peptides in comparison to Comp Y and Comp X.

| Cmpd | EC50 (µM) |
|---|---|
| Substance P | 0.36 |
| Icatibant | 16.44 |
| SEQ ID NO. | |
| 56 (comp) | 38.5 |
| 149 (comp) | 50.4 |
| 151 (comp) | 32.9 |
| 118 | >100 |
| 125 | >100 |
| 145 | >100 |
| 219 | 88.2 |
| 161 | >50 |
| 162 | >50 |
| 163 | >100 |
| 165 | >100 |
| 166 | >100 |
| 167 | >50 |
| 215 | >100 |
| 234 | 49.2 |
| 212 | >300 |
| 217 | >300 |
| 223 | >300 |
| 238 | 36.7 |
| 243 | >300 |
| 218 | >300 |
| 213 | >300 |
| 236 | 74.1 |
| 241 | >300 |
| 237 | >300 |
| 242 | >300 |
| 233 | >300 |
| 231 | 47.5 |
| 168 | >300 |

Example 16: Assessment of Effect on Blood Pressure

The effect of the compounds on systolic blood pressure was determined in telemetry studies in Sprague Dawley rats at a dosage of 0.1 mg/kg SC.

The rats were previously implanted with a telemetry device (DSI, Saint-Paul, USA, HD-S10, HD-S11 or HD S21) and allowed to recover for a minimum period of 2 weeks before treatment with vehicle or the different peptides. Blood pressure (BP) was recorded through a catheter inserted into the abdominal aorta. The device body was placed in the abdomen. The animals were allowed to recover from surgery for at least 10 days before the first administration of test drug or vehicle.

The chronically instrumented rats of the telemetry studies were individually housed immediately after surgery and then housed in pairs with a non-instrumented companion after recovery.

Systolic blood pressure was recorded for one hour before treatment (basal period). Thereafter, the subcutaneous administration of the test compound or its vehicle was performed, under continuous recording of the signal up to 48 hours, analysed and expressed as % change from baseline.

Representative data are presented in Table 13 below, in which "Duration of action" indicates the last time point for which an effect on BP was still observed (n=2 animals/peptide)

TABLE 13

| | Systolic blood pressure (Mean) | | | |
|---|---|---|---|---|
| | % change from baseline | | | Duration of |
| SEQ ID No | 8 h | 12 h | 24 h | action (h) |
| 110 | −19 | −10 | −6 | 20 |
| 100 | −22 | −12 | −9 | >24 |
| 118 | −24 | −17 | −4 | >24 |
| 113 | −31 | −24 | −7 | >24 |
| 203 | −18 | −11 | 2 | 23 |
| 125 | −25 | −16 | 1 | 22 |
| 189 | −27 | −25 | −13 | >24 |
| 145 | −23 | −21 | −14 | >24 |
| 144 | −22 | −17 | 1 | 23 |
| 193 | −20 | −12 | −8 | >24 |
| 194 | −13 | −3 | 18 | 19 |
| 233 | 1 | −8 | −11 | >24 |
| 218 | −13 | −17 | −16 | >24 |
| 213 | −10 | −18 | −13 | >24 |
| 231 | −3 | −3 | −12 | >24 |
| 206 | −12 | −16 | −13 | >24 |
| 219 | −10 | −13 | −10 | >24 |
| 215 | −12 | −14 | −16 | >24 |
| 209 | −18 | −11 | 3 | 23 |
| 220 | −17 | −14 | −11 | >24 |
| 229 | −12 | −9 | −5 | >24 |
| 210 | −13 | −13 | −6 | >24 |
| 230 | −15 | −16 | 3 | 23 |
| 235 | −8 | −7 | −12 | >24 |
| 10 | −24 | −11 | 2 | 18 |
| 33 | −22 | −11 | 16 | 17 |
| 19 | −21 | 0 | 10 | 11 |
| 43 | −18 | −1 | 13 | 12 |
| 40 | −30 | −18 | 7 | 23 |
| 64 | −25 | −13 | 3 | 23 |
| 55 | −31 | −23 | 0 | 23 |
| ~~56~~ | ~~−32~~ | ~~−23~~ | ~~−4~~ | ~~>24~~ |
| 51 | −27 | −19 | −1 | 24 |
| 52 | −28 | −17 | 4 | 23 |
| 47 | −14 | −6 | 2 | 23 |
| 57 | −34 | −25 | −2 | >24 |
| 82 | −33 | −4 | 11 | 14 |
| 165 | −30 | −20 | 2 | 23 |
| 158 | −11 | −7 | 3 | 23 |

All sequences disclosed herein are listed in Table 2 and the appended sequence listing with the albumin binding moieties shown in Table 2, the entire content of which forms a part of this specification.

All publications, patent applications, patents, and other references mentioned herein are incorporated by reference in their entirety. In addition, the materials, methods, and examples given are illustrative only and not intended to be limiting. Unless otherwise defined, all technical and scientific terms used herein have the same meaning as commonly understood by one of ordinary skill in the art to which this invention belongs. It is to be understood that while the disclosure has been described in conjunction with the detailed description thereof, the foregoing description is intended to illustrate and not limit the scope of the invention, which is defined by the scope of the appended claims. other aspects, advantages, and modifications are within the scope of the claims.

The invention claimed is:

1. A compound comprising a peptide or a pharmaceutically acceptable salt thereof, comprising the amino acid sequence of formula (I):

```
(I)
X1-X2-X3-X4-X5-X6-X7-X8-X9-X10-X11-X12-X13-X14-
X15-X16-X17-X18-X19-X20-X21-X22-X23-X24-X25-X26-
X27-X28-X29-X30-X31-X32-X33-X34-X35-X36-X37-X38
```

wherein

X1 is absent or isoleucine (I) with Isoleucine in L or D configuration;

X2 is valine (V) with valine in L or D configuration;

X3 is leucine (L);

X4 is serine(S);

X5 is leucine (L);

X6 is aspartate (D);

X7 is valine (V) or D-valine (v);

X8 is proline (P);

X9 is isoleucine (I);

X10 is lysine (K), alanine (A) or glycine (G);

X11 is leucine (L), isoleucine (I), alpha-methyl-leucine (αMeL) or 2-aminoisobutyric acid (Aib);

X12 is lysine (K), wherein the epsilon-amino group of the lysine side chain is covalently bound to an albumin-binding moiety;

X13 is lysine (K), glutamine (Q) or alanine (A);

X14 is isoleucine (I) or 2-aminoisobutyric acid (Aib);

X15 is leucine (L), alpha-methyl-leucine (αMeL) or 2-aminoisobutyric acid (Aib);

X16 is leucine (L);

X17 is glutamate (E) or lysine (K);

X18 is glutamine (Q);

X19 is glutamate (E);

X20 is lysine (K), arginine (R) or alanine (A);

X21 is glutamine (Q);

X22 is lysine (K) or alanine (A);

X23 is alanine (A) or glutamate (E);

X24 is glutamine (Q);

X25 is arginine (R), alanine (A), alpha-methyl-leucine (αMeL) or 2-aminoisobutyric acid (Aib);

X26 is glutamate (E) or 2-aminoisobutyric acid (Aib);

X27 is glutamine (Q);

X28 is alanine (A);

X29 is glutamate (E);

X30 is lysine (K) or threonine (T);

X31 asparagine (N), glutamine (Q) or alanine (A);

X32 is lysine (K), valine (V), threonine (T), 2-aminoisobutyric acid (Aib), glutamate (E), alanine (A), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); or 1-aminocyclopropanecarboxylic acid (Cpx);

X33 is glutamine (Q);

X34 is isoleucine (I);

X35 is leucine (L);

X36 is alanine (A) or glutamate (E);

X37 is glutamine (Q);

X38 is valine (V);

and wherein:

when X1 is isoleucine, then X7 is D-valine, and X32 is selected from valine (V), threonine (T), 2-aminoisobutyric acid (Aib), alanine (A), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); or 1-aminocyclopropanecarboxylic acid (Cpx).

2. The compound of claim 1, wherein:

X1 is absent or an N-terminally acetylated or N-methylated isoleucine (I);

X2 is valine (V), wherein when X1 is absent said valine is N-terminally acylated or alkylated;

X7 is D-valine (v);

X9 is isoleucine (I);

X10 is lysine (K);

X11 is leucine (L) or alpha-methyl-leucine (αMeL);

X14 is isoleucine (I);

X15 is leucine (L);

X20 is lysine (K);

X23 is alanine (A) or glutamate (E);

X25 is arginine (R);

X26 is glutamate (E);

X31 is asparagine (N);

X32 is glutamate (E), valine (V), threonine (T), 2-aminoisobutyric acid (Aib), alanine (A), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); or 1-aminocyclopropanecarboxylic acid (Cpx); and wherein when X1 is an N-terminally acetylated or N-methylated isoleucine (I), X7 is D-valine, and X32 is selected from valine (V), threonine (T), 2-aminoisobutyric acid (Aib), alanine (A), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); or 1-aminocyclopentane-1-carboxylic acid (Cpex).

3. The compound of claim 1, wherein at least one of X10, X11, X13, X15, X20, X22, X23, X25, X31 and X32 is selected as:

X10 being alanine (A) or glycine (G);

X11 being isoleucine (I), alpha-methyl-leucine (αMeL) or 2-aminoisobutyric acid (Aib);

X13 being glutamine (Q) or alanine (A);

X15 being alpha-methyl-leucine (αMeL) or 2-aminoisobutyric acid (Aib);

X20 being arginine (R) or alanine (A);

X22 being alanine (A);

X23 being alanine (A) or glutamate (E);

X25 being alanine (A); alpha-methyl-leucine (αMeL) or 2-aminoisobutyric acid (Aib););

X31 being glutamine (Q) or alanine (A);

X32 being glutamate (E), 2-aminoisobutyric acid (Aib), alanine (A), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx);

1-aminocyclopentane-1-carboxylic acid (Cpex); or 1-aminocyclopropanecarboxylic acid (Cpx).

4. The compound of claim 1, wherein:

X1 is absent or an N-terminally acetylated or N-methylated isoleucine (I);

X2 is valine (V), wherein when X1 is absent, said valine is N-terminally acylated or alkylated;

X7 is D-valine (v);

X9 is isoleucine (I);

X10 is lysine (K);

X11 is leucine (L) or alpha-methyl-leucine (αMeL);

X14 is isoleucine (I);

X15 is leucine (L);

X20 is lysine (K);

X23 is glutamate (E);

X25 is arginine (R);

X26 is glutamate (E);

X31 is asparagine (N);

X32 is glutamate (E), 2-aminoisobutyric acid (Aib), or 4-Amino-piperidine-4-carboxylic acid (4-Pip); and wherein when X1 is an N-terminally acetylated or N-methylated isoleucine (I), then X7 is D-valine, and X32 is selected from 2-aminoisobutyric acid (Aib), 2-aminobutyric acid (Abu); 4-amino-tetrahydro-2H-pyran-4-yl-acetic acid (ThP) or 4-Amino-piperidine-4-carboxylic acid (4-Pip).

5. The compound of claim 1, wherein:

X1 is absent;

X2 is valine (V) N-terminally acetylated or alkylated with a group selected from an N-methyl, a propanoyl group, a butanoyl group, a pentanoyl group or an isopropanoyl group and X32 is selected from glutamate (E), valine (V), threonine (T), 2-aminoisobutyric acid (Aib), alanine (A), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-amino-cyclopentane-1-carboxylic acid (Cpex); or 1-aminocyclopropanecarboxylic acid (Cpx).

6. The compound of claim 1, wherein the compound is a peptide of the amino acid sequence of formula (I), wherein when X1 is absent, X2 is valine with valine in L or D configuration, with said valine being N-terminally acylated with a C1-20 alkanoyl.

7. The compound of claim 1, wherein the compound is a peptide of the amino acid sequence of formula (I), wherein when X1 is absent, X2 is valine with valine in L or D configuration, with said valine being N-terminally acylated or alkylated; and X32 is selected from valine (V), threonine (T), 2-aminoisobutyric acid (Aib), alanine (A), 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); or 1-aminocyclopropanecarboxylic acid (Cpx).

8. The compound of claim 1, wherein the albumin-binding moiety is a group of the formula (II):

$$-Y-Z-C(O)R^1 \quad \text{(II)}$$

wherein

Y is AEEA, {AEEA}$_2$, {AEEA}$_3$, Gly, {Gly}$_2$, {Gly}$_3$, N-MeGly, {N-MeGly}$_2$, {N-MeGly}$_3$ or absent, wherein AEEA denotes [2-(2-aminoethoxy) ethoxy]-acetyl;

Z is gGlu, {gGlu}$_2$ or absent; and $R^1$ is $—(CH_2)_xCOOH$ or $—(CH_2)_xCH_3$, wherein x is an integer from 10 to 22.

9. The compound of claim 8, wherein the albumin-binding moiety is selected from the following groups:

-{AEEA}-gGlu-C(O)$(CH_2)_{10}$COOH;

-{AEEA}-gGlu-C(O)$(CH_2)_{12}$COOH;

-{AEEA}-gGlu-C(O)$(CH_2)_{14}$COOH;

-{AEEA}-gGlu-C(O)$(CH_2)_{16}$COOH;

-{AEEA}-gGlu-C(O)$(CH_2)_{18}$COOH;

-{AEEA}$_2$-gGlu-C(O)$(CH_2)_{10}$COOH;

-{AEEA}$_2$-gGlu-C(O)$(CH_2)_{12}$COOH;

-{AEEA}$_2$-gGlu-C(O)$(CH_2)_{14}$COOH;

-{AEEA}$_2$-gGlu-C(O)$(CH_2)_{16}$COOH;

-{AEEA}$_2$-gGlu-C(O)$(CH_2)_{18}$COOH;

-{AEEA}$_2$-{gGlu}$_2$-C(O)$(CH_2)_{10}$COOH;

-{AEEA}$_2$-{gGlu}$_2$-C(O)$(CH_2)_{12}$COOH;

-{AEEA}$_2$-{gGlu}$_2$-C(O)$(CH_2)_{14}$COOH;

-{AEEA}$_2$-{gGlu}$_2$-C(O)$(CH_2)_{16}$COOH;

-{AEEA}$_2$-{gGlu}$_2$-C(O)$(CH_2)_{18}$COOH;

-gGlu-C(O)$(CH_2)_{10}$COOH; -gGlu-C(O)$(CH_2)_{12}$COOH;

-gGlu-C(O)$(CH_2)_{14}$COOH; -gGlu-C(O)$(CH_2)_{16}$COOH;

-gGlu-C(O)$(CH_2)_{18}$COOH; -{gGlu}$_2$-C(O)$(CH_2)_{10}$COOH;

-{gGlu}$_2$-C(O)$(CH_2)_{12}$COOH; -{gGlu}$_2$-C(O)$(CH_2)_{14}$COOH;

-{gGlu}$_2$-C(O)$(CH_2)_{16}$COOH; and

-{gGlu}$_2$-C(O)$(CH_2)_{18}$COOH.

10. The compound of claim 8, wherein the albumin-binding moiety is -gGlu-C(O)$(CH_2)_{12}$COOH; -gGlu-C(O)$(CH_2)_{14}$COOH; -gGlu-C(O)$(CH_2)_{16}$COOH; -gGlu-C(O)$(CH_2)_{18}$COOH; -{AEEA}$_2$-gGlu-C(O)$(CH_2)_{12}$COOH, -{AEEA}$_2$-gGlu-C(O)$(CH_2)$ 16COOH; -{AEEA}$_2$-gGlu-C(O)$(CH_2)_{18}$COOH and -{AEEA}$_2$-{gGlu}$_2$-C(O)$(CH_2)_{16}$COOH.

11. The compound of claim 1, wherein the compound is a peptide of any one of SEQ ID NOs 62, 74, 76, 88, 90, 131, 144, 152, 154, 161, 168, 169, 176, 187, 189, 212, 213, 217, 218, 222, 231, 232, 233, 236, 237, 240, 241, 242, or 244, or a pharmaceutically acceptable salt thereof.

12. A pharmaceutical composition comprising a compound of claim 1 and a pharmaceutically acceptable excipient, diluent or carrier.

13. The compound of claim 1, wherein said X1 isoleucine is N-terminally acetylated or N-methylated.

14. A compound comprising a peptide or a pharmaceutically acceptable salt thereof comprising the amino acid sequence of formula (I):

(I)

X1-X2-X3-X4-X5-X6-X7-X8-X9-X10-X11-X12-X13-X14-X15-X16-X17-X18-X19-X20-X21-X22-X23-X24-X25-X26-X27-X28-X29-X30-X31-X32-X33-X34-X35-X36-X37-X38 wherein
- X1 is isoleucine (I) with isoleucine in L or D configuration;
- X2 is valine (V) with valine in L or D configuration;
- X3 is leucine (L);
- X4 is serine(S);
- X5 is leucine (L);
- X6 is aspartate (D);
- X7 is D-valine (v);
- X8 is proline (P);
- X9 is isoleucine (I);
- X10 is lysine (K) or glycine (G);
- X11 is leucine (L);
- X12 is lysine (K), wherein the epsilon-amino group of the lysine side chain is covalently bound to an albumin-binding moiety;
- X13 is lysine (K);
- X14 is isoleucine (I);
- X15 is leucine (L);
- X16 is leucine (L);
- X17 is glutamate (E);
- X18 is glutamine (Q);
- X19 is glutamate (E);
- X20 is lysine (K);
- X21 is glutamine (Q);
- X22 is lysine (K);
- X23 is lysine (K), alanine (A), or 2-aminoisobutyric acid (Aib);
- X24 is glutamine (Q);
- X25 is arginine (R);
- X26 is glutamate (E);
- X27 is glutamine (Q);
- X28 is alanine (A);
- X29 is glutamate (E);
- X30 is threonine (T);
- X31 is asparagine (N);
- X32 is 2-aminobutyric acid (Abu); norvaline (Nva); α-methyl-lysine (αMeK); 2,3-diaminopropionic acid (Dap); 4-Amino-piperidine-4-carboxylic acid (4-Pip); 4-amino-tetrahydro-2H-pyran-4-yl-acetic acid (ThP); 1-aminocyclohexanecarboxylic acid (Chx); 1-aminocyclopentane-1-carboxylic acid (Cpex); or 1-aminocyclopropanecarboxylic acid (Cpx);
- X33 is glutamine (Q);
- X34 is isoleucine (I);
- X35 is leucine (L);
- X36 is alanine (A);
- X37 is glutamine (Q); and
- X38 is valine (V).

15. The compound of claim 14, wherein said X1 isoleucine is N-terminally acetylated or N-methylated.

16. The compound of claim 14, wherein the compound is a peptide of any one of SEQ ID NOs 51, 52, 54, 55, 57, 58, 59, 60, 61, 62, 63, 69, 70, 72, 73, 76, 77, 83, 84, 90, 91, 104, 105, 106, 107, 109, 114, 115, 117, 127, 128, 129, 131, 132, 133, 134, 135, 136, 139, 140, 141, 143, 152, 153, 154, 155, 169, 170, 172, 173, 175, 183, 184, 187, 188, 196, 198, 199, 207, 208, 210, or 227, or a pharmaceutically acceptable salt thereof.

17. A compound comprising a peptide or a pharmaceutically acceptable salt thereof comprising the amino acid sequence of formula (I):

(I)

X1-X2-X3-X4-X5-X6-X7-X8-X9-X10-X11-X12-X13-X14-X15-X16-X17-X18-X19-X20-X21-X22-X23-X24-X25-X26-X27-X28-X29-X30-X31-X32-X33-X34-X35-X36-X37-X38 wherein
- X1 is absent;
- X2 is valine (V); with valine in L or D configuration;
- X3 is leucine (L);
- X4 is serine(S);
- X5 is leucine (L);
- X6 is aspartate (D);
- X7 is valine (V) or D-valine (v);
- X8 is proline (P);
- X9 is isoleucine (I);
- X10 is lysine (K) or glycine (G);
- X11 is leucine (L) or alpha-methyl-leucine (αMeL);
- X12 is lysine (K), wherein the epsilon-amino group of the lysine side chain is covalently bound to an albumin-binding moiety;
- X13 is lysine (K) or glutamine (Q);
- X14 is isoleucine (I) or 2-aminoisobutyric acid (Aib);
- X15 is leucine (L);
- X16 is leucine (L);
- X17 is glutamate (E) or lysine (K);
- X18 is glutamine (Q);
- X19 is glutamate (E);
- X20 is lysine (K), arginine (R) or alanine (A);
- X21 is glutamine (Q);
- X22 is lysine (K);
- X23 is lysine (K), alanine (A), or 2-aminoisobutyric acid (Aib);
- X24 is glutamine (Q);
- X25 is arginine (R);
- X26 is glutamate (E);
- X27 is glutamine (Q);
- X28 is alanine (A);
- X29 is glutamate (E);
- X30 is lysine (K) or threonine (T);
- X31 is asparagine (N);
- X32 is lysine (K), valine (V), 2-aminoisobutyric acid (Aib), alanine (A), or 4-Amino-piperidine-4-carboxylic acid (4-Pip);
- X33 is glutamine (Q);
- X34 is isoleucine (I);
- X35 is leucine (L);
- X36 is alanine (A) or glutamate (E);
- X37 is glutamine (Q); and
- X38 is valine (V).

18. The compound of claim 17, wherein the X2 valine is N-terminally acylated with an alkanoyl group selected from ethanoyl, methanoyl, propanoyl, butanoyl, pentanoyl, hexanoyl or heptanoyl.

19. The compound of claim 17, wherein the compound is a peptide of any one of SEQ ID NOs 3, 4, 6, 7, 8, 9, 22, 29, 33, 34, 35, 36, 37, 45, 46, 78, 79, 80, 81, 86, 92, 93, 94, 95, 96, 120, 121, 122, 123, 124, 156, 157, 158, 159, 160, 193, 194, 195, 201, 202, 219, 220, 221, 222, 223, 224, 225, 228, or 235, or a pharmaceutically acceptable salt thereof.

* * * * *

SEQUENCE LISTING

```
Sequence total quantity: 244
SEQ ID NO: 1           moltype = AA  length = 38
FEATURE                Location/Qualifiers
source                 1..38
                       mol_type = protein
                       organism = synthetic construct
VARIANT                1
                       note = absent or I
VARIANT                2
                       note = Valine or D-valine
VARIANT                7
                       note = Valine or D-valine
VARIANT                11
                       note = L or I or alpha-methyl-leucine or Aib
MOD_RES                12
                       note = the epsilon-amino group of the lysine side chain is
                        covalentlybound to an albumin -binding moiety
VARIANT                13
                       note = K or Q
VARIANT                14
                       note = I or Aib
VARIANT                15
                       note = L or alpha-methyl-leucine or Aib
VARIANT                17
                       note = E or K
VARIANT                20
                       note = K or R
VARIANT                23
                       note = K or A or Aib
VARIANT                25
                       note = R or alpha-methyl-leucine or Aib
VARIANT                26
                       note = E or Aib
VARIANT                30
                       note = K or T
VARIANT                31
                       note = N or Q or A
VARIANT                32
                       note = K or V or T or Aib or E or A or Abu or Nva
                        oralpha-methyl-leucine or Dap or 4-Pip or Thp or Chx or
                        Cpex or Cpx
VARIANT                36
                       note = A or E
SEQUENCE: 1
XXLSLDXPIK XKXXXLXQEX QKXQXXQAEX XXQILXQV                          38

SEQ ID NO: 2           moltype = AA  length = 38
FEATURE                Location/Qualifiers
source                 1..38
                       mol_type = protein
                       organism = synthetic construct
MOD_RES                1
                       note = ACETYLATION
SITE                   7
                       note = D-valine
MOD_RES                12
                       note = the epsilon-amino group of the lysine side chain is
                        covalentlybound to an albumin -binding moiety
MOD_RES                38
                       note = AMIDATION
SEQUENCE: 2
IVLSLDXPIK LKQILLKQER QKKQREQAEK NKQILEQV                          38

SEQ ID NO: 3           moltype = AA  length = 37
FEATURE                Location/Qualifiers
source                 1..37
```

-continued

```
                       mol_type = protein
                       organism = synthetic construct
MOD_RES                1
                       note = ACETYLATION
SITE                   6
                       note = D-valine
MOD_RES                11
                       note = the epsilon-amino group of the lysine side chain is
                        covalentlybound to an albumin -binding moiety
MOD_RES                37
                       note = AMIDATION
SEQUENCE: 3
VLSLDXPIKL KQILLKQERQ KKQREQAEKN KQILEQV                          37

SEQ ID NO: 4           moltype = AA  length = 37
FEATURE                Location/Qualifiers
source                 1..37
                       mol_type = protein
                       organism = synthetic construct
SITE                   6
                       note = D-valine
MOD_RES                11
                       note = the epsilon-amino group of the lysine side chain is
                        covalentlybound to an albumin -binding moiety
MOD_RES                37
                       note = AMIDATION
SEQUENCE: 4
VLSLDXPIKL KQILLKQERQ KKQREQAEKN KQILEQV                          37

SEQ ID NO: 5           moltype = AA  length = 38
FEATURE                Location/Qualifiers
source                 1..38
                       mol_type = protein
                       organism = synthetic construct
MOD_RES                1
                       note = met
SITE                   7
                       note = D-valine
MOD_RES                12
                       note = the epsilon-amino group of the lysine side chain is
                        covalentlybound to an albumin -binding moiety
MOD_RES                38
                       note = AMIDATION
SEQUENCE: 5
IVLSLDXPIK LKQILLKQER QKKQREQAEK NKQILEQV                         38

SEQ ID NO: 6           moltype = AA  length = 37
FEATURE                Location/Qualifiers
source                 1..37
                       mol_type = protein
                       organism = synthetic construct
MOD_RES                1
                       note = Acetylated with a propanoyl group
SITE                   6
                       note = D-valine
MOD_RES                11
                       note = the epsilon-amino group of the lysine side chain is
                        covalentlybound to an albumin -binding moiety
MOD_RES                37
                       note = AMIDATION
SEQUENCE: 6
VLSLDVPIKL KQILLKQERQ KKQREQAEKN KQILEQV                          37

SEQ ID NO: 7           moltype = AA  length = 37
FEATURE                Location/Qualifiers
source                 1..37
                       mol_type = protein
                       organism = synthetic construct
MOD_RES                1
                       note = Acetylated with a butanoyl group
SITE                   6
                       note = D-Valine
MOD_RES                11
                       note = the epsilon-amino group of the lysine side chain is
                        covalentlybound to an albumin -binding moiety
MOD_RES                37
                       note = AMIDATION
SEQUENCE: 7
VLSLDVPIKL KQILLKQERQ KKQREQAEKN KQILEQV                          37
```

-continued

```
SEQ ID NO: 8            moltype = AA  length = 37
FEATURE                 Location/Qualifiers
source                  1..37
                        mol_type = protein
                        organism = synthetic construct
MOD_RES                 1
                        note = Acetylated with a pentanoyl group
SITE                    6
                        note = D-valine
MOD_RES                 11
                        note = the epsilon-amino group of the lysine side chain is
                         covalentlybound to an albumin -binding moiety
MOD_RES                 37
                        note = AMIDATION
SEQUENCE: 8
VLSLDVPIKL KQILLKQERQ KKQREQAEKN KQILEQV                           37

SEQ ID NO: 9            moltype = AA  length = 37
FEATURE                 Location/Qualifiers
source                  1..37
                        mol_type = protein
                        organism = synthetic construct
MOD_RES                 1
                        note = Acetylated with a isopentanoyl group
SITE                    6
                        note = D-valine
MOD_RES                 11
                        note = the epsilon-amino group of the lysine side chain is
                         covalentlybound to an albumin -binding moiety
MOD_RES                 37
                        note = AMIDATION
SEQUENCE: 9
VLSLDVPIKL KQILLKQERQ KKQREQAEKN KQILEQV                           37

SEQ ID NO: 10           moltype = AA  length = 38
FEATURE                 Location/Qualifiers
source                  1..38
                        mol_type = protein
                        organism = synthetic construct
SITE                    7
                        note = D-valine
MOD_RES                 12
                        note = the epsilon-amino group of the lysine side chain is
                         covalentlybound to an albumin -binding moiety
MOD_RES                 32
                        note = X is Aib
MOD_RES                 38
                        note = AMIDATION
SEQUENCE: 10
IVLSLDVPIK LKQILLKQER QKKQREQAEK NXQILEQV                          38

SEQ ID NO: 11           moltype = AA  length = 38
FEATURE                 Location/Qualifiers
source                  1..38
                        mol_type = protein
                        organism = synthetic construct
SITE                    7
                        note = D-valine
MOD_RES                 12
                        note = the epsilon-amino group of the lysine side chain is
                         covalentlybound to an albumin -binding moiety
MOD_RES                 32
                        note = X is Aib
MOD_RES                 38
                        note = AMIDATION
SEQUENCE: 11
IVLSLDVPIK LKKILLEQEK QKKQREQAET NXQILAQV                          38

SEQ ID NO: 12           moltype = AA  length = 38
FEATURE                 Location/Qualifiers
source                  1..38
                        mol_type = protein
                        organism = synthetic construct
SITE                    7
                        note = D-valine
MOD_RES                 12
                        note = the epsilon-amino group of the lysine side chain is
                         covalentlybound to an albumin -binding moiety
```

-continued

```
MOD_RES                32
                       note = X is Aib
MOD_RES                38
                       note = AMIDATION
SEQUENCE: 12
IVLSLDVPIK LKKILLEQEK QKKQREQAET NXQILAQV                          38

SEQ ID NO: 13          moltype = AA  length = 38
FEATURE                Location/Qualifiers
source                 1..38
                       mol_type = protein
                       organism = synthetic construct
SITE                   7
                       note = D-valine
MOD_RES                12
                       note = the epsilon-amino group of the lysine side chain is
                        covalentlybound to an albumin -binding moiety
MOD_RES                38
                       note = AMIDATION
SEQUENCE: 13
IVLSLDVPIK LKQILLKQER QKKQREQAEK NVQILEQV                          38

SEQ ID NO: 14          moltype = AA  length = 38
FEATURE                Location/Qualifiers
source                 1..38
                       mol_type = protein
                       organism = synthetic construct
SITE                   7
                       note = D-valine
MOD_RES                12
                       note = the epsilon-amino group of the lysine side chain is
                        covalentlybound to an albumin -binding moiety
MOD_RES                38
                       note = AMIDATION
SEQUENCE: 14
IVLSLDVPIK LKQILLKQER QKKQREQAEK NTQILEQV                          38

SEQ ID NO: 15          moltype = AA  length = 37
FEATURE                Location/Qualifiers
source                 1..37
                       mol_type = protein
                       organism = synthetic construct
SITE                   6
                       note = D-valine
MOD_RES                11
                       note = the epsilon-amino group of the lysine side chain is
                        covalentlybound to an albumin -binding moiety
MOD_RES                22
                       note = X is Aib
MOD_RES                31
                       note = X is Aib
MOD_RES                37
                       note = AMIDATION
SEQUENCE: 15
VLSLDVPIKL KKILLEQEKQ KXQREQAETN XQILAQV                           37

SEQ ID NO: 16          moltype = AA  length = 38
FEATURE                Location/Qualifiers
source                 1..38
                       mol_type = protein
                       organism = synthetic construct
MOD_RES                1
                       note = ACETYLATION
SITE                   7
                       note = D-valine
MOD_RES                12
                       note = the epsilon-amino group of the lysine side chain is
                        covalentlybound to an albumin -binding moiety
MOD_RES                32
                       note = X is Aib
MOD_RES                38
                       note = AMIDATION
SEQUENCE: 16
IVLSLDVPIK LKQILLKQER QKKQREQAEK NXQILEQV                          38

SEQ ID NO: 17          moltype = AA  length = 38
FEATURE                Location/Qualifiers
source                 1..38
                       mol_type = protein
```

-continued

```
                         organism = synthetic construct
MOD_RES                  1
                         note = ACETYLATION
SITE                     7
                         note = D-valine
MOD_RES                  12
                         note = the epsilon-amino group of the lysine side chain is
                          covalentlybound to an albumin -binding moiety
MOD_RES                  38
                         note = AMIDATION
SEQUENCE: 17
IVLSLDVPIK LKQILLKQER QKKQREQAEK NEQILEQV                          38

SEQ ID NO: 18            moltype = AA  length = 38
FEATURE                  Location/Qualifiers
source                   1..38
                         mol_type = protein
                         organism = synthetic construct
MOD_RES                  1
                         note = ACETYLATION
SITE                     7
                         note = D-valine
MOD_RES                  12
                         note = the epsilon-amino group of the lysine side chain is
                          covalentlybound to an albumin -binding moiety
MOD_RES                  14
                         note = X is Aib
MOD_RES                  38
                         note = AMIDATION
SEQUENCE: 18
IVLSLDVPIK LKQXLLKQER QKKQREQAEK NVQILEQV                          38

SEQ ID NO: 19            moltype = AA  length = 38
FEATURE                  Location/Qualifiers
source                   1..38
                         mol_type = protein
                         organism = synthetic construct
MOD_RES                  1
                         note = ACETYLATION
MOD_RES                  11
                         note = X is alpha-methyl-leucine
MOD_RES                  12
                         note = the epsilon-amino group of the lysine side chain is
                          covalentlybound to an albumin -binding moiety
MOD_RES                  32
                         note = X is Aib
MOD_RES                  38
                         note = AMIDATION
SEQUENCE: 19
IVLSLDVPIK XKQILLKQER QKKQREQAEK NXQILEQV                          38

SEQ ID NO: 20            moltype = AA  length = 38
FEATURE                  Location/Qualifiers
source                   1..38
                         mol_type = protein
                         organism = synthetic construct
MOD_RES                  1
                         note = ACETYLATION
MOD_RES                  11
                         note = X is alpha-methyl-leucine
MOD_RES                  12
                         note = the epsilon-amino group of the lysine side chain is
                          covalentlybound to an albumin -binding moiety
MOD_RES                  14
                         note = X is Aib
MOD_RES                  32
                         note = X is Aib
MOD_RES                  38
                         note = AMIDATION
SEQUENCE: 20
IVLSLDVPIK XKQXLLKQER QKKQREQAEK NXQILEQV                          38

SEQ ID NO: 21            moltype = AA  length = 38
FEATURE                  Location/Qualifiers
source                   1..38
                         mol_type = protein
                         organism = synthetic construct
MOD_RES                  1
                         note = ACETYLATION
```

-continued

```
SITE                    7
                        note = D-valine
MOD_RES                 12
                        note = the epsilon-amino group of the lysine side chain is
                         covalentlybound to an albumin -binding moiety
MOD_RES                 32
                        note = X is Aib
MOD_RES                 38
                        note = AMIDATION
SEQUENCE: 21
IVLSLDVPIK LKKILLKQER QKKQREQAEK NXQILEQV                          38

SEQ ID NO: 22           moltype = AA  length = 37
FEATURE                 Location/Qualifiers
source                  1..37
                        mol_type = protein
                        organism = synthetic construct
MOD_RES                 1
                        note = Acetylated with a pentanoyl group
SITE                    6
                        note = D-valine
MOD_RES                 11
                        note = the epsilon-amino group of the lysine side chain is
                         covalentlybound to an albumin -binding moiety
MOD_RES                 13
                        note = X is Aib
MOD_RES                 37
                        note = AMIDATION
SEQUENCE: 22
VLSLDVPIKL KQXLLKQERQ KKQREQAEKN VQILEQV                           37

SEQ ID NO: 23           moltype = AA  length = 38
FEATURE                 Location/Qualifiers
source                  1..38
                        mol_type = protein
                        organism = synthetic construct
MOD_RES                 1
                        note = METHYLATION
SITE                    7
                        note = D-valine
MOD_RES                 12
                        note = the epsilon-amino group of the lysine side chain is
                         covalentlybound to an albumin -binding moiety
MOD_RES                 32
                        note = X is Aib
MOD_RES                 38
                        note = AMIDATION
SEQUENCE: 23
IVLSLDVPIK LKQILLKQER QKKQREQAEK NXQILEQV                          38

SEQ ID NO: 24           moltype = AA  length = 38
FEATURE                 Location/Qualifiers
source                  1..38
                        mol_type = protein
                        organism = synthetic construct
MOD_RES                 1
                        note = METHYLATION
SITE                    7
                        note = D-valine
MOD_RES                 12
                        note = the epsilon-amino group of the lysine side chain is
                         covalentlybound to an albumin -binding moiety
MOD_RES                 38
                        note = AMIDATION
SEQUENCE: 24
IVLSLDVPIK LKQILLKQER QKKQREQAEK NAQILEQV                          38

SEQ ID NO: 25           moltype = AA  length = 38
FEATURE                 Location/Qualifiers
source                  1..38
                        mol_type = protein
                        organism = synthetic construct
MOD_RES                 12
                        note = the epsilon-amino group of the lysine side chain is
                         covalentlybound to an albumin -binding moiety
MOD_RES                 14
                        note = X is Aib
MOD_RES                 32
                        note = X is Aib
```

```
MOD_RES                 38
                        note = AMIDATION
SEQUENCE: 25
IVLSLDVPIK LKQXLLKQER QKKQREQAEK NXQILEQV                         38

SEQ ID NO: 26           moltype = AA  length = 38
FEATURE                 Location/Qualifiers
source                  1..38
                        mol_type = protein
                        organism = synthetic construct
MOD_RES                 1
                        note = ACETYLATION
MOD_RES                 12
                        note = the epsilon-amino group of the lysine side chain is
                         covalentlybound to an albumin -binding moiety
MOD_RES                 14
                        note = X is Aib
MOD_RES                 32
                        note = X is Aib
MOD_RES                 38
                        note = AMIDATION
SEQUENCE: 26
IVLSLDVPIK LKQXLLKQER QKKQREQAEK NXQILEQV                         38

SEQ ID NO: 27           moltype = AA  length = 38
FEATURE                 Location/Qualifiers
source                  1..38
                        mol_type = protein
                        organism = synthetic construct
MOD_RES                 1
                        note = ACETYLATION
SITE                    7
                        note = D-valine
MOD_RES                 12
                        note = the epsilon-amino group of the lysine side chain is
                         covalentlybound to an albumin -binding moiety
MOD_RES                 14
                        note = X is Aib
MOD_RES                 38
                        note = AMIDATION
SEQUENCE: 27
IVLSLDVPIK LKQXLLKQER QKKQREQAEK NVQILEQV                         38

SEQ ID NO: 28           moltype = AA  length = 38
FEATURE                 Location/Qualifiers
source                  1..38
                        mol_type = protein
                        organism = synthetic construct
MOD_RES                 1
                        note = METHYLATION
SITE                    7
                        note = D-valine
MOD_RES                 12
                        note = the epsilon-amino group of the lysine side chain is
                         covalentlybound to an albumin -binding moiety
MOD_RES                 14
                        note = X is Aib
MOD_RES                 38
                        note = AMIDATION
SEQUENCE: 28
IVLSLDVPIK LKQXLLKQER QKKQREQAEK NVQILEQV                         38

SEQ ID NO: 29           moltype = AA  length = 37
FEATURE                 Location/Qualifiers
source                  1..37
                        mol_type = protein
                        organism = synthetic construct
MOD_RES                 1
                        note = Acetylated with a pentanoyl group
SITE                    6
                        note = D-valine
MOD_RES                 11
                        note = the epsilon-amino group of the lysine side chain is
                         covalentlybound to an albumin -binding moiety
MOD_RES                 13
                        note = X is Aib
MOD_RES                 37
                        note = AMIDATION
SEQUENCE: 29
```

-continued

```
VLSLDVPIKL KQXLLKQERQ KKQREQAEKN VQILEQV                    37

SEQ ID NO: 30          moltype = AA  length = 38
FEATURE                Location/Qualifiers
source                 1..38
                       mol_type = protein
                       organism = synthetic construct
MOD_RES                1
                       note = ACETYLATION
SITE                   7
                       note = D-valine
MOD_RES                12
                       note = the epsilon-amino group of the lysine side chain is
                        covalentlybound to an albumin -binding moiety
MOD_RES                32
                       note = X is Aib
MOD_RES                38
                       note = AMIDATION
SEQUENCE: 30
IVLSLDVPIK LKQILLKQER QKKQREQAEK NXQILEQV                   38

SEQ ID NO: 31          moltype = AA  length = 38
FEATURE                Location/Qualifiers
source                 1..38
                       mol_type = protein
                       organism = synthetic construct
MOD_RES                1
                       note = METHYLATION
SITE                   7
                       note = D-valine
MOD_RES                12
                       note = the epsilon-amino group of the lysine side chain is
                        covalentlybound to an albumin -binding moiety
MOD_RES                32
                       note = X is Aib
MOD_RES                38
                       note = AMIDATION
SEQUENCE: 31
IVLSLDVPIK LKQILLKQER QKKQREQAEK NXQILEQV                   38

SEQ ID NO: 32          moltype = AA  length = 37
FEATURE                Location/Qualifiers
source                 1..37
                       mol_type = protein
                       organism = synthetic construct
MOD_RES                1
                       note = Acetylated with a pentanoyl group
SITE                   6
                       note = D-valine
MOD_RES                11
                       note = the epsilon-amino group of the lysine side chain is
                        covalentlybound to an albumin -binding moiety
MOD_RES                31
                       note = X is Aib
MOD_RES                37
                       note = AMIDATION
SEQUENCE: 32
VLSLDVPIKL KQILLKQERQ KKQREQAEKN XQILEQV                    37

SEQ ID NO: 33          moltype = AA  length = 37
FEATURE                Location/Qualifiers
source                 1..37
                       mol_type = protein
                       organism = synthetic construct
MOD_RES                1
                       note = ACETYLATION
SITE                   6
                       note = D-valine
MOD_RES                11
                       note = the epsilon-amino group of the lysine side chain is
                        covalentlybound to an albumin -binding moiety
MOD_RES                37
                       note = AMIDATION
SEQUENCE: 33
VLSLDVPIKL KKILLEQEKQ KKQREQAETN KQILAQV                    37

SEQ ID NO: 34          moltype = AA  length = 37
FEATURE                Location/Qualifiers
source                 1..37
```

```
                         mol_type = protein
                         organism = synthetic construct
SITE                     6
                         note = D-valine
MOD_RES                  11
                         note = the epsilon-amino group of the lysine side chain is
                          covalentlybound to an albumin -binding moiety
MOD_RES                  37
                         note = AMIDATION
SEQUENCE: 34
VLSLDVPIKL KKILLEQEKQ KKQREQAETN KQILAQV                              37

SEQ ID NO: 35            moltype = AA  length = 37
FEATURE                  Location/Qualifiers
source                   1..37
                         mol_type = protein
                         organism = synthetic construct
MOD_RES                  1
                         note = Acetylated with a propanoyl group
SITE                     6
                         note = D-valine
MOD_RES                  11
                         note = the epsilon-amino group of the lysine side chain is
                          covalentlybound to an albumin -binding moiety
MOD_RES                  37
                         note = AMIDATION
SEQUENCE: 35
VLSLDVPIKL KKILLEQEKQ KKQREQAETN KQILAQV                              37

SEQ ID NO: 36            moltype = AA  length = 37
FEATURE                  Location/Qualifiers
source                   1..37
                         mol_type = protein
                         organism = synthetic construct
MOD_RES                  1
                         note = Acetylated with a butanoyl group
SITE                     6
                         note = D-valine
MOD_RES                  11
                         note = the epsilon-amino group of the lysine side chain is
                          covalentlybound to an albumin -binding moiety
MOD_RES                  37
                         note = AMIDATION
SEQUENCE: 36
VLSLDVPIKL KKILLEQEKQ KKQREQAETN KQILAQV                              37

SEQ ID NO: 37            moltype = AA  length = 37
FEATURE                  Location/Qualifiers
source                   1..37
                         mol_type = protein
                         organism = synthetic construct
MOD_RES                  1
                         note = Acetylated with a pentanoyl group
SITE                     6
                         note = D-valine
MOD_RES                  11
                         note = the epsilon-amino group of the lysine side chain is
                          covalentlybound to an albumin -binding moiety
MOD_RES                  37
                         note = AMIDATION
SEQUENCE: 37
VLSLDVPIKL KKILLEQEKQ KKQREQAETN KQILAQV                              37

SEQ ID NO: 38            moltype = AA  length = 38
FEATURE                  Location/Qualifiers
source                   1..38
                         mol_type = protein
                         organism = synthetic construct
MOD_RES                  11
                         note = X is alpha-methyl-leucine
MOD_RES                  12
                         note = the epsilon-amino group of the lysine side chain is
                          covalentlybound to an albumin -binding moiety
MOD_RES                  32
                         note = X is Aib
MOD_RES                  38
                         note = AMIDATION
SEQUENCE: 38
IVLSLDVPIK XKKILLEQEK QKKQREQAET NXQILAQV                             38
```

```
SEQ ID NO: 39          moltype = AA  length = 38
FEATURE                Location/Qualifiers
source                 1..38
                       mol_type = protein
                       organism = synthetic construct
MOD_RES                1
                       note = ACETYLATION
MOD_RES                12
                       note = the epsilon-amino group of the lysine side chain is
                        covalentlybound to an albumin -binding moiety
MOD_RES                32
                       note = X is Aib
MOD_RES                38
                       note = AMIDATION
SEQUENCE: 39
IVLSLDVPIK LKKILLEQEK QKKQREQAET NXQILAQV                          38

SEQ ID NO: 40          moltype = AA  length = 38
FEATURE                Location/Qualifiers
source                 1..38
                       mol_type = protein
                       organism = synthetic construct
MOD_RES                1
                       note = ACETYLATION
SITE                   7
                       note = D-valine
MOD_RES                12
                       note = the epsilon-amino group of the lysine side chain is
                        covalentlybound to an albumin -binding moiety
MOD_RES                32
                       note = X is Aib
MOD_RES                38
                       note = AMIDATION
SEQUENCE: 40
IVLSLDVPIK LKKILLEQEK QKKQREQAET NXQILAQV                          38

SEQ ID NO: 41          moltype = AA  length = 38
FEATURE                Location/Qualifiers
source                 1..38
                       mol_type = protein
                       organism = synthetic construct
MOD_RES                1
                       note = ACETYLATION
SITE                   7
                       note = D-valine
MOD_RES                12
                       note = the epsilon-amino group of the lysine side chain is
                        covalentlybound to an albumin -binding moiety
MOD_RES                32
                       note = X is Aib
MOD_RES                38
                       note = AMIDATION
SEQUENCE: 41
IVLSLDVPIK LKKILLEQEK QKKQREQAET NXQILAQV                          38

SEQ ID NO: 42          moltype = AA  length = 38
FEATURE                Location/Qualifiers
source                 1..38
                       mol_type = protein
                       organism = synthetic construct
MOD_RES                1
                       note = ACETYLATION
SITE                   7
                       note = D-valine
MOD_RES                12
                       note = the epsilon-amino group of the lysine side chain is
                        covalentlybound to an albumin -binding moiety
MOD_RES                32
                       note = X is Aib
MOD_RES                38
                       note = AMIDATION
SEQUENCE: 42
IVLSLDVPIK LKKILLEQEK QKKQREQAET NXQILAQV                          38

SEQ ID NO: 43          moltype = AA  length = 38
FEATURE                Location/Qualifiers
source                 1..38
                       mol_type = protein
```

```
                        organism = synthetic construct
MOD_RES                 1
                        note = ACETYLATION
MOD_RES                 11
                        note = X is alpha-methyl-leucine
MOD_RES                 12
                        note = the epsilon-amino group of the lysine side chain is
                         covalentlybound to an albumin -binding moiety
MOD_RES                 32
                        note = X is Aib
MOD_RES                 38
                        note = AMIDATION
SEQUENCE: 43
IVLSLDVPIK XKKILLEQEK QKKQREQAET NXQILAQV                     38

SEQ ID NO: 44           moltype = AA  length = 38
FEATURE                 Location/Qualifiers
source                  1..38
                        mol_type = protein
                        organism = synthetic construct
MOD_RES                 1
                        note = ACETYLATION
SITE                    7
                        note = D-valine
MOD_RES                 11
                        note = X is alpha-methyl-leucine
MOD_RES                 12
                        note = the epsilon-amino group of the lysine side chain is
                         covalentlybound to an albumin -binding moiety
MOD_RES                 32
                        note = X is Aib
MOD_RES                 38
                        note = AMIDATION
SEQUENCE: 44
IVLSLDVPIK XKKILLEQEK QKKQREQAET NXQILAQV                     38

SEQ ID NO: 45           moltype = AA  length = 37
FEATURE                 Location/Qualifiers
source                  1..37
                        mol_type = protein
                        organism = synthetic construct
MOD_RES                 1
                        note = ACETYLATION
SITE                    6
                        note = D-valine
MOD_RES                 11
                        note = the epsilon-amino group of the lysine side chain is
                         covalentlybound to an albumin -binding moiety
MOD_RES                 31
                        note = X is Aib
MOD_RES                 37
                        note = AMIDATION
SEQUENCE: 45
VLSLDVPIKL KKILLEQEKQ KKQREQAETN XQILAQV                      37

SEQ ID NO: 46           moltype = AA  length = 37
FEATURE                 Location/Qualifiers
source                  1..37
                        mol_type = protein
                        organism = synthetic construct
MOD_RES                 1
                        note = ACETYLATION
SITE                    6
                        note = D-valine
MOD_RES                 10
                        note = X is alpha-methyl-leucine
MOD_RES                 11
                        note = the epsilon-amino group of the lysine side chain is
                         covalentlybound to an albumin -binding moiety
MOD_RES                 31
                        note = X is Aib
MOD_RES                 37
                        note = AMIDATION
SEQUENCE: 46
VLSLDVPIKX KKILLEQEKQ KKQREQAETN XQILAQV                      37

SEQ ID NO: 47           moltype = AA  length = 38
FEATURE                 Location/Qualifiers
source                  1..38
```

-continued

```
                         mol_type = protein
                         organism = synthetic construct
MOD_RES                  1
                         note = ACETYLATION
SITE                     7
                         note = D-valine
MOD_RES                  12
                         note = the epsilon-amino group of the lysine side chain is
                          covalentlybound to an albumin -binding moiety
MOD_RES                  38
                         note = AMIDATION
SEQUENCE: 47
IVLSLDVPIK LKKILLEQEK QKKQREQAET NAQILAQV                            38

SEQ ID NO: 48            moltype = AA  length = 38
FEATURE                  Location/Qualifiers
source                   1..38
                         mol_type = protein
                         organism = synthetic construct
MOD_RES                  1
                         note = ACETYLATION
SITE                     7
                         note = D-valine
MOD_RES                  12
                         note = the epsilon-amino group of the lysine side chain is
                          covalentlybound to an albumin -binding moiety
MOD_RES                  38
                         note = AMIDATION
SEQUENCE: 48
IVLSLDVPIK LKKILLEQEK QKKQREQAET NVQILAQV                            38

SEQ ID NO: 49            moltype = AA  length = 38
FEATURE                  Location/Qualifiers
source                   1..38
                         mol_type = protein
                         organism = synthetic construct
MOD_RES                  1
                         note = ACETYLATION
MOD_RES                  11
                         note = X is alpha-methyl-leucine
MOD_RES                  12
                         note = the epsilon-amino group of the lysine side chain is
                          covalentlybound to an albumin -binding moiety
MOD_RES                  38
                         note = ACETYLATION
SEQUENCE: 49
IVLSLDVPIK XKKILLEQEK QKKQREQAET NVQILAQV                            38

SEQ ID NO: 50            moltype = AA  length = 38
FEATURE                  Location/Qualifiers
source                   1..38
                         mol_type = protein
                         organism = synthetic construct
MOD_RES                  1
                         note = ACETYLATION
SITE                     7
                         note = D-valine
MOD_RES                  11
                         note = X is alpha-methyl-leucine
MOD_RES                  12
                         note = the epsilon-amino group of the lysine side chain is
                          covalentlybound to an albumin -binding moiety
MOD_RES                  38
                         note = AMIDATION
SEQUENCE: 50
IVLSLDVPIK XKKILLEQEK QKKQREQAET NVQILAQV                            38

SEQ ID NO: 51            moltype = AA  length = 38
FEATURE                  Location/Qualifiers
source                   1..38
                         mol_type = protein
                         organism = synthetic construct
MOD_RES                  1
                         note = ACETYLATION
SITE                     7
                         note = D-valine
MOD_RES                  12
                         note = the epsilon-amino group of the lysine side chain is
                          covalentlybound to an albumin -binding moiety
```

-continued

```
MOD_RES                32
                       note = X is Abu
MOD_RES                38
                       note = AMIDATION
SEQUENCE: 51
IVLSLDVPIK LKKILLEQEK QKKQREQAET NXQILAQV                          38

SEQ ID NO: 52          moltype = AA  length = 38
FEATURE                Location/Qualifiers
source                 1..38
                       mol_type = protein
                       organism = synthetic construct
MOD_RES                1
                       note = ACETYLATION
SITE                   7
                       note = D-valine
MOD_RES                12
                       note = the epsilon-amino group of the lysine side chain is
                        covalentlybound to an albumin -binding moiety
MOD_RES                32
                       note = X is Nva
MOD_RES                38
                       note = AMIDATION
SEQUENCE: 52
IVLSLDVPIK LKKILLEQEK QKKQREQAET NXQILAQV                          38

SEQ ID NO: 53          moltype = AA  length = 38
FEATURE                Location/Qualifiers
source                 1..38
                       mol_type = protein
                       organism = synthetic construct
MOD_RES                1
                       note = ACETYLATION
SITE                   7
                       note = D-valine
MOD_RES                11
                       note = X is alpha-methyl-leucine
MOD_RES                12
                       note = the epsilon-amino group of the lysine side chain is
                        covalentlybound to an albumin -binding moiety
MOD_RES                38
                       note = AMIDATION
SEQUENCE: 53
IVLSLDVPIK XKKILLEQEK QKKQREQAET DKQILAQV                          38

SEQ ID NO: 54          moltype = AA  length = 39
FEATURE                Location/Qualifiers
source                 1..39
                       mol_type = protein
                       organism = synthetic construct
MOD_RES                1
                       note = ACETYLATION
SITE                   7
                       note = D-valine
MOD_RES                12
                       note = the epsilon-amino group of the lysine side chain is
                        covalentlybound to an albumin -binding moiety
MOD_RES                32
                       note = X is alpha-methyl-leucine
MOD_RES                38
                       note = AMIDATION
SEQUENCE: 54
IVLSLDVPIK LKKILLEQEK QKKQREQAET NXKQILAQV                         39

SEQ ID NO: 55          moltype = AA  length = 38
FEATURE                Location/Qualifiers
source                 1..38
                       mol_type = protein
                       organism = synthetic construct
MOD_RES                1
                       note = ACETYLATION
SITE                   7
                       note = D-valine
MOD_RES                12
                       note = the epsilon-amino group of the lysine side chain is
                        covalentlybound to an albumin -binding moiety
MOD_RES                32
                       note = X is Dap
MOD_RES                38
```

-continued

```
                         note = AMIDATION
SEQUENCE: 55
IVLSLDVPIK LKKILLEQEK QKKQREQAET NXQILAQV                            38

SEQ ID NO: 56            moltype = AA  length = 38
FEATURE                  Location/Qualifiers
source                   1..38
                         mol_type = protein
                         organism = synthetic construct
MOD_RES                  1
                         note = ACETYLATION
SITE                     7
                         note = D-valine
MOD_RES                  12
                         note = the epsilon-amino group of the lysine side chain is
                          covalentlybound to an albumin -binding moiety
MOD_RES                  38
                         note = AMIDATION
SEQUENCE: 56
IVLSLDVPIK LKKILLEQEK QKKQREQAET NEQILAQV                            38

SEQ ID NO: 57            moltype = AA  length = 38
FEATURE                  Location/Qualifiers
source                   1..38
                         mol_type = protein
                         organism = synthetic construct
MOD_RES                  1
                         note = ACETYLATION
SITE                     7
                         note = D-valine
MOD_RES                  12
                         note = the epsilon-amino group of the lysine side chain is
                          covalentlybound to an albumin -binding moiety
MOD_RES                  32
                         note = X is 4-Pip
MOD_RES                  38
                         note = AMIDATION
SEQUENCE: 57
IVLSLDVPIK LKKILLEQEK QKKQREQAET NXQILAQV                            38

SEQ ID NO: 58            moltype = AA  length = 38
FEATURE                  Location/Qualifiers
source                   1..38
                         mol_type = protein
                         organism = synthetic construct
MOD_RES                  1
                         note = ACETYLATION
SITE                     7
                         note = D-valine
MOD_RES                  12
                         note = the epsilon-amino group of the lysine side chain is
                          covalentlybound to an albumin -binding moiety
MOD_RES                  32
                         note = X is Thp
MOD_RES                  38
                         note = AMIDATION
SEQUENCE: 58
IVLSLDVPIK LKKILLEQEK QKKQREQAET NXQILAQV                            38

SEQ ID NO: 59            moltype = AA  length = 38
FEATURE                  Location/Qualifiers
source                   1..38
                         mol_type = protein
                         organism = synthetic construct
MOD_RES                  1
                         note = ACETYLATION
SITE                     7
                         note = D-valine
MOD_RES                  12
                         note = the epsilon-amino group of the lysine side chain is
                          covalentlybound to an albumin -binding moiety
MOD_RES                  32
                         note = X is Chx
MOD_RES                  38
                         note = AMIDATION
SEQUENCE: 59
IVLSLDVPIK LKKILLEQEK QKKQREQAET NXQILAQV                            38

SEQ ID NO: 60            moltype = AA  length = 38
```

```
FEATURE                Location/Qualifiers
source                 1..38
                       mol_type = protein
                       organism = synthetic construct
MOD_RES                1
                       note = ACETYLATION
SITE                   7
                       note = D-valine
MOD_RES                12
                       note = the epsilon-amino group of the lysine side chain is
                        covalentlybound to an albumin -binding moiety
MOD_RES                32
                       note = X is Cpex
MOD_RES                38
                       note = AMIDATION
SEQUENCE: 60
IVLSLDVPIK LKKILLEQEK QKKQREQAET NXQILAQV                          38

SEQ ID NO: 61          moltype = AA  length = 38
FEATURE                Location/Qualifiers
source                 1..38
                       mol_type = protein
                       organism = synthetic construct
MOD_RES                1
                       note = ACETYLATION
SITE                   7
                       note = D-valine
MOD_RES                12
                       note = the epsilon-amino group of the lysine side chain is
                        covalentlybound to an albumin -binding moiety
MOD_RES                32
                       note = X is Cpx
MOD_RES                38
                       note = AMIDATION
SEQUENCE: 61
IVLSLDVPIK LKKILLEQEK QKKQREQAET NXQILAQV                          38

SEQ ID NO: 62          moltype = AA  length = 38
FEATURE                Location/Qualifiers
source                 1..38
                       mol_type = protein
                       organism = synthetic construct
MOD_RES                1
                       note = ACETYLATION
SITE                   7
                       note = D-valine
MOD_RES                12
                       note = the epsilon-amino group of the lysine side chain is
                        covalentlybound to an albumin -binding moiety
MOD_RES                32
                       note = X is 4-Pip
MOD_RES                38
                       note = AMIDATION
SEQUENCE: 62
IVLSLDVPIK LKKILLEQEK QKAQREQAET NXQILAQV                          38

SEQ ID NO: 63          moltype = AA  length = 38
FEATURE                Location/Qualifiers
source                 1..38
                       mol_type = protein
                       organism = synthetic construct
MOD_RES                1
                       note = ACETYLATION
SITE                   7
                       note = D-valine
MOD_RES                12
                       note = the epsilon-amino group of the lysine side chain is
                        covalentlybound to an albumin -binding moiety
MOD_RES                23
                       note = X is Aib
MOD_RES                32
                       note = X is 4-Pip
SEQUENCE: 63
IVLSLDVPIK LKKILLEQEK QKXQREQAET NXQILAQV                          38

SEQ ID NO: 64          moltype = AA  length = 38
FEATURE                Location/Qualifiers
source                 1..38
                       mol_type = protein
```

```
                        organism = synthetic construct
MOD_RES                 1
                        note = METHYLATION
SITE                    7
                        note = D-valine
MOD_RES                 12
                        note = the epsilon-amino group of the lysine side chain is
                         covalentlybound to an albumin -binding moiety
MOD_RES                 32
                        note = X is Aib
MOD_RES                 38
                        note = AMIDATION
SEQUENCE: 64
IVLSLDVPIK LKKILLEQEK QKKQREQAET NXQILAQV                           38

SEQ ID NO: 65           moltype = AA  length = 38
FEATURE                 Location/Qualifiers
source                  1..38
                        mol_type = protein
                        organism = synthetic construct
MOD_RES                 1
                        note = METHYLATION
SITE                    7
                        note = D-valine
MOD_RES                 11
                        note = X is alpha-methyl-leucine
MOD_RES                 12
                        note = the epsilon-amino group of the lysine side chain is
                         covalentlybound to an albumin -binding moiety
MOD_RES                 32
                        note = X is Aib
MOD_RES                 38
                        note = AMIDATION
SEQUENCE: 65
IVLSLDVPIK XKKILLEQEK QKKQREQAET NXQILAQV                           38

SEQ ID NO: 66           moltype = AA  length = 38
FEATURE                 Location/Qualifiers
source                  1..38
                        mol_type = protein
                        organism = synthetic construct
MOD_RES                 1
                        note = METHYLATION
SITE                    7
                        note = D-valine
MOD_RES                 12
                        note = the epsilon-amino group of the lysine side chain is
                         covalentlybound to an albumin -binding moiety
MOD_RES                 38
                        note = AMIDATION
SEQUENCE: 66
IVLSLDVPIK LKKILLEQEK QKKQREQAET NVQILAQV                           38

SEQ ID NO: 67           moltype = AA  length = 38
FEATURE                 Location/Qualifiers
source                  1..38
                        mol_type = protein
                        organism = synthetic construct
MOD_RES                 1
                        note = METHYLATION
SITE                    7
                        note = D-valine
MOD_RES                 11
                        note = X is alpha-methyl-leucine
MOD_RES                 12
                        note = the epsilon-amino group of the lysine side chain is
                         covalentlybound to an albumin -binding moiety
MOD_RES                 38
                        note = AMIDATION
SEQUENCE: 67
IVLSLDVPIK XKKILLEQEK QKKQREQAET NVQILAQV                           38

SEQ ID NO: 68           moltype = AA  length = 38
FEATURE                 Location/Qualifiers
source                  1..38
                        mol_type = protein
                        organism = synthetic construct
MOD_RES                 1
                        note = METHYLATION
```

-continued

```
SITE                    7
                        note = D-valine
MOD_RES                 12
                        note = the epsilon-amino group of the lysine side chain is
                         covalentlybound to an albumin -binding moiety
MOD_RES                 38
                        note = AMIDATION
SEQUENCE: 68
IVLSLDVPIK LKKILLEQEK QKKQREQAET NAQILAQV                          38

SEQ ID NO: 69           moltype = AA  length = 38
FEATURE                 Location/Qualifiers
source                  1..38
                        mol_type = protein
                        organism = synthetic construct
MOD_RES                 1
                        note = METHYLATION
SITE                    7
                        note = D-valine
MOD_RES                 12
                        note = the epsilon-amino group of the lysine side chain is
                         covalentlybound to an albumin -binding moiety
MOD_RES                 32
                        note = X is Abu
MOD_RES                 38
                        note = AMIDATION
SEQUENCE: 69
IVLSLDVPIK LKKILLEQEK QKKQREQAET NXQILAQV                          38

SEQ ID NO: 70           moltype = AA  length = 38
FEATURE                 Location/Qualifiers
source                  1..38
                        mol_type = protein
                        organism = synthetic construct
MOD_RES                 1
                        note = METHYLATION
SITE                    7
                        note = D-valine
MOD_RES                 12
                        note = the epsilon-amino group of the lysine side chain is
                         covalentlybound to an albumin -binding moiety
MOD_RES                 32
                        note = X is Dap
MOD_RES                 38
                        note = AMIDATION
SEQUENCE: 70
IVLSLDVPIK LKKILLEQEK QKKQREQAET NXQILAQV                          38

SEQ ID NO: 71           moltype = AA  length = 38
FEATURE                 Location/Qualifiers
source                  1..38
                        mol_type = protein
                        organism = synthetic construct
MOD_RES                 1
                        note = METHYLATION
SITE                    7
                        note = D-valine
MOD_RES                 12
                        note = the epsilon-amino group of the lysine side chain is
                         covalentlybound to an albumin -binding moiety
MOD_RES                 38
                        note = AMIDATION
SEQUENCE: 71
IVLSLDVPIK LKKILLEQEK QKKQREQAET NEQILAQV                          38

SEQ ID NO: 72           moltype = AA  length = 38
FEATURE                 Location/Qualifiers
source                  1..38
                        mol_type = protein
                        organism = synthetic construct
MOD_RES                 1
                        note = METHYLATION
SITE                    7
                        note = D-valine
MOD_RES                 12
                        note = the epsilon-amino group of the lysine side chain is
                         covalentlybound to an albumin -binding moiety
MOD_RES                 32
                        note = X is 4-Pip
```

```
MOD_RES                 38
                        note = AMIDATION
SEQUENCE: 72
IVLSLDVPIK LKKILLEQEK QKKQREQAET NXQILAQV                          38

SEQ ID NO: 73           moltype = AA  length = 38
FEATURE                 Location/Qualifiers
source                  1..38
                        mol_type = protein
                        organism = synthetic construct
MOD_RES                 1
                        note = METHYLATION
SITE                    7
                        note = D-valine
MOD_RES                 12
                        note = the epsilon-amino group of the lysine side chain is
                         covalentlybound to an albumin -binding moiety
MOD_RES                 32
                        note = X is Thp
MOD_RES                 38
                        note = AMIDATION
SEQUENCE: 73
IVLSLDVPIK LKKILLEQEK QKKQREQAET NXQILAQV                          38

SEQ ID NO: 74           moltype = AA  length = 38
FEATURE                 Location/Qualifiers
source                  1..38
                        mol_type = protein
                        organism = synthetic construct
MOD_RES                 1
                        note = METHYLATION
SITE                    7
                        note = D-valine
MOD_RES                 12
                        note = the epsilon-amino group of the lysine side chain is
                         covalentlybound to an albumin -binding moiety
MOD_RES                 32
                        note = X is Aib
MOD_RES                 38
                        note = AMIDATION
SEQUENCE: 74
IVLSLDVPIK LKKILLEQEK QKAQREQAET NXQILAQV                          38

SEQ ID NO: 75           moltype = AA  length = 38
FEATURE                 Location/Qualifiers
source                  1..38
                        mol_type = protein
                        organism = synthetic construct
MOD_RES                 1
                        note = METHYLATION
SITE                    7
                        note = D-valine
MOD_RES                 12
                        note = the epsilon-amino group of the lysine side chain is
                         covalentlybound to an albumin -binding moiety
MOD_RES                 23
                        note = X is Aib
MOD_RES                 32
                        note = X is Aib
SEQUENCE: 75
IVLSLDVPIK LKKILLEQEK QKXQREQAET NXQILAQV                          38

SEQ ID NO: 76           moltype = AA  length = 38
FEATURE                 Location/Qualifiers
source                  1..38
                        mol_type = protein
                        organism = synthetic construct
MOD_RES                 1
                        note = METHYLATION
SITE                    7
                        note = D-valine
MOD_RES                 12
                        note = the epsilon-amino group of the lysine side chain is
                         covalentlybound to an albumin -binding moiety
MOD_RES                 32
                        note = X is 4-Pip
MOD_RES                 38
                        note = AMIDATION
SEQUENCE: 76
```

-continued

```
IVLSLDVPIK LKKILLEQEK QKAQREQAET NXQILAQV                         38

SEQ ID NO: 77          moltype = AA  length = 38
FEATURE                Location/Qualifiers
source                 1..38
                       mol_type = protein
                       organism = synthetic construct
MOD_RES                1
                       note = METHYLATION
SITE                   7
                       note = D-valine
MOD_RES                12
                       note = the epsilon-amino group of the lysine side chain is
                        covalentlybound to an albumin -binding moiety
MOD_RES                23
                       note = X is Aib
MOD_RES                32
                       note = X is 4-Pip
SEQUENCE: 77
IVLSLDVPIK LKKILLEQEK QKXQREQAET NXQILAQV                         38

SEQ ID NO: 78          moltype = AA  length = 37
FEATURE                Location/Qualifiers
source                 1..37
                       mol_type = protein
                       organism = synthetic construct
MOD_RES                1
                       note = Acetylated with a propanoyl group
SITE                   6
                       note = D-valine
MOD_RES                11
                       note = the epsilon-amino group of the lysine side chain is
                        covalentlybound to an albumin -binding moiety
MOD_RES                31
                       note = X is Aib
MOD_RES                37
                       note = AMIDATION
SEQUENCE: 78
VLSLDVPIKL KKILLEQEKQ KKQREQAETN XQILAQV                          37

SEQ ID NO: 79          moltype = AA  length = 37
FEATURE                Location/Qualifiers
source                 1..37
                       mol_type = protein
                       organism = synthetic construct
MOD_RES                1
                       note = Acetylated with a butanoyl group
SITE                   6
                       note = D-valine
MOD_RES                11
                       note = the epsilon-amino group of the lysine side chain is
                        covalentlybound to an albumin -binding moiety
MOD_RES                31
                       note = X is Aib
MOD_RES                37
                       note = AMIDATION
SEQUENCE: 79
VLSLDVPIKL KKILLEQEKQ KKQREQAETN XQILAQV                          37

SEQ ID NO: 80          moltype = AA  length = 37
FEATURE                Location/Qualifiers
source                 1..37
                       mol_type = protein
                       organism = synthetic construct
MOD_RES                1
                       note = Acetylated with a pentanoyl group
SITE                   6
                       note = D-valine
MOD_RES                11
                       note = the epsilon-amino group of the lysine side chain is
                        covalentlybound to an albumin -binding moiety
MOD_RES                31
                       note = X is Aib
MOD_RES                37
                       note = AMIDATION
SEQUENCE: 80
VLSLDVPIKL KKILLEQEKQ KKQREQAETN XQILAQV                          37

SEQ ID NO: 81          moltype = AA  length = 37
```

-continued

```
FEATURE                Location/Qualifiers
source                 1..37
                       mol_type = protein
                       organism = synthetic construct
MOD_RES                1
                       note = Acetylated with a pentanoyl group
SITE                   6
                       note = D-valine
MOD_RES                11
                       note = the epsilon-amino group of the lysine side chain is
                        covalentlybound to an albumin -binding moiety
MOD_RES                37
                       note = AMIDATION
SEQUENCE: 81
VLSLDVPIKL KKILLEQEKQ KKQREQAETN VQILAQV                          37

SEQ ID NO: 82          moltype = AA  length = 38
FEATURE                Location/Qualifiers
source                 1..38
                       mol_type = protein
                       organism = synthetic construct
MOD_RES                1
                       note = ACETYLATION
SITE                   7
                       note = D-valine
MOD_RES                12
                       note = the epsilon-amino group of the lysine side chain is
                        covalentlybound to an albumin -binding moiety
MOD_RES                32
                       note = X is Aib
MOD_RES                38
                       note = AMIDATION
SEQUENCE: 82
IVLSLDVPIK LKKILLEQEK QKKQREQAET NXQILAQV                         38

SEQ ID NO: 83          moltype = AA  length = 38
FEATURE                Location/Qualifiers
source                 1..38
                       mol_type = protein
                       organism = synthetic construct
MOD_RES                1
                       note = ACETYLATION
SITE                   7
                       note = D-valine
MOD_RES                12
                       note = the epsilon-amino group of the lysine side chain is
                        covalentlybound to an albumin -binding moiety
MOD_RES                32
                       note = X is Abu
MOD_RES                38
                       note = AMIDATION
SEQUENCE: 83
IVLSLDVPIK LKKILLEQEK QKKQREQAET NXQILAQV                         38

SEQ ID NO: 84          moltype = AA  length = 38
FEATURE                Location/Qualifiers
source                 1..38
                       mol_type = protein
                       organism = synthetic construct
MOD_RES                1
                       note = ACETYLATION
SITE                   7
                       note = D-valine
MOD_RES                12
                       note = the epsilon-amino group of the lysine side chain is
                        covalentlybound to an albumin -binding moiety
MOD_RES                32
                       note = X is 4-Pip
MOD_RES                38
                       note = AMIDATION
SEQUENCE: 84
IVLSLDVPIK LKKILLEQEK QKKQREQAET NXQILAQV                         38

SEQ ID NO: 85          moltype = AA  length = 38
FEATURE                Location/Qualifiers
source                 1..38
                       mol_type = protein
                       organism = synthetic construct
MOD_RES                1
```

```
                        note = ACETYLATION
SITE                    7
                        note = D-valine
MOD_RES                 12
                        note = the epsilon-amino group of the lysine side chain is
                         covalentlybound to an albumin -binding moiety
MOD_RES                 38
                        note = AMIDATION
SEQUENCE: 85
IVLSLDVPIK LKKILLEQEK QKKQREQAET NEQILAQV                            38

SEQ ID NO: 86           moltype = AA  length = 37
FEATURE                 Location/Qualifiers
source                  1..37
                        mol_type = protein
                        organism = synthetic construct
MOD_RES                 1
                        note = Acetylated with a pentanoyl group
SITE                    6
                        note = D-valine
MOD_RES                 11
                        note = the epsilon-amino group of the lysine side chain is
                         covalentlybound to an albumin -binding moiety
MOD_RES                 31
                        note = X is Aib
MOD_RES                 37
                        note = AMIDATION
SEQUENCE: 86
VLSLDVPIKL KKILLEQEKQ KKQREQAETN XQILAQV                             37

SEQ ID NO: 87           moltype = AA  length = 38
FEATURE                 Location/Qualifiers
source                  1..38
                        mol_type = protein
                        organism = synthetic construct
MOD_RES                 1
                        note = METHYLATION
SITE                    7
                        note = D-valine
MOD_RES                 12
                        note = the epsilon-amino group of the lysine side chain is
                         covalentlybound to an albumin -binding moiety
MOD_RES                 32
                        note = X is Aib
MOD_RES                 38
                        note = AMIDATION
SEQUENCE: 87
IVLSLDVPIK LKKILLEQEK QKKQREQAET NXQILAQV                            38

SEQ ID NO: 88           moltype = AA  length = 38
FEATURE                 Location/Qualifiers
source                  1..38
                        mol_type = protein
                        organism = synthetic construct
MOD_RES                 1
                        note = METHYLATION
SITE                    7
                        note = D-valine
MOD_RES                 12
                        note = the epsilon-amino group of the lysine side chain is
                         covalentlybound to an albumin -binding moiety
MOD_RES                 32
                        note = X is Aib
MOD_RES                 38
                        note = AMIDATION
SEQUENCE: 88
IVLSLDVPIK LKKILLEQEK QKAQREQAET NXQILAQV                            38

SEQ ID NO: 89           moltype = AA  length = 38
FEATURE                 Location/Qualifiers
source                  1..38
                        mol_type = protein
                        organism = synthetic construct
MOD_RES                 1
                        note = METHYLATION
SITE                    7
                        note = D-valine
MOD_RES                 12
                        note = the epsilon-amino group of the lysine side chain is
```

-continued

```
                        covalentlybound to an albumin -binding moiety
MOD_RES                 23
                        note = X is Aib
MOD_RES                 32
                        note = X is Aib
MOD_RES                 38
                        note = AMIDATION
SEQUENCE: 89
IVLSLDVPIK LKKILLEQEK QKXQREQAET NXQILAQV                          38

SEQ ID NO: 90           moltype = AA  length = 38
FEATURE                 Location/Qualifiers
source                  1..38
                        mol_type = protein
                        organism = synthetic construct
MOD_RES                 1
                        note = ACETYLATION
SITE                    7
                        note = D-valine
MOD_RES                 12
                        note = the epsilon-amino group of the lysine side chain is
                        covalentlybound to an albumin -binding moiety
MOD_RES                 32
                        note = X is 4-Pip
MOD_RES                 38
                        note = AMIDATION
SEQUENCE: 90
IVLSLDVPIK LKKILLEQEK QKAQREQAET NXQILAQV                          38

SEQ ID NO: 91           moltype = AA  length = 38
FEATURE                 Location/Qualifiers
source                  1..38
                        mol_type = protein
                        organism = synthetic construct
MOD_RES                 1
                        note = ACETYLATION
SITE                    7
                        note = D-valine
MOD_RES                 12
                        note = the epsilon-amino group of the lysine side chain is
                        covalentlybound to an albumin -binding moiety
MOD_RES                 23
                        note = X is Aib
MOD_RES                 32
                        note = X is 4-Pip
MOD_RES                 38
                        note = AMIDATION
SEQUENCE: 91
IVLSLDVPIK LKKILLEQEK QKXQREQAET NXQILAQV                          38

SEQ ID NO: 92           moltype = AA  length = 37
FEATURE                 Location/Qualifiers
source                  1..37
                        mol_type = protein
                        organism = synthetic construct
MOD_RES                 1
                        note = ACETYLATION
SITE                    6
                        note = D-valine
MOD_RES                 11
                        note = the epsilon-amino group of the lysine side chain is
                        covalentlybound to an albumin -binding moiety
MOD_RES                 37
                        note = AMIDATION
SEQUENCE: 92
VLSLDVPIKL KKILLEQEKQ KKQREQAETN KQILAQV                           37

SEQ ID NO: 93           moltype = AA  length = 37
FEATURE                 Location/Qualifiers
source                  1..37
                        mol_type = protein
                        organism = synthetic construct
SITE                    6
                        note = D-valine
MOD_RES                 11
                        note = the epsilon-amino group of the lysine side chain is
                        covalentlybound to an albumin -binding moiety
MOD_RES                 37
                        note = AMIDATION
```

-continued

```
SEQUENCE: 93
VLSLDVPIKL KKILLEQEKQ KKQREQAETN KQILAQV                        37

SEQ ID NO: 94          moltype = AA  length = 37
FEATURE                Location/Qualifiers
source                 1..37
                       mol_type = protein
                       organism = synthetic construct
MOD_RES                1
                       note = Acetylated with a propanoyl group
MOD_RES                11
                       note = the epsilon-amino group of the lysine side chain is
                        covalentlybound to an albumin -binding moiety
MOD_RES                37
                       note = AMIDATION
SEQUENCE: 94
VLSLDVPIKL KKILLEQEKQ KKQREQAETN KQILAQV                        37

SEQ ID NO: 95          moltype = AA  length = 37
FEATURE                Location/Qualifiers
source                 1..37
                       mol_type = protein
                       organism = synthetic construct
MOD_RES                1
                       note = Acetylated with a butanoyl group
MOD_RES                11
                       note = the epsilon-amino group of the lysine side chain is
                        covalentlybound to an albumin -binding moiety
MOD_RES                37
                       note = AMIDATION
SEQUENCE: 95
VLSLDVPIKL KKILLEQEKQ KKQREQAETN KQILAQV                        37

SEQ ID NO: 96          moltype = AA  length = 37
FEATURE                Location/Qualifiers
source                 1..37
                       mol_type = protein
                       organism = synthetic construct
MOD_RES                1
                       note = Acetylated with a pentanoyl group
MOD_RES                11
                       note = the epsilon-amino group of the lysine side chain is
                        covalentlybound to an albumin -binding moiety
MOD_RES                37
                       note = AMIDATION
SEQUENCE: 96
VLSLDVPIKL KKILLEQEKQ KKQREQAETN KQILAQV                        37

SEQ ID NO: 97          moltype = AA  length = 38
FEATURE                Location/Qualifiers
source                 1..38
                       mol_type = protein
                       organism = synthetic construct
MOD_RES                1
                       note = ACETYLATION
MOD_RES                12
                       note = the epsilon-amino group of the lysine side chain is
                        covalentlybound to an albumin -binding moiety
MOD_RES                32
                       note = X is Aib
MOD_RES                38
                       note = AMIDATION
SEQUENCE: 97
IVLSLDVPIK LKKILLEQEK QKKQREQAET NXQILAQV                       38

SEQ ID NO: 98          moltype = AA  length = 38
FEATURE                Location/Qualifiers
source                 1..38
                       mol_type = protein
                       organism = synthetic construct
MOD_RES                1
                       note = ACETYLATION
SITE                   7
                       note = D-valine
MOD_RES                12
                       note = the epsilon-amino group of the lysine side chain is
                        covalentlybound to an albumin -binding moiety
MOD_RES                32
                       note = X is Aib
```

```
MOD_RES                38
                       note = AMIDATION
SEQUENCE: 98
IVLSLDVPIK LKKILLEQEK QKKQREQAET NXQILAQV                   38

SEQ ID NO: 99          moltype = AA  length = 37
FEATURE                Location/Qualifiers
source                 1..37
                       mol_type = protein
                       organism = synthetic construct
MOD_RES                1
                       note = ACETYLATION
SITE                   6
                       note = D-valine
MOD_RES                11
                       note = the epsilon-amino group of the lysine side chain is
                        covalentlybound to an albumin -binding moiety
MOD_RES                31
                       note = X is Aib
MOD_RES                37
                       note = AMIDATION
SEQUENCE: 99
VLSLDVPIKL KKILLEQEKQ KKQREQAETN XQILAQV                    37

SEQ ID NO: 100         moltype = AA  length = 38
FEATURE                Location/Qualifiers
source                 1..38
                       mol_type = protein
                       organism = synthetic construct
MOD_RES                1
                       note = ACETYLATION
SITE                   7
                       note = D-valine
MOD_RES                12
                       note = the epsilon-amino group of the lysine side chain is
                        covalentlybound to an albumin -binding moiety
MOD_RES                38
                       note = AMIDATION
SEQUENCE: 100
IVLSLDVPIK LKKILLEQEK QKKQREQAET NAQILAQV                   38

SEQ ID NO: 101         moltype = AA  length = 37
FEATURE                Location/Qualifiers
source                 1..37
                       mol_type = protein
                       organism = synthetic construct
MOD_RES                1
                       note = ACETYLATION
SITE                   6
                       note = D-valine
MOD_RES                11
                       note = the epsilon-amino group of the lysine side chain is
                        covalentlybound to an albumin -binding moiety
MOD_RES                37
                       note = AMIDATION
SEQUENCE: 101
VLSLDVPIKL KKILLEQEKQ KKQREQAETN AQILAQV                    37

SEQ ID NO: 102         moltype = AA  length = 38
FEATURE                Location/Qualifiers
source                 1..38
                       mol_type = protein
                       organism = synthetic construct
MOD_RES                1
                       note = ACETYLATION
MOD_RES                12
                       note = the epsilon-amino group of the lysine side chain is
                        covalentlybound to an albumin -binding moiety
MOD_RES                38
                       note = AMIDATION
SEQUENCE: 102
IVLSLDVPIK LKKILLEQEK QKKQREQAET NVQILAQV                   38

SEQ ID NO: 103         moltype = AA  length = 38
FEATURE                Location/Qualifiers
source                 1..38
                       mol_type = protein
                       organism = synthetic construct
MOD_RES                1
```

-continued

```
                        note = ACETYLATION
SITE                    7
                        note = D-valine
MOD_RES                 12
                        note = the epsilon-amino group of the lysine side chain is
                         covalentlybound to an albumin -binding moiety
MOD_RES                 38
                        note = AMIDATION
SEQUENCE: 103
IVLSLDVPIK LKKILLEQEK QKKQREQAET NVQILAQV                          38

SEQ ID NO: 104          moltype = AA  length = 38
FEATURE                 Location/Qualifiers
source                  1..38
                        mol_type = protein
                        organism = synthetic construct
MOD_RES                 1
                        note = ACETYLATION
SITE                    7
                        note = D-valine
MOD_RES                 12
                        note = the epsilon-amino group of the lysine side chain is
                         covalentlybound to an albumin -binding moiety
MOD_RES                 32
                        note = X is Abu
MOD_RES                 38
                        note = AMIDATION
SEQUENCE: 104
IVLSLDVPIK LKKILLEQEK QKKQREQAET NXQILAQV                          38

SEQ ID NO: 105          moltype = AA  length = 38
FEATURE                 Location/Qualifiers
source                  1..38
                        mol_type = protein
                        organism = synthetic construct
MOD_RES                 1
                        note = ACETYLATION
SITE                    7
                        note = D-valine
MOD_RES                 12
                        note = the epsilon-amino group of the lysine side chain is
                         covalentlybound to an albumin -binding moiety
MOD_RES                 32
                        note = X is Nva
MOD_RES                 38
                        note = AMIDATION
SEQUENCE: 105
IVLSLDVPIK LKKILLEQEK QKKQREQAET NXQILAQV                          38

SEQ ID NO: 106          moltype = AA  length = 38
FEATURE                 Location/Qualifiers
source                  1..38
                        mol_type = protein
                        organism = synthetic construct
MOD_RES                 1
                        note = ACETYLATION
SITE                    7
                        note = D-valine
MOD_RES                 12
                        note = the epsilon-amino group of the lysine side chain is
                         covalentlybound to an albumin -binding moiety
MOD_RES                 32
                        note = X is alpha-methyl-leucine
MOD_RES                 38
                        note = AMIDATION
SEQUENCE: 106
IVLSLDVPIK LKKILLEQEK QKKQREQAET NXQILAQV                          38

SEQ ID NO: 107          moltype = AA  length = 38
FEATURE                 Location/Qualifiers
source                  1..38
                        mol_type = protein
                        organism = synthetic construct
MOD_RES                 1
                        note = ACETYLATION
SITE                    7
                        note = D-valine
MOD_RES                 12
                        note = the epsilon-amino group of the lysine side chain is
```

-continued

```
                       covalentlybound to an albumin -binding moiety
MOD_RES                32
                       note = X is Dap
MOD_RES                38
                       note = AMIDATION
SEQUENCE: 107
IVLSLDVPIK LKKILLEQEK QKKQREQAET NXQILAQV                          38

SEQ ID NO: 108         moltype = AA  length = 38
FEATURE                Location/Qualifiers
source                 1..38
                       mol_type = protein
                       organism = synthetic construct
MOD_RES                1
                       note = ACETYLATION
SITE                   7
                       note = D-valine
MOD_RES                12
                       note = the epsilon-amino group of the lysine side chain is
                        covalentlybound to an albumin -binding moiety
MOD_RES                38
                       note = AMIDATION
SEQUENCE: 108
IVLSLDVPIK LKKILLEQEK QKKQREQAET NEQILAQV                          38

SEQ ID NO: 109         moltype = AA  length = 38
FEATURE                Location/Qualifiers
source                 1..38
                       mol_type = protein
                       organism = synthetic construct
MOD_RES                1
                       note = ACETYLATION
SITE                   7
                       note = D-valine
MOD_RES                12
                       note = the epsilon-amino group of the lysine side chain is
                        covalentlybound to an albumin -binding moiety
MOD_RES                32
                       note = X is 4-Pip
MOD_RES                38
                       note = AMIDATION
SEQUENCE: 109
IVLSLDVPIK LKKILLEQEK QKKQREQAET NXQILAQV                          38

SEQ ID NO: 110         moltype = AA  length = 38
FEATURE                Location/Qualifiers
source                 1..38
                       mol_type = protein
                       organism = synthetic construct
MOD_RES                1
                       note = ACETYLATION
SITE                   7
                       note = D-valine
MOD_RES                11
                       note = X is alpha-methyl-leucine
MOD_RES                12
                       note = the epsilon-amino group of the lysine side chain is
                        covalentlybound to an albumin -binding moiety
MOD_RES                32
                       note = X is Aib
MOD_RES                38
                       note = AMIDATION
SEQUENCE: 110
IVLSLDVPIK XKKILLEQEK QKKQREQAET NXQILAQV                          38

SEQ ID NO: 111         moltype = AA  length = 38
FEATURE                Location/Qualifiers
source                 1..38
                       mol_type = protein
                       organism = synthetic construct
MOD_RES                1
                       note = ACETYLATION
SITE                   7
                       note = D-valine
MOD_RES                11
                       note = X is alpha-methyl-leucine
MOD_RES                12
                       note = the epsilon-amino group of the lysine side chain is
                        covalentlybound to an albumin -binding moiety
```

-continued

```
MOD_RES                  38
                         note = AMIDATION
SEQUENCE: 111
IVLSLDVPIK XKKILLEQEK QKKQREQAET NVQILAQV                         38

SEQ ID NO: 112           moltype = AA  length = 38
FEATURE                  Location/Qualifiers
source                   1..38
                         mol_type = protein
                         organism = synthetic construct
MOD_RES                  1
                         note = ACETYLATION
SITE                     7
                         note = D-valine
MOD_RES                  11
                         note = X is alpha-methyl-leucine
MOD_RES                  12
                         note = the epsilon-amino group of the lysine side chain is
                          covalentlybound to an albumin -binding moiety
MOD_RES                  38
                         note = AMIDATION
SEQUENCE: 112
IVLSLDVPIK XKKILLEQEK QKKQREQAET NAQILAQV                         38

SEQ ID NO: 113           moltype = AA  length = 38
FEATURE                  Location/Qualifiers
source                   1..38
                         mol_type = protein
                         organism = synthetic construct
MOD_RES                  1
                         note = METHYLATION
SITE                     7
                         note = D-valine
MOD_RES                  12
                         note = the epsilon-amino group of the lysine side chain is
                          covalentlybound to an albumin -binding moiety
MOD_RES                  38
                         note = AMIDATION
SEQUENCE: 113
IVLSLDVPIK LKKILLEQEK QKKQREQAET NAQILAQV                         38

SEQ ID NO: 114           moltype = AA  length = 38
FEATURE                  Location/Qualifiers
source                   1..38
                         mol_type = protein
                         organism = synthetic construct
MOD_RES                  1
                         note = METHYLATION
SITE                     7
                         note = D-valine
MOD_RES                  12
                         note = the epsilon-amino group of the lysine side chain is
                          covalentlybound to an albumin -binding moiety
MOD_RES                  32
                         note = X is Abu
MOD_RES                  38
                         note = AMIDATION
SEQUENCE: 114
IVLSLDVPIK LKKILLEQEK QKKQREQAET NXQILAQV                         38

SEQ ID NO: 115           moltype = AA  length = 38
FEATURE                  Location/Qualifiers
source                   1..38
                         mol_type = protein
                         organism = synthetic construct
MOD_RES                  1
                         note = METHYLATION
SITE                     7
                         note = D-valine
MOD_RES                  12
                         note = the epsilon-amino group of the lysine side chain is
                          covalentlybound to an albumin -binding moiety
MOD_RES                  32
                         note = X is Dap
MOD_RES                  38
                         note = AMIDATION
SEQUENCE: 115
IVLSLDVPIK LKKILLEQEK QKKQREQAET NXQILAQV                         38
```

-continued

```
SEQ ID NO: 116          moltype = AA  length = 38
FEATURE                 Location/Qualifiers
source                  1..38
                        mol_type = protein
                        organism = synthetic construct
MOD_RES                 1
                        note = METHYLATION
SITE                    7
                        note = D-valine
MOD_RES                 12
                        note = the epsilon-amino group of the lysine side chain is
                         covalentlybound to an albumin -binding moiety
MOD_RES                 38
                        note = AMIDATION
SEQUENCE: 116
IVLSLDVPIK LKKILLEQEK QKKQREQAET NEQILAQV                          38

SEQ ID NO: 117          moltype = AA  length = 38
FEATURE                 Location/Qualifiers
source                  1..38
                        mol_type = protein
                        organism = synthetic construct
MOD_RES                 1
                        note = METHYLATION
SITE                    7
                        note = D-valine
MOD_RES                 12
                        note = the epsilon-amino group of the lysine side chain is
                         covalentlybound to an albumin -binding moiety
MOD_RES                 32
                        note = X is 4-Pip
MOD_RES                 38
                        note = AMIDATION
SEQUENCE: 117
IVLSLDVPIK LKKILLEQEK QKKQREQAET NXQILAQV                          38

SEQ ID NO: 118          moltype = AA  length = 38
FEATURE                 Location/Qualifiers
source                  1..38
                        mol_type = protein
                        organism = synthetic construct
MOD_RES                 1
                        note = METHYLATION
SITE                    7
                        note = D-valine
MOD_RES                 12
                        note = the epsilon-amino group of the lysine side chain is
                         covalentlybound to an albumin -binding moiety
MOD_RES                 32
                        note = X is Aib
MOD_RES                 38
                        note = AMIDATION
SEQUENCE: 118
IVLSLDVPIK LKKILLEQEK QKKQREQAET NXQILAQV                          38

SEQ ID NO: 119          moltype = AA  length = 38
FEATURE                 Location/Qualifiers
source                  1..38
                        mol_type = protein
                        organism = synthetic construct
MOD_RES                 1
                        note = METHYLATION
SITE                    7
                        note = D-valine
MOD_RES                 11
                        note = X is alpha-methyl-leucine
MOD_RES                 12
                        note = the epsilon-amino group of the lysine side chain is
                         covalentlybound to an albumin -binding moiety
MOD_RES                 32
                        note = X is Aib
MOD_RES                 38
                        note = AMIDATION
SEQUENCE: 119
IVLSLDVPIK XKKILLEQEK QKKQREQAET NXQILAQV                          38

SEQ ID NO: 120          moltype = AA  length = 37
FEATURE                 Location/Qualifiers
source                  1..37
```

```
                         mol_type = protein
                         organism = synthetic construct
MOD_RES                  1
                         note = Acetylated with a pentanoyl group
SITE                     6
                         note = D-valine
MOD_RES                  11
                         note = the epsilon-amino group of the lysine side chain is
                          covalentlybound to an albumin -binding moiety
MOD_RES                  31
                         note = X is Aib
MOD_RES                  37
                         note = AMIDATION
SEQUENCE: 120
VLSLDVPIKL KKILLEQEKQ KKQREQAETN XQILAQV                          37

SEQ ID NO: 121           moltype = AA  length = 37
FEATURE                  Location/Qualifiers
source                   1..37
                         mol_type = protein
                         organism = synthetic construct
MOD_RES                  1
                         note = Acetylated with a pentanoyl group
SITE                     6
                         note = D-valine
MOD_RES                  11
                         note = the epsilon-amino group of the lysine side chain is
                          covalentlybound to an albumin -binding moiety
MOD_RES                  37
                         note = AMIDATION
SEQUENCE: 121
VLSLDVPIKL KKILLEQEKQ KKQREQAETN VQILAQV                          37

SEQ ID NO: 122           moltype = AA  length = 37
FEATURE                  Location/Qualifiers
source                   1..37
                         mol_type = protein
                         organism = synthetic construct
MOD_RES                  1
                         note = Acetylated with a pentanoyl group
SITE                     6
                         note = D-valine
MOD_RES                  11
                         note = the epsilon-amino group of the lysine side chain is
                          covalentlybound to an albumin -binding moiety
MOD_RES                  37
                         note = AMIDATION
SEQUENCE: 122
VLSLDVPIKL KKILLEQEKQ KKQREQAETN AQILAQV                          37

SEQ ID NO: 123           moltype = AA  length = 37
FEATURE                  Location/Qualifiers
source                   1..37
                         mol_type = protein
                         organism = synthetic construct
MOD_RES                  1
                         note = Acetylated with a pentanoyl group
SITE                     5
                         note = D-valine
MOD_RES                  10
                         note = X is alpha-methyl-leucine
MOD_RES                  11
                         note = the epsilon-amino group of the lysine side chain is
                          covalentlybound to an albumin -binding moiety
MOD_RES                  31
                         note = X is Aib
MOD_RES                  37
                         note = AMIDATION
SEQUENCE: 123
VLSLDVPIKX KKILLEQEKQ KKQREQAETN XQILAQV                          37

SEQ ID NO: 124           moltype = AA  length = 37
FEATURE                  Location/Qualifiers
source                   1..37
                         mol_type = protein
                         organism = synthetic construct
MOD_RES                  1
                         note = Acetylated with a pentanoyl group
SITE                     7
```

-continued

```
                        note = D-valine
MOD_RES                 10
                        note = X is alpha-methyl-leucine
MOD_RES                 11
                        note = the epsilon-amino group of the lysine side chain is
                         covalentlybound to an albumin -binding moiety
MOD_RES                 37
                        note = AMIDATION
SEQUENCE: 124
VLSLDVPIKX KKILLEQEKQ KKQREQAETN VQILAQV                            37

SEQ ID NO: 125          moltype = AA  length = 38
FEATURE                 Location/Qualifiers
source                  1..38
                        mol_type = protein
                        organism = synthetic construct
MOD_RES                 1
                        note = ACETYLATION
SITE                    7
                        note = D-valine
MOD_RES                 12
                        note = the epsilon-amino group of the lysine side chain is
                         covalentlybound to an albumin -binding moiety
MOD_RES                 32
                        note = X is Aib
MOD_RES                 38
                        note = AMIDATION
SEQUENCE: 125
IVLSLDVPIK LKKILLEQEK QKKQREQAET NXQILAQV                           38

SEQ ID NO: 126          moltype = AA  length = 38
FEATURE                 Location/Qualifiers
source                  1..38
                        mol_type = protein
                        organism = synthetic construct
MOD_RES                 1
                        note = ACETYLATION
SITE                    7
                        note = D-valine
MOD_RES                 12
                        note = the epsilon-amino group of the lysine side chain is
                         covalentlybound to an albumin -binding moiety
MOD_RES                 38
                        note = AMIDATION
SEQUENCE: 126
IVLSLDVPIK LKKILLEQEK QKKQREQAET NAQILAQV                           38

SEQ ID NO: 127          moltype = AA  length = 38
FEATURE                 Location/Qualifiers
source                  1..38
                        mol_type = protein
                        organism = synthetic construct
MOD_RES                 1
                        note = ACETYLATION
SITE                    7
                        note = D-valine
MOD_RES                 12
                        note = the epsilon-amino group of the lysine side chain is
                         covalentlybound to an albumin -binding moiety
MOD_RES                 32
                        note = X is Abu
MOD_RES                 38
                        note = AMIDATION
SEQUENCE: 127
IVLSLDVPIK LKKILLEQEK QKKQREQAET NXQILAQV                           38

SEQ ID NO: 128          moltype = AA  length = 38
FEATURE                 Location/Qualifiers
source                  1..38
                        mol_type = protein
                        organism = synthetic construct
MOD_RES                 1
                        note = ACETYLATION
SITE                    7
                        note = D-valine
MOD_RES                 12
                        note = the epsilon-amino group of the lysine side chain is
                         covalentlybound to an albumin -binding moiety
MOD_RES                 32
```

-continued

```
                        note = X is Dap
MOD_RES                 38
                        note = AMIDATION
SEQUENCE: 128
IVLSLDVPIK LKKILLEQEK QKKQREQAET NXQILAQV                           38

SEQ ID NO: 129          moltype = AA  length = 38
FEATURE                 Location/Qualifiers
source                  1..38
                        mol_type = protein
                        organism = synthetic construct
MOD_RES                 1
                        note = ACETYLATION
SITE                    7
                        note = D-valine
MOD_RES                 12
                        note = the epsilon-amino group of the lysine side chain is
                         covalentlybound to an albumin -binding moiety
MOD_RES                 32
                        note = X is 4-Pip
MOD_RES                 38
                        note = AMIDATION
SEQUENCE: 129
IVLSLDVPIK LKKILLEQEK QKKQREQAET NXQILAQV                           38

SEQ ID NO: 130          moltype = AA  length = 38
FEATURE                 Location/Qualifiers
source                  1..38
                        mol_type = protein
                        organism = synthetic construct
MOD_RES                 1
                        note = ACETYLATION
SITE                    7
                        note = D-valine
MOD_RES                 12
                        note = the epsilon-amino group of the lysine side chain is
                         covalentlybound to an albumin -binding moiety
MOD_RES                 38
                        note = AMIDATION
SEQUENCE: 130
IVLSLDVPIK LKKILLEQEK QKKQREQAET NEQILAQV                           38

SEQ ID NO: 131          moltype = AA  length = 38
FEATURE                 Location/Qualifiers
source                  1..38
                        mol_type = protein
                        organism = synthetic construct
MOD_RES                 1
                        note = ACETYLATION
SITE                    7
                        note = D-valine
MOD_RES                 12
                        note = the epsilon-amino group of the lysine side chain is
                         covalentlybound to an albumin -binding moiety
MOD_RES                 32
                        note = X is 4-Pip
MOD_RES                 38
                        note = AMIDATION
SEQUENCE: 131
IVLSLDVPIK LKKILLEQEK QKAQREQAET NXQILAQV                           38

SEQ ID NO: 132          moltype = AA  length = 38
FEATURE                 Location/Qualifiers
source                  1..38
                        mol_type = protein
                        organism = synthetic construct
MOD_RES                 1
                        note = ACETYLATION
SITE                    7
                        note = D-valine
MOD_RES                 12
                        note = the epsilon-amino group of the lysine side chain is
                         covalentlybound to an albumin -binding moiety
MOD_RES                 23
                        note = X is Aib
MOD_RES                 32
                        note = X is 4-Pip
MOD_RES                 38
                        note = AMIDATION
```

```
SEQUENCE: 132
IVLSLDVPIK LKKILLEQEK QKKQREQAET NXQILAQV                          38

SEQ ID NO: 133          moltype = AA  length = 38
FEATURE                 Location/Qualifiers
source                  1..38
                        mol_type = protein
                        organism = synthetic construct
MOD_RES                 1
                        note = ACETYLATION
SITE                    7
                        note = D-valine
MOD_RES                 12
                        note = the epsilon-amino group of the lysine side chain is
                         covalentlybound to an albumin -binding moiety
MOD_RES                 32
                        note = X is Thp
MOD_RES                 38
                        note = AMIDATION
SEQUENCE: 133
IVLSLDVPIK LKKILLEQEK QKKQREQAET NXQILAQV                          38

SEQ ID NO: 134          moltype = AA  length = 38
FEATURE                 Location/Qualifiers
source                  1..38
                        mol_type = protein
                        organism = synthetic construct
MOD_RES                 1
                        note = ACETYLATION
SITE                    7
                        note = D-valine
MOD_RES                 12
                        note = the epsilon-amino group of the lysine side chain is
                         covalentlybound to an albumin -binding moiety
MOD_RES                 32
                        note = X is Chx
MOD_RES                 38
                        note = AMIDATION
SEQUENCE: 134
IVLSLDVPIK LKKILLEQEK QKKQREQAET NXQILAQV                          38

SEQ ID NO: 135          moltype = AA  length = 38
FEATURE                 Location/Qualifiers
source                  1..38
                        mol_type = protein
                        organism = synthetic construct
MOD_RES                 1
                        note = ACETYLATION
SITE                    7
                        note = D-valine
MOD_RES                 12
                        note = the epsilon-amino group of the lysine side chain is
                         covalentlybound to an albumin -binding moiety
MOD_RES                 32
                        note = X is Cpex
MOD_RES                 38
                        note = AMIDATION
SEQUENCE: 135
IVLSLDVPIK LKKILLEQEK QKKQREQAET NXQILAQV                          38

SEQ ID NO: 136          moltype = AA  length = 38
FEATURE                 Location/Qualifiers
source                  1..38
                        mol_type = protein
                        organism = synthetic construct
MOD_RES                 1
                        note = ACETYLATION
SITE                    7
                        note = D-valine
MOD_RES                 12
                        note = the epsilon-amino group of the lysine side chain is
                         covalentlybound to an albumin -binding moiety
MOD_RES                 32
                        note = X is Cpx
MOD_RES                 38
                        note = AMIDATION
SEQUENCE: 136
IVLSLDVPIK LKKILLEQEK QKKQREQAET NXQILAQV                          38
```

-continued

```
SEQ ID NO: 137          moltype = AA  length = 38
FEATURE                 Location/Qualifiers
source                  1..38
                        mol_type = protein
                        organism = synthetic construct
MOD_RES                 1
                        note = METHYLATION
SITE                    7
                        note = D-valine
MOD_RES                 12
                        note = the epsilon-amino group of the lysine side chain is
                         covalentlybound to an albumin -binding moiety
MOD_RES                 32
                        note = X is Aib
MOD_RES                 38
                        note = AMIDATION
SEQUENCE: 137
IVLSLDVPIK LKKILLEQEK QKKQREQAET NXQILAQV                           38

SEQ ID NO: 138          moltype = AA  length = 38
FEATURE                 Location/Qualifiers
source                  1..38
                        mol_type = protein
                        organism = synthetic construct
MOD_RES                 1
                        note = METHYLATION
SITE                    7
                        note = D-valine
MOD_RES                 12
                        note = the epsilon-amino group of the lysine side chain is
                         covalentlybound to an albumin -binding moiety
MOD_RES                 38
                        note = AMIDATION
SEQUENCE: 138
IVLSLDVPIK LKKILLEQEK QKKQREQAET NAQILAQV                           38

SEQ ID NO: 139          moltype = AA  length = 38
FEATURE                 Location/Qualifiers
source                  1..38
                        mol_type = protein
                        organism = synthetic construct
MOD_RES                 1
                        note = METHYLATION
SITE                    7
                        note = D-valine
MOD_RES                 12
                        note = the epsilon-amino group of the lysine side chain is
                         covalentlybound to an albumin -binding moiety
MOD_RES                 32
                        note = X is Abu
MOD_RES                 38
                        note = AMIDATION
SEQUENCE: 139
IVLSLDVPIK LKKILLEQEK QKKQREQAET NXQILAQV                           38

SEQ ID NO: 140          moltype = AA  length = 38
FEATURE                 Location/Qualifiers
source                  1..38
                        mol_type = protein
                        organism = synthetic construct
MOD_RES                 1
                        note = METHYLATION
SITE                    7
                        note = D-valine
MOD_RES                 12
                        note = the epsilon-amino group of the lysine side chain is
                         covalentlybound to an albumin -binding moiety
MOD_RES                 32
                        note = X is Dap
MOD_RES                 38
                        note = AMIDATION
SEQUENCE: 140
IVLSLDVPIK LKKILLEQEK QKKQREQAET NXQILAQV                           38

SEQ ID NO: 141          moltype = AA  length = 38
FEATURE                 Location/Qualifiers
source                  1..38
                        mol_type = protein
                        organism = synthetic construct
```

-continued

```
MOD_RES                 1
                        note = METHYLATION
SITE                    7
                        note = D-valine
MOD_RES                 12
                        note = the epsilon-amino group of the lysine side chain is
                         covalentlybound to an albumin -binding moiety
MOD_RES                 32
                        note = X is 4-Pip
MOD_RES                 38
                        note = AMIDATION
SEQUENCE: 141
IVLSLDVPIK LKKILLEQEK QKKQREQAET NXQILAQV                          38

SEQ ID NO: 142          moltype = AA  length = 38
FEATURE                 Location/Qualifiers
source                  1..38
                        mol_type = protein
                        organism = synthetic construct
MOD_RES                 1
                        note = METHYLATION
SITE                    7
                        note = D-valine
MOD_RES                 12
                        note = the epsilon-amino group of the lysine side chain is
                         covalentlybound to an albumin -binding moiety
MOD_RES                 38
                        note = AMIDATION
SEQUENCE: 142
IVLSLDVPIK LKKILLEQEK QKKQREQAET NEQILAQV                          38

SEQ ID NO: 143          moltype = AA  length = 38
FEATURE                 Location/Qualifiers
source                  1..38
                        mol_type = protein
                        organism = synthetic construct
MOD_RES                 1
                        note = METHYLATION
SITE                    7
                        note = D-valine
MOD_RES                 12
                        note = the epsilon-amino group of the lysine side chain is
                         covalentlybound to an albumin -binding moiety
MOD_RES                 32
                        note = X is Thp
MOD_RES                 38
                        note = AMIDATION
SEQUENCE: 143
IVLSLDVPIK LKKILLEQEK QKKQREQAET NXQILAQV                          38

SEQ ID NO: 144          moltype = AA  length = 38
FEATURE                 Location/Qualifiers
source                  1..38
                        mol_type = protein
                        organism = synthetic construct
MOD_RES                 1
                        note = METHYLATION
SITE                    7
                        note = D-valine
MOD_RES                 12
                        note = the epsilon-amino group of the lysine side chain is
                         covalentlybound to an albumin -binding moiety
MOD_RES                 32
                        note = X is Aib
MOD_RES                 38
                        note = AMIDATION
SEQUENCE: 144
IVLSLDVPIK LKKILLEQEK QKAQREQAET NXQILAQV                          38

SEQ ID NO: 145          moltype = AA  length = 38
FEATURE                 Location/Qualifiers
source                  1..38
                        mol_type = protein
                        organism = synthetic construct
MOD_RES                 1
                        note = METHYLATION
SITE                    7
                        note = D-valine
MOD_RES                 12
```

```
                        note = the epsilon-amino group of the lysine side chain is
                         covalentlybound to an albumin -binding moiety
MOD_RES                 23
                        note = X is Aib
MOD_RES                 32
                        note = X is Aib
MOD_RES                 38
                        note = AMIDATION
SEQUENCE: 145
IVLSLDVPIK LKKILLEQEK QKXQREQAET NXQILAQV                          38

SEQ ID NO: 146          moltype = AA  length = 38
FEATURE                 Location/Qualifiers
source                  1..38
                        mol_type = protein
                        organism = synthetic construct
REGION                  1..38
                        note = Comp 3
SITE                    7
                        note = D-valine
MOD_RES                 12
                        note = the epsilon-amino group of the lysine side chain is
                         covalentlybound to an albumin -binding moiety
MOD_RES                 38
                        note = AMIDATION
SEQUENCE: 146
IVLSLDVPIK LKQILLKQER QKKQREQAEK NKQILEQV                          38

SEQ ID NO: 147          moltype = AA  length = 38
FEATURE                 Location/Qualifiers
source                  1..38
                        mol_type = protein
                        organism = synthetic construct
REGION                  1..38
                        note = Comp 2
SITE                    7
                        note = D-valine
MOD_RES                 12
                        note = the epsilon-amino group of the lysine side chain is
                         covalentlybound to an albumin -binding moiety
MOD_RES                 38
                        note = AMIDATION
SEQUENCE: 147
IVLSLDVPIK LKQILLKQER QKKQREQAEK NKQILEQV                          38

SEQ ID NO: 148          moltype = AA  length = 38
FEATURE                 Location/Qualifiers
source                  1..38
                        mol_type = protein
                        organism = synthetic construct
SITE                    7
                        note = D-valine
MOD_RES                 12
                        note = the epsilon-amino group of the lysine side chain is
                         covalentlybound to an albumin -binding moiety
MOD_RES                 38
                        note = AMIDATION
SEQUENCE: 148
IVLSLDVPIK LKQILLKQER QKKQREQAEK NKQILEQV                          38

SEQ ID NO: 149          moltype = AA  length = 38
FEATURE                 Location/Qualifiers
source                  1..38
                        mol_type = protein
                        organism = synthetic construct
SITE                    7
                        note = D-valine
MOD_RES                 12
                        note = the epsilon-amino group of the lysine side chain is
                         covalentlybound to an albumin -binding moiety
MOD_RES                 38
                        note = AMIDATION
SEQUENCE: 149
IVLSLDVPIK LKKILLEQEK QKKQREQAET NKQILAQV                          38

SEQ ID NO: 150          moltype = AA  length = 38
FEATURE                 Location/Qualifiers
source                  1..38
                        mol_type = protein
```

-continued

```
                        organism = synthetic construct
SITE                    7
                        note = D-valine
MOD_RES                 12
                        note = the epsilon-amino group of the lysine side chain is
                         covalentlybound to an albumin -binding moiety
MOD_RES                 38
                        note = AMIDATION
SEQUENCE: 150
IVLSLDVPIK LKQILLKQER QKKQREQAEK NKQILEQV                           38

SEQ ID NO: 151          moltype = AA  length = 38
FEATURE                 Location/Qualifiers
SITE                    7
                        note = D-valine
MOD_RES                 12
                        note = the epsilon-amino group of the lysine side chain is
                         covalentlybound to an albumin -binding moiety
MOD_RES                 38
                        note = AMIDATION
source                  1..38
                        mol_type = protein
                        organism = synthetic construct
SEQUENCE: 151
IVLSLDVPIK LKQILLKQER QKKQREQAEK NKQILEQV                           38

SEQ ID NO: 152          moltype = AA  length = 38
FEATURE                 Location/Qualifiers
source                  1..38
                        mol_type = protein
                        organism = synthetic construct
MOD_RES                 1
                        note = Acetylated
SITE                    7
                        note = D-valine
MOD_RES                 12
                        note = Lysine is bound to an albumine-binding moiety
MOD_RES                 32
                        note = X is 4-Pip
MOD_RES                 38
                        note = Amidation
SEQUENCE: 152
IVLSLDVPIK LKKILLEQEK QKAQREQAET NXQILAQV                           38

SEQ ID NO: 153          moltype = AA  length = 38
FEATURE                 Location/Qualifiers
source                  1..38
                        mol_type = protein
                        organism = synthetic construct
MOD_RES                 1
                        note = Acetylated
SITE                    7
                        note = D-valine
MOD_RES                 12
                        note = Lysine is bound to an albumine-binding moiety
MOD_RES                 23
                        note = X is Aib
MOD_RES                 32
                        note = X is 4-Pip
MOD_RES                 38
                        note = AMIDATION
SEQUENCE: 153
IVLSLDVPIK LKKILLEQEK QKXQREQAET NXQILAQV                           38

SEQ ID NO: 154          moltype = AA  length = 38
FEATURE                 Location/Qualifiers
source                  1..38
                        mol_type = protein
                        organism = synthetic construct
MOD_RES                 1
                        note = N-Methylated
SITE                    7
                        note = D-valine
MOD_RES                 32
                        note = X is 4-Pip
MOD_RES                 38
                        note = Amidation
MOD_RES                 12
                        note = Lisine is bound to an albumin binding moiety
```

-continued

```
SEQUENCE: 154
IVLSLDVPIK LKKILLEQEK QKAQREQAET NXQILAQV                    38

SEQ ID NO: 155         moltype = AA  length = 38
FEATURE                Location/Qualifiers
source                 1..38
                       mol_type = protein
                       organism = synthetic construct
MOD_RES                1
                       note = N-Methylated
MOD_RES                23
                       note = X is Aib
MOD_RES                32
                       note = X is 4-Pip
MOD_RES                38
                       note = Amidation
SITE                   7
                       note = D-valine
MOD_RES                12
                       note = Lysine is bound to an albumin binding moiety
SEQUENCE: 155
IVLSLDVPIK LKKILLEQEK QKXQREQAET NXQILAQV                    38

SEQ ID NO: 156         moltype = AA  length = 37
FEATURE                Location/Qualifiers
source                 1..37
                       mol_type = protein
                       organism = synthetic construct
MOD_RES                1
                       note = Acylated with Hexanoyl
SITE                   6
                       note = D-valine
MOD_RES                31
                       note = X is Aib
MOD_RES                37
                       note = Amidation
MOD_RES                11
                       note = Lysine is bound to an albumin binding moiety
SEQUENCE: 156
VLSLDVPIKL KKILLEQEKQ KKQREQAETN XQILAQV                     37

SEQ ID NO: 157         moltype = AA  length = 37
FEATURE                Location/Qualifiers
source                 1..37
                       mol_type = protein
                       organism = synthetic construct
MOD_RES                1
                       note = Acylated with Hexanoyl
SITE                   6
                       note = D-valine
MOD_RES                31
                       note = X is 4-Pip
MOD_RES                37
                       note = Amidation
MOD_RES                11
                       note = Lysine is bound to an albumin binding moiety
SEQUENCE: 157
VLSLDVPIKL KKILLEQEKQ KKQREQAETN XQILAQV                     37

SEQ ID NO: 158         moltype = AA  length = 37
FEATURE                Location/Qualifiers
source                 1..37
                       mol_type = protein
                       organism = synthetic construct
MOD_RES                1
                       note = Acylation with Decanoyl
SITE                   6
                       note = D-valine
MOD_RES                11
                       note = Lysine is bound to an albumin binding moiety
MOD_RES                31
                       note = X is Aib
MOD_RES                37
                       note = Amidation
SEQUENCE: 158
VLSLDVPIKL KKILLEQEKQ KKQREQAETN XQILAQV                     37

SEQ ID NO: 159         moltype = AA  length = 37
FEATURE                Location/Qualifiers
```

```
source                  1..37
                        mol_type = protein
                        organism = synthetic construct
MOD_RES                 1
                        note = N-Methylated
SITE                    6
                        note = D-valine
MOD_RES                 11
                        note = Lysine is bound to an albumin binding moiety
MOD_RES                 31
                        note = X is Aib
MOD_RES                 37
                        note = amidation
SEQUENCE: 159
VLSLDVPIKL KKILLEQEKQ KKQREQAETN XQILAQV                            37

SEQ ID NO: 160          moltype = AA  length = 37
FEATURE                 Location/Qualifiers
source                  1..37
                        mol_type = protein
                        organism = synthetic construct
MOD_RES                 1
                        note = N-Methylated
SITE                    6
                        note = D-valine
MOD_RES                 11
                        note = Lysine is bound to an albumin binding moiety
MOD_RES                 31
                        note = X is 4-Pip
MOD_RES                 37
                        note = amidation
SEQUENCE: 160
VLSLDVPIKL KKILLEQEKQ KKQREQAETN XQILAQV                            37

SEQ ID NO: 161          moltype = AA  length = 38
FEATURE                 Location/Qualifiers
source                  1..38
                        mol_type = protein
                        organism = synthetic construct
MOD_RES                 1
                        note = Acetylated
MOD_RES                 7
                        note = X is D-valine
MOD_RES                 32
                        note = X is Aib
MOD_RES                 38
                        note = Amidation
MOD_RES                 12
                        note = Lysine side chain is bound to an albumin-binding
                         moiety
SEQUENCE: 161
IVLSLDXPIK LKKILLEQEK QKAQREQAET NXQILAQV                           38

SEQ ID NO: 162          moltype = AA  length = 38
FEATURE                 Location/Qualifiers
source                  1..38
                        mol_type = protein
                        organism = synthetic construct
MOD_RES                 1
                        note = Acetylated
MOD_RES                 7
                        note = X is D-valine
MOD_RES                 12
                        note = Lysine is bound to an albumin binding moiety
MOD_RES                 7
                        note = X is Aib
MOD_RES                 38
                        note = Amidation
SEQUENCE: 162
IVLSLDXPIK LKKILLEQEK QKXQREQAET NXQILAQV                           38

SEQ ID NO: 163          moltype = AA  length = 38
FEATURE                 Location/Qualifiers
source                  1..38
                        mol_type = protein
                        organism = synthetic construct
MOD_RES                 1
                        note = acetylation
MOD_RES                 7
```

-continued

```
                         note = X is D-valine
MOD_RES                  12
                         note = Lysine is bound to an albumin binding moiety
MOD_RES                  38
                         note = amidation
SEQUENCE: 163
IVLSLDXPIA LKKILLEQEK QKKQREQAET NXQILAQV                         38

SEQ ID NO: 164           moltype = AA  length = 38
FEATURE                  Location/Qualifiers
source                   1..38
                         mol_type = protein
                         organism = synthetic construct
MOD_RES                  1
                         note = Acetylated
MOD_RES                  7
                         note = X is D-valine
MOD_RES                  12
                         note = Lysine is bound to an albumin binding moiety
MOD_RES                  32
                         note = X is Aib
MOD_RES                  38
                         note = Amidation
SEQUENCE: 164
IVLSLDXPIK LKAILLEQEK QKKQREQAET NXQILAQV                         38

SEQ ID NO: 165           moltype = AA  length = 38
FEATURE                  Location/Qualifiers
source                   1..38
                         mol_type = protein
                         organism = synthetic construct
MOD_RES                  1
                         note = Acetylated
MOD_RES                  7
                         note = X is D-valine
MOD_RES                  12
                         note = Lysine is bound to an albumin binding moiety
MOD_RES                  32
                         note = X is Aib
MOD_RES                  38
                         note = amidation
SEQUENCE: 165
IVLSLDXPIK LKKILLEQEA QKKQREQAET NXQILAQV                         38

SEQ ID NO: 166           moltype = AA  length = 38
FEATURE                  Location/Qualifiers
source                   1..38
                         mol_type = protein
                         organism = synthetic construct
MOD_RES                  1
                         note = acetylation
MOD_RES                  7
                         note = X is D-valine
MOD_RES                  12
                         note = Lysine is bound to an albumin binding moiety
MOD_RES                  32
                         note = X is Aib
MOD_RES                  38
                         note = amidation
SEQUENCE: 166
IVLSLDXPIK LKKILLEQEK QAKQREQAET NXQILAQV                         38

SEQ ID NO: 167           moltype = AA  length = 38
FEATURE                  Location/Qualifiers
source                   1..38
                         mol_type = protein
                         organism = synthetic construct
MOD_RES                  1
                         note = acetylation
MOD_RES                  7
                         note = X is D-valine
MOD_RES                  12
                         note = Lysine is bound to an albumin binding moiety
MOD_RES                  32
                         note = X is Aib
MOD_RES                  38
                         note = Amidation
SEQUENCE: 167
IVLSLDXPIK LKKILLEQEK QKKQAEQAET NXQILAQV                         38
```

```
SEQ ID NO: 168         moltype = AA  length = 38
FEATURE                Location/Qualifiers
source                 1..38
                       mol_type = protein
                       organism = synthetic construct
MOD_RES                1
                       note = Acetylation
MOD_RES                7
                       note = X is D-valine
MOD_RES                12
                       note = Lysine is bound to an albumin binding moiety
MOD_RES                32
                       note = X is Aib
MOD_RES                38
                       note = Amidation
SEQUENCE: 168
IVLSLDXPIK LKKILLEQEK QKEQREQAET NXQILAQV                          38

SEQ ID NO: 169         moltype = AA  length = 38
FEATURE                Location/Qualifiers
source                 1..38
                       mol_type = protein
                       organism = synthetic construct
MOD_RES                1
                       note = Acetylation
MOD_RES                7
                       note = X is D-valine
MOD_RES                12
                       note = Lysine is bound to an albumin binding moiety
MOD_RES                32
                       note = X is 4-Pip
MOD_RES                38
                       note = amidation
SEQUENCE: 169
IVLSLDXPIK LKKILLEQEK QKAQREQAET NXQILAQV                          38

SEQ ID NO: 170         moltype = AA  length = 38
FEATURE                Location/Qualifiers
source                 1..38
                       mol_type = protein
                       organism = synthetic construct
MOD_RES                1
                       note = acetylation
MOD_RES                7
                       note = X is D-valine
MOD_RES                23
                       note = X is Aib
MOD_RES                32
                       note = X is 4-Pip
MOD_RES                38
                       note = amidation
SEQUENCE: 170
IVLSLDXPIK LKKILLEQEK QKXQREQAET NXQILAQV                          38

SEQ ID NO: 171         moltype = AA  length = 38
FEATURE                Location/Qualifiers
source                 1..38
                       mol_type = protein
                       organism = synthetic construct
MOD_RES                1
                       note = acetylated
MOD_RES                7
                       note = X is D-valine
MOD_RES                12
                       note = Lysine is bound to an albumin binding moiety
MOD_RES                32
                       note = X is Aib
MOD_RES                38
                       note = Amidation
SEQUENCE: 171
IVLSLDXPIK LKKILLEQEK QKKQREQAET NXQILAQV                          38

SEQ ID NO: 172         moltype = AA  length = 38
FEATURE                Location/Qualifiers
source                 1..38
                       mol_type = protein
                       organism = synthetic construct
MOD_RES                1
```

```
                        note = Acetylated
MOD_RES                 7
                        note = X is D-valine
MOD_RES                 12
                        note = Lysine is bound to an albumin binding moiety
MOD_RES                 32
                        note = X is 4-Pip
MOD_RES                 38
                        note = amidation
SEQUENCE: 172
IVLSLDXPIK LKKILLEQEK QKKQREQAET NXQILAQV                            38

SEQ ID NO: 173          moltype = AA  length = 38
FEATURE                 Location/Qualifiers
source                  1..38
                        mol_type = protein
                        organism = synthetic construct
MOD_RES                 1
                        note = acetylation
MOD_RES                 7
                        note = X is D-valine
MOD_RES                 12
                        note = Lysine is bound to an albumin binding moiety
MOD_RES                 23
                        note = X is Aib
MOD_RES                 32
                        note = X is 4-Pip
MOD_RES                 38
                        note = amidation
SEQUENCE: 173
IVLSLDXPIK LKKILLEQEK QKXQREQAET NXQILAQV                            38

SEQ ID NO: 174          moltype = AA  length = 38
FEATURE                 Location/Qualifiers
source                  1..38
                        mol_type = protein
                        organism = synthetic construct
MOD_RES                 1
                        note = acetylation
MOD_RES                 7
                        note = X is D-valine
MOD_RES                 12
                        note = Lysine is bound to an albumin binding moeity
MOD_RES                 32
                        note = X is Aib
MOD_RES                 38
                        note = amidation
SEQUENCE: 174
IVLSLDXPIK LKKILLEQEK QKKQREQAET NXQILAQV                            38

SEQ ID NO: 175          moltype = AA  length = 38
FEATURE                 Location/Qualifiers
source                  1..38
                        mol_type = protein
                        organism = synthetic construct
MOD_RES                 1
                        note = acetylation
MOD_RES                 7
                        note = X is D-valine
MOD_RES                 12
                        note = Lysine is bound to an albumin binding moiety
MOD_RES                 32
                        note = X is 4-Pip
MOD_RES                 38
                        note = amidation
SEQUENCE: 175
IVLSLDXPIK LKKILLEQEK QKKQREQAET NXQILAQV                            38

SEQ ID NO: 176          moltype = AA  length = 38
FEATURE                 Location/Qualifiers
source                  1..38
                        mol_type = protein
                        organism = synthetic construct
MOD_RES                 1
                        note = N-Methylated
MOD_RES                 7
                        note = X is D-valine
MOD_RES                 12
                        note = Lysine is bound to an albumin binding moiety
```

```
MOD_RES                 32
                        note = X is Aib
MOD_RES                 38
                        note = Amidation
SEQUENCE: 176
IVLSLDXPIK LKKILLEQEK QKAQREQAET NXQILAQV                    38

SEQ ID NO: 177          moltype = AA  length = 38
FEATURE                 Location/Qualifiers
source                  1..38
                        mol_type = protein
                        organism = synthetic construct
MOD_RES                 1
                        note = N-Methylated
MOD_RES                 7
                        note = X is D-valine
MOD_RES                 12
                        note = Lysine is bound to an albumin binding moiety
MOD_RES                 23
                        note = X is Aib
MOD_RES                 32
                        note = X is Aib
MOD_RES                 38
                        note = amidation
SEQUENCE: 177
IVLSLDXPIK LKKILLEQEK QKXQREQAET NXQILAQV                    38

SEQ ID NO: 178          moltype = AA  length = 38
FEATURE                 Location/Qualifiers
source                  1..38
                        mol_type = protein
                        organism = synthetic construct
MOD_RES                 1
                        note = N-Methylated
MOD_RES                 7
                        note = X is D-valine
MOD_RES                 12
                        note = Lysine is bound to an albumin binding moiety
MOD_RES                 32
                        note = X is Aib
MOD_RES                 38
                        note = amidation
SEQUENCE: 178
IVLSLDXPIK LKKILLEQEK QKKQREQAET NXQILAQV                    38

SEQ ID NO: 179          moltype = AA  length = 38
FEATURE                 Location/Qualifiers
source                  1..38
                        mol_type = protein
                        organism = synthetic construct
MOD_RES                 1
                        note = N-Methylated
MOD_RES                 7
                        note = X is D-valine
MOD_RES                 12
                        note = Lysine is bound to an albumin binding moiety
MOD_RES                 32
                        note = X is Aib
MOD_RES                 38
                        note = amidation
SEQUENCE: 179
IVLSLDXPIK LKKILLEQEK QKKQREQAET NXQILAQV                    38

SEQ ID NO: 180          moltype = AA  length = 37
FEATURE                 Location/Qualifiers
source                  1..37
                        mol_type = protein
                        organism = synthetic construct
MOD_RES                 1
                        note = Acylation with Pentanoyl
MOD_RES                 6
                        note = X is D-valine
MOD_RES                 11
                        note = Lysine is bound to an albulin binding moiety
MOD_RES                 31
                        note = X is Aib
MOD_RES                 37
                        note = Amidation
SEQUENCE: 180
```

```
VLSLDXPIKL KKILLEQEKQ KKQREQAETN XQILAQV                          37

SEQ ID NO: 181         moltype = AA  length = 37
FEATURE                Location/Qualifiers
source                 1..37
                       mol_type = protein
                       organism = synthetic construct
MOD_RES                1
                       note = Acylation with Pentanoyl
MOD_RES                6
                       note = X is D-valine
MOD_RES                11
                       note = Lysine is bound to an albumin binding moiety
MOD_RES                31
                       note = X is Aib
MOD_RES                37
                       note = amidation
SEQUENCE: 181
VLSLDXPIKL KKILLEQEKQ KKQREQAETN XQILAQV                          37

SEQ ID NO: 182         moltype = AA  length = 38
FEATURE                Location/Qualifiers
source                 1..38
                       mol_type = protein
                       organism = synthetic construct
MOD_RES                1
                       note = Acetylation
MOD_RES                7
                       note = X is D-valine
MOD_RES                12
                       note = Lysine is bound to an albumin binding moiety
MOD_RES                32
                       note = X is Aib
MOD_RES                38
                       note = amidation
SEQUENCE: 182
IVLSLDXPIK LKKILLEQEK QKKQREQAET NXQILAQV                         38

SEQ ID NO: 183         moltype = AA  length = 38
FEATURE                Location/Qualifiers
source                 1..38
                       mol_type = protein
                       organism = synthetic construct
MOD_RES                1
                       note = Acetylation
MOD_RES                7
                       note = X is D-valine
MOD_RES                12
                       note = Lysine is bound to an albumin binding moiety
MOD_RES                32
                       note = X is 4-Pip
MOD_RES                38
                       note = Amidation
SEQUENCE: 183
IVLSLDXPIK LKKILLEQEK QKKQREQAET NXQILAQV                         38

SEQ ID NO: 184         moltype = AA  length = 38
FEATURE                Location/Qualifiers
source                 1..38
                       mol_type = protein
                       organism = synthetic construct
MOD_RES                1
                       note = Acetylation
MOD_RES                7
                       note = X is D-valine
MOD_RES                12
                       note = Lysine is bound to an albumin binding moiety
MOD_RES                23
                       note = X is Aib
MOD_RES                32
                       note = X is 4-Pip
MOD_RES                38
                       note = Amidation
SEQUENCE: 184
IVLSLDXPIK LKKILLEQEK QKXQREQAET NXQILAQV                         38

SEQ ID NO: 185         moltype = AA  length = 37
FEATURE                Location/Qualifiers
source                 1..37
```

```
                        mol_type = protein
                        organism = synthetic construct
MOD_RES                 1
                        note = Acylation with Pentanoyl
MOD_RES                 6
                        note = X is D-valine
MOD_RES                 11
                        note = Lysine is bound to an albumin binding moiety
MOD_RES                 31
                        note = X is Aib
MOD_RES                 37
                        note = Amidation
SEQUENCE: 185
VLSLDXPIKL KKILLEQEKQ KKQREQAETN XQILAQV                            37

SEQ ID NO: 186          moltype = AA  length = 38
FEATURE                 Location/Qualifiers
source                  1..38
                        mol_type = protein
                        organism = synthetic construct
MOD_RES                 1
                        note = N-Methylated
MOD_RES                 7
                        note = X is D-valine
MOD_RES                 12
                        note = Lysine is bound to an albumin binding moiety
MOD_RES                 32
                        note = X is Aib
MOD_RES                 38
                        note = Amidation
SEQUENCE: 186
IVLSLDXPIK LKKILLEQEK QKKQREQAET NXQILAQV                           38

SEQ ID NO: 187          moltype = AA  length = 38
FEATURE                 Location/Qualifiers
source                  1..38
                        mol_type = protein
                        organism = synthetic construct
MOD_RES                 1
                        note = Acetylation
MOD_RES                 7
                        note = X is D-valine
MOD_RES                 12
                        note = Lysine is bound to an albumin binding moiety
MOD_RES                 32
                        note = X is 4-Pip
MOD_RES                 38
                        note = Amidation
SEQUENCE: 187
IVLSLDXPIK LKKILLEQEK QKAQREQAET NXQILAQV                           38

SEQ ID NO: 188          moltype = AA  length = 38
FEATURE                 Location/Qualifiers
source                  1..38
                        mol_type = protein
                        organism = synthetic construct
MOD_RES                 1
                        note = Acetylation
MOD_RES                 7
                        note = X is D-valine
MOD_RES                 12
                        note = Lysine is bound to an albumin binding moiety
MOD_RES                 23
                        note = X is Aib
MOD_RES                 32
                        note = X is 4-Pip
MOD_RES                 38
                        note = Amidation
SEQUENCE: 188
IVLSLDXPIK LKKILLEQEK QKXQREQAET NXQILAQV                           38

SEQ ID NO: 189          moltype = AA  length = 38
FEATURE                 Location/Qualifiers
source                  1..38
                        mol_type = protein
                        organism = synthetic construct
MOD_RES                 1
                        note = Acetylation
MOD_RES                 7
```

```
                        note = X is D-valine
MOD_RES                 12
                        note = Lysine is bound to an albumin binding moiety
MOD_RES                 32
                        note = X is Aib
MOD_RES                 38
                        note = Amidation
SEQUENCE: 189
IVLSLDXPIK LKKILLEQEK QKAQREQAET NXQILAQV                         38

SEQ ID NO: 190          moltype = AA  length = 38
FEATURE                 Location/Qualifiers
source                  1..38
                        mol_type = protein
                        organism = synthetic construct
MOD_RES                 1
                        note = Acetylation
MOD_RES                 7
                        note = X is D-valine
MOD_RES                 12
                        note = Lysine is bound to an albumin binding moiety
MOD_RES                 23
                        note = X is Aib
MOD_RES                 32
                        note = X is Aib
MOD_RES                 38
                        note = Amidation
SEQUENCE: 190
IVLSLDXPIK LKKILLEQEK QKXQREQAET NXQILAQV                         38

SEQ ID NO: 191          moltype = AA  length = 38
FEATURE                 Location/Qualifiers
source                  1..38
                        mol_type = protein
                        organism = synthetic construct
MOD_RES                 1
                        note = Acetylated
MOD_RES                 7
                        note = X is D-valine
MOD_RES                 12
                        note = Lysine is bound to an albumin binding moiety
MOD_RES                 32
                        note = X is Aib
MOD_RES                 38
                        note = Amidation
SEQUENCE: 191
IVLSLDXPIG LKKILLEQEK QKKQREQAET NXQILAQV                         38

SEQ ID NO: 192          moltype = AA  length = 38
FEATURE                 Location/Qualifiers
source                  1..38
                        mol_type = protein
                        organism = synthetic construct
MOD_RES                 1
                        note = N-Methylated
MOD_RES                 7
                        note = X is D-valine
MOD_RES                 12
                        note = Lysine is bound to an albumin binding moiety
MOD_RES                 32
                        note = X is Aib
MOD_RES                 38
                        note = amidation
SEQUENCE: 192
IVLSLDXPIG LKKILLEQEK QKKQREQAET NXQILAQV                         38

SEQ ID NO: 193          moltype = AA  length = 37
FEATURE                 Location/Qualifiers
source                  1..37
                        mol_type = protein
                        organism = synthetic construct
MOD_RES                 1
                        note = Acylation with Pentanoyl
MOD_RES                 6
                        note = X is D-valine
MOD_RES                 11
                        note = Lysine is bound to an albumin binding moiety
MOD_RES                 31
                        note = X is Aib
```

-continued

```
MOD_RES                 37
                        note = Amidation
SEQUENCE: 193
VLSLDXPIKL KKILLEQEKQ KKQREQAETN XQILAQV                    37

SEQ ID NO: 194          moltype = AA  length = 37
FEATURE                 Location/Qualifiers
source                  1..37
                        mol_type = protein
                        organism = synthetic construct
MOD_RES                 1
                        note = Acylation with Pentanoyl
MOD_RES                 6
                        note = X is D-valine
MOD_RES                 11
                        note = Lysine is bound to an albumin binding moiety
MOD_RES                 31
                        note = X is Aib
MOD_RES                 37
                        note = Amidation
SEQUENCE: 194
VLSLDXPIKL KKILLEQEKQ KXQREQAETN XQILAQV                    37

SEQ ID NO: 195          moltype = AA  length = 37
FEATURE                 Location/Qualifiers
source                  1..37
                        mol_type = protein
                        organism = synthetic construct
MOD_RES                 1
                        note = Acylation with Pentanoyl
MOD_RES                 6
                        note = X is D-valine
MOD_RES                 11
                        note = Lysine is bound to an albumin binding moiety
MOD_RES                 31
                        note = X is Aib
MOD_RES                 37
                        note = Amidation
SEQUENCE: 195
VLSLDXPIGL KKILLEQEKQ KKQREQAETN XQILAQV                    37

SEQ ID NO: 196          moltype = AA  length = 38
FEATURE                 Location/Qualifiers
source                  1..38
                        mol_type = protein
                        organism = synthetic construct
MOD_RES                 1
                        note = Acetylation
MOD_RES                 7
                        note = X is D-valine
MOD_RES                 12
                        note = Lysine is bound to an albulin binding moiety
MOD_RES                 23
                        note = X is Aib
MOD_RES                 32
                        note = X is 4-Pip
MOD_RES                 38
                        note = Amidation
SEQUENCE: 196
IVLSLDXPIK LKKILLEQEK QKXQREQAET NXQILAQV                   38

SEQ ID NO: 197          moltype = AA  length = 38
FEATURE                 Location/Qualifiers
source                  1..38
                        mol_type = protein
                        organism = synthetic construct
MOD_RES                 1
                        note = Acetylation
MOD_RES                 7
                        note = X is D-valine
MOD_RES                 12
                        note = Lysine is bound to an albumin binding moiety
MOD_RES                 23
                        note = X is Aib
MOD_RES                 32
                        note = X is Aib
MOD_RES                 38
                        note = Amidation
SEQUENCE: 197
```

```
IVLSLDXPIK LKKILLEQEK QKXQREQAET NXQILAQV                        38

SEQ ID NO: 198          moltype = AA  length = 38
FEATURE                 Location/Qualifiers
source                  1..38
                        mol_type = protein
                        organism = synthetic construct
MOD_RES                 1
                        note = Acetylation
MOD_RES                 7
                        note = X is D-valine
MOD_RES                 12
                        note = Lysine is bound to an albumin binding moiety
MOD_RES                 32
                        note = X is Thp
MOD_RES                 38
                        note = amidation
SEQUENCE: 198
IVLSLDXPIK LKKILLEQEK QKKQREQAET NXQILAQV                        38

SEQ ID NO: 199          moltype = AA  length = 38
FEATURE                 Location/Qualifiers
source                  1..38
                        mol_type = protein
                        organism = synthetic construct
MOD_RES                 1
                        note = Acetylation
MOD_RES                 7
                        note = X is D-valine
MOD_RES                 12
                        note = Lysine is bound to an albumn binding moiety
MOD_RES                 32
                        note = X is Thp
MOD_RES                 38
                        note = Amidation
SEQUENCE: 199
IVLSLDXPIK LKKILLEQEK QKKQREQAET NXQILAQV                        38

SEQ ID NO: 200          moltype = AA  length = 38
FEATURE                 Location/Qualifiers
source                  1..38
                        mol_type = protein
                        organism = synthetic construct
MOD_RES                 1
                        note = N-Methylated
MOD_RES                 7
                        note = X is D-valine
MOD_RES                 12
                        note = Lysine is bound to an labumin binding moiety
MOD_RES                 23
                        note = X is Aib
MOD_RES                 32
                        note = X is Aib
MOD_RES                 38
                        note = Amidation
SEQUENCE: 200
IVLSLDXPIK LKKILLEQEK QKXQREQAET NXQILAQV                        38

SEQ ID NO: 201          moltype = AA  length = 37
FEATURE                 Location/Qualifiers
source                  1..37
                        mol_type = protein
                        organism = synthetic construct
MOD_RES                 1
                        note = Acylation with Pentanoyl
MOD_RES                 6
                        note = X is D-valine
MOD_RES                 11
                        note = Lysine is bound to an albumin binding moiety
MOD_RES                 31
                        note = X is Aib
MOD_RES                 37
                        note = Amidation
SEQUENCE: 201
VLSLDXPIKL KKILLEQEKQ KKQREQAETN XQILAQV                         37

SEQ ID NO: 202          moltype = AA  length = 37
FEATURE                 Location/Qualifiers
source                  1..37
```

```
                        mol_type = protein
                        organism = synthetic construct
MOD_RES                 1
                        note = Acylation with Pentanoyl
MOD_RES                 6
                        note = X is D-valine
MOD_RES                 11
                        note = Lysine is bound to an albumin binding moiety
MOD_RES                 22
                        note = X is Aib
MOD_RES                 31
                        note = X is Aib
SEQUENCE: 202
VLSLDXPIKL KKILLEQEKQ KXQREQAETN XQILAQV                    37

SEQ ID NO: 203          moltype = AA  length = 38
FEATURE                 Location/Qualifiers
source                  1..38
                        mol_type = protein
                        organism = synthetic construct
MOD_RES                 1
                        note = Acetylation
MOD_RES                 7
                        note = X is D-valine
MOD_RES                 12
                        note = Lysine is bound to an albumin binding moiety
MOD_RES                 32
                        note = X is Aib
MOD_RES                 38
                        note = Amidation
SEQUENCE: 203
IVLSLDXPIK LKKILLEQEK QKKQREQAET NXQILAQV                   38

SEQ ID NO: 204          moltype = AA  length = 38
FEATURE                 Location/Qualifiers
source                  1..38
                        mol_type = protein
                        organism = synthetic construct
MOD_RES                 1
                        note = Acetylation
MOD_RES                 7
                        note = X is D-valine
MOD_RES                 12
                        note = Lysine is bound to an albumin binding moiety
MOD_RES                 32
                        note = X is Aib
MOD_RES                 38
                        note = Amidation
SEQUENCE: 204
IVLSLDXPIK LKKILLEQEK QKKQREQAET NXQILAQV                   38

SEQ ID NO: 205          moltype = AA  length = 38
FEATURE                 Location/Qualifiers
source                  1..38
                        mol_type = protein
                        organism = synthetic construct
MOD_RES                 1
                        note = Acetylation
MOD_RES                 7
                        note = X is D-valine
MOD_RES                 12
                        note = Lysine is bound to an albumin binding moiety
MOD_RES                 32
                        note = X is Aib
SEQUENCE: 205
IVLSLDXPIK LKKILLEQEK QKKQREQAET NXQILAQV                   38

SEQ ID NO: 206          moltype = AA  length = 38
FEATURE                 Location/Qualifiers
source                  1..38
                        mol_type = protein
                        organism = synthetic construct
MOD_RES                 1
                        note = Acetylation
MOD_RES                 7
                        note = X is D-valine
MOD_RES                 12
                        note = Lysine is bound to an albumin binding moiety
MOD_RES                 32
```

-continued

```
                        note = X is Aib
MOD_RES                 38
                        note = Amidation
SEQUENCE: 206
IVLSLDXPIK LKKILLEQEK QKKQREQAET NXQILAQV                            38

SEQ ID NO: 207          moltype = AA  length = 38
FEATURE                 Location/Qualifiers
source                  1..38
                        mol_type = protein
                        organism = synthetic construct
MOD_RES                 1
                        note = Acetylated
MOD_RES                 7
                        note = X is D-valine
MOD_RES                 12
                        note = Lysine is bound to an albumin binding moiety
MOD_RES                 32
                        note = X is 4-Pip
MOD_RES                 38
                        note = Amidation
SEQUENCE: 207
IVLSLDXPIK LKKILLEQEK QKKQREQAET NXQILAQV                            38

SEQ ID NO: 208          moltype = AA  length = 38
FEATURE                 Location/Qualifiers
source                  1..38
                        mol_type = protein
                        organism = synthetic construct
MOD_RES                 1
                        note = Acetylated
MOD_RES                 7
                        note = X is D-valine
MOD_RES                 12
                        note = Lysine is bound to an albumin binding moiety
MOD_RES                 23
                        note = X is Aib
MOD_RES                 32
                        note = X is 4-Pip
MOD_RES                 38
                        note = Amidation
SEQUENCE: 208
IVLSLDXPIK LKKILLEQEK QKXQREQAET NXQILAQV                            38

SEQ ID NO: 209          moltype = AA  length = 38
FEATURE                 Location/Qualifiers
source                  1..38
                        mol_type = protein
                        organism = synthetic construct
MOD_RES                 1
                        note = Acetylated
MOD_RES                 7
                        note = X is D-valine
MOD_RES                 12
                        note = Lysine is bound to an albumin binding moiety
MOD_RES                 23
                        note = X is Aib
MOD_RES                 32
                        note = X is Aib
MOD_RES                 38
                        note = Amidation
SEQUENCE: 209
IVLSLDXPIK LKKILLEQEK QKXQREQAET NXQILAQV                            38

SEQ ID NO: 210          moltype = AA  length = 38
FEATURE                 Location/Qualifiers
source                  1..38
                        mol_type = protein
                        organism = synthetic construct
MOD_RES                 1
                        note = Acetylated
MOD_RES                 7
                        note = X is D-valine
MOD_RES                 12
                        note = Lysine is bound to an albumin binding moiety
MOD_RES                 32
                        note = X is Thp
MOD_RES                 38
                        note = Amidation
```

```
SEQUENCE: 210
IVLSLDXPIK LKKILLEQEK QKKQREQAET NXQILAQV                          38

SEQ ID NO: 211          moltype = AA  length = 38
FEATURE                 Location/Qualifiers
source                  1..38
                        mol_type = protein
                        organism = synthetic construct
MOD_RES                 1
                        note = Acetylated
MOD_RES                 7
                        note = X is D-valine
MOD_RES                 12
                        note = Lysine is bound to an albumin binding moiety
MOD_RES                 32
                        note = X is Aib
MOD_RES                 38
                        note = amidation
SEQUENCE: 211
IVLSLDXPIK LKKILLEQEA QKKQREQAET NXQILAQV                          38

SEQ ID NO: 212          moltype = AA  length = 38
FEATURE                 Location/Qualifiers
source                  1..38
                        mol_type = protein
                        organism = synthetic construct
MOD_RES                 1
                        note = acetylated
MOD_RES                 7
                        note = X is D-valine
MOD_RES                 12
                        note = Lysine is bound to an albumin binding moiety
MOD_RES                 32
                        note = X is Aib
MOD_RES                 38
                        note = Amidation
SEQUENCE: 212
IVLSLDXPIK LKKILLEQEK QKAQREQAET NXQILAQV                          38

SEQ ID NO: 213          moltype = AA  length = 38
FEATURE                 Location/Qualifiers
source                  1..38
                        mol_type = protein
                        organism = synthetic construct
MOD_RES                 1
                        note = acetylated
MOD_RES                 7
                        note = X is D-valine
MOD_RES                 12
                        note = Lysine is bound to an albumin binding moiety
MOD_RES                 32
                        note = X is Aib
MOD_RES                 38
                        note = Amidation
SEQUENCE: 213
IVLSLDXPIK LKKILLEQEK QKEQREQAET NXQILAQV                          38

SEQ ID NO: 214          moltype = AA  length = 38
FEATURE                 Location/Qualifiers
source                  1..38
                        mol_type = protein
                        organism = synthetic construct
MOD_RES                 1
                        note = N-Methylation
MOD_RES                 7
                        note = X is D-valine
MOD_RES                 12
                        note = Lysine is bound to an albumin binding moiety
MOD_RES                 32
                        note = X is Aib
MOD_RES                 38
                        note = Amidation
SEQUENCE: 214
IVLSLDXPIK LKKILLEQEK QKKQREQAET NXQILAQV                          38

SEQ ID NO: 215          moltype = AA  length = 38
FEATURE                 Location/Qualifiers
source                  1..38
                        mol_type = protein
```

```
                        organism = synthetic construct
MOD_RES                 1
                        note = N-Methylated
MOD_RES                 7
                        note = X is D-valine
MOD_RES                 12
                        note = Lysine is bound to an albumin binding moiety
MOD_RES                 23
                        note = X is Aib
MOD_RES                 32
                        note = X is Aib
MOD_RES                 38
                        note = Amidation
SEQUENCE: 215
IVLSLDXPIK LKKILLEQEK QKXQREQAET NXQILAQV                           38

SEQ ID NO: 216          moltype = AA  length = 38
FEATURE                 Location/Qualifiers
source                  1..38
                        mol_type = protein
                        organism = synthetic construct
MOD_RES                 1
                        note = N-Methylated
MOD_RES                 7
                        note = X is D-valine
MOD_RES                 12
                        note = Lysine is bound to an albumin binding moiety
MOD_RES                 32
                        note = X is Aib
MOD_RES                 38
                        note = Amidation
SEQUENCE: 216
IVLSLDXPIK LKKILLEQEA QKKQREQAET NXQILAQV                           38

SEQ ID NO: 217          moltype = AA  length = 38
FEATURE                 Location/Qualifiers
source                  1..38
                        mol_type = protein
                        organism = synthetic construct
MOD_RES                 1
                        note = N-Methylated
MOD_RES                 7
                        note = X is D-valine
MOD_RES                 12
                        note = Lysine is bound to an albumin binding moiety
MOD_RES                 32
                        note = X is Aib
MOD_RES                 38
                        note = Amidation
SEQUENCE: 217
IVLSLDXPIK LKKILLEQEK QKAQREQAET NXQILAQV                           38

SEQ ID NO: 218          moltype = AA  length = 38
FEATURE                 Location/Qualifiers
source                  1..38
                        mol_type = protein
                        organism = synthetic construct
MOD_RES                 1
                        note = N-Methylated
MOD_RES                 7
                        note = X is D-valine
MOD_RES                 12
                        note = Lysine is bound to an albumin binding moiety
MOD_RES                 32
                        note = X is Aib
MOD_RES                 38
                        note = Amidation
SEQUENCE: 218
IVLSLDXPIK LKKILLEQEK QKEQREQAET NXQILAQV                           38

SEQ ID NO: 219          moltype = AA  length = 37
FEATURE                 Location/Qualifiers
source                  1..37
                        mol_type = protein
                        organism = synthetic construct
MOD_RES                 1
                        note = Acylated with Pentanoyl
MOD_RES                 6
                        note = X is D-valine
```

```
MOD_RES                 11
                        note = Lysine is bound to an albumin binding moiety
MOD_RES                 31
                        note = X is Aib
MOD_RES                 37
                        note = Amidation
SEQUENCE: 219
VLSLDXPIKL KKILLEQEKQ KKQREQAETN XQILAQV                         37

SEQ ID NO: 220          moltype = AA  length = 37
FEATURE                 Location/Qualifiers
source                  1..37
                        mol_type = protein
                        organism = synthetic construct
MOD_RES                 1
                        note = Acylated with Pentanoyl
MOD_RES                 6
                        note = X is D-valine
MOD_RES                 11
                        note = Lysine is bound to an albumin binding moiety
MOD_RES                 22
                        note = X is Aib
MOD_RES                 31
                        note = X is Aib
MOD_RES                 37
                        note = Amidation
SEQUENCE: 220
VLSLDXPIKL KKILLEQEKQ KXQREQAETN XQILAQV                         37

SEQ ID NO: 221          moltype = AA  length = 37
FEATURE                 Location/Qualifiers
source                  1..37
                        mol_type = protein
                        organism = synthetic construct
MOD_RES                 1
                        note = Acylated with Pentanoyl
MOD_RES                 6
                        note = X is D-valine
MOD_RES                 11
                        note = Lysine is bound to an albumin binding moiety
MOD_RES                 31
                        note = X is Aib
MOD_RES                 37
                        note = Amidation
SEQUENCE: 221
VLSLDXPIKL KKILLEQEAQ KKQREQAETN XQILAQV                         37

SEQ ID NO: 222          moltype = AA  length = 37
FEATURE                 Location/Qualifiers
source                  1..37
                        mol_type = protein
                        organism = synthetic construct
MOD_RES                 1
                        note = Acylated with Pentanoyl
MOD_RES                 6
                        note = X is D-valine
MOD_RES                 11
                        note = Lysine is bound to an albumin binding moiety
MOD_RES                 31
                        note = X is Aib
MOD_RES                 37
                        note = Amidation
SEQUENCE: 222
VLSLDXPIKL KKILLEQEKQ KAQREQAETN XQILAQV                         37

SEQ ID NO: 223          moltype = AA  length = 37
FEATURE                 Location/Qualifiers
source                  1..37
                        mol_type = protein
                        organism = synthetic construct
MOD_RES                 1
                        note = Acylation with Decanoyl
MOD_RES                 6
                        note = X is D-valine
MOD_RES                 11
                        note = Lysine is bound to an albumin binding moiety
MOD_RES                 31
                        note = X is Aib
MOD_RES                 37
```

```
                        note = Amidation
SEQUENCE: 223
VLSLDXPIKL KKILLEQEKQ KKQREQAETN XQILAQV                        37

SEQ ID NO: 224          moltype = AA  length = 37
FEATURE                 Location/Qualifiers
source                  1..37
                        mol_type = protein
                        organism = synthetic construct
MOD_RES                 1
                        note = Acylation with Dodecanoyl
MOD_RES                 6
                        note = X is D-valine
MOD_RES                 11
                        note = Lysine is bound to an albumin binding moiety
MOD_RES                 31
                        note = X is Aib
MOD_RES                 37
                        note = Amidation
SEQUENCE: 224
VLSLDXPIKL KKILLEQEKQ KKQREQAETN XQILAQV                        37

SEQ ID NO: 225          moltype = AA  length = 37
FEATURE                 Location/Qualifiers
source                  1..37
                        mol_type = protein
                        organism = synthetic construct
MOD_RES                 1
                        note = Acylation with Tetradecanoyl
MOD_RES                 6
                        note = X is D-valine
MOD_RES                 11
                        note = Lysine is bound to an albumin binding moiety
MOD_RES                 31
                        note = X is Aib
MOD_RES                 37
                        note = Amidation
SEQUENCE: 225
VLSLDXPIKL KKILLEQEKQ KKQREQAETN XQILAQV                        37

SEQ ID NO: 226          moltype = AA  length = 38
FEATURE                 Location/Qualifiers
source                  1..38
                        mol_type = protein
                        organism = synthetic construct
MOD_RES                 1
                        note = Acetylated
MOD_RES                 7
                        note = X is D-valine
MOD_RES                 12
                        note = Lysine is bound to an albumin binding moiety
MOD_RES                 32
                        note = X is Aib
MOD_RES                 38
                        note = Amidation
SEQUENCE: 226
IVLSLDXPIG LKKILLEQEK QKKQREQAET NXQILAQV                       38

SEQ ID NO: 227          moltype = AA  length = 38
FEATURE                 Location/Qualifiers
source                  1..38
                        mol_type = protein
                        organism = synthetic construct
MOD_RES                 1
                        note = Acetylated
MOD_RES                 7
                        note = X is D-valine
MOD_RES                 12
                        note = Lysine is bound to an albumin binding moiety
MOD_RES                 32
                        note = X is 4-Pip
MOD_RES                 38
                        note = Amidation
SEQUENCE: 227
IVLSLDXPIG LKKILLEQEK QKKQREQAET NXQILAQV                       38

SEQ ID NO: 228          moltype = AA  length = 37
FEATURE                 Location/Qualifiers
source                  1..37
```

-continued

```
                        mol_type = protein
                        organism = synthetic construct
MOD_RES                 1
                        note = Acylation with Pentanoyl
MOD_RES                 6
                        note = X is D-valine
MOD_RES                 11
                        note = Lysine is bound to an albumin binding moiety
MOD_RES                 31
                        note = X is Aib
MOD_RES                 37
                        note = Amidation
SEQUENCE: 228
VLSLDXPIGL KKILLEQEKQ KKQREQAETN XQILAQV                            37

SEQ ID NO: 229          moltype = AA  length = 38
FEATURE                 Location/Qualifiers
source                  1..38
                        mol_type = protein
                        organism = synthetic construct
MOD_RES                 1
                        note = N-Methylated
MOD_RES                 7
                        note = X is D-valine
MOD_RES                 12
                        note = Lysine is bound to an albumin binding moiety
MOD_RES                 32
                        note = X is Aib
MOD_RES                 38
                        note = Amidation
SEQUENCE: 229
IVLSLDXPIG LKKILLEQEK QKKQREQAET NXQILAQV                           38

SEQ ID NO: 230          moltype = AA  length = 38
FEATURE                 Location/Qualifiers
source                  1..38
                        mol_type = protein
                        organism = synthetic construct
MOD_RES                 1
                        note = Acetylated
MOD_RES                 7
                        note = X is D-valine
MOD_RES                 12
                        note = Lysine is bound to an albumin binding moiety
MOD_RES                 32
                        note = X is Aib
MOD_RES                 38
                        note = Amidation
SEQUENCE: 230
IVLSLDXPIK LKKILLEQEK QKKQREQAET NXQILAQV                           38

SEQ ID NO: 231          moltype = AA  length = 38
FEATURE                 Location/Qualifiers
source                  1..38
                        mol_type = protein
                        organism = synthetic construct
MOD_RES                 1
                        note = Acetylated
MOD_RES                 7
                        note = X is D-valine
MOD_RES                 12
                        note = Lysine is bound to an albumin binding moiety
MOD_RES                 32
                        note = X is Aib
MOD_RES                 38
                        note = Amidation
SEQUENCE: 231
IVLSLDXPIK LKKILLEQEK QKEQREQAET NXQILAQV                           38

SEQ ID NO: 232          moltype = AA  length = 38
FEATURE                 Location/Qualifiers
source                  1..38
                        mol_type = protein
                        organism = synthetic construct
MOD_RES                 1
                        note = Acetylated
MOD_RES                 7
                        note = X is D-valine
MOD_RES                 12
```

```
                        note = Lysine is bound to an albumin binding moiety
MOD_RES                 32
                        note = X is Aib
MOD_RES                 38
                        note = Amidation
SEQUENCE: 232
IVLSLDXPIK LKKILLEQEK QKAQREQAET NXQILAQV                          38

SEQ ID NO: 233          moltype = AA  length = 38
FEATURE                 Location/Qualifiers
source                  1..38
                        mol_type = protein
                        organism = synthetic construct
MOD_RES                 1
                        note = N-Methylated
MOD_RES                 7
                        note = X is D-valine
MOD_RES                 12
                        note = Lysine is bound to an albumin binding moiety
MOD_RES                 32
                        note = X is Aib
MOD_RES                 38
                        note = Amidation
SEQUENCE: 233
IVLSLDXPIK LKKILLEQEK QKEQREQAET NXQILAQV                          38

SEQ ID NO: 234          moltype = AA  length = 38
FEATURE                 Location/Qualifiers
source                  1..38
                        mol_type = protein
                        organism = synthetic construct
MOD_RES                 1
                        note = N-Methylated
MOD_RES                 7
                        note = X is D-valine
MOD_RES                 12
                        note = Lysine is bound to an albumin binding moiety
MOD_RES                 32
                        note = X is Aib
MOD_RES                 38
                        note = Amidation
MOD_RES                 23
                        note = X is Aib
SEQUENCE: 234
IVLSLDXPIK LKKILLEQEK QKXQREQAET NXQILAQV                          38

SEQ ID NO: 235          moltype = AA  length = 37
FEATURE                 Location/Qualifiers
source                  1..37
                        mol_type = protein
                        organism = synthetic construct
MOD_RES                 1
                        note = Acylation with Pentanoyl
MOD_RES                 6
                        note = X is D-valine
MOD_RES                 11
                        note = Lysine is bound to an albumin binding moiety
MOD_RES                 31
                        note = X is Aib
MOD_RES                 37
                        note = Amidation
SEQUENCE: 235
VLSLDXPIKL KKILLEQEKQ KKQREQAETN XQILAQV                           37

SEQ ID NO: 236          moltype = AA  length = 38
FEATURE                 Location/Qualifiers
source                  1..38
                        mol_type = protein
                        organism = synthetic construct
MOD_RES                 1
                        note = Acetylated
MOD_RES                 7
                        note = X is D-valine
MOD_RES                 12
                        note = Lysine is bound to an albumin binding moiety
MOD_RES                 32
                        note = X is Aib
MOD_RES                 38
                        note = Amidation
```

-continued

```
SEQUENCE: 236
IVLSLDXPIK LKKILLEQEK QKEQREQAET NXQILAQV                   38

SEQ ID NO: 237          moltype = AA  length = 38
FEATURE                 Location/Qualifiers
source                  1..38
                        mol_type = protein
                        organism = synthetic construct
MOD_RES                 1
                        note = N-Methylated
MOD_RES                 7
                        note = X is D-valine
MOD_RES                 12
                        note = Lysine is bound to an albumin binding moiety
MOD_RES                 32
                        note = X is Aib
MOD_RES                 38
                        note = Amidation
SEQUENCE: 237
IVLSLDXPIK LKKILLEQEK QKEQREQAET NXQILAQV                   38

SEQ ID NO: 238          moltype = AA  length = 38
FEATURE                 Location/Qualifiers
source                  1..38
                        mol_type = protein
                        organism = synthetic construct
MOD_RES                 1
                        note = Acetylated
MOD_RES                 7
                        note = X is D-valine
MOD_RES                 12
                        note = Lysine is bound to an albumin binding moiety
MOD_RES                 32
                        note = X is Aib
MOD_RES                 38
                        note = Amidation
SEQUENCE: 238
IVLSLDXPIK LKKILLEQEK QKKQREQAET NXQILAQV                   38

SEQ ID NO: 239          moltype = AA  length = 38
FEATURE                 Location/Qualifiers
source                  1..38
                        mol_type = protein
                        organism = synthetic construct
MOD_RES                 1
                        note = N-Methylated
MOD_RES                 7
                        note = X is D-valine
MOD_RES                 12
                        note = Lysine is bound to an albumin binding moiety
MOD_RES                 23
                        note = X is Aib
MOD_RES                 32
                        note = X is Aib
MOD_RES                 38
                        note = Amidation
SEQUENCE: 239
IVLSLDXPIK LKKILLEQEK QKXQREQAET NXQILAQV                   38

SEQ ID NO: 240          moltype = AA  length = 38
FEATURE                 Location/Qualifiers
source                  1..38
                        mol_type = protein
                        organism = synthetic construct
MOD_RES                 1
                        note = Acetylated
MOD_RES                 7
                        note = X is D-valine
MOD_RES                 32
                        note = X is Aib
MOD_RES                 38
                        note = Amidation
SEQUENCE: 240
IVLSLDXPIK LKKILLEQEK QKAQREQAET NXQILAQV                   38

SEQ ID NO: 241          moltype = AA  length = 38
FEATURE                 Location/Qualifiers
source                  1..38
                        mol_type = protein
```

-continued

```
                         organism = synthetic construct
MOD_RES                  1
                         note = Acetylated
SITE                     7
                         note = D-valine
MOD_RES                  12
                         note = Lysine is bound to an albumin binding moiety
MOD_RES                  32
                         note = X is Aib
MOD_RES                  38
                         note = Amidation
SEQUENCE: 241
IVLSLDXPIK LKKILLEQEK QKEQREQAET NXQILAQV                          38

SEQ ID NO: 242           moltype = AA  length = 38
FEATURE                  Location/Qualifiers
source                   1..38
                         mol_type = protein
                         organism = synthetic construct
MOD_RES                  1
                         note = N-Methylated
MOD_RES                  7
                         note = X is D-valine
MOD_RES                  12
                         note = Lysine is bound to an albumin binding moiety
MOD_RES                  32
                         note = X is Aib
MOD_RES                  38
                         note = Amidation
SEQUENCE: 242
IVLSLDXPIK LKKILLEQEK QKEQREQAET NXQILAQV                          38

SEQ ID NO: 243           moltype = AA  length = 38
FEATURE                  Location/Qualifiers
source                   1..38
                         mol_type = protein
                         organism = synthetic construct
MOD_RES                  1
                         note = Acetylated
MOD_RES                  7
                         note = X is D-valine
MOD_RES                  12
                         note = Lysine is bound to an albumin binding moiety
MOD_RES                  32
                         note = X is Aib
MOD_RES                  38
                         note = Amidation
SEQUENCE: 243
IVLSLDXPIK LKKILLEQEK QKKQREQAET NXQILAQV                          38

SEQ ID NO: 244           moltype = AA  length = 38
FEATURE                  Location/Qualifiers
source                   1..38
                         mol_type = protein
                         organism = synthetic construct
MOD_RES                  1
                         note = Acetylated
MOD_RES                  7
                         note = X is D-valine
MOD_RES                  12
                         note = Lysine is bound to an albumin binding moiety
MOD_RES                  32
                         note = X is Aib
MOD_RES                  38
                         note = Amidation
SEQUENCE: 244
IVLSLDXPIK LKKILLEQEK QKAQREQAET NXQILAQV                          38
```